United States Patent
Comita-Prevoir et al.

(10) Patent No.: US 10,800,778 B2
(45) Date of Patent: Oct. 13, 2020

(54) BETA-LACTAMASE INHIBITOR COMPOUNDS

(71) Applicant: Entasis Therapeutics Limited, Altrincham, Cheshire (GB)

(72) Inventors: Janelle Comita-Prevoir, Northborough, MA (US); Thomas Francois Durand-Reville, Belmont, MA (US); Lise Gauthier, Waltham, MA (US); John O'Donnell, Mattapoisett, MA (US); Jan Romero, Arlington, MA (US); Ruben Tommasi, Stow, MA (US); Jeroen Cunera Verheijen, Westborough, MA (US); Frank Wu, Shrewsbury, MA (US); Xiaoyun Wu, Westborough, MA (US); Jing Zhang, Sudbury, MA (US)

(73) Assignee: Entasis Therapeutics Limited, Altricham (GB)

( * ) Notice: Subject to any disclaimer, the term of this patent is extended or adjusted under 35 U.S.C. 154(b) by 0 days.

(21) Appl. No.: 16/333,900

(22) PCT Filed: Sep. 15, 2017

(86) PCT No.: PCT/US2017/051692
§ 371 (c)(1),
(2) Date: Mar. 15, 2019

(87) PCT Pub. No.: WO2018/053215
PCT Pub. Date: Mar. 22, 2018

(65) Prior Publication Data
US 2019/0202832 A1    Jul. 4, 2019

Related U.S. Application Data

(60) Provisional application No. 62/456,423, filed on Feb. 8, 2017, provisional application No. 62/395,464, filed on Sep. 16, 2016.

(51) Int. Cl.
| | | |
|---|---|---|
| *C07D 471/08* | (2006.01) | |
| *C07D 211/78* | (2006.01) | |
| *A61P 31/04* | (2006.01) | |
| *A61K 31/546* | (2006.01) | |
| *A61K 45/06* | (2006.01) | |
| *A61K 31/46* | (2006.01) | |
| *A61K 31/439* | (2006.01) | |

(52) U.S. Cl.
CPC .......... *C07D 471/08* (2013.01); *A61K 31/439* (2013.01); *A61K 31/46* (2013.01); *A61K 31/546* (2013.01); *A61K 45/06* (2013.01); *A61P 31/04* (2018.01); *C07D 211/78* (2013.01); *Y02A 50/404* (2018.01); *Y02A 50/406* (2018.01); *Y02A 50/473* (2018.01)

(58) Field of Classification Search
CPC ............................ C07D 471/08; C07D 211/78
See application file for complete search history.

(56) References Cited

U.S. PATENT DOCUMENTS

| | | |
|---|---|---|
| 7,112,592 B2 | 9/2006 | Lampilas et al. |
| 7,612,087 B2 | 11/2009 | Aszodi et al. |
| 9,309,245 B2 | 4/2016 | McGuire et al. |
| 9,623,014 B2 | 4/2017 | McGuire et al. |
| 9,968,593 B2 | 5/2018 | DeJonge et al. |
| 10,376,499 B2 | 8/2019 | DeJonge et al. |
| 2004/0157826 A1 | 8/2004 | Lampilas et al. |
| 2005/0020572 A1 | 1/2005 | Aszodi et al. |
| 2005/0245505 A1 | 11/2005 | Aszodi et al. |

(Continued)

FOREIGN PATENT DOCUMENTS

| | | |
|---|---|---|
| CN | 1655781 A | 8/2005 |
| EP | 2135959 A1 | 12/2009 |

(Continued)

OTHER PUBLICATIONS

STN Registry No. 1055320-07-4, 1 page, Sep. 30, 2008.

(Continued)

*Primary Examiner* — Bruck Kifle
(74) *Attorney, Agent, or Firm* — McCarter & English, LLP; Steven G. Davis; Michael J. DeGrazia

(57) ABSTRACT

The present invention is directed to compounds which are beta-lactamase inhibitors. The compounds and their pharmaceutically acceptable salts are useful in combination with beta-lactam antibiotics, for the treatment of bacterial infections, including infections caused by drug resistant organisms, including multi-drug resistant organisms. The present invention includes compounds according to Formula (I): or a pharmaceutically acceptable salt thereof, wherein the values of $R^1$, $R^2$, $R^3$, $R^4$, $R^5$ and $R^6$ are described herein.

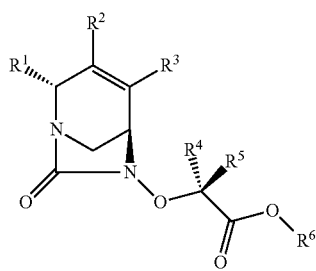

25 Claims, No Drawings

(56) References Cited

U.S. PATENT DOCUMENTS

| | | |
|---|---|---|
| 2006/0046995 A1 | 3/2006 | Lampilas et al. |
| 2009/0018329 A1 | 1/2009 | Lampilas et al. |
| 2010/0087648 A1 | 4/2010 | Lampilas et al. |
| 2010/0092443 A1 | 4/2010 | Levasseur et al. |
| 2010/0093784 A1 | 4/2010 | Ledoussal et al. |
| 2010/0137355 A1 | 6/2010 | Lampilas et al. |
| 2011/0046102 A1 | 2/2011 | Ledoussal et al. |
| 2013/0225554 A1 | 8/2013 | Maiti et al. |
| 2013/0289012 A1 | 10/2013 | Gu et al. |
| 2013/0296555 A1 | 11/2013 | Gu et al. |
| 2014/0094447 A1 | 4/2014 | Bhagwat et al. |

FOREIGN PATENT DOCUMENTS

| | | |
|---|---|---|
| JP | 2004-505088 A | 2/2004 |
| JP | 2005-518333 A | 6/2005 |
| JP | 2005-523897 A | 8/2005 |
| JP | 2006-512335 A | 4/2006 |
| JP | 2011-510012 A | 3/2011 |
| WO | 1995/18129 A1 | 7/1995 |
| WO | 2002/010172 A1 | 2/2002 |
| WO | 2009/091856 A2 | 7/2009 |
| WO | 2009/133442 A1 | 11/2009 |
| WO | 2011/042560 A1 | 4/2011 |
| WO | 2013/014497 A1 | 1/2013 |
| WO | 2013/30733 A1 | 3/2013 |
| WO | 2013/30735 A1 | 3/2013 |
| WO | 2013/38330 A1 | 3/2013 |
| WO | 2013/122888 A2 | 8/2013 |
| WO | 2013/149121 A1 | 10/2013 |
| WO | 2013/149136 A1 | 10/2013 |
| WO | 2013/150296 A1 | 10/2013 |
| WO | 2013/180197 A1 | 12/2013 |
| WO | 2014/33560 A1 | 3/2014 |
| WO | 2014/033561 A1 | 3/2014 |
| WO | 2014/122468 A1 | 8/2014 |
| WO | 2014/141132 A1 | 9/2014 |
| WO | 2016/081452 A1 | 5/2016 |

OTHER PUBLICATIONS

STN Registry No. 1057653-58-3, 1 page, Oct. 6, 2008.
STN Registry No. 1062174-54-7, 1 page, Oct. 16, 2008.
Akova, Sulbactam-containing beta-lactamase inhibitor combinations. Clin Microbiol Infect. 2008;14(Suppl. 1)185-188.
Aszodi et al., Design and synthesis of bridged gamma-lactams as analogues of beta-lactam antibiotics. Bioorg Med Chem Lett. May 17, 2004;14(10):2489-92.
Bonnefoy et al., In vitro activity of AVE1330A, an innovative broad-spectrum non-beta-lactam beta-lactamase Inhibitor. J Antimicrob Chemother. Aug. 2004;54(2):410-7.
Kanematsu et al., Significance of beta-Lactamase Inhibitor in the Treatment of Urinary Tract Infection. Chemotherapy. 1984;32(suppl. 4):494-503.
Sawai et al., Mechanism of beta-lactamase inhibition: differences between sulbactam and other inhibitors. Diagn Microbiol Infect Dis. Jul.-Aug. 1989;12(4 Suppl):121S-129S.
Shlaes et al., New beta-lactam-beta-lactamase inhibitor combinations in clinical development. Ann N Y Acad Sci. Jan. 2013;1277:105-14.
International Search Report and Written Opinion for Application No. PCT/US2015/061076, dated Jan. 25, 2016. 13 pages.
International Search Report and Written Opinion for Application No. PCT/GB2013/050869, dated May 15, 2013, 9 pages.
International Search Report and Written Opinion for Application No. PCT/US2017/051692, dated Feb. 15, 2018, 16 pages.
International Search Report and Written Opinion for Application No. PCT/GB2017/051489, dated Aug. 21, 2017, 9 pages.
Copending U.S. Appl. No. 16/451,498, filed Jun. 25, 2019.

BETA-LACTAMASE INHIBITOR COMPOUNDS

RELATED APPLICATIONS

This application is a 35 U.S.C. § 371 national stage filing of International Application No. PCT/US2017/051692, filed Sep. 15, 2017, which claims priority to U.S. Provisional Application No. 62/395,464, filed Sep. 16, 2016 and U.S. Provisional Application No. 62/456,423, filed Feb. 8, 2017, the entire contents of each of which are incorporated herein by reference.

FIELD OF THE INVENTION

The present invention relates to novel oral beta-lactamase inhibitors, their pharmaceutical compositions and methods of use. In addition, the present invention relates to therapeutic methods for the treatment of bacterial infections, including overcoming bacterial antibiotic resistance.

BACKGROUND OF THE INVENTION

The international microbiological and infectious disease community continues to express serious concern that the continuing evolution of antibacterial resistance could result in bacterial strains against which currently available antibacterial agents will be ineffective. The outcome of such an occurrence could have considerable morbidity and mortality. In general, bacterial pathogens may be classified as either Gram-positive or Gram-negative pathogens. Antibiotic compounds with effective activity against both Gram-positive and Gram-negative pathogens are typically regarded as having a broad spectrum of activity.

In the fight against bacterial infection, beta-lactam antibiotics are essential. Beta-lactams are a broad class of drugs which all have a beta-lactam in their core molecular structure, and typically show effectiveness against a broad spectrum of Gram-positive and Gram-negative bacteria by inhibiting the cell wall synthesis of the bacterium. Because the drug target has no eukaryotic analog, their toxicity is low and they are generally well-tolerated. They remain among the most widely prescribed, safe and effective drugs available to combat bacterial infection. However, their effectiveness is limited by highly resistant infectious strains such as methicillin-resistant *Staphylococcus aureus* (MRSA) and multi-drug resistant (MDR) strains of *Pseudomonas aeruginosa, Acinetobacter baumannii, Escherichia coli, Klebsiella pneumoniae*, and other Enterobacteriaceae. Such resistant bacteria are major causes of patient morbidity and mortality. Helfand, β-*lactams Against Emerging 'Superbugs': Progress and Pitfalls*, Expert Rev. Clin. Pharmacol. 1(4):559-571 (2008).

Beta-lactam antibiotics, alone and in combination with beta-lactamase inhibitors, continue to represent an essential portion of the antibacterial agents used to combat disease. Beta-lactam resistance for Gram-negative infections is primarily driven by beta-lactamase activity; and the significant dependence on beta-lactam antibiotics has lead to the diversification and increased prevalence of beta-lactamases. These beta-lactamases are driving resistance to even the newest beta-lactam antibiotics. Llarrull, et al., *The Future of Beta-Lactams*, Current Opinion in Microbiology, 13:551-557 (2010).

A major threat to the efficacy of these drugs is the increasing prevalence of extended-spectrum beta-lactamases (ESBLs). Beta-lactamases are enzymes that are produced by some bacteria that ring open the beta-lactam portion of a beta-lactam antibiotic and thereby deactivate it. There are currently, four classes of beta-lactamases, denoted as Class A, Class B, Class C and Class D. Class A, Class C and Class D beta-lactamases are serine beta-lactamases, while Class B beta-lactamases are metallo-beta-lactamases (MBLs). Bush & Jacoby, *Updated Functional Classification of β-Lactamases*, Antimicrobial Agents and Chemotherapy, 54(3):969-976 (Mar. 2010).

To help improve the effectiveness of beta-lactam antibiotics, some beta-lactamase inhibitors have been developed. However, the currently available beta-lactamase inhibitors in many instances are insufficient to counter the constantly increasing diversity of beta-lactamases. The three most common serine beta-lactamase agents currently used—clavulanic acid, tazobactam and sulbactam—have activity only against certain Class A enzymes, which severely limits their utility. Additionally, novel beta-lactamase inhibitors recently approved or currently in clinical trials, such as avibactam and MK-7655, are only available for intravenous use and work primarily on Class A and C enzymes, with minimal effectiveness against Class D beta-lactamases. Bebrone, et al., *Current Challenges in Antimicrobial Chemotherapy: Focus on β-Lactamase Inhibition*, Drugs, 70(6):651-679 (2010). While these agents represent a considerable improvement over the currently available beta-lactamase inhibitors, agents which effectively hit all three classes of serine beta-lactamases, with the added benefit of an orally effective dose form for use outside of the hospital setting are desirable for combating the significant beta-lactam resistance seen today. Currently, there are no approved beta-lactamase inhibitors which are administered orally and effective against Class C or Class D beta-lactamases, yet resistance rates to conventional antibiotics are continuing to rise.

Compounds similar to the ones disclosed herein, also with broad beta-lactamase inhibition profiles (being effective against most Class A, Class C and Class D beta-lactamases), were described in WO 2013/150296. This patent application featured compounds according to the following formula:

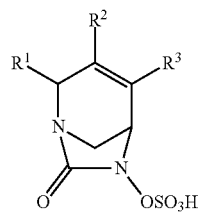

While the compounds of the WO 2013/150296 application represent a significant improvement in the spectrum of beta-lactamase inhibitors presently on the market or in the clinic, the compounds described therein can only be administered intravenously (IV) because they are not orally bioavailable. Moreover, the compounds disclosed therein could not be made to be orally bioavailable by using a prodrug on the sulfate activating group on the molecule. Therefore, these potent beta-lactamase inhibitors are limited to intravenous or parenteral administration, which typically happens only in a hospital setting. Accordingly, there are limited treatment options for patients with serious, resistant infections but who are otherwise healthy and do not need to be admitted into the hospital, or patients who could be discharged from a hospital but who would benefit from antibacterial treatment in an outpatient setting (also known as "oral switch therapy"). The compounds of the WO 2013/150296 application have the potential to provide patients with more effective and broader beta-lactamase inhibition than anything yet identified, but the compounds currently require intravenous administration in a hospital setting.

There is a critical need for a new, broad spectrum, oral beta-lactamase inhibitor that would provide a significant benefit for patients infected with resistant pathogens who may be able to be treated outside of the hospital setting, or who are admitted to a hospital but may not have reliable venous access. Such patients may have serious, complicated infections from pathogens which produce one or multiple beta-lactamases, but who may not require treatment in a hospital setting, or those recovering from infections which were initially successfully treated with an IV beta-lactam/beta-lactamase inhibitor combination in the hospital, but who would benefit from continued beta-lactam/beta-lactamase inhibitor combination therapy outside of the hospital setting—which would be possible only with an orally active, broad-spectrum beta-lactamase inhibitor such as described herein.

Furthermore, for patients with resistant bacterial infections which require hospital admission for initial treatment, compounds according to the present invention, as described in Formulae (Ia), (IIa), (IIIa), (IVa) and (Va), can be administered intravenously in the hospital setting until a patient is stable enough to be discharged into the community setting. Upon discharge, the patient can continue therapy with the same medication by administration of a compound according to one of Formulae (I), (II), (III), (IV), or (V), in a community setting, while maintaining a consistent treatment until the bacterial infection is resolved. There are currently no Class A, C and D β-lactamase inhibitors which can be administered initially by IV with the additional benefit of oral administration once a patient is well enough to be discharged from the hospital. The ability for a doctor to tailor the care to a patient's needs would allow for earlier discharge of patients who require hospitalization, and significantly lessen the costs of treatment overall by avoiding prolonged hospital stays.

There is an urgent need for new, orally-active beta-lactamase inhibitors which are effective against more than one of Class A, C and D beta-lactamases.

SUMMARY OF THE INVENTION

The present invention is directed to compounds which are orally available beta-lactamase inhibitors. The compounds, and their pharmaceutically acceptable salts, are useful in combination with beta-lactam antibiotics for the treatment of bacterial infections, including infections caused by drug resistant organisms, including multi-drug resistant organisms.

More particularly, the invention relates to compounds of formula (I):

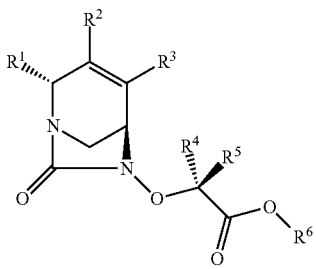

or a pharmaceutically acceptable salt thereof; wherein:
$R^1$ is $-C(O)NR^7R^8$, $-CN$, phenyl, a 5-7 membered heteroaryl, $-C(O)NR'NR'C(O)R^9$, $-C(O)NR'OR^{10}$, or a $C_1$-$C_6$ alkyl group, wherein the alkyl group is substituted with one to three groups consisting of halo, $C_1$-$C_3$ alkoxy, $-OH$, $-CN$, $-NR^7R^8$, $-NR^7COR^9$, a 5-7 membered heteroaryl and a 5-7 membered heterocyclyl, and wherein the phenyl and heteroaryl represented by $R^1$ are optionally and independently substituted with 1-3 groups selected from halo, $-OH$, $C_1$-$C_3$ alkoxy, $-CN$, $-NR^7R^8$, and $-CONR^7R^8$;
$R^2$ and $R^3$ are independently selected from hydrogen, halo, $C_1$-$C_3$ alkyl, and $C_3$-$C_6$ cycloalkyl;
$R^4$ and $R^5$ are independently selected from hydrogen, halo, $-CN$, $-CO_2R^9$, $C_1$-$C_3$ alkyl, and $C_1$-$C_3$ haloalkyl;
$R^6$ is hydrogen, $C_1$-$C_{12}$ alkyl, $C_1$-$C_4$alkyl-$C_1$-$C_3$alkoxy-(NR'$C_1$-$C_6$alkyl)-$C_1$-$C_3$alkoxy, $C_1$-$C_4$alkyl-$C_1$-$C_3$alkoxy-$C_1$-$C_3$alkoxy, $C_2$-$C_{12}$ alkenyl, $C_3$-$C_{10}$ cycloalkyl, a 5-7 membered heteroaryl and a 5-7 membered heterocyclyl, wherein the alkyl, alkenyl, cycloalkyl, heteroaryl and heterocyclyl are optionally and independently substituted 1-6 groups selected from a carboxyl, halo, $C_1$-$C_6$ alkoxy, $C_1$-$C_6$ alkyl and phenyl. Alternatively, $R^6$ is $C_1$-$C_{12}$ alkyl, $C_1$-$C_4$alkyl-$C_1$-$C_3$alkoxy-(NR'$C_1$-$C_6$alkyl)-$C_1$-$C_3$alkoxy, $C_1$-$C_4$alkyl-$C_1$-$C_3$alkoxy-$C_1$-$C_3$alkoxy, $C_2$-$C_{12}$ alkenyl, $C_3$-$C_{10}$ cycloalkyl, a 5-7 membered heteroaryl and a 5-7 membered heterocyclyl, wherein the alkyl, alkenyl, cycloalkyl, heteroaryl and heterocyclyl are optionally and independently substituted 1-6 groups selected from a carboxyl, halo, $C_1$-$C_6$ alkoxy, $C_1$-$C_6$ alkyl and phenyl;
each $R^7$ and $R^8$ are independently hydrogen, $C_1$-$C_3$ alkyl, $C_1$-$C_3$ alkoxy, phenyl, $C_3$-$C_6$ cycloalkyl, 4-7 membered heterocyclyl, or 5-7 membered heteroaryl, wherein the alkyl, alkoxy, phenyl, cycloalkyl, heterocyclyl or heteroaryl represented by $R^7$ or $R^8$ is optionally and independently substituted with 1-6 groups selected from a 5-6 membered heterocyclyl optionally substituted with one or two $-F$ atoms, carboxyl or $-CO(OC_{1-6}$ alkyl), 5-6 membered heteroaryl, $-CN$, $-OH$, $C_1$-$C_3$ alkyl optionally substituted with $-NH_2$ or $-OH$, $C_1$-$C_3$ haloalkyl, $C_1$-$C_3$ haloalkoxy, $C_1$-$C_3$ alkoxy $-NHCO(C_1$-$C_3$alkyl), $-NHCO(C_1$-$C_3$alkoxy), $-S(O)_2NR'R''$, $-NHS(O)_2NR'R''$, $-NHS(O)_2(C_1$-$C_3$alkyl), $-NR'R''$, and $-C(O)NR'R''$; each $R^9$ is $C_1$-$C_6$ alkyl, $C_1$-$C_6$ haloalkyl, $C_1$-$C_6$ haloalkoxy or $C_1$-$C_6$ alkoxy;
each $R^{10}$ is a $C_1$-$C_3$ alkyl optionally substituted with 1-6 groups selected from a 5-6 membered heterocyclyl optionally substituted with one or two $-F$ atoms, carboxyl or $-CO(OC_{1-6}$ alkyl), a $C_3$-$C_6$ cycloalkyl, a 5-6 membered heteroaryl, $-CN$, $-OH$, $-NHCO(C_1$-$C_3$alkyl), $-NHCO(C_1$-$C_3$alkoxy), $-S(O)_2NR'R''$, $-NHS(O)_2NR'R''$, $-NHS(O)_2(C_1$-$C_3$alkyl), $-NR'R''$, or $-C(O)NR'R''$; and
each R' and R'' is independently hydrogen, methyl, ethyl or propyl; or R' and R'' are taken together with the nitrogen to which they are attached to form a 5-6 membered heterocyclyl; provided that at least one of $R^2$ and $R^3$ is other than hydrogen.

DETAILED DESCRIPTION OF THE INVENTION

In one aspect of the invention is an oral beta-lactamase inhibitor compound according to formula (I); as described above.

In another aspect of the invention, $R^1$ in formula (I) is —C(O)NR$^7$R$^8$, —CN, phenyl, a 5-6 membered heteroaryl, —C(O)NR'NR'C(O)R$^9$, —C(O)NR'OR$^{10}$, or a $C_1$-$C_6$ alkyl group, wherein the alkyl group is substituted with one to three groups consisting of halo, $C_1$-$C_3$ alkoxy, —OH, —CN, —NR$^7$R$^8$, —NR$^7$COR$^9$, a 5-6 membered heteroaryl and a 5-7 membered heterocyclyl, and wherein the phenyl and heteroaryl represented by $R^1$ are optionally and independently substituted with 1-3 groups selected from halo, —OH, $C_1$-$C_3$ alkoxy, —CN, —NR$^7$R$^8$, and —CONR$^7$R$^8$;

$R^6$ is hydrogen, $C_1$-$C_{12}$ alkyl, $C_1$-$C_4$alkyl-$C_1$-$C_3$alkoxy-(NR'C$_1$-$C_6$alkyl)-$C_1$-$C_3$alkoxy, $C_1$-$C_4$alkyl-$C_1$-$C_3$alkoxy-$C_1$-$C_3$alkoxy, $C_2$-$C_{12}$ alkenyl, $C_3$-$C_{10}$ cycloalkyl, a 5-6 membered heteroaryl and a 5-7 membered heterocyclyl, wherein the alkyl, alkenyl, cycloalkyl, heteroaryl and heterocyclyl are optionally and independently substituted 1-6 groups selected from a carboxyl, halo, $C_1$-$C_6$ alkoxy, $C_1$-$C_6$ alkyl and phenyl (alternatively, $R^6$ is $C_1$-$C_{12}$ alkyl, $C_1$-$C_4$alkyl-$C_1$-$C_3$alkoxy-(NR'C$_1$-$C_6$alkyl)-$C_1$-$C_3$alkoxy, $C_1$-$C_4$alkyl-$C_1$-$C_3$alkoxy-$C_1$-$C_3$alkoxy, $C_2$-$C_{12}$ alkenyl, $C_3$-$C_{10}$ cycloalkyl, a 5-6 membered heteroaryl and a 5-7 membered heterocyclyl, wherein the alkyl, alkenyl, cycloalkyl, heteroaryl and heterocyclyl are optionally and independently substituted 1-6 groups selected from a carboxyl, halo, $C_1$-$C_6$ alkoxy, $C_1$-$C_6$ alkyl and phenyl); and each $R^7$ and $R^8$ are independently hydrogen, $C_1$-$C_3$ alkyl, $C_1$-$C_3$ alkoxy, phenyl, $C_3$-$C_6$ cycloalkyl, 4-7 membered heterocyclyl, or 5-6 membered heteroaryl, wherein the alkyl, alkoxy, phenyl, cycloalkyl, heterocyclyl or heteroaryl represented by $R^7$ or $R^8$ is optionally and independently substituted with 1-6 groups selected from a 5-6 membered heterocyclyl optionally substituted with one or two —F atoms, carboxyl or —CO(OC$_{1-6}$ alkyl), 5-6 membered heteroaryl, —CN, —OH, $C_1$-$C_3$ alkyl optionally substituted with —NH$_2$ or —OH, $C_1$-$C_3$ haloalkyl, $C_1$-$C_3$ haloalkoxy, $C_1$-$C_3$ alkoxy —NHCO(C$_1$-$C_3$alkyl), —NHCO(C$_1$-C$_3$alkoxy), —S(O)$_2$NR'R", —NHS(O)$_2$NR'R", —NHS(O)$_2$(C$_1$-$C_3$alkyl), —NR'R", and —C(O)NR'R"; each $R^9$ is $C_1$-$C_6$ alkyl, $C_1$-$C_6$ haloalkyl, $C_1$-$C_6$ haloalkoxy or $C_1$-$C_6$ alkoxy;

In another aspect of the invention is a compound according to Formula (II):

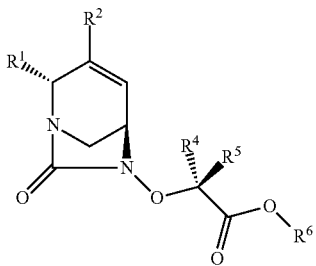

(II)

or a pharmaceutically acceptable salt thereof, wherein the variables $R^1$, $R^2$, $R^4$, $R^5$ and $R^6$ are as defined for formula (I).

In one aspect of the invention is a compound according to Formula (III):

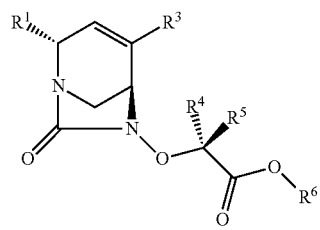

(III)

or a pharmaceutically acceptable salt thereof, wherein the variables $R^1$, $R^3$, $R^4$, $R^5$ and $R^6$ are as defined for formula (I).

In a further aspect of the invention is a compound according to Formula (IV):

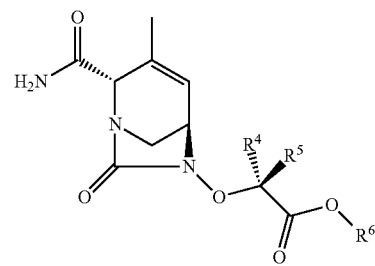

(IV)

or a pharmaceutically acceptable salt thereof, wherein the variables $R^4$, $R^5$ and $R^6$ are as defined for formula (I).

In a further aspect of the invention is a compound according to Formula (V):

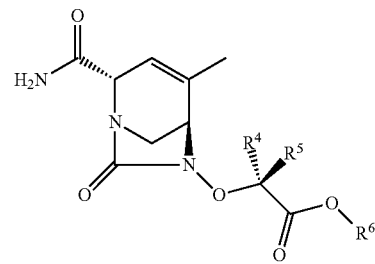

(V)

or a pharmaceutically acceptable salt thereof, wherein the variables $R^4$, $R^5$ and $R^6$ are as defined for formula (I).

In a further aspect of the invention is a compound according to Formula (Ia):

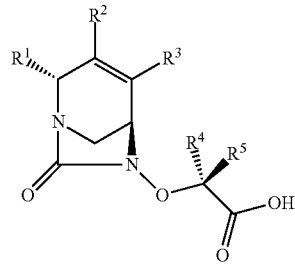

or a pharmaceutically acceptable salt thereof; wherein: $R^1$ is —C(O)NR$^7$R$^8$, —CN, phenyl, a 5-7 membered heteroaryl, —C(O)NR'NR'C(O)R$^9$, —C(O)NR'OR$^{10}$, or a C$_1$-C$_6$ alkyl group, wherein the alkyl group is substituted with one to three groups consisting of halo, C$_1$-C$_3$ alkoxy, —OH, —CN, —NR$^7$R$^8$, —NR$^7$COR$^9$, a 5-7 membered heteroaryl and a 5-7 membered heterocyclyl, and wherein the phenyl and heteroaryl represented by R$^1$ are optionally and independently substituted with 1-3 groups selected from halo, —OH, C$_1$-C$_3$ alkoxy, —CN, —NR$^7$R$^8$, and —CONR$^7$R$^8$; R$^2$ and R$^3$ are independently selected from hydrogen, halo, C$_1$-C$_3$ alkyl, and C$_3$-C$_6$ cycloalkyl; R$^4$ and R$^5$ are independently selected from hydrogen, halo, —CN, —CO$_2$R$^9$, C$_1$-C$_3$ alkyl, and C$_1$-C$_3$ haloalkyl; each R$^7$ and R$^8$ are independently hydrogen, C$_1$-C$_3$ alkyl, C$_1$-C$_3$ alkoxy, phenyl, C$_3$-C$_6$ cycloalkyl, 4-7 membered heterocyclyl, or 5-7 membered heteroaryl, wherein the alkyl, alkoxy, phenyl, cycloalkyl, heterocyclyl or heteroaryl represented by R$^7$ or R$^8$ is optionally and independently substituted with 1-6 groups selected from a 5-6 membered heterocyclyl optionally substituted with one or two —F atoms, carboxyl or —CO(OC$_{1-6}$ alkyl), 5-6 membered heteroaryl, —CN, —OH, C$_1$-C$_3$ alkyl optionally substituted with —NH$_2$ or —OH, C$_1$-C$_3$ haloalkyl, C$_1$-C$_3$ haloalkoxy, C$_1$-C$_3$ alkoxy —NHCO(C$_1$-C$_3$alkyl), —NHCO(C$_1$-C$_3$alkoxy), —S(O)$_2$NR'R'', —NHS(O)$_2$NR'R'', —NHS(O)$_2$(C$_1$-C$_3$alkyl), —NR'R'', and —C(O)NR'R''; each R$^9$ is C$_1$-C$_6$ alkyl, C$_1$-C$_6$ haloalkyl, C$_1$-C$_6$ haloalkoxy or C$_1$-C$_6$ alkoxy; each R$^{10}$ is a C$_1$-C$_3$ alkyl optionally substituted with 1-6 groups selected from a 5-6 membered heterocyclyl optionally substituted with one or two —F atoms, carboxyl or —CO(OC$_{1-6}$ alkyl), a C$_3$-C$_6$ cycloalkyl, a 5-6 membered heteroaryl, —CN, —OH, —NHCO(C$_1$-C$_3$alkyl), —NHCO(C$_1$-C$_3$alkoxy), —S(O)$_2$NR'R'', —NHS(O)$_2$NR'R'', —NHS(O)$_2$(C$_1$-C$_3$alkyl), —NR'R'', or —C(O)NR'R''; and each R' and R'' is independently hydrogen, methyl, ethyl or propyl; or R' and R'' are taken together with the nitrogen to which they are attached to form a 5-6 membered heterocyclyl; provided that at least one of R$^2$ and R$^3$ is other than hydrogen.

In a further aspect of the invention is a compound according to Formula (Ia):

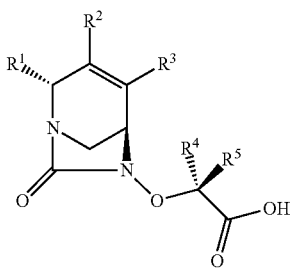

(Ia)

or a pharmaceutically acceptable salt thereof; wherein: R$^1$ is —C(O)NR$^7$R$^8$, —CN, phenyl, a 5-6 membered heteroaryl, —C(O)NR'NR'C(O)R$^9$, —C(O)NR'OR$^{10}$, or a C$_1$-C$_6$ alkyl group, wherein the alkyl group is substituted with one to three groups consisting of halo, C$_1$-C$_3$ alkoxy, —OH, —CN, —NR$^7$R$^8$, —NR$^7$COR$^9$, a 5-6 membered heteroaryl and a 5-7 membered heterocyclyl, and wherein the phenyl and heteroaryl represented by R$^1$ are optionally and independently substituted with 1-3 groups selected from halo, —OH, C$_1$-C$_3$ alkoxy, —CN, —NR$^7$R$^8$, and —CONR$^7$R$^8$; R$^2$ and R$^3$ are independently selected from hydrogen, halo, C$_1$-C$_3$ alkyl, and C$_3$-C$_6$ cycloalkyl; R$^4$ and R$^5$ are independently selected from hydrogen, halo, —CN, —CO$_2$R$^9$, C$_1$-C$_3$ alkyl, and C$_1$-C$_3$ haloalkyl; each R$^7$ and R$^8$ are independently hydrogen, C$_1$-C$_3$ alkyl, C$_1$-C$_3$ alkoxy, phenyl, C$_3$-C$_6$ cycloalkyl, 4-7 membered heterocyclyl, or 5-6 membered heteroaryl, wherein the alkyl, alkoxy, phenyl, cycloalkyl, heterocyclyl or heteroaryl represented by R$^7$ or R$^8$ is optionally and independently substituted with 1-6 groups selected from a 5-6 membered heterocyclyl optionally substituted with one or two —F atoms, carboxyl or —CO(OC$_{1-6}$ alkyl), 5-6 membered heteroaryl, —CN, —OH, C$_1$-C$_3$ alkyl optionally substituted with —NH$_2$ or —OH, C$_1$-C$_3$ haloalkyl, C$_1$-C$_3$ haloalkoxy, C$_1$-C$_3$ alkoxy —NHCO(C$_1$-C$_3$alkyl), —NHCO(C$_1$-C$_3$alkoxy), —S(O)$_2$NR'R'', —NHS(O)$_2$NR'R'', —NHS(O)$_2$(C$_1$-C$_3$alkyl), —NR'R'', and —C(O)NR'R''; each R$^9$ is C$_1$-C$_6$ alkyl, C$_1$-C$_6$ haloalkyl, C$_1$-C$_6$ haloalkoxy or C$_1$-C$_6$ alkoxy; each R$^{10}$ is a C$_1$-C$_3$ alkyl optionally substituted with 1-6 groups selected from a 5-6 membered heterocyclyl optionally substituted with one or two —F atoms, carboxyl or —CO(OC$_{1-6}$ alkyl), a C$_3$-C$_6$ cycloalkyl, a 5-6 membered heteroaryl, —CN, —OH, —NHCO(C$_1$-C$_3$alkyl), —NHCO(C$_1$-C$_3$alkoxy), —S(O)$_2$NR'R'', —NHS(O)$_2$NR'R'', —NHS(O)$_2$(C$_1$-C$_3$alkyl), —NR'R'', or —C(O)NR'R''; and each R' and R'' is independently hydrogen, methyl, ethyl or propyl; or R' and R'' are taken together with the nitrogen to which they are attached to form a 5-6 membered heterocyclyl; provided that at least one of R$^2$ and R$^3$ is other than hydrogen.

In another aspect of the invention is a compound according to Formula (IIa):

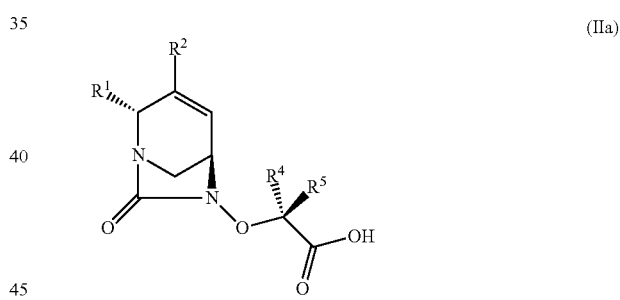

(IIa)

or a pharmaceutically acceptable salt thereof, wherein the variables R$^1$, R$^2$, R$^4$ and R$^5$ are as defined for formula (Ia).

In one aspect of the invention is a compound according to Formula (IIIa):

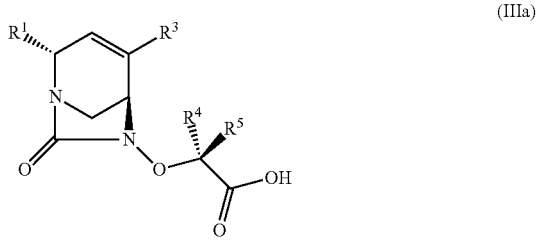

(IIIa)

or a pharmaceutically acceptable salt thereof, wherein the variables R$^1$, R$^3$, R$^4$ and R$^5$ are as defined for formula (Ia).

In a further aspect of the invention is a compound according to Formula (IVa):

(IVa)

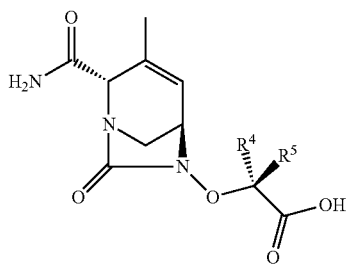

or a pharmaceutically acceptable salt thereof, wherein the variables $R^4$ and $R^5$ are as defined for formula (Ia).

In a further aspect of the invention is a compound according to Formula (Va):

(Va)

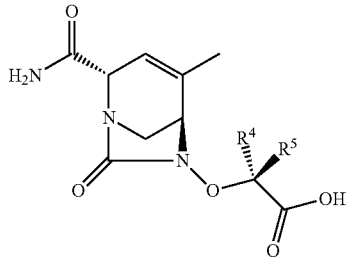

or a pharmaceutically acceptable salt thereof, wherein the variables $R^4$ and $R^5$ are as defined for formula (Ia).

In one aspect of the inventions, for Formulae (I), (Ia), (II), or (IIa), $R^2$ is $C_1$-$C_3$ alkyl. In another aspect of the invention, for Formulae (I), (Ia), (II), or (IIa), $R^2$ is methyl.

In one aspect of the invention, for Formula (I), (Ia), (III), and (IIIa), $R^3$ is $C_1$-$C_3$ alkyl. In another aspect of the invention, for Formula (I), (Ia), (III), and (IIIa), $R^3$ is methyl.

In one aspect of the invention, for Formula (I), (Ia), (II), (IIa), (III), and (IIIa), $R^1$ is selected from an oxadiazole, —C(O)NHNHC(O)($C_1$-$C_3$ alkyl), —CH$_2$NH$_2$, —CH$_2$NHCO($C_1$-$C_3$ alkoxy), —CH$_2$NHCO($C_1$-$C_3$ alkyl), or —CH$_2$NHCO($C_1$-$C_3$ haloalkyl), wherein the oxadiazole of $R^1$ is optionally substituted with —OH, $C_1$-$C_3$ alkoxy, —NR$^7$R$^8$, or —CONR$^7$R$^8$. In one aspect of the invention, for Formula (I), (Ia), (II), (IIa), (III), and (IIIa), $R^1$ is selected from —CH$_2$NH$_2$,

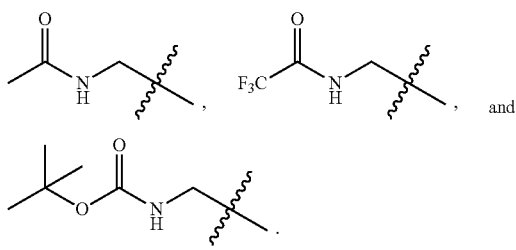

In a further aspect, for Formula (I), (Ia), (II), (IIa), (III), and (IIIa), $R^1$ is —CN,

1.

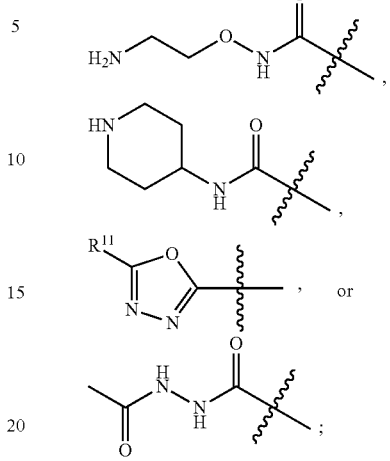

wherein $R^{11}$ is hydrogen or —C(O)NH$_2$. In one aspect of the invention, for Formula (I), (Ia), (II), (IIa), (III), and (IIIa), $R^1$ is —CN or —C(O)NH$_2$. In one aspect of the invention, for Formula (I), (Ia), (II), (IIa), (III), and (IIIa), $R^1$ is —CN. In one aspect of the invention, for Formula (I), (Ia), (II), (IIa), (III), and (IIIa), $R^1$ is —C(O)NH$_2$. In one aspect of the invention, for Formula (I), (Ia), (II), (IIa), (III), and (IIIa), $R^1$ is —C(O)NR$^7$R$^8$. In one aspect of the invention, for Formula (I), (Ia), (II), (IIa), (III), and (IIIa), when $R^1$ is —C(O)NR$^7$R$^8$, $R^7$ is hydrogen and $R^8$ is 1) a phenyl optionally substituted with a $C_1$-$C_3$ alkyl or $C_1$-$C_3$ alkyl-NH$_2$, 2) an $C_1$-$C_3$ alkyl or 3) $C_1$-$C_3$ alkoxy, wherein each alkyl or alkoxy of represented by $R^8$ is optionally and independently substituted with a $C_3$-$C_6$ cycloalkyl, —CN, —OH, —NH$_2$, —SO$_2$NH$_2$, —NHSO$_2$NH$_2$, —C(O)NH$_2$, —NHC(O)($C_1$-$C_3$ alkyl), pyrazinyl, oxytanyl, oxazolyl, or a pyrrolidinyl optionally substituted with one or more carboxyl, fluoro, or —C(O)O($C_1$-$C_6$ alkyl). In one aspect of the invention, for Formula (I), (Ia), (II), (IIa), (III), and (IIIa), when $R^1$ is —C(O)NR$^7$R$^8$, $R^7$ is hydrogen and $R^8$ is selected from the group consisting of:

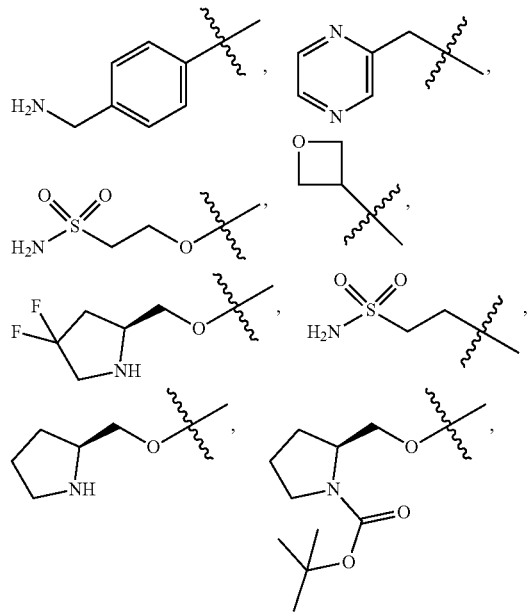

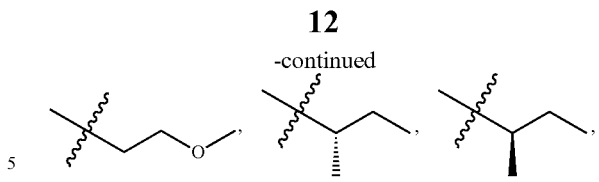

—CH$_2$CN, and —CH$_2$OH.

In one aspect of the invention, for any one of Formulae (I), (II), (III), (IV) or (V), R$^6$ is C$_1$-C$_{12}$ alkyl. In one aspect of the invention, for any one of Formulae (I), (II), (III), (IV) or (V), R$^6$ is ethyl, isopropyl, 2-butyl or isopentyl. In one aspect of the invention, for any one of Formulae (I), (II), (III), (IV) or (V), R$^6$ is isopropyl. In one aspect of the invention, for any one of Formulae (I), (II), (III), (IV) or (V), R$^6$ is C$_1$-C$_4$alkyl-OC(O)—(NHC$_1$-C$_6$alkyl)-C(O)C$_1$-C$_3$alkoxy, C$_1$-C$_4$alkyl-OC(O)—C$_1$-C$_4$alkyl or C$_1$-C$_4$alkyl-OC(O)—C$_1$-C$_3$alkoxy. In one aspect of the invention, for any one of Formulae (I), (II), (III), (IV) or (V), R$^6$ is selected from the group consisting of:

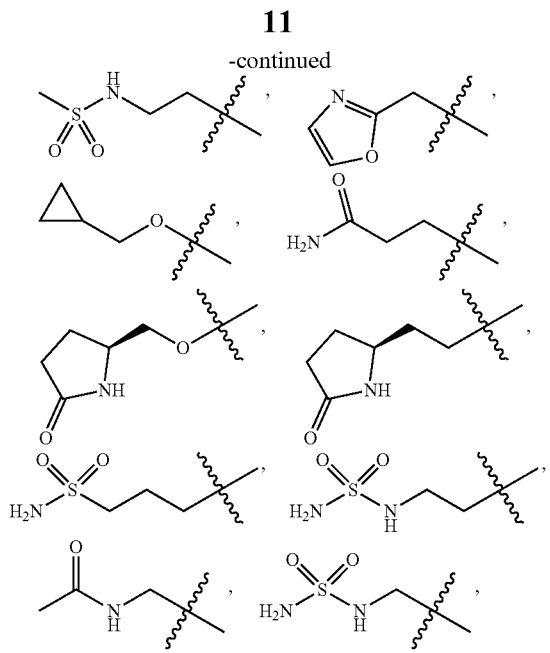

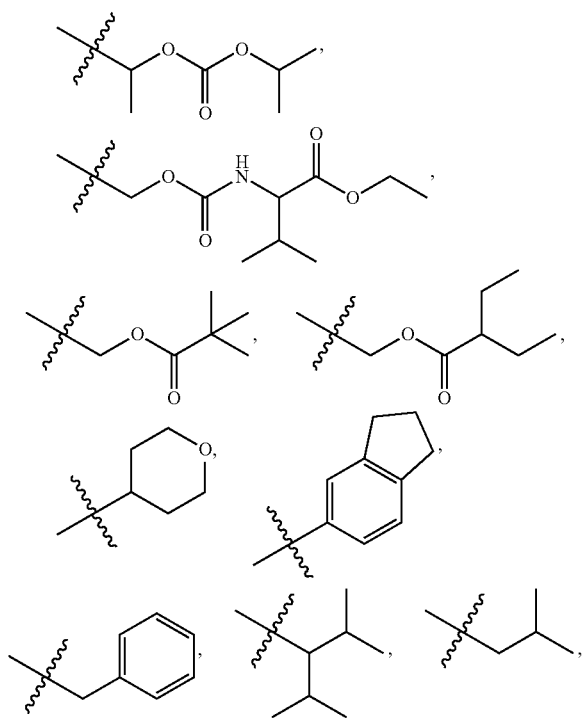

methyl, n-propyl, n-butyl, n-pentyl, n-hexyl, n-septyl, n-octyl, or n-nonyl.

In one aspect of the invention, for any one of Formulae (I), (Ia), (II), (IIa), (III), (IIIa), (IV), (IVa), (V) or (Va), R$^4$ and R$^5$ are independently H, methyl or fluoro. In another aspect of the invention, for any one of Formulae (I), (Ia), (II), (IIa), (III), (IIIa), (IV), (IVa), (V) or (Va), one of R$^4$ and R$^5$ is hydrogen and the other is fluoro. In another aspect of the invention, for any one of Formulae (I), (Ia), (II), (IIa), (III), (IIIa), (IV), (IVa), (V) or (Va), R$^4$ is fluoro and R$^5$ is hydrogen. In another aspect of the invention, for any one of Formulae (I), (Ia), (II), (IIa), (III), (IIIa), (IV), (IVa), (V) or (Va), R$^4$ is hydrogen and R$^5$ is fluoro. In another aspect of the invention, for any one of Formulae (I), (Ia), (II), (IIa), (III), (IIIa), (IV), (IVa), (V) or (Va), both R$^4$ and R$^5$ are hydrogen.

In another aspect of the invention, for any one of Formulae (I), (Ia), (II), (IIa), (III), (IIIa), (IV), (IVa), (V) or (Va), both R$^4$ and R$^5$ are fluoro.

Any embodiment described herein can be combined with any other suitable embodiment described herein to provide additional embodiments. For example, where one embodiment individually or collectively describes possible groups for R$^1$ and a separate embodiment describes possible groups for R$^2$, it is understood that these embodiments can be combined to provide an additional embodiment utilizing any of the possible groups for R$^1$ with any of the possible groups for R$^2$. Analogously, the invention encompasses any embodiments called out individually for R$^1$, R$^2$, R$^3$, R$^4$, R$^5$ and R$^6$ in combination with any specific embodiments called out for each of the remaining variables.

Compounds of Formulae (I), (II), (III), (IV) and (V), and pharmaceutically acceptable salts thereof, possess beneficial beta-lactamase inhibition spectrum and are suitable for oral administration. Compounds of Formulae (Ia), (IIa), (IIIa), (IVa) and (Va), and pharmaceutically acceptable salts thereof, possess beneficial beta-lactamase inhibition spectrum and are suitable for intravenous, intraperitoneal, intramuscular or subcutaneous administration, e.g., intravenous administration. As such, compounds of Formulae (Ia), (IIa), (IIIa), (IVa) and (Va), and pharmaceutically acceptable salts thereof can be advantageously used when a patient is unable to take antibiotics orally, such as in a hospital setting, urgent care setting or nursing home setting. Once the patient has improved sufficiently to take antibiotics orally, the treatment can be switched such that a compound of Formulae (I), (II), (III), (IV) and (V), or a pharmaceutically acceptable salt thereof can be administered orally to the patient. Additionally, compounds of Formulae (Ia), (IIa), (IIIa), (IVa), (Va), (I), (II), (III), (IV) and (V), and pharmaceutically acceptable salts thereof, may possess beneficial efficacious, metabolic, toxicological and/or pharmacodynamic properties.

One aspect of the invention includes a compound according to one of the examples, or a pharmaceutically acceptable salt thereof, namely:

| Ex. # | Structure | Compound Name |
|---|---|---|
| 1 | 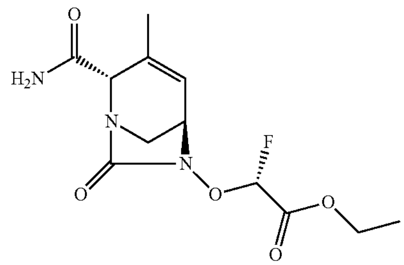 | (R)-ethyl 2-((2S,5R)-2-carbamoyl-3-methyl-7-oxo-1,6-diazabicyclo[3.2.1]oct-3-en-6-yloxy)-2-fluoroacetate |
| 2 | 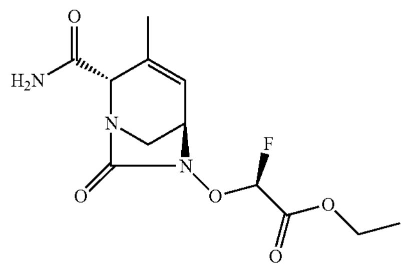 [SMILES: CCOC(=O)[C@H](F)ON1C(=O)N2C[C@H]1C=C(C)[C@H]2C(N)=O] | (S)-ethyl 2-((2S,5R)-2-carbamoyl-3-methyl-7-oxo-1,6-diazabicyclo[3.2.1]oct-3-en-6-yloxy)-2-fluoroacetate |
| 3 | 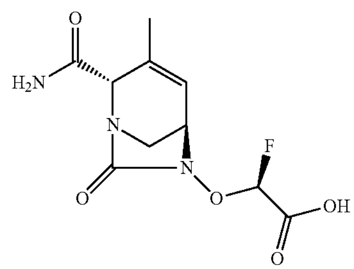 [SMILES: CC1=C[C@@H]2CN(C(=O)N2O[C@@H](F)C(=O)O)[C@@H]1C(N)=O] | (2S)-{[(2S,5R)-2-carbamoyl-3-methyl-7-oxo-1,6-diazabicyclo[3.2.1]oct-3-en-6-yl]oxy}(fluoro)ethanoic acid lithium salt |
| 4 | 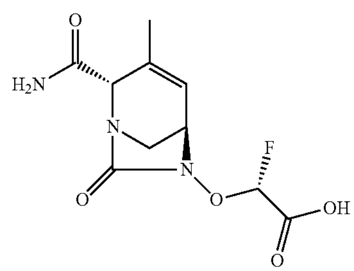 [SMILES: CC1=C[C@@H]2CN(C(=O)N2O[C@H](F)C(=O)O)[C@@H]1C(N)=O] | (2R)-{[(2S,5R)-2-carbamoyl-3-methyl-7-oxo-1,6-diazabicyclo[3.2.1]oct-3-en-6-yl]oxy}(fluoro)ethanoic acid lithium salt |
| 5 | 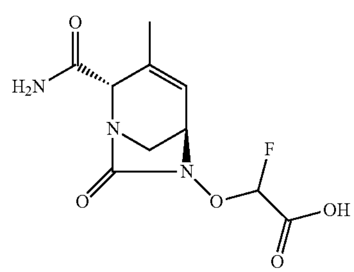 [SMILES: CC1=C[C@@H]2CN(C(=O)N2OC(F)C(=O)O)[C@@H]1C(N)=O] | {[(2S,5R)-2-carbamoyl-3-methyl-7-oxo-1,6-diazabicyclo[3.2.1]oct-3-en-6-yl]oxy}(fluoro)acetic acid lithium salt |
| 6 | 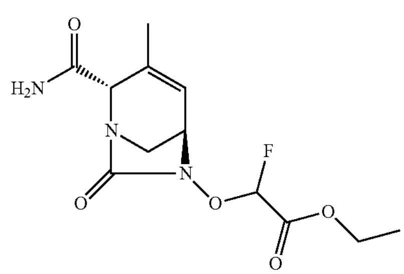 | ethyl {[(2S,5R)-2-carbamoyl-3-methyl-7-oxo-1,6-diazabicyclo[3.2.1]oct-3-en-6-yl]oxy}(fluoro)acetate |

| Ex. # | Structure | Compound Name |
|---|---|---|
| 7 | 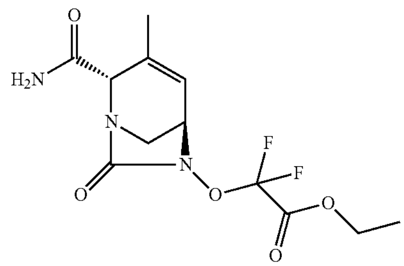 | ethyl {[(2S,5R)-2-carbamoyl-3-methyl-7-oxo-1,6-diazabicyclo[3.2.1]oct-3-en-6-yl]oxy}(difluoro)acetate |
| 8 | 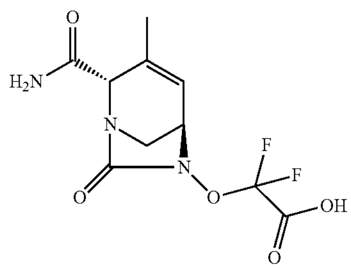 [SMILES: CC1=C[C@@H]2CN(C(=O)N2OC(F)(F)C(=O)O)[C@@H]1C(N)=O] | {[(2S,5R)-2-carbamoyl-3-methyl-7-oxo-1,6-diazabicyclo[3.2.1]oct-3-en-6-yl]oxy}(difluoro)acetic acid lithium salt |
| 9 | 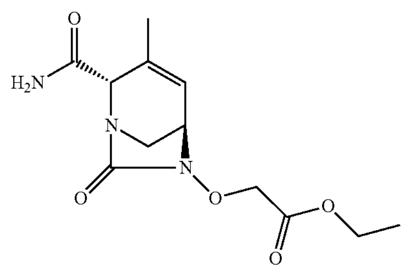 | ethyl {[(2S,5R)-2-carbamoyl-3-methyl-7-oxo-1,6-diazabicyclo[3.2.1]oct-3-en-6-yl]oxy}acetate |
| 10 | 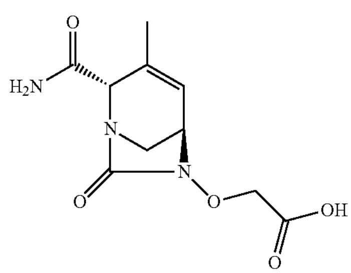 [SMILES: CC1=C[C@@H]2CN(C(=O)N2OCC(=O)O)[C@@H]1C(N)=O] | {[(2S,5R)-2-carbamoyl-3-methyl-7-oxo-1,6-diazabicyclo[3.2.1]oct-3-en-6-yl]oxy}acetic acid lithium salt |
| 11 | 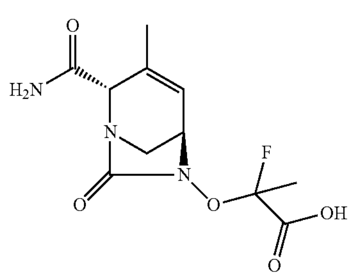 [SMILES: CC1=C[C@@H]2CN(C(=O)N2OC(C)(F)C(=O)O)[C@@H]1C(N)=O] | 2-{[(2S,5R)-2-carbamoyl-3-methyl-7-oxo-1,6-diazabicyclo[3.2.1]oct-3-en-6-yl]oxy}-2-fluoropropanoic acid lithium salt |

-continued

| Ex. # | Structure | Compound Name |
|---|---|---|
| 12 | 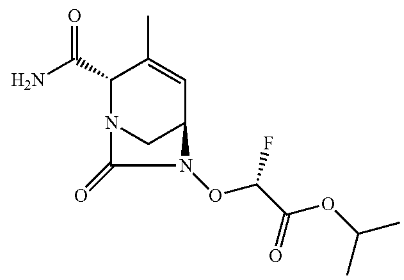 [SMILES: CC1=C[C@@H]2CN(C(=O)N2O[C@H](F)C(=O)OC(C)C)[C@@H]1C(N)=O] | propan-2-yl (2R)-{[(2S,5R)-2-carbamoyl-3-methyl-7-oxo-1,6-diazabicyclo[3.2.1]oct-3-en-6-yl]oxy}(fluoro)ethanoate |
| 13 | 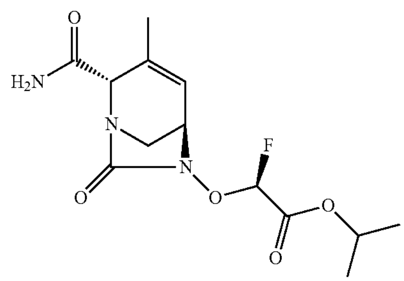 | propan-2-yl (2S)-{[(2S,5R)-2-carbamoyl-3-methyl-7-oxo-1,6-diazabicyclo[3.2.1]oct-3-en-6-yl]oxy}(fluoro)ethanoate |
| 14 | 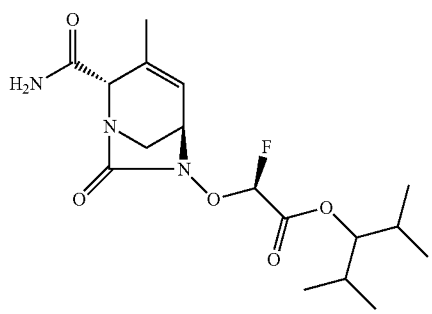 [SMILES: CC1=C[C@@H]2CN(C(=O)N2O[C@@H](F)C(=O)OC(C(C)C)C(C)C)[C@@H]1C(N)=O] | 2,4-dimethylpentan-3-yl (2S)-{[(2S,5R)-2-carbamoyl-3-methyl-7-oxo-1,6-diazabicyclo[3.2.1]oct-3-en-6-yl]oxy}(fluoro)ethanoate |
| 15 | 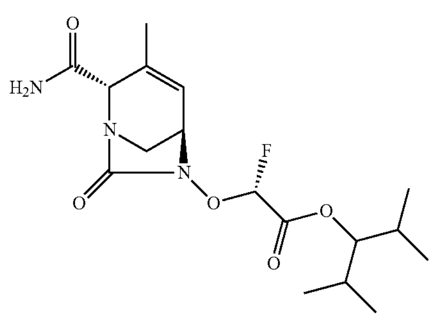 [SMILES: CC1=C[C@@H]2CN(C(=O)N2O[C@H](F)C(=O)OC(C(C)C)C(C)C)[C@@H]1C(N)=O] | 2,4-dimethylpentan-3-yl (2R)-{[(2S,5R)-2-carbamoyl-3-methyl-7-oxo-1,6-diazabicyclo[3.2.1]oct-3-en-6-yl]oxy}(fluoro)ethanoate |
| 16 | 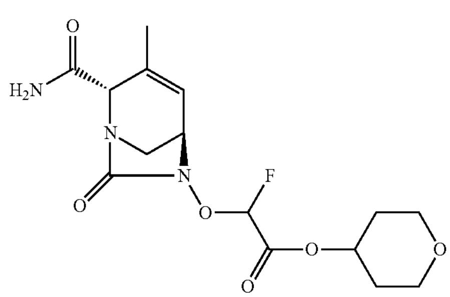 [SMILES: CC1=C[C@@H]2CN(C(=O)N2OC(F)C(=O)OC2CCOCC2)[C@@H]1C(N)=O] | tetrahydro-2H-pyran-4-yl {[(2S,5R)-2-carbamoyl-3-methyl-7-oxo-1,6-diazabicyclo[3.2.1]oct-3-en-6-yl]oxy}(fluoro)acetate |

-continued

| Ex. # | Structure | Compound Name |
|---|---|---|
| 17 | 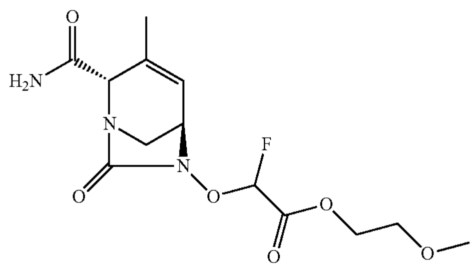 [SMILES: COCCOC(=O)C(F)ON1C(=O)N2C[C@H]1C=C(C)[C@H]2C(N)=O] | 2-methoxyethyl {[(2S,5R)-2-carbamoyl-3-methyl-7-oxo-1,6-diazabicyclo[3.2.1]oct-3-en-6-yl]oxy}(fluoro)acetate |
| 18 | 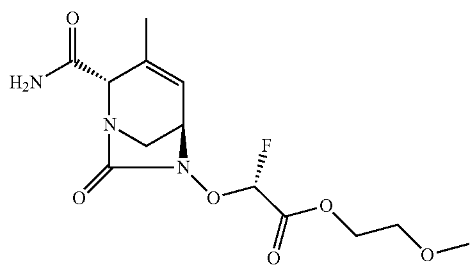 [SMILES: COCCOC(=O)[C@@H](F)ON1C(=O)N2C[C@H]1C=C(C)[C@H]2C(N)=O] | 2-methoxyethyl (2R)-{[(2S,5R)-2-carbamoyl-3-methyl-7-oxo-1,6-diazabicyclo[3.2.1]oct-3-en-6-yl]oxy}(fluoro)ethanoate |
| 19 | 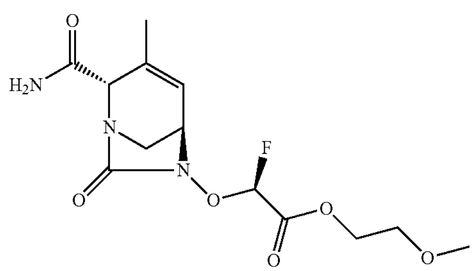 [SMILES: COCCOC(=O)[C@H](F)ON1C(=O)N2C[C@H]1C=C(C)[C@H]2C(N)=O] | 2-methoxyethyl (2S)-{[(2S,5R)-2-carbamoyl-3-methyl-7-oxo-1,6-diazabicyclo[3.2.1]oct-3-en-6-yl]oxy}(fluoro)ethanoate |
| 20 | 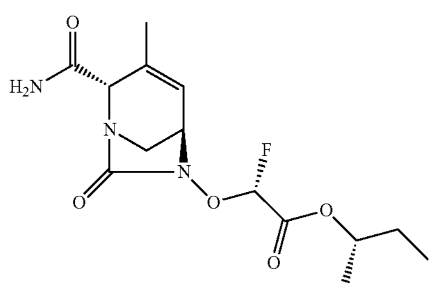 [SMILES: CC[C@H](C)OC(=O)[C@@H](F)ON1C(=O)N2C[C@H]1C=C(C)[C@H]2C(N)=O] | (2R)-(S)-sec-butyl 2-(((2S,5R)-2-carbamoyl-3-methyl-7-oxo-1,6-diazabicyclo[3.2.1]oct-3-en-6-yl)oxy)-2-fluoroacetate |
| 21 | 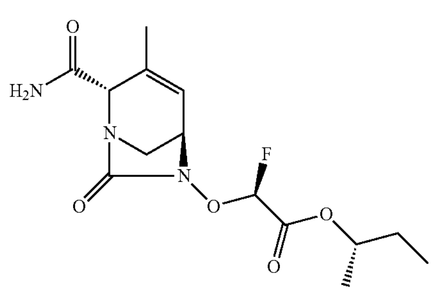 [SMILES: CC[C@H](C)OC(=O)[C@H](F)ON1C(=O)N2C[C@H]1C=C(C)[C@H]2C(N)=O] | (2S)-(S)-sec-butyl 2-(((2S,5R)-2-carbamoyl-3-methyl-7-oxo-1,6-diazabicyclo[3.2.1]oct-3-en-6-yl)oxy)-2-fluoroacetate |

| Ex. # | Structure | Compound Name |
|---|---|---|
| 22 | 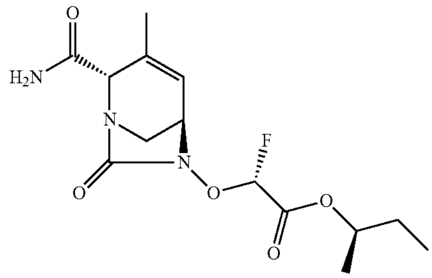 [SMILES: CC[C@@H](C)OC(=O)[C@@H](F)ON1C(=O)N2C[C@H]1C=C(C)[C@H]2C(N)=O] | (2R)-(R)-sec-butyl 2-(((2S,5R)-2-carbamoyl-3-methyl-7-oxo-1,6-diazabicyclo[3.2.1]oct-3-en-6-yl)oxy)-2-fluoroacetate |
| 23 | 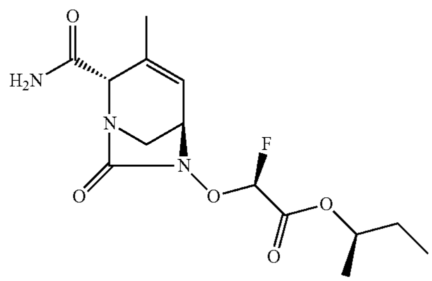 [SMILES: CC[C@@H](C)OC(=O)[C@H](F)ON1C(=O)N2C[C@H]1C=C(C)[C@H]2C(N)=O] | (2S)-(R)-sec-butyl 2-(((2S,5R)-2-carbamoyl-3-methyl-7-oxo-1,6-diazabicyclo[3.2.1]oct-3-en-6-yl)oxy)-2-fluoroacetate |
| 24 | 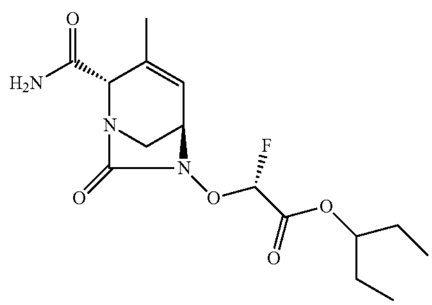 [SMILES: CCC(CC)OC(=O)[C@@H](F)ON1C(=O)N2C[C@H]1C=C(C)[C@H]2C(N)=O] | (R)-pentan-3-yl 2-((2S,5R)-2-carbamoyl-3-methyl-7-oxo-1,6-diazabicyclo[3.2.1]oct-3-en-6-yloxy)-2-fluoroacetate |
| 25 | 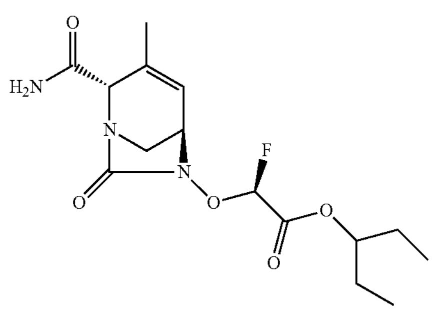 [SMILES: CCC(CC)OC(=O)[C@H](F)ON1C(=O)N2C[C@H]1C=C(C)[C@H]2C(N)=O] | (S)-pentan-3-yl 2-((2S,5R)-2-carbamoyl-3-methyl-7-oxo-1,6-diazabicyclo[3.2.1]oct-3-en-6-yloxy)-2-fluoroacetate |
| 26 | 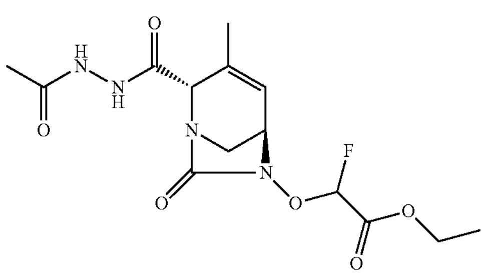 [SMILES: CCOC(=O)C(F)ON1C(=O)N2C[C@H]1C=C(C)[C@H]2C(=O)NNC(C)=O] | ethyl 2-(((2S,5R)-2-(2-acetylhydrazinecarbonyl)-3-methyl-7-oxo-1,6-diazabicyclo[3.2.1]oct-3-en-6-yl)oxy)-2-fluoroacetate |

| Ex. # | Structure | Compound Name |
|---|---|---|
| 27 | 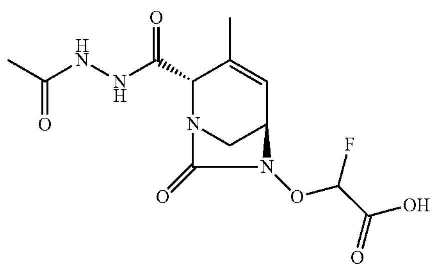 [SMILES: CC(=O)NNC(=O)[C@@H]1C(C)=C[C@@H]2CN1C(=O)N2OC(F)C(=O)O] | 2-(((2S,5R)-2-(2-acetylhydrazinecarbonyl)-3-methyl-7-oxo-1,6-diazabicyclo[3.2.1]oct-3-en-6-yl)oxy)-2-fluoroacetic acid lithium salt |
| 28 | 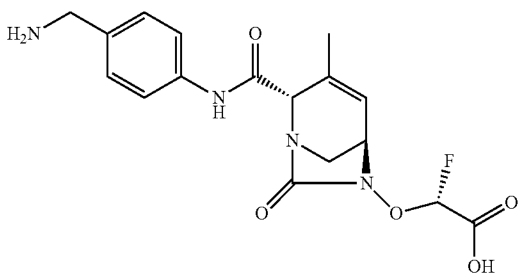 [SMILES: CC1=C[C@@H]2CN(C(=O)N2O[C@H](F)C(=O)O)[C@@H]1C(=O)Nc1ccc(CN)cc1] | (R)-2-((2S,5R)-2-(4-(aminomethyl)phenylcarbamoyl)-3-methyl-7-oxo-1,6-diazabicyclo[3.2.1]oct-3-en-6-yloxy)-2-fluoroacetic acid TFA salt |
| 29 | 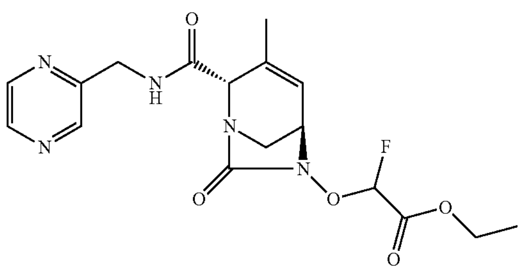 [SMILES: CCOC(=O)C(F)ON1C(=O)N2C[C@H]1C=C(C)[C@H]2C(=O)NCc1cnccn1] | ethyl 2-fluoro-2-(((2S,5R)-3-methyl-7-oxo-2-((pyrazin-2-ylmethyl)carbamoyl)-1,6-diazabicyclo[3.2.1]oct-3-en-6-yl)oxy)acetate |
| 30 | 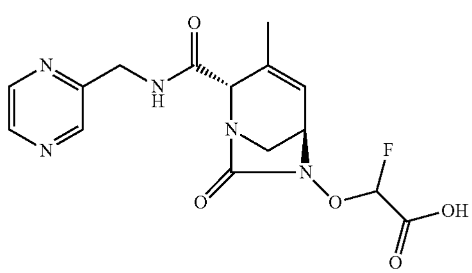 [SMILES: CC1=C[C@@H]2CN(C(=O)N2OC(F)C(=O)O)[C@@H]1C(=O)NCc1cnccn1] | 2-fluoro-2-(((2S,5R)-3-methyl-7-oxo-2-((pyrazin-2-ylmethyl)carbamoyl)-1,6-diazabicyclo[3.2.1]oct-3-en-6-yl)oxy)acetic acid lithium salt |
| 31 | 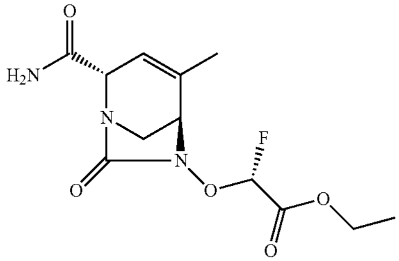 [SMILES: CCOC(=O)[C@@H](F)ON1C(=O)N2C[C@H]1C(C)=C[C@H]2C(N)=O] | (2R)-ethyl 2-(((2S,5R)-2-carbamoyl-4-methyl-7-oxo-1,6-diazabicyclo[3.2.1]oct-3-en-6-yl)oxy)-2-fluoroacetate |

-continued

| Ex. # | Structure | Compound Name |
|---|---|---|
| 32 | 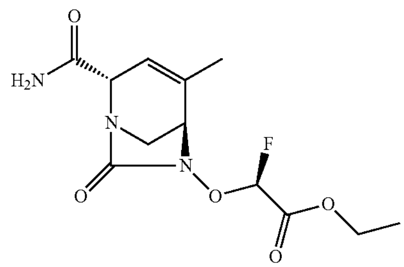 [SMILES: CCOC(=O)[C@H](F)ON1C(=O)N2C[C@H]1C(C)=C[C@H]2C(N)=O] | (2S)-ethyl 2-(((2S,5R)-2-carbamoyl-4-methyl-7-oxo-1,6-diazabicyclo[3.2.1]oct-3-en-6-yl)oxy)-2-fluoroacetate |
| 33 | 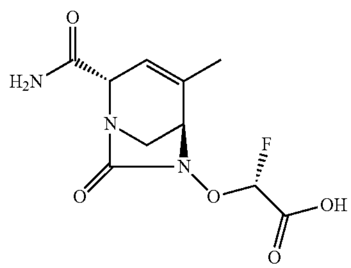 [SMILES: CC1=C[C@@H](C(N)=O)N2C[C@@H]1N(O[C@H](F)C(=O)O)C2=O] | (2R)-2-(((2S,5R)-2-carbamoyl-4-methyl-7-oxo-1,6-diazabicyclo[3.2.1]oct-3-en-6-yl)oxy)-2-fluoroacetic acid lithium salt |
| 34 | 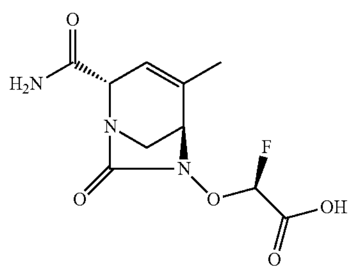 [SMILES: CC1=C[C@@H](C(N)=O)N2C[C@@H]1N(O[C@@H](F)C(=O)O)C2=O] | (2S)-2-(((2S,5R)-2-carbamoyl-4-methyl-7-oxo-1,6-diazabicyclo[3.2.1]oct-3-en-6-yl)oxy)-2-fluoroacetic acid lithium salt |
| 35 | 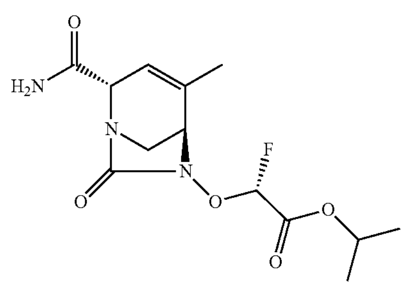 [SMILES: CC1=C[C@@H](C(N)=O)N2C[C@@H]1N(O[C@H](F)C(=O)OC(C)C)C2=O] | (2R)-isopropyl 2-(((2S,5R)-2-carbamoyl-4-methyl-7-oxo-1,6-diazabicyclo[3.2.1]oct-3-en-6-yl)oxy)-2-fluoroacetate |
| 36 | 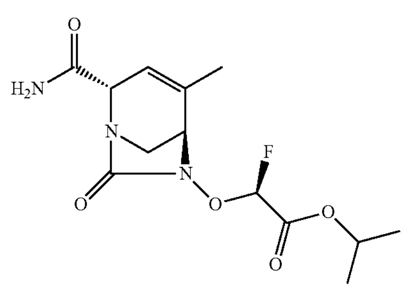 [SMILES: CC1=C[C@@H](C(N)=O)N2C[C@@H]1N(O[C@@H](F)C(=O)OC(C)C)C2=O] | (2S)-isopropyl 2-(((2S,5R)-2-carbamoyl-4-methyl-7-oxo-1,6-diazabicyclo[3.2.1]oct-3-en-6-yl)oxy)-2-fluoroacetate |

| Ex. # | Structure | Compound Name |
|---|---|---|
| 37 | 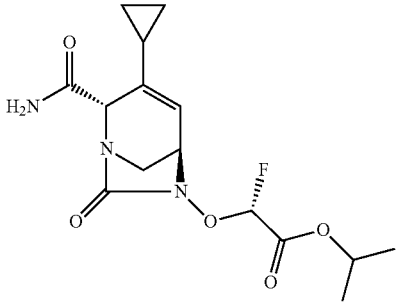 [SMILES: CC(C)OC(=O)[C@@H](F)ON1C(=O)N2C[C@H]1C=C(C1CC1)[C@H]2C(N)=O] | (2R)-isopropyl 2-(((2S,5R)-2-carbamoyl-3-cyclopropyl-7-oxo-1,6-diazabicyclo[3.2.1]oct-3-en-6-yl)oxy)-2-fluoroacetate |
| 38 | 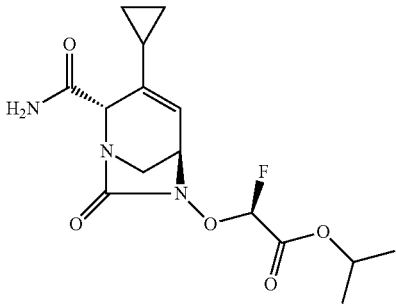 | (2S)-isopropyl 2-(((2S,5R)-2-carbamoyl-3-cyclopropyl-7-oxo-1,6-diazabicyclo[3.2.1]oct-3-en-6-yl)oxy)-2-fluoroacetate |
| 39 | 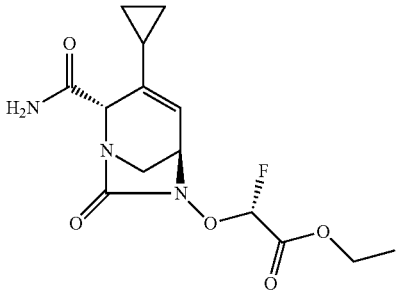 [SMILES: CCOC(=O)[C@@H](F)ON1C(=O)N2C[C@H]1C=C(C1CC1)[C@H]2C(N)=O] | (2R)-ethyl 2-(((2S,5R)-2-carbamoyl-3-cyclopropyl-7-oxo-1,6-diazabicyclo[3.2.1]oct-3-en-6-yl)oxy)-2-fluoroacetate |
| 40 | 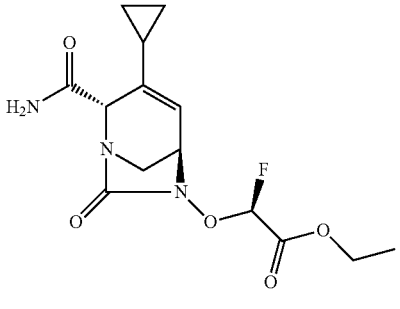 [SMILES: CCOC(=O)[C@H](F)ON1C(=O)N2C[C@H]1C=C(C1CC1)[C@H]2C(N)=O] | (2S)-ethyl 2-(((2S,5R)-2-carbamoyl-3-cyclopropyl-7-oxo-1,6-diazabicyclo[3.2.1]oct-3-en-6-yl)oxy)-2-fluoroacetate |
| 41 | 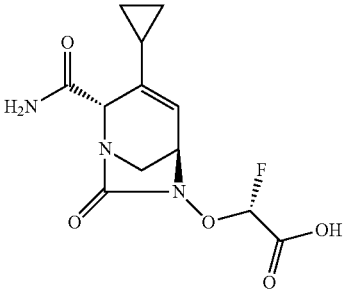 | (2R)-2-(((2S,5R)-2-carbamoyl-3-cyclopropyl-7-oxo-1,6-diazabicyclo[3.2.1]oct-3-en-6-yl)oxy)-2-fluoroacetic acid lithium salt |

| Ex. # | Structure | Compound Name |
|---|---|---|
| 42 | 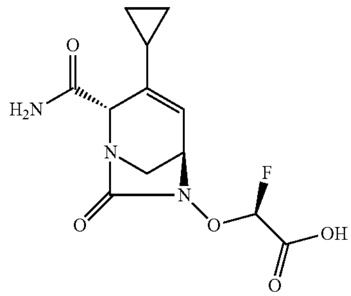 [SMILES: NC(=O)[C@@H]1C(C2CC2)=C[C@@H]2CN1C(=O)N2O[C@@H](F)C(=O)O] | (2R)-2-(((2S,5R)-2-carbamoyl-3-cyclopropyl-7-oxo-1,6-diazabicyclo[3.2.1]oct-3-en-6-yl)oxy)-2-fluoroacetic acid lithium salt |
| 43 | 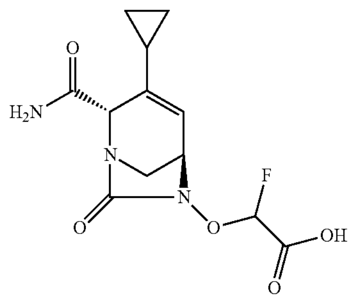 [SMILES: NC(=O)[C@@H]1C(C2CC2)=C[C@@H]2CN1C(=O)N2OC(F)C(=O)O] | 2-(((2S,5R)-2-carbamoyl-3-cyclopropyl-7-oxo-1,6-diazabicyclo[3.2.1]oct-3-en-6-yl)oxy)-2-fluoroacetic acid lithium salt |
| 44 | 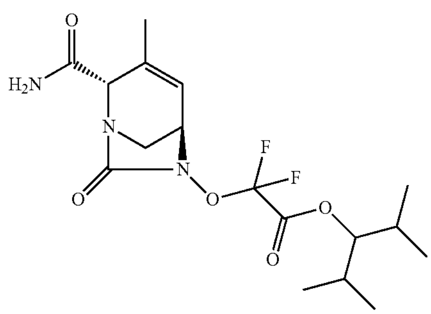 [SMILES: CC1=C[C@@H]2CN(C(=O)N2OC(F)(F)C(=O)OC(C(C)C)C(C)C)[C@@H]1C(N)=O] | (1-isopropyl-2-methyl-propyl) 2-[[(2S,5R)-2-carbamoyl-3-methyl-7-oxo-1,6-diazabicyclo[3.2.1]oct-3-en-6-yl]oxy]-2,2-difluoro-acetate |
| 45 | 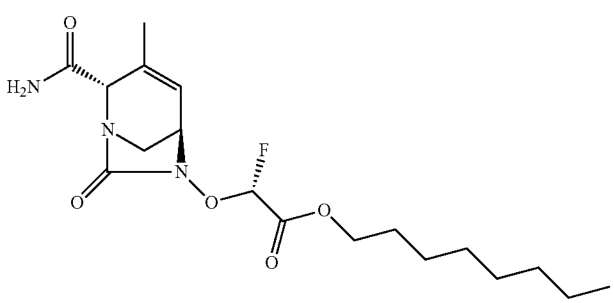 [SMILES: CCCCCCCCOC(=O)[C@@H](F)ON1C(=O)N2C[C@H]1C=C(C)[C@H]2C(N)=O] | octyl (2R)-2-[[(2S,5R)-2-carbamoyl-3-methyl-7-oxo-1,6-diazabicyclo[3.2.1]oct-3-en-6-yl]oxy]-2-fluoro-acetate |
| 46 | 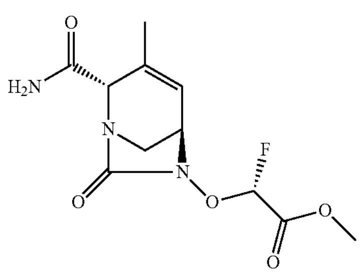 [SMILES: COC(=O)[C@@H](F)ON1C(=O)N2C[C@H]1C=C(C)[C@H]2C(N)=O] | methyl (2R)-2-[[(2S,5R)-2-carbamoyl-3-methyl-7-oxo-1,6-diazabicyclo[3.2.1]oct-3-en-6-yl]oxy]-2-fluoro-acetate |

-continued

| Ex. # | Structure | Compound Name |
|---|---|---|
| 47 | 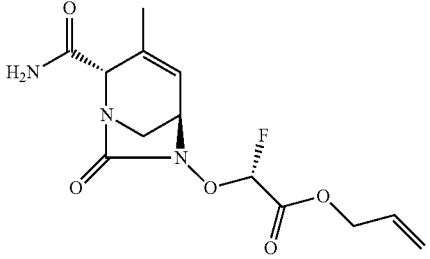 [SMILES: C=CCOC(=O)[C@@H](F)ON1C(=O)N2C[C@H]1C=C(C)[C@H]2C(N)=O] | allyl (2R)-2-[[(2S,5R)-2-carbamoyl-3-methyl-7-oxo-1,6-diazabicyclo[3.2.1]oct-3-en-6-yl]oxy]-2-fluoro-acetate |
| 48 | 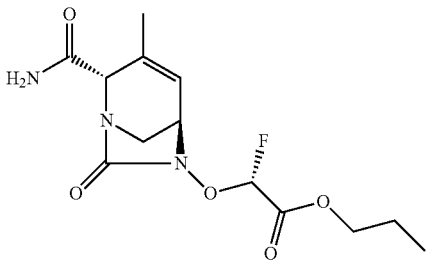 | propyl (2R)-2-[[(2S,5R)-2-carbamoyl-3-methyl-7-oxo-1,6-diazabicyclo[3.2.1]oct-3-en-6-yl]oxy]-2-fluoro-acetate |
| 49 | 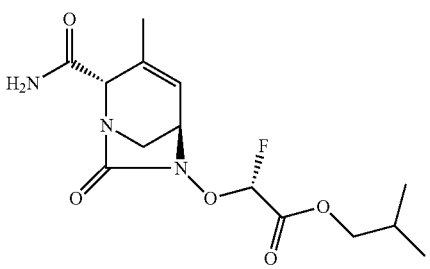 [SMILES: CC1=C[C@@H]2CN(C(=O)N2O[C@H](F)C(=O)OCC(C)C)[C@@H]1C(N)=O] | isobutyl (2R)-2-[[(2S,5R)-2-carbamoyl-3-methyl-7-oxo-1,6-diazabicyclo[3.2.1]oct-3-en-6-yl]oxy]-2-fluoro-acetate |
| 50 | 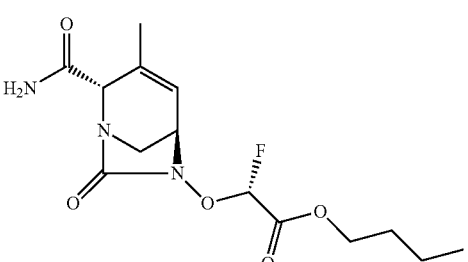 | butyl (2R)-2-[[(2S,5R)-2-carbamoyl-3-methyl-7-oxo-1,6-diazabicyclo[3.2.1]oct-3-en-6-yl]oxy]-2-fluoro-acetate |
| 51 | 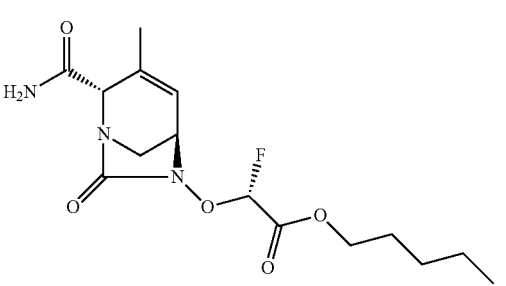 [SMILES: CCCCCOC(=O)[C@@H](F)ON1C(=O)N2C[C@H]1C=C(C)[C@H]2C(N)=O] | pentyl (2R)-2-[[(2S,5R)-2-carbamoyl-3-methyl-7-oxo-1,6-diazabicyclo[3.2.1]oct-3-en-6-yl]oxy]-2-fluoro-acetate |

| Ex. # | Structure | Compound Name |
|---|---|---|
| 52 | 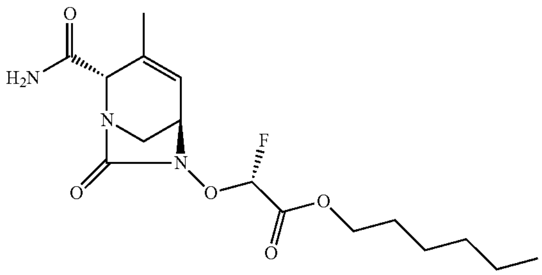 [SMILES: CCCCCCOC(=O)[C@@H](F)ON1C(=O)N2C[C@H]1C=C(C)[C@H]2C(N)=O] | hexyl (2R)-2-[[(2S,5R)-2-carbamoyl-3-methyl-7-oxo-1,6-diazabicyclo[3.2.1]oct-3-en-6-yl]oxy]-2-fluoro-acetate |
| 53 | 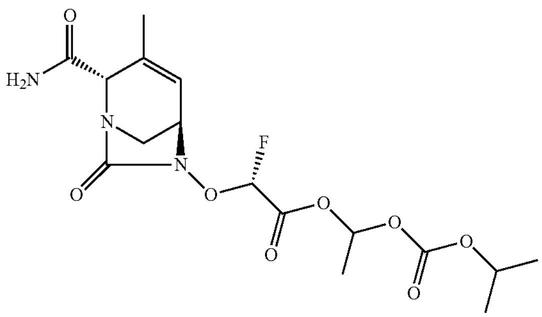 [SMILES: CC1=C[C@@H]2CN(C(=O)N2O[C@H](F)C(=O)OC(C)OC(=O)OC(C)C)[C@@H]1C(N)=O] | 1-isopropoxycarbonyloxyethyl (2R)-2-[[(2S,5R)-2-carbamoyl-3-methyl-7-oxo-1,6-diazabicyclo[3.2.1]oct-3-en-6-yl]oxy]-2-fluoro-acetate |
| 54 | 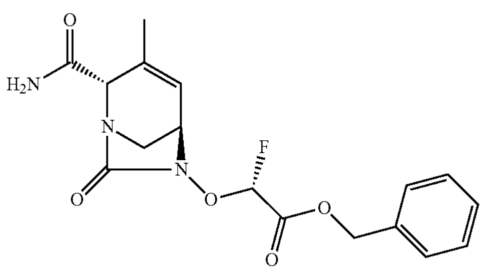 [SMILES: CC1=C[C@@H]2CN(C(=O)N2O[C@H](F)C(=O)OCc2ccccc2)[C@@H]1C(N)=O] | (2R)-benzyl 2-(((2S,5R)-2-carbamoyl-3-methyl-7-oxo-1,6-diazabicyclo[3.2.1]oct-3-en-6-yl)oxy)-2-fluoroacetate |
| 55 | 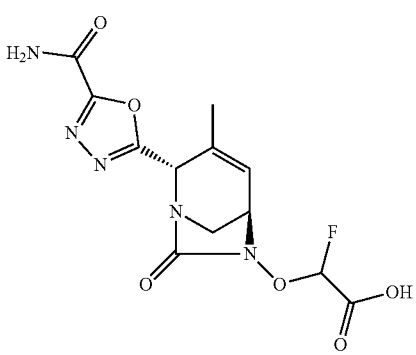 [SMILES: CC1=C[C@@H]2CN(C(=O)N2OC(F)C(=O)O)[C@@H]1c1nnc(C(N)=O)o1] | 2-[[(2S,5R)-2-(5-carbamoyl-1,3,4-oxadiazol-2-yl)-3-methyl-7-oxo-1,6-diazabicyclo[3.2.1]oct-3-en-6-yl]oxy]-2-fluoro-acetic acid lithium salt |
| 56 | 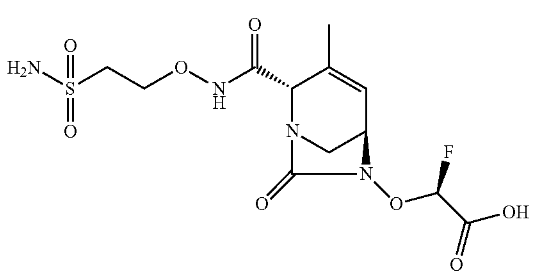 [SMILES: CC1=C[C@@H]2CN(C(=O)N2O[C@@H](F)C(=O)O)[C@@H]1C(=O)NOCCS(N)(=O)=O] | (2S)-2-fluoro-2-[[(2S,5R)-3-methyl-7-oxo-2-(2-sulfamoylethoxycarbamoyl)-1,6-diazabicyclo[3.2.1]oct-3-en-6-yl]oxy]acetic acid lithium salt |

-continued

| Ex. # | Structure | Compound Name |
|---|---|---|
| 57 | 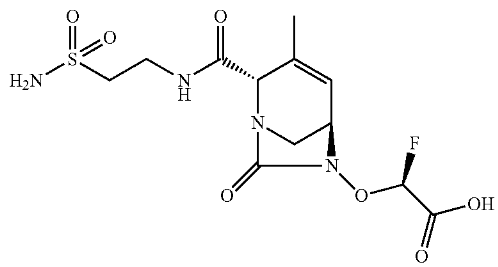 [SMILES: CC1=C[C@@H]2CN(C(=O)N2O[C@@H](F)C(=O)O)[C@@H]1C(=O)NCCS(N)(=O)=O] | (2S)-2-fluoro-2-[[(2S,5R)-3-methyl-7-oxo-2-(2-sulfamoylethylcarbamoyl)-1,6-diazabicyclo[3.2.1]oct-3-en-6-yl]oxy]acetic acid lithium salt |
| 58 | 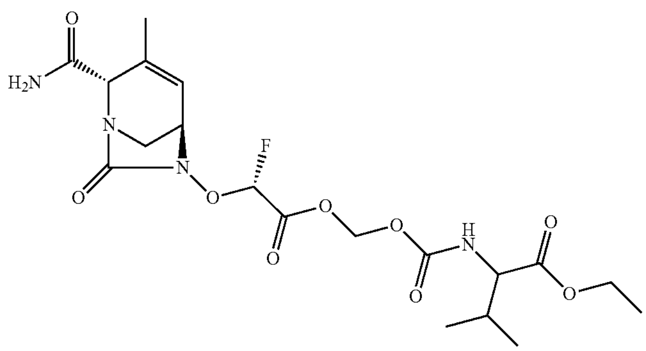 [SMILES: CCOC(=O)C(NC(=O)OCOC(=O)[C@@H](F)ON1C(=O)N2C[C@H]1C=C(C)[C@H]2C(N)=O)C(C)C] | ethyl 2-[[(2R)-2-[[(2S,5R)-2-carbamoyl-3-methyl-7-oxo-1,6-diazabicyclo[3.2.1]oct-3-en-6-yl]oxy]-2-fluoro-acetyl]oxymethoxycarbonylamino]-3-methyl-butanoate |
| 59 | 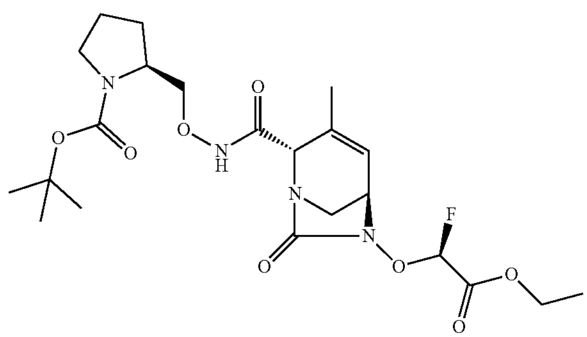 [SMILES: CCOC(=O)[C@H](F)ON1C(=O)N2C[C@H]1C=C(C)[C@H]2C(=O)NOC[C@@H]1CCCN1C(=O)OC(C)(C)C] | tert-butyl (2S)-2-(((((2S,5R)-6-((S)-2-ethoxy-1-fluoro-2-oxoethoxy)-3-methyl-7-oxo-1,6-diazabicyclo[3.2.1]oct-3-ene-2-carboxamido)oxy)methyl)pyrrolidine-1-carboxylate |
| 60 | 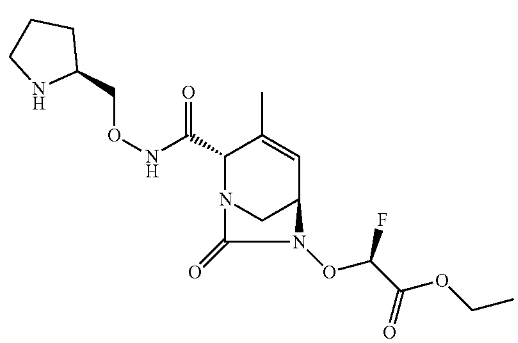 [SMILES: CCOC(=O)[C@H](F)ON1C(=O)N2C[C@H]1C=C(C)[C@H]2C(=O)NOC[C@@H]1CCCN1] | ethyl (2S)-2-fluoro-2-(((2S,5R)-3-methyl-7-oxo-2-(((((S)-pyrrolidin-2-yl)methoxy)carbamoyl)-1,6-diazabicyclo[3.2.1]oct-3-en-6-yl)oxy)acetate TFA salt |

-continued

| Ex. # | Structure | Compound Name |
|---|---|---|
| 61 | 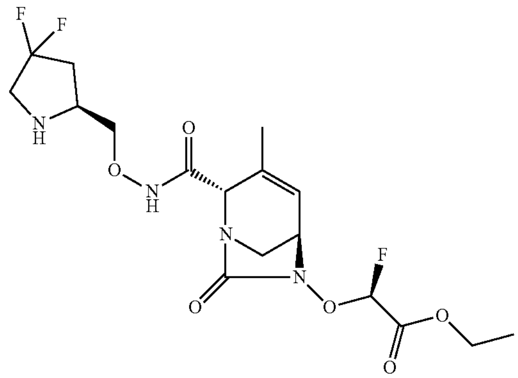 [SMILES: CCOC(=O)[C@H](F)ON1C(=O)N2C[C@H]1C=C(C)[C@H]2C(=O)NOC[C@@H]1CC(F)(F)CN1] | ethyl (2S)-2-(((2S,5R)-2-((((S)-4,4-difluoropyrrolidin-2-yl)methoxy)carbamoyl)-3-methyl-7-oxo-1,6-diazabicyclo[3.2.1]oct-3-en-6-yl)oxy)-2-fluoroacetate TFA salt |
| 62 | 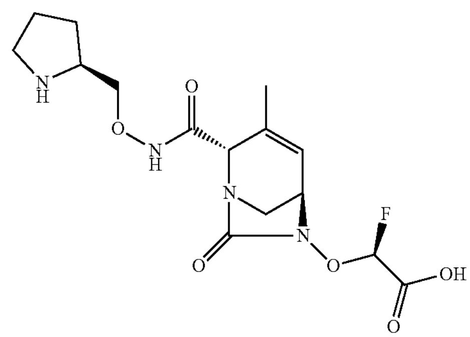 [SMILES: CC1=C[C@@H]2CN(C(=O)N2O[C@@H](F)C(=O)O)[C@@H]1C(=O)NOC[C@@H]1CCCN1] | (2S)-2-fluoro-2-[[(2S,5R)-3-methyl-7-oxo-2-[[(2S)-pyrrolidin-2-yl]methoxycarbamoyl]-1,6-diazabicyclo[3.2.1]oct-3-en-6-yl]oxy]acetic acid TFA salt |
| 63 | 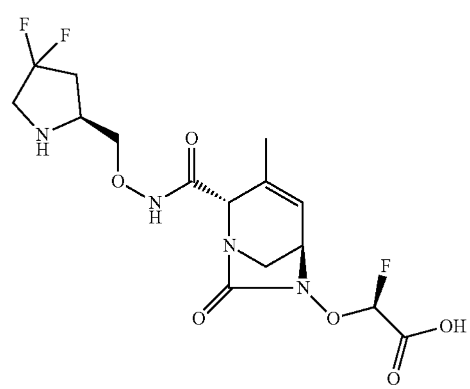 [SMILES: CC1=C[C@@H]2CN(C(=O)N2O[C@@H](F)C(=O)O)[C@@H]1C(=O)NOC[C@@H]1CC(F)(F)CN1] | (2S)-2-(((2S,5R)-2-((((S)-4,4-difluoropyrrolidin-2-yl)methoxy)carbamoyl)-3-methyl-7-oxo-1,6-diazabicyclo[3.2.1]oct-3-en-6-yl)oxy)-2-fluoroacetic acid TFA salt |
| 64 | 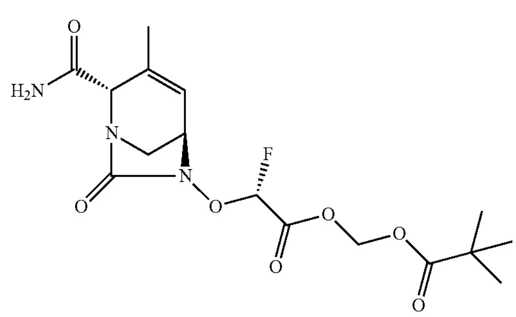 [SMILES: CC1=C[C@@H]2CN(C(=O)N2O[C@H](F)C(=O)OCOC(=O)C(C)(C)C)[C@@H]1C(N)=O] | [(2R)-2-[[(2S,5R)-2-carbamoyl-3-methyl-7-oxo-1,6-diazabicyclo[3.2.1]oct-3-en-6-yl]oxy]-2-fluoro-acetyl]oxymethyl 2,2-dimethylpropanoate |

-continued

| Ex. # | Structure | Compound Name |
|---|---|---|
| 65 | 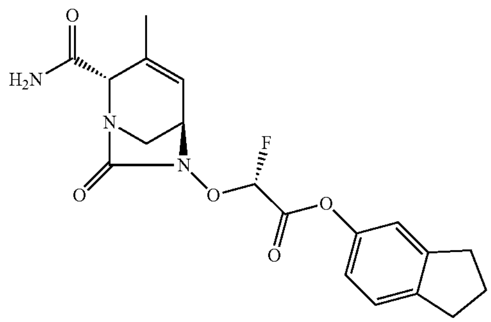 [SMILES: CC1=C[C@@H]2CN(C(=O)N2O[C@H](F)C(=O)Oc2ccc3c(c2)CCC3)[C@@H]1C(N)=O] | indan-5-yl (2R)-2-[[(2S,5R)-2-carbamoyl-3-methyl-7-oxo-1,6-diazabicyclo[3.2.1]oct-3-en-6-yl]oxy]-2-fluoro-acetate |
| 66 | 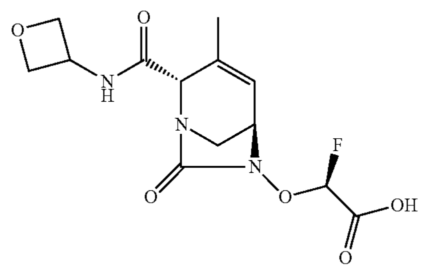 [SMILES: CC1=C[C@@H]2CN(C(=O)N2O[C@@H](F)C(=O)O)[C@@H]1C(=O)NC1COC1] | (2S)-2-fluoro-2-[[(2S,5R)-3-methyl-2-(oxetan-3-ylcarbamoyl)-7-oxo-1,6-diazabicyclo[3.2.1]oct-3-en-6-yl]oxy]acetic acid lithium salt |
| 67 | 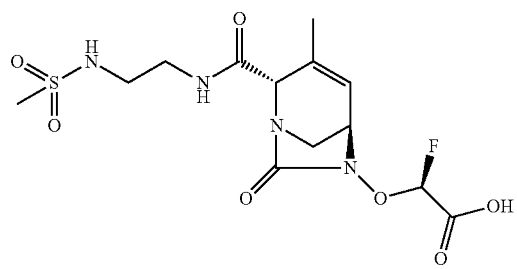 [SMILES: CC1=C[C@@H]2CN(C(=O)N2O[C@@H](F)C(=O)O)[C@@H]1C(=O)NCCNS(C)(=O)=O] | (2S)-2-fluoro-2-[[(2S,5R)-2-[2-(methanesulfonamido)ethylcarbamoyl]-3-methyl-7-oxo-1,6-diazabicyclo[3.2.1]oct-3-en-6-yl]oxy]acetic acid lithium salt |
| 68 | 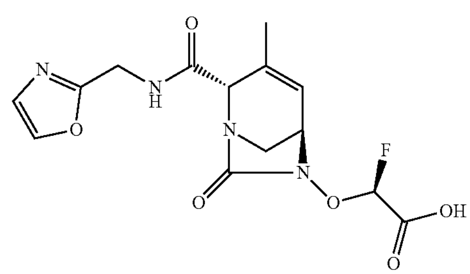 [SMILES: CC1=C[C@@H]2CN(C(=O)N2O[C@@H](F)C(=O)O)[C@@H]1C(=O)NCc1ncco1] | (2S)-2-fluoro-2-[[(2S,5R)-3-methyl-2-(oxazol-2-ylmethylcarbamoyl)-7-oxo-1,6-diazabicyclo[3.2.1]oct-3-en-6-yl]oxy]acetic acid lithium salt |
| 69 | 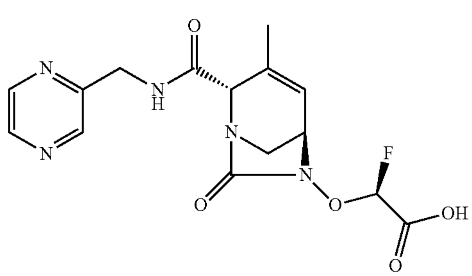 [SMILES: CC1=C[C@@H]2CN(C(=O)N2O[C@@H](F)C(=O)O)[C@@H]1C(=O)NCc1cnccn1] | (2S)-2-fluoro-2-[[(2S,5R)-3-methyl-7-oxo-2-(pyrazin-2-ylmethylcarbamoyl)-1,6-diazabicyclo[3.2.1]oct-3-en-6-yl]oxy]acetic acid lithium salt |

-continued

| Ex. # | Structure | Compound Name |
|---|---|---|
| 70 | 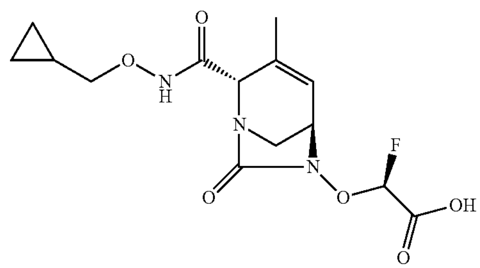 [SMILES: CC1=C[C@@H]2CN(C(=O)N2O[C@@H](F)C(=O)O)[C@@H]1C(=O)NOCC1CC1] | (2S)-2-[[(2S,5R)-2-(cyclopropylmethoxycarbamoyl)-3-methyl-7-oxo-1,6-diazabicyclo[3.2.1]oct-3-en-6-yl]oxy]-2-fluoro-acetic acid lithium salt |
| 71 | 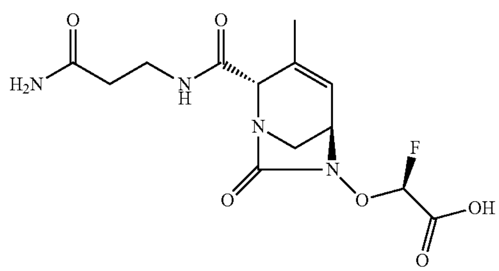 [SMILES: CC1=C[C@@H]2CN(C(=O)N2O[C@@H](F)C(=O)O)[C@@H]1C(=O)NCCC(N)=O] | (2S)-2-[[(2S,5R)-2-[(3-amino-3-oxo-propyl)carbamoyl]-3-methyl-7-oxo-1,6-diazabicyclo[3.2.1]oct-3-en-6-yl]oxy]-2-fluoro-acetic acid lithium salt |
| 72 | 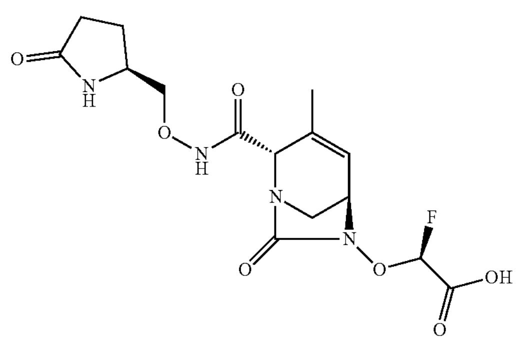 [SMILES: CC1=C[C@@H]2CN(C(=O)N2O[C@@H](F)C(=O)O)[C@@H]1C(=O)NOC[C@@H]1CCC(=O)N1] | (2S)-2-fluoro-2-[[(2S,5R)-3-methyl-7-oxo-2-[(5-oxopyrrolidin-2-yl)methoxycarbamoyl]-1,6-diazabicyclo[3.2.1]oct-3-en-6-yl]oxy]acetic acid lithium salt |
| 73 | 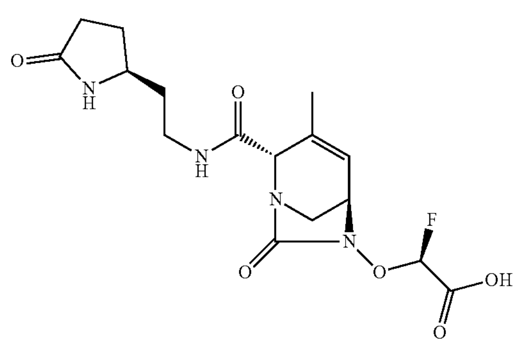 [SMILES: CC1=C[C@@H]2CN(C(=O)N2O[C@@H](F)C(=O)O)[C@@H]1C(=O)NCC[C@@H]1CCC(=O)N1] | (2S)-2-fluoro-2-[[(2S,5R)-3-methyl-7-oxo-2-[2-(5-oxopyrrolidin-2-yl)ethylcarbamoyl]-1,6-diazabicyclo[3.2.1]oct-3-en-6-yl]oxy]acetic acid lithium salt |
| 74 | 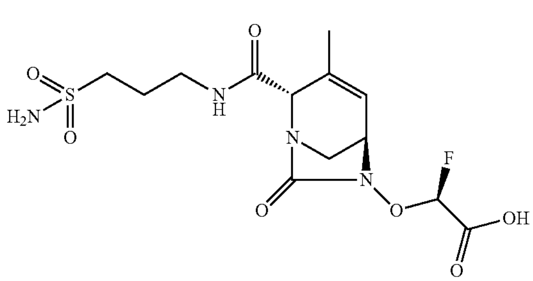 [SMILES: CC1=C[C@@H]2CN(C(=O)N2O[C@@H](F)C(=O)O)[C@@H]1C(=O)NCCCS(N)(=O)=O] | (2S)-2-fluoro-2-[[(2S,5R)-3-methyl-7-oxo-2-(3-sulfamoylpropylcarbamoyl)-1,6-diazabicyclo[3.2.1]oct-3-en-6-yl]oxy]acetic acid lithium salt |

-continued

| Ex. # | Structure | Compound Name |
|---|---|---|
| 75 | 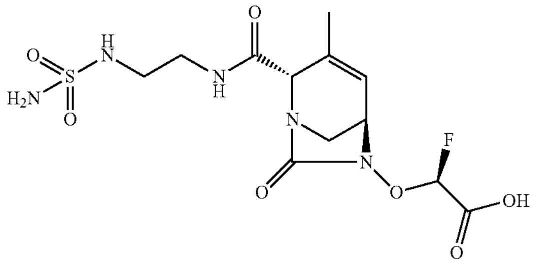 [SMILES: CC1=C[C@@H]2CN(C(=O)N2O[C@@H](F)C(=O)O)[C@@H]1C(=O)NCCNS(N)(=O)=O] | (2S)-2-fluoro-2-[[(2S,5R)-3-methyl-7-oxo-2-[2-(sulfamoylamino) ethylcarbamoyl]-1,6-diazabicyclo[3.2.1]oct-3-en-6-yl]oxy]acetic acid lithium salt |
| 76 | 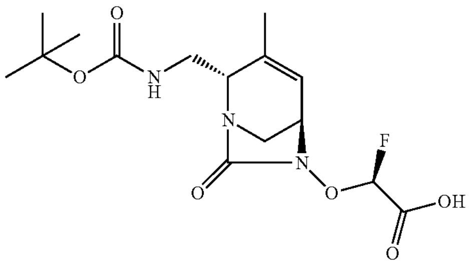 [SMILES: CC1=C[C@@H]2CN(C(=O)N2O[C@@H](F)C(=O)O)[C@@H]1CNC(=O)OC(C)(C)C] | (2S)-2-[[(2S,5R)-2-[(tert-butoxycarbonylamino)methyl]-3-methyl-7-oxo-1,6-diazabicyclo[3.2.1]oct-3-en-6-yl]oxy]-2-fluoro-acetic acid lithium salt |
| 77 | 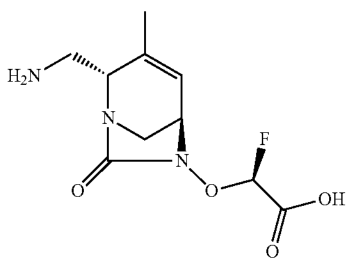 [SMILES: CC1=C[C@@H]2CN(C(=O)N2O[C@@H](F)C(=O)O)[C@@H]1CN] | (2S)-2-[[(2S,5R)-2-(aminomethyl)-3-methyl-7-oxo-1,6-diazabicyclo[3.2.1]oct-3-en-6-yl]oxy]-2-fluoro-acetic acid |
| 78 | 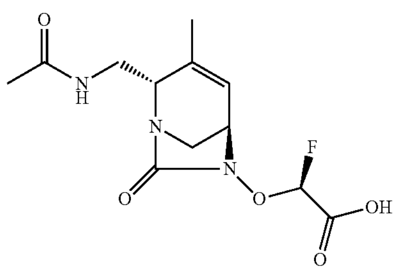 [SMILES: CC(=O)NC[C@@H]1C(C)=C[C@@H]2CN1C(=O)N2O[C@@H](F)C(=O)O] | (2S)-2-[[(2S,5R)-2-(acetamidomethyl)-3-methyl-7-oxo-1,6-diazabicyclo[3.2.1]oct-3-en-6-yl]oxy]-2-fluoro-acetic acid lithium salt |
| 79 | 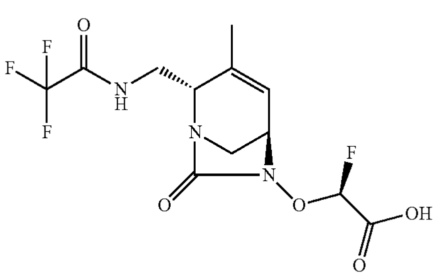 [SMILES: CC1=C[C@@H]2CN(C(=O)N2O[C@@H](F)C(=O)O)[C@@H]1CNC(=O)C(F)(F)F] | (2S)-2-fluoro-2-[[(2S,5R)-3-methyl-7-oxo-2-[[(2,2,2-trifluoroacetyl)amino]methyl]-1,6-diazabicyclo[3.2.1]oct-3-en-6-yl]oxy]acetic acid lithium salt |

-continued

| Ex. # | Structure | Compound Name |
|---|---|---|
| 80 | 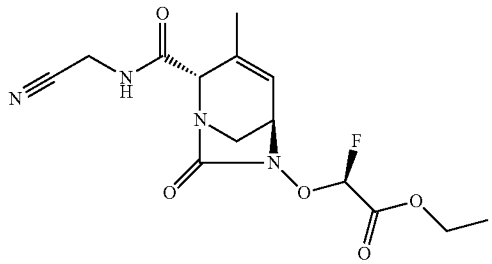 [SMILES: CCOC(=O)[C@H](F)ON1C(=O)N2C[C@H]1C=C(C)[C@H]2C(=O)NCC#N] | ethyl (2S)-2-fluoro-2-[[(2S,5R)-2-(cyanomethylcarbamoyl)-3-methyl-7-oxo-1,6-diazabicyclo[3.2.1]oct-3-en-6-yl]oxy]acetate |
| 81 | 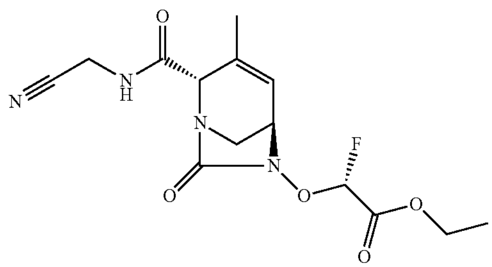 [SMILES: CCOC(=O)[C@@H](F)ON1C(=O)N2C[C@H]1C=C(C)[C@H]2C(=O)NCC#N] | ethyl (2R)-2-fluoro-2-[[(2S,5R)-2-(cyanomethylcarbamoyl)-3-methyl-7-oxo-1,6-diazabicyclo[3.2.1]oct-3-en-6-yl]oxy]acetate |
| 82 | 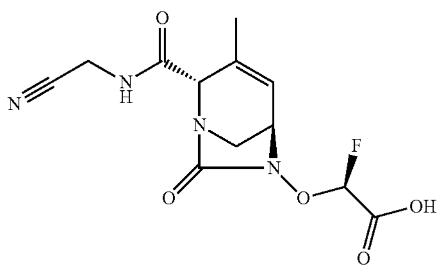 [SMILES: CC1=C[C@@H]2CN(C(=O)N2O[C@@H](F)C(=O)O)[C@@H]1C(=O)NCC#N] | (2S)-2-fluoro-2-[[(2S,5R)-2-(cyanomethylcarbamoyl)-3-methyl-7-oxo-1,6-diazabicyclo[3.2.1]oct-3-en-6-yl]oxy]acetic acid lithium salt |
| 83 | 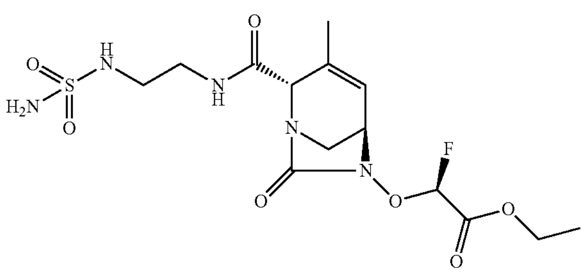 [SMILES: CCOC(=O)[C@H](F)ON1C(=O)N2C[C@H]1C=C(C)[C@H]2C(=O)NCCNS(N)(=O)=O] | ethyl (2S)-2-fluoro-2-[[(2S,5R)-2-(cyanomethylcarbamoyl)-3-methyl-7-oxo-1,6-diazabicyclo[3.2.1]oct-3-en-6-yl]oxy]acetate |
| 84 | 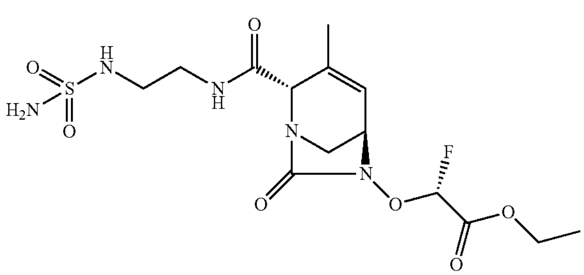 [SMILES: CCOC(=O)[C@@H](F)ON1C(=O)N2C[C@H]1C=C(C)[C@H]2C(=O)NCCNS(N)(=O)=O] | ethyl (2R)-2-fluoro-2-[[(2S,5R)-2-(cyanomethylcarbamoyl)-3-methyl-7-oxo-1,6-diazabicyclo[3.2.1]oct-3-en-6-yl]oxy]acetate |

-continued

| Ex. # | Structure | Compound Name |
|---|---|---|
| 85 | 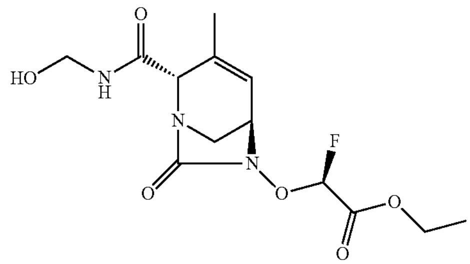 [SMILES: CCOC(=O)[C@H](F)ON1C(=O)N2C[C@H]1C=C(C)[C@H]2C(=O)NCO] | ethyl (2S)-2-fluoro-2-[[(2S,5R)-2-(hydroxymethylcarbamoyl)-3-methyl-7-oxo-1,6-diazabicyclo[3.2.1]oct-3-en-6-yl]oxy]acetate |
| 86 | 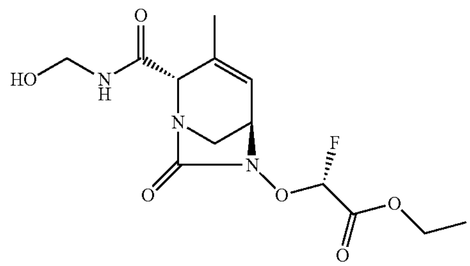 [SMILES: CCOC(=O)[C@@H](F)ON1C(=O)N2C[C@H]1C=C(C)[C@H]2C(=O)NCO] | ethyl (2R)-2-fluoro-2-[[(2S,5R)-2-(hydroxymethylcarbamoyl)-3-methyl-7-oxo-1,6-diazabicyclo[3.2.1]oct-3-en-6-yl]oxy]acetate |
| 87 | 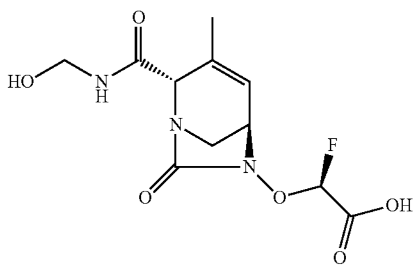 [SMILES: CC1=C[C@@H]2CN(C(=O)N2O[C@@H](F)C(=O)O)[C@@H]1C(=O)NCO] | (2S)-2-fluoro-2-[[(2S,5R)-2-(hydroxymethylcarbamoyl)-3-methyl-7-oxo-1,6-diazabicyclo[3.2.1]oct-3-en-6-yl]oxy]acetic acid lithium salt |
| 88 | 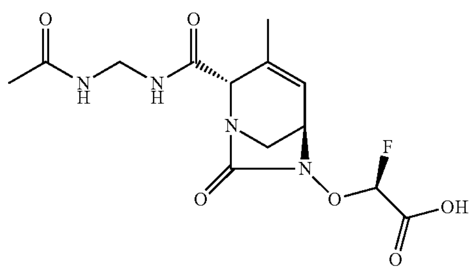 [SMILES: CC(=O)NCNC(=O)[C@@H]1C(C)=C[C@@H]2CN1C(=O)N2O[C@@H](F)C(=O)O] | (2S)-2-fluoro-2-[[(2S,5R)-2-(acetamidomethylcarbamoyl)-3-methyl-7-oxo-1,6-diazabicyclo[3.2.1]oct-3-en-6-yl]oxy]acetic acid lithium salt |
| 89 | 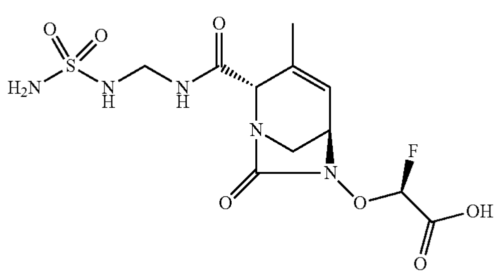 [SMILES: CC1=C[C@@H]2CN(C(=O)N2O[C@@H](F)C(=O)O)[C@@H]1C(=O)NCNS(N)(=O)=O] | (2S)-2-fluoro-2-[[(2S,5R)-3-methyl-7-oxo-2-[(sulfamoylamino)methylcarbamoyl]-1,6-diazabicyclo[3.2.1]oct-3-en-6-yl]oxy]acetic acid lithium salt |
| 90 | 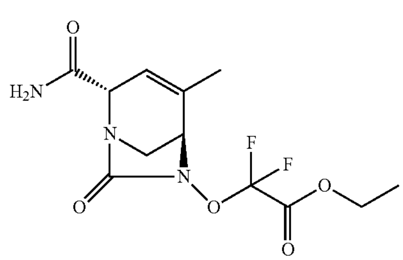 [SMILES: CCOC(=O)C(F)(F)ON1C(=O)N2C[C@H]1C(C)=C[C@H]2C(N)=O] | ethyl 2-(((2S,5R)-2-carbamoyl-4-methyl-7-oxo-1,6-diazabicyclo[3.2.1]oct-3-en-6-yl)oxy)-2,2-difluoroacetate |

-continued

| Ex. # | Structure | Compound Name |
|---|---|---|
| 91 | 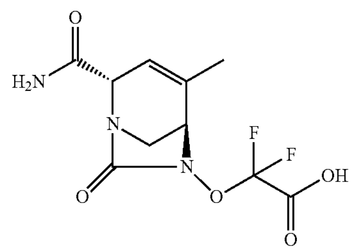 [SMILES: CC1=C[C@@H](C(N)=O)N2C[C@@H]1N(OC(F)(F)C(=O)O)C2=O] | 2-(((2S,5R)-2-carbamoyl-4-methyl-7-oxo-1,6-diazabicyclo[3.2.1]oct-3-en-6-yl)oxy)-2,2-difluoroacetic acid lithium salt |
| 92 | 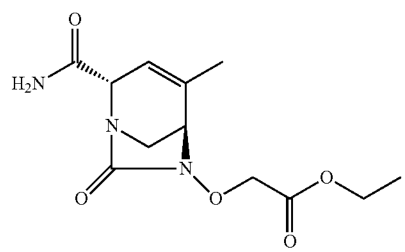 [SMILES: CCOC(=O)CON1C(=O)N2C[C@H]1C(C)=C[C@H]2C(N)=O] | ethyl 2-(((2S,5R)-2-carbamoyl-4-methyl-7-oxo-1,6-diazabicyclo[3.2.1]oct-3-en-6-yl)oxy)acetate |
| 93 | 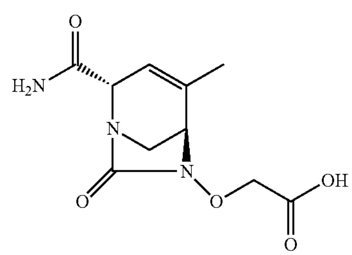 [SMILES: CC1=C[C@@H](C(N)=O)N2C[C@@H]1N(OCC(=O)O)C2=O] | 2-(((2S,5R)-2-carbamoyl-4-methyl-7-oxo-1,6-diazabicyclo[3.2.1]oct-3-en-6-yl)oxy)acetic acid lithium salt |
| 94 | 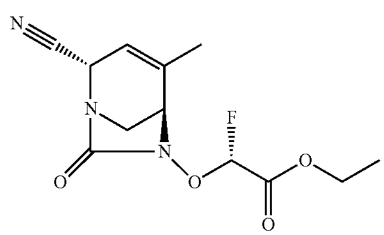 [SMILES: CCOC(=O)[C@@H](F)ON1C(=O)N2C[C@H]1C(C)=C[C@H]2C#N] | ethyl (2R)-2-(((2S,5R)-2-cyano-4-methyl-7-oxo-1,6-diazabicyclo[3.2.1]oct-3-en-6-yl)oxy)-2-fluoroacetate |
| 95 | 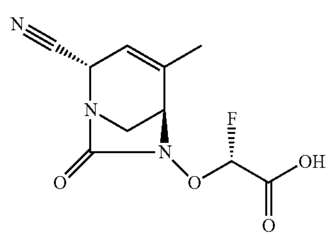 [SMILES: CC1=C[C@@H](C#N)N2C[C@@H]1N(O[C@H](F)C(=O)O)C2=O] | (2R)-2-(((2S,5R)-2-cyano-4-methyl-7-oxo-1,6-diazabicyclo[3.2.1]oct-3-en-6-yl)oxy)-2-fluoroacetic acid lithium salt |
| 96 | 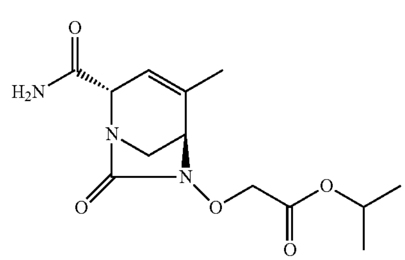 [SMILES: CC1=C[C@@H](C(N)=O)N2C[C@@H]1N(OCC(=O)OC(C)C)C2=O] | isopropyl 2-(((2S,5R)-2-carbamoyl-4-methyl-7-oxo-1,6-diazabicyclo[3.2.1]oct-3-en-6-yl)oxy)acetate |

Compounds of the invention include those of formulae (I), (Ia), (II), (IIa), (III), (IIIa), (IV), (IVa), (V), (Va) in free base (uncharged) state, as well as pharmaceutically acceptable salts thereof.

Alkyl—As used herein the term "alkyl" refers to both straight and branched chain saturated hydrocarbon radicals having the specified number of carbon atoms. References to individual alkyl groups such as "propyl" are specific for the straight chain version only and references to individual branched chain alkyl groups such as 'isopropyl' and "3-pentyl" are specific for the branched chain version only. In one aspect, "alkyl" is methyl.

Halo—As used herein, the term "halo" is intended to include fluoro, chloro, bromo and iodo. In one aspect, the "halo" may refer fluoro, chloro, and bromo. In another aspect, "halo" may refer to fluoro or chloro. In still another aspect, "halo" may refer to fluoro. In yet another aspect, "halo" may refer to chloro.

Haloalkyl—As used herein is an "alkyl" moiety as defined above substituted with one or more halogen atoms. In one aspect, a "haloalkyl" may be —$CHF_2$, —$CH_2F$ or —$CF_3$.

Cycloalkyl—In one aspect, "cycloalkyl" refers to a saturated monocyclic carbon ring, of which one or more —$CH_2$— groups may be optionally replaced with a corresponding number of —C(O)— groups. Illustrative examples of "cycloalkyl" include cyclopropyl, cyclobutyl, cyclopentyl, and cyclopentenyl. In one aspect, "3- to 5-membered carbocyclyl" may be cyclopropyl.

5-7 Membered Heterocyclyl—The term "5-7 membered heterocyclyl" refers to a saturated or partially saturated, non-aromatic monocyclic ring containing 5 to 7 ring atoms, of which at least one ring atom is selected from nitrogen, sulfur, and oxygen, and of which a —$CH_2$— group may be optionally replaced by a —C(O)— group. Analogously, "5-6 membered heterocyclyl" refers to a saturated or partially saturated, non-aromatic monocyclic ring containing 5 to 6 ring atoms, of which at least one ring atom is selected from nitrogen, sulfur, and oxygen, and of which a —$CH_2$— group may be optionally replaced by a —C(O)— group. Unless otherwise specified, "5-7 membered heterocyclyl" and "5-6 membered heterocyclyl" groups may be carbon or nitrogen linked. Ring nitrogen atoms may be optionally oxidized to form an N-oxide. Ring sulfur atoms may be optionally oxidized to form S-oxides or sulphones. Illustrative examples of "5-7 membered heterocyclyl" and "5-6 membered heterocyclyl" include, but are not limited to, azetidinyl, dioxidotetrahydrothiophenyl, 2,4-dioxoimidazolidinyl, 3,5-dioxopiperidinyl, furanyl, imidazolyl, isothiazolyl, isoxazolyl, morpholinyl, oxazolyl, oxetanyl, oxoimidazolidinyl, 3-oxo-1-piperazinyl, 2-oxopyrrolidinyl, 2-oxotetrahydrofuranyl, oxo-1,3-thiazolidinyl, piperazinyl, piperidyl, 2H-pyranyl, pyrazolyl, pyridinyl, pyrrolyl, pyrrolidinyl, pyrimidinyl, pyrazinyl, pyrazolyl, pyridazinyl, 4-pyridonyl, tetrahydrofuranyl, tetrahydropyranyl, thiazolyl, 1,3,4-thiadiazolyl, thiazolidinyl, thiomorpholinyl, thiophenyl, 4H-1,2,4-triazolyl, pyridine-N-oxidyl, tetrazolyl, oxadiazolyl, triazolyl, pyrazinyl, triazinyl, and homopiperidinyl. In one embodiment, the terms "5-7 membered heterocyclyl" and "5-6 membered heterocyclyl" includes siderophores of 5-7 or 5-6 members which contain at least one heteroatom.

5- or 6-Membered Heteroaryl—The term "5-6 membered heteroaryl" refers to a monocyclic, aromatic heterocyclyl ring containing 5 or 6 ring atoms, of which at least one ring atom is selected from nitrogen, sulfur, and oxygen. Unless otherwise specified, "5-6 membered heteroaryl" groups may be carbon or nitrogen linked. Ring nitrogen atoms may be optionally oxidized to form an N-oxide. Ring sulfur atoms may be optionally oxidized to form S-oxides. Illustrative examples of "5-6 membered heteroaryl" include furanyl, imidazolyl, isothiazolyl, isoxazole, oxazolyl, pyrazinyl, pyrazolyl, pyridazinyl, pyrimidinyl, pyridinyl, pyrrolyl, tetrazolyl, thiadiazolyl, thiazolyl, thiophenyl, and triazolyl.

Optionally substituted—As used herein, the phrase "optionally substituted" indicates that substitution is optional and therefore it is possible for the designated group to be either substituted or unsubstituted. In the event a substitution is desired, the appropriate number of hydrogens on the designated group may be replaced with a selection from the indicated substituents, provided that the normal valency of the atoms on a particular substituent is not exceeded, and that the substitution results in a stable compound.

In one aspect, when a particular group is designated as being optionally substituted with one or more substituents, the particular group may be unsubstituted. In another aspect, the particular group may bear one substituent. In another aspect, the particular substituent may bear two substituents. In still another aspect, the particular group may bear three substituents. In yet another aspect, the particular group may bear four substituents. In a further aspect, the particular group may bear one or two substituents. In still a further aspect, the particular group may be unsubstituted, or may bear one or two substituents.

Pharmaceutically Acceptable—As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Prodrug—As used herein, the term "prodrug" refers to a chemically modified version of a pharmacologically active agent that is transformed in vivo to release an active drug. (See Rautio, J., et al., *Prodrugs: Design and Clinical Applications*, Nature Rev., vol. 7, page 255 (March 2008)). In the present invention, prodrugs are used to make active beta-lactamase inhibitor compounds orally bioavailable following absorption from the gastrointestinal tract.

Effective Amount—As used herein, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

Compounds of Formulae (I), (Ia), (II), (IIa), (III), (IIIa), (IV), (IVa), (V), and (Va) may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

When a compound disclosed herein is depicted by name or structure and has one or more chiral centers, and where the name or structure encompasses more than one stereoisomer, e.g., does not indicate the stereochemistry at one or more chiral centers, it is to be understood that the name or structure encompasses all such stereoisomers and mixtures thereof.

The synthesis of optically active forms may be carried out by standard techniques of organic chemistry well known in the art, for example by synthesis from optically active starting materials or by resolution of a racemic form. Racemates may be separated into individual enantiomers using known procedures (see, for example, Advanced Organic Chemistry: 3rd Edition: author J March, p 104-107). A suitable procedure involves formation of diastereomeric derivatives by reaction of the racemic material with a chiral auxiliary, followed by separation, for example by chromatography, of the diastereomers and then cleavage of the auxiliary species. Similarly, the above-mentioned activity may be evaluated using the standard laboratory techniques referred to hereinafter.

Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent.

When a specific stereoisomer is designated, structurally or by name, it is favorably provided or substantially isolated from other stereoisomers of the same compound. In one aspect, a mixture containing a particular stereoisomer of a compound of Formulae (I), (Ia), (II), (IIa), (III), (IIIa), (IV), (IVa), (V), or (Va) may contain less than 30%, particularly less than 20%, and more particularly less than 10% by weight of other stereoisomers of the same compound. In another aspect, a mixture containing a particular stereoisomer of a compound of Formulae (I), (Ia), (II), (IIa), (III), (IIIa), (IV), (IVa), (V), or (Va) may contain less than 6%, particularly less than 3%, and more particularly less than 2% by weight of other stereoisomers of the compound. In another aspect, a mixture containing a particular stereoisomer of a compound of Formulae (I), (Ia), (II), (IIa), (III), (IIIa), (IV), (IVa), (V), or (Va) may contain less than 1%, particularly less than 0.5%, and more particularly less than 0.3%, and still more particularly less 0.1% by weight of other stereoisomers of the compound.

In one aspect, the terms "infection" and "bacterial infection" may refer to a gynecological infection. In another aspect the terms "infection" and "bacterial infection" may refer to a respiratory tract infection (RTI). In still another, the terms "infection" and "bacterial infection" may refer to a sexually transmitted disease. In yet another aspect, the terms "infection" and "bacterial infection" may refer to an uncomplicated urinary tract infection (UTI). In yet another aspect, the terms "infection" and "bacterial infection" may refer to a complicated urinary tract infection (cUTI). In a further aspect, the terms "infection" and "bacterial infection" may refer to acute exacerbation of chronic bronchitis (ACEB). In yet a further aspect, the terms "infection" and "bacterial infection" may refer to acute otitis media. In one aspect, the terms "infection" and "bacterial infection" may refer to acute sinusitis. In another aspect, the terms "infection" and "bacterial infection" may refer to an infection caused by drug resistant bacteria. In still another aspect, the terms "infection" and "bacterial infection" may refer to catheter-related sepsis. In yet another aspect, the terms "infection" and "bacterial infection" may refer to chancroid. In a further aspect, the terms "infection" and "bacterial infection" may refer to chlamydia. In still a further aspect, the terms "infection" and "bacterial infection" may refer to community-acquired pneumonia (CAP). In yet a further aspect, the terms "infection" and "bacterial infection" may refer to complicated skin and skin structure infection. In one aspect, the terms "infection" and "bacterial infection" may refer to uncomplicated skin and skin structure infection (SSSI). In another aspect, the terms "infection" and "bacterial infection" may refer to endocarditis. In still another aspect, the terms "infection" and "bacterial infection" may refer to febrile neutropenia. In yet another aspect, the terms "infection" and "bacterial infection" may refer to gonococcal cervicitis. In a further aspect, the terms "infection" and "bacterial infection" may refer to gonococcal urethritis. In still a further aspect, the terms "infection" and "bacterial infection" may refer to hospital-acquired pneumonia (HAP). In yet another aspect, the terms "infection" and "bacterial infection" may refer to osteomyelitis. In a further aspect, the terms "infection" and "bacterial infection" may refer to sepsis. In still a further aspect, the terms "infection" and "bacterial infection" may refer to syphilis. In a further aspect, the terms "infection" and "bacterial infection" may refer to an intra-abdominal infection (IAI). In one aspect of the invention, the terms "infection" and "bacterial infection" may refer to an infection selected from the group consisting of complicated urinary tract infection, uncomplicated urinary tract infection, kidney infection, lower respiratory tract infection, hospital-acquired bacterial pneumonia, pneumonia, acute bacterial prostatitis, acute bacterial skin and soft tissue infection, sepsis, intra-abdominal infection, and diabetic foot infection.

In one embodiment of the invention, the terms "infection" and "bacterial infection" refer to an infection caused by Gram-negative bacteria, also referred to as a "Gram-negative infection". In one aspect of this embodiment, the Gram-negative infection is an infection resistant to one or more antibiotics. In one aspect of this embodiment, the Gram-negative infection is a multi-drug resistant infection. In one aspect of this embodiment, the Gram-negative infection is caused by one or more Enterobacteriaceae spp. pathogens. In one aspect of this embodiment, the one or more Enterobacteriaceae spp. pathogens includes one or more *E. coli, K. pneumoniae, K. oxytoca, C. freundii, C. koseri, E. cloacae, P. mirabilis, M. morganii* and/or *S. marcescens*. In one aspect of this embodiment, the one or more Enterobacteriaceae spp. pathogens includes one or more *E. coli* or *K. pneumoniae* pathogen. In another aspect of this embodiment, the Gram-negative infection is caused by one or more biothreat pathogens. In one aspect of this embodiment, the one or more biothreat pathogens is *Burkholderia* spp., *Y. pestis*, and/or *F. tularensis*. In any of these aspects of the embodiment, the one or more Gram-negative pathogens may express one or more serine beta-lactamase enzymes. In one aspect of this embodiment, the one or more serine beta-lactamase enzymes includes one or more Class A, Class C and/or Class D beta-lactamase.

All the above mentioned infections can be caused by a variety of bacteria that potentially could be treatable with the claimed agents in combination with penicillin-binding protein inhibitors, or by itself. In one embodiment of the invention is a method of treating one or more of the infections listed above comprising administering to a subject suffering from a bacterial infection an effective amount of a compound of Formulae (I), (Ia), (II), (IIa), (III), (IIIa), (IV), (IVa), (V), or (Va) or a pharmaceutically acceptable salt thereof, in combination with an additional antibiotic agent. In one aspect of this embodiment, the additional antibiotic agent is a beta-lactam antibiotic. In one aspect of this embodiment, the additional antibiotic agent is a penicillin-binding protein inhibitor.

In one aspect, there is provided the use of a compound of Formulae (I), (Ia), (II), (IIa), (III), (IIIa), (IV), (IVa), (V), or (Va), or a pharmaceutically acceptable salt thereof, in the manufacture of a medicament for the production of a bacterial peptidoglycan inhibitory effect, either alone or in combination with a penicillin-binding protein inhibitor, in a warm-blooded animal such as man.

In another aspect, there is provided the use of a compound of Formulae (I), (Ia), (II), (IIa), (III), (IIIa), (IV), (IVa), (V), or (Va), or a pharmaceutically acceptable salt thereof, in the manufacture of a medicament for the treatment of a bacterial infection in a warm-blooded animal such as man. In one aspect, the compound of Formulae (I), (Ia), (II), (IIa), (III), (IIIa), (IV), (IVa), (V), or (Va), or a pharmaceutically acceptable salt thereof, is administered in combination with an additional antibiotic agent, such as a beta-lactam antibiotic. In one aspect of this embodiment, the additional antibiotic agent is a penicillin-binding protein inhibitor. In one aspect of this embodiment, the additional antibiotic agent is a beta-lactam antibiotic. In one aspect of this embodiment, the beta-lactam antibiotic is selected from cefpodoxime, cefuroxime, tigemonam, loracarbef, cefixime, cephalexin, cefadroxil, cefetamet, cefprozil, ceftibuten, cefditoren, faropenem, tebipenem, amoxicillin, carbenicillin, cefdinir, ampicillin, cefditoren, or a prodrug thereof. In one aspect of this embodiment, the beta-lactam antibiotic is cefpodoxime proxetil. In one aspect of this embodiment, the beta-lactam antibiotic is cefuroxime axetil. In one aspect of this embodiment, the beta-lactam antibiotic is cefpodoxime, or a prodrug thereof. In one aspect of this embodiment, the beta-lactam antibiotic is cefuroxime, or a prodrug thereof.

In still another aspect, there is provided the use of a compound of Formulae (I), (Ia), (II), (IIa), (III), (IIIa), (IV), (IVa), (V), or (Va), or a pharmaceutically acceptable salt thereof, in the manufacture of a medicament for the treatment of complicated urinary tract infection, uncomplicated urinary tract infection, kidney infection, lower respiratory tract infection, hospital-acquired bacterial pneumonia, pneumonia, acute bacterial prostatitis, acute bacterial skin and soft tissue infection, sepsis, intra-abdominal infection, and diabetic foot infections, in a warm-blooded animal such as man. In one aspect of the invention, is the use of a compound of Formulae (I), (Ia), (II), (IIa), (III), (IIIa), (IV), (IVa), (V), or (Va), or a pharmaceutically acceptable salt thereof, in the manufacture of a medicament for the treatment of complicated urinary tract infections. In one aspect of the preceding two embodiments, the compound of Formulae (I), (Ia), (II), (IIa), (III), (IIIa), (IV), (IVa), (V), or (Va) is administered in combination with an additional antibiotic agent. In one aspect of this embodiment, the additional antibiotic agent is a penicillin-binding protein inhibitor. In one aspect of this embodiment, the additional antibiotic agent is a beta-lactam antibiotic. In one aspect of this embodiment, the beta-lactam antibiotic is selected from cefpodoxime, cefuroxime, tigemonam, loracarbef, cefixime, cephalexin, cefadroxil, cefetamet, cefprozil, ceftibuten, cefditoren, faropenem, tebipenem, amoxicillin, carbenicillin, cefdinir, ampicillin, cefditoren and prodrugs thereof. In one aspect of this embodiment, the beta-lactam antibiotic is cefpodoxime proxetil. In one aspect of this embodiment, the beta-lactam antibiotic is cefuroxime axetil. In one aspect of this embodiment, the beta-lactam antibiotic is cefpodoxime, or a prodrug thereof. In one aspect of this embodiment, the beta-lactam antibiotic is cefuroxime, or a prodrug thereof.

In another aspect, there is provided a method for producing a bacterial peptidoglycan inhibitory effect, either alone or in combination with a penicillin-binding protein inhibitor, in a warm-blooded animal such as man, said method comprising administering to said animal an effective amount of a compound of Formulae (I), (Ia), (II), (IIa), (III), (IIIa), (IV), (IVa), (V), or (Va), or a pharmaceutically acceptable salt thereof.

In a further aspect, there is provided a method for treating a bacterial infection in a warm-blooded animal such as man, said method comprising administering to said animal an effective amount of a compound of Formulae (I), (Ia), (II), (IIa), (III), (IIIa), (IV), (IVa), (V), or (Va), or a pharmaceutically acceptable salt thereof. In one aspect of this embodiment, the compound is as described for Formulae (I), (II), (III), (IV) or (V), or a pharmaceutically acceptable salt thereof. In one aspect of this embodiment, for a compound of Formulae (I), (II), (III), (IV) or (V), the compound is administered orally. In another aspect of this embodiment, the compound of Formulae (I), (II), (III), (IV) or (V), or a pharmaceutically acceptable salt thereof, is administered in combination with an additional antibiotic agent. In one aspect of this embodiment, the additional antibiotic agent is a penicillin-binding protein inhibitor. In one aspect, the additional antibiotic agent is a beta-lactam antibiotic. In one aspect of this embodiment, the beta-lactam antibiotic is selected from cefpodoxime, cefuroxime, tigemonam, loracarbef, cefixime, cephalexin, cefadroxil, cefetamet, cefprozil, ceftibuten, cefditoren, faropenem, tebipenem, amoxicillin, carbenicillin, cefdinir, ampicillin, cefditoren and prodrugs thereof. In one aspect of this embodiment, the beta-lactam antibiotic is cefpodoxime proxetil. In one aspect of this embodiment, the beta-lactam antibiotic is cefuroxime axetil. In one aspect of this embodiment, the beta-lactam antibiotic is cefpodoxime, or a prodrug thereof. In one aspect of this embodiment, the beta-lactam antibiotic is cefuroxime, or a prodrug thereof.

In a further embodiment, there is provided a method for treating a bacterial infection in a subject in need thereof, comprising administering to the subject an effective amount of a compound of Formulae (Ia), (IIa), (IIIa), (IVa) or (Va), or a pharmaceutically acceptable salt thereof intravenously, intraperitoneally, intramuscularly or subcutaneously, preferably intravenously. As such, a compound of Formulae (Ia), (IIa), (IIIa), (IVa) or (Va), or a pharmaceutically acceptable salt thereof are advantageously used when a patient is not able to take medication by mouth, e.g., in a hospital setting (e.g., in an intensive care unit, an emergency room setting, on a cardiology floor and the like), in an urgent care setting and a nursing home setting. In one aspect of this embodiment, the compound of Formulae (Ia), (IIa), (IIIa), (IVa) or (Va), or a pharmaceutically acceptable salt thereof, is administered intravenously (IV). In one apsect of this embodiment, the compound of Formulae (Ia), (IIa), (IIIa), (IVa) or (Va), or a pharmaceutically acceptable salt thereof, is administered until the patient is able to take medication orally, e.g.,for the duration of the hospital stay or urgent care stay, until such time the subject is able to be discharged from a hospital setting or urgent care setting or until such time until the patient's condition has improved so that the patient can take medication orally, e.g., until the patient is able to orally take medication in a nursing home setting. In one aspect of this embodiment, the compound of Formulae (Ia), (IIa), (IIIa), (IVa) or (Va), or a pharmaceutically acceptable salt thereof, is administered with a beta-lactam antibiotic. In one aspect of this embodiment, the beta-lactam antibiotic is selected from cefpodoxime, cefuroxime, tigemonam, loracarbef, cefixime, cephalexin, cefadroxil, cefetamet, cefprozil, ceftibuten, cefditoren, faropenem, tebipenem, amoxicillin, carbenicillin, cefdinir, ampicillin, cefditoren and prodrugs thereof. In one aspect of this embodiment, the beta-lactam antibiotic is cefpodoxime, or a prodrug thereof. In one aspect of this embodiment, the beta-lactam antibiotic is cefuroxime, or a prodrug thereof. In another aspect of this embodiment, the method further comprises administering an effective amount of a compound of Formula (I), (II), (III), (IV) or (V), or a pharmaceutically acceptable salt thereof, to the subject in a community setting, after discharge from the hospital setting or urgent care setting or when the subject has improved sufficiently so that the subject is able to take medication orally, e.g., in a nursing home setting. In one aspect of this embodiment, the compound of Formula (I), (II), (III), (IV) or (V), or a pharmaceutically acceptable salt thereof, is administered orally in a community setting. In one aspect of this embodiment, the compound of Formula (I), (II), (III), (IV) or (V), or a pharmaceutically acceptable salt thereof, is administered in combination with the same beta-lactam antibiotic that the compound of Formulae (Ia), (IIa), (IIIa), (IVa) or (Va) is paired with in the hospital setting, urgent care setting or nursing home setting. In one aspect of this embodiment, the administration of a compound of Formulae (Ia), (IIa), (IIIa), (IVa) or (Va) is followed by oral administration of a compound of Formula (I), (II), (III), (IV) or (V), or a pharmaceutically acceptable salt thereof, once the patient is able to take medication by mouth, e.g., once the patient has been discharged from the hospital setting or urgent care setting and is in a community setting or whose condition has sufficiently improved in a nursing home setting to orally take medication. Preferably, the switch from intravenous, intraperitoneal, intramuscular or subcutaneous (compound of Formulae (Ia), (IIa), (IIIa), (IVa) or (Va)) to oral administration (compound of Formulae (I), (II), (III), (IV) or (V)) occurs without any gaps in the treatment of the patient.

In still a further aspect, there is provided a method for treating complicated urinary tract infection, uncomplicated urinary tract infection, kidney infection, lower respiratory tract infection, hospital-acquired bacterial pneumonia (HAP), pneumonia, acute bacterial prostatitis, acute bacterial skin and soft tissue infection, sepsis, intra-abdominal infection, and diabetic foot infections, in a warm-blooded animal such as man, said method comprising administering to said animal an effective amount of a compound of Formulae (I), (Ia), (II), (IIa), (III), (IIIa), (IV), (IVa), (V), or (Va), or a pharmaceutically acceptable salt thereof. In still a further aspect, there is provided a method for treating complicated urinary tract infections, in a warm-blooded animal such as man, said method comprising administering to said animal an effective amount of a compound of Formulae (I), (Ia), (II), (IIa), (III), (IIIa), (IV), (IVa), (V), or (Va), or a pharmaceutically acceptable salt thereof. In one aspect of either of the preceeding embodiment, the compound of Formulae(I), (Ia), (II), (IIa), (III), (IIIa), (IV), (IVa), (V), or (Va), or a pharmaceutically acceptable salt thereof, is administered in combination with an additional antibiotic agent. In one aspect of this embodiment, the additional antibiotic agent is a penicillin-binding protein inhibitor. In one aspect, the additional antibiotic agent is a beta-lactam antibiotic. In one aspect of this embodiment, the beta-lactam antibiotic is selected from cefpodoxime, cefuroxime, tigemonam, loracarbef, cefixime, cephalexin, cefadroxil, cefetamet, cefprozil, ceftibuten, cefditoren, faropenem, tebipenem, amoxicillin, carbenicillin, cefdinir, ampicillin, cefditoren and prodrugs thereof. In one aspect of this embodiment, the beta-lactam antibiotic is cefpodoxime proxetil. In one aspect of this embodiment, the beta-lactam antibiotic is cefuroxime axetil. In one aspect of this embodiment, the beta-lactam antibiotic is cefpodoxime, or a prodrug thereof. In one aspect of this embodiment, the beta-lactam antibiotic is cefuroxime, or a prodrug thereof.

In yet a further aspect, there is provided a compound of Formulae (I), (Ia), (II), (IIa), (III), (IIIa), (IV), (IVa), (V), or (Va), or a pharmaceutically acceptable salt thereof, for use in producing a bacterial peptidoglycan inhibitory effect, either alone or in combination with a penicillin-binding protein inhibitor, in a warm-blooded animal such as man. In one aspect, there is provided a compound of Formulae (I), (Ia), (II), (IIa), (III), (IIIa), (IV), (IVa), (V), or (Va), or a pharmaceutically acceptable salt thereof, for use in treating Gram-negative bacterial infections, either alone or in combination with a beta-lactam antibiotic. In one aspect of this embodiment, the beta-lactam antibiotic is selected from cefpodoxime, cefuroxime, tigemonam, loracarbef, cefixime, cephalexin, cefadroxil, cefetamet, cefprozil, ceftibuten, cefditoren, faropenem, tebipenem, amoxicillin, carbenicillin, cefdinir, ampicillin, cefditoren and prodrugs thereof. In one aspect of this embodiment, the beta-lactam antibiotic is cefpodoxime proxetil. In one aspect of this embodiment, the beta-lactam antibiotic is cefuroxime axetil. In one aspect of this embodiment, the beta-lactam antibiotic is cefpodoxime, or a prodrug thereof. In one aspect of this embodiment, the beta-lactam antibiotic is cefuroxime, or a prodrug thereof.

In one aspect of the invention, there is provided a method of inhibiting one or more beta-lactamase enzyme comprising administering a compound of Formulae (I), (Ia), (II), (IIa), (III), (IIIa), (IV), (IVa), (V), or (Va), or a pharmaceutically acceptable salt thereof, to an animal in need thereof. In a further aspect, the one or more beta-lactamase enzyme is a serine beta-lactamase enzyme. In a further aspect, the one or more beta-lactamase enzyme is selected from the group consisting of Class A, Class C and Class D. In a further aspect, the one or more beta-lactamase enzyme is a Class A enzyme. In a further aspect, the one or more beta-lactamase enzyme is a Class C enzyme. In a further aspect, the one or more beta-lactamase enzyme is a Class D enzyme. In a further aspect, the one or more beta-lactamase enzyme is a Class D enzyme and one or more of Class A and C enzymes. In a further aspect, the one or more beta-lactamase enzyme is all three of Class A, C and D enzymes.

The beta-lactamase inhibitors of Formulae (I), (Ia), (II), (IIa), (III), (IIIa), (IV), (IVa), (V), or (Va) can be administered in combination with any beta-lactam antibiotic belonging, but not limited to, the classes of clavams, carbapenems, monobactams, penems, penicillins, and or cephalosporins, or with any other compound susceptible to serine beta-lactamases. In one aspect of the invention, a compound of Formulae (I), (Ia), (II), (IIa), (III), (IIIa), (IV), (IVa), (V), or (Va) is combined with one or more of: penicillin, methicillin, oxacillin, nafcillin, cloxacillin, dicloxacillin, flucloxacillin, temocillin, amoxicillin, ampicillin, co-amoxiclav, azlocillin, carbenicillin, ticarcillin, mezlocillin, piperacillin, cephalexin, cephalothin, CXA-101, cefazolin, cefaclor, cefuroxime, cefamandole, cefotetan, cefoxitin, ceftriaxone, cefotaxime, cefpodoxime, cefixime, ceftazidime, ceftobiprole medocaril, cefepime, cefpirome, ceftaroline, imipenem, meropenem, ertapenem, faropenem, sulopenem, doripenem, PZ-601 (Protez Pharmaceuticals), ME1036 (Forest Labs), BAL30072, MC-1, tomopenem, tebipenemn, aztreonam, tigemonam, nocardicin A, or tabtoxinine-beta-lactam. In one aspect of the invention, a compound of Formulae (I), (Ia), (II), (IIa), (III), (IIIa), (IV), (IVa), (V), or (Va) is combined with cefpodoxime, cefuroxime, tigemonam, cefixime or faropenem. In one aspect of the invention, a compound of Formulae (I), (Ia), (II), (IIa), (III), (IIIa), (IV), (IVa), (V), or (Va) is combined with an antibacterial compound from the group consisting of penicillin V, cloxacillin, dicloxacillin, nafcillin, oxacillin, amoxicillin, ampicillin, bacampicillin, amoxicillin-clavulanate, carbenicillin, cefadroxil, cephalexin, cephradine, cefaclor, cefprozil, cefuroxime axetil, cefdinir, loracabef, cefixime, cefpodoxime, and ceftibuten, or a prodrug or salt thereof. In one aspect of the invention, a compound of Formulae (I), (Ia), (II), (IIa), (III), (IIIa), (IV), (IVa), (V), or (Va) is combined with an antibacterial compound from the group consisting of cefpodoxime, cefuroxime, tigemonam, loracarbef, cefixime, cephalexin, cefadroxil, cefetamet, cefprozil, ceftibuten, cefditoren, faropenem, tebipenem, amoxicillin, carbenicillin, cefdinir, ampicillin, cefditoren and prodrugs thereof. In one aspect of the invention, a compound of Formulae (I), (Ia), (II), (IIa), (III), (IIIa), (IV), (IVa), (V), or (Va) is combined with cefpodoxime, or a prodrug thereof, such as cefpodoxime proxetil. In one aspect of the invention, a compound of Formulae (I), (Ia), (II), (IIa), (III), (IIIa), (IV), (IVa), (V), or (Va) is combined with cefuroxime or a prodrug thereof, such as cefuroxime axetil.

In another aspect of the invention, the compound of Formulae (I), (II), (III) or (IV) is administered in combination with a beta-lactam antibiotic and an additional antibiotic and/or an additional beta-lactamase inhibitor. In one aspect of the invention, the additional antibiotic agent is selected from one of the classes of aminoglycosides, spectinomycins, macrolides, ketolides, streptogramins, oxazolidinones, tetracyclines, fluoroquinolones, quinolones, coumarin antibiotics, glycopeptides, lipoglycopeptides, nitroimidazoles, ansamycins, phenicols, mupirocyn, fosfomycin, tobramycin, linezolid, daptomycin, vancomycin, beta-lactams and the classes mentioned in ANTIMICROBIAL AGENTS (ASM Press, Ed: A. Bryskier (2005)).

In one aspect of the invention, the compound of Formulae (I), (Ia), (II), (IIa), (III), (IIIa), (IV), (IVa), (V), or (Va) is administered in combination with a beta-lactam antibiotic and a second agent which is designed to address beta-lactam resistance. In one aspect of the invention, the second agent designed to address beta-lactam resistance may be a metallo-beta-lactamase (MBL) inhibitor, also known as a Class B inhibitor.

In one aspect, there is provided a compound of Formulae (I), (Ia), (II), (IIa), (III), (IIIa), (IV), (IVa), (V), or (Va), or a pharmaceutically acceptable salt thereof, for use in treating a bacterial infection in a warm-blooded animal, such as man.

In another aspect, there is provided a compound of Formulae (I), (Ia), (II), (IIa), (III), (IIIa), (IV), (IVa), (V), or (Va), or a pharmaceutically acceptable salt thereof, for use in treating complicated urinary tract infection, uncomplicated urinary tract infection, kidney infection, lower respiratory tract infection, hospital-acquired bacterial pneumonia, pneumonia, acute bacterial prostatitis, acute bacterial skin and soft tissue infection, sepsis, intra-abdominal infection, and diabetic foot infections, in a warm-blooded animal such as man. In another aspect, there is provided a compound of Formulae (I), (Ia), (II), (IIa), (III), (IIIa), (IV), (IVa), (V), or (Va), or a pharmaceutically acceptable salt thereof, for use in treating complicated urinary tract infections in a warm-blooded animal such as man.

In still another aspect, there is provided a pharmaceutical composition comprising a compound of Formulae (I), (Ia), (II), (IIa), (III), (IIIa), (IV), (IVa), (V), or (Va), or a pharmaceutically acceptable salt thereof, and at least one pharmaceutically acceptable carrier, diluent, or excipient. In one aspect of this embodiment, the pharmaceutical composition further comprises a beta-lactam antibiotic. In one apsect of this embodiment, the beta-lactam antibiotic is selected from cefpodoxime, cefuroxime, tigemonam, loracarbef, cefixime, cephalexin, cefadroxil, cefetamet, cefprozil, ceftibuten, cefditoren, faropenem, tebipenem, amoxicillin, carbenicillin, cefdinir, ampicillin, cefditoren and prodrugs thereof.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). In one aspect of the invention, the compound of Formulae (Ia), (IIa), (IIIa), (IVa), or (Va), or a pharmaceutically acceptable salt thereof, is administered intravenously. In another aspect of the invention, the compound of Formulae (Ia), (IIa), (IIIa), (IVa), or (Va), or a pharmaceutically acceptable salt thereof, is administered intravenously in combination with one or more other antibacterial agent. In one aspect of the invention, the compound of Formulae (I), (II), (III), (IV), or (V), or a pharmaceutically acceptable salt thereof, is administered orally. In another aspect of the invention, the compound of Formulae (I), (II), (III), (IV), or (V), or a pharmaceutically acceptable salt thereof, is administered orally in combination with one or more other antibacterial agent. In one aspect of any of these embodiments, the compound of Formulae (I), (Ia), (II), (IIa), (III), (IIIa), (IV), (IVa), (V), or (Va), or a pharmaceutically acceptable salt thereof, is administered simultaneously with one or more other antibacterial agents. In another aspect of this embodiment, the compound of Formulae (I), (Ia), (II), (IIa), (III), (IIIa), (IV), (IVa), (V), or (Va), or a pharmaceutically acceptable salt thereof, is administered consecutively with one or more other antibacterial agents, such as a beta-lactam antibiotic.

In one embodiment of the invention is a method of treating a bacterial infection in a person in need thereof, comprising administering to said person an effective amount of a compound of one of Formulae (Ia), (IIa), (IIIa), (IVa) or (Va) intravenously in combination with one or more additional antibacterial agent in a hospital setting, urgent care setting or nursing home setting followed by administering to said person an effective amount of a compound of one of Formulae (I), (II), (III), (IV) or (V) orally in combination with one or more additional antibacterial agent outside of, for example, a hospital setting, urgent care setting or nursing home setting once the patient is again able to take medication by mouth.

In one embodiment of the invention is a method of treating a bacterial infection in a person in need thereof, comprising orally administering to said person an effective amount of a compound of one of Formulae (I), (II), (III), (IV) or (V) in combination with one or more additional antibacterial agent as an oral switch therapy following administering to said person an effective amount of one or more intravenously, intraperitoneally, intramuscularly or subcutaneously-administered antibacterial agent, e.g., a compound of Formulae (Ia), (IIa), (IIIa), (IVa) or (Va) or a pharmaceutically acceptable salt thereof. The nature, dose and duration of the antibiotic therapy and timing to switch from an intravenous, intraperitoneal, intramuscular or subcutaneous to oral medication are usually chosen by physician and can depend on the patient's health, his or her ability to receive an oral treatment and the type of infections from which said person suffers. The patient may be switched from intravenous, intraperitoneal, intramuscular or subcutaneous to oral treatment when the patient becomes asymptomatic, has no fever or reduced fever (e.g., below 100.5° F., 100° F., 99.5° F. and the like), is removed from a ventilator or is no longer in need of intravenous fluids.

The compositions of the invention may be obtained by conventional procedures using conventional pharmaceutical excipients well known in the art. Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

The amount of active ingredient that is combined with one or more excipients to produce a single dosage form will necessarily vary depending upon the host treated and the particular route of administration. For example, a formulation intended for oral administration to humans will generally contain, for example, active agent compounded with an appropriate and convenient amount of excipients which may vary from about 5 to about 98 percent by weight of the total composition. Dosage unit forms will generally contain about 100 mg to about 4000 mg of an active ingredient. For oral administration, e.g., of compound of Formulae (I), (II), (III), (IV) or (V) or pharmaceutically acceptable salts thereof, 0.1 g to 10 g equiv of active ingredient per day are suitable; and for intravenous administration, e.g., of compound of Formulae (Ia), (IIa), (IIIa), (IVa) or (Va) or pharmaceutically acceptable salts thereof, 0.5 to 8 g equiv of active ingredient per day are suitable.

In addition to the compounds of the present invention, the pharmaceutical composition of this invention may also contain or be co-administered (simultaneously, sequentially or separately) with one or more known drugs selected from other clinically useful classes of antibacterial agents (for example, macrolides, quinolones, beta-lactams or aminoglycosides) and/or other anti-infective agents (for example, an antifungal triazole or amphotericin). These may include carbapenems, for example meropenem or imipenem, to broaden the therapeutic effectiveness. Compounds of this invention may also contain or be co-administered with bactericidal/permeability-increasing protein (BPI) products or efflux pump inhibitors to improve activity against Gram-negative bacteria and bacteria resistant to antimicrobial agents.

As stated above the size of the dose required for the therapeutic or prophylactic treatment of a particular disease state will necessarily be varied depending on the host treated, the route of administration and the severity of the illness being treated. Accordingly, the optimum dosage may be determined by the practitioner who is treating any particular patient.

Compounds of Formulae (I), (Ia), (II), (IIa), (III), (IIIa), (IV), (IVa), (V), or (Va) may be prepared in a variety of ways. The processes shown below illustrates a method for synthesizing compounds of Formula (I) (wherein $R^1$, $R^2$, and $R^3$ unless otherwise defined, are as defined hereinabove). The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used. The Schemes and Processes are not intended to present an exhaustive list of methods for preparing the compounds of Formulae (I), (Ia), (II), (IIa), (III), (IIIa), (IV), (IVa), (V), or (Va); rather, additional techniques of which the skilled chemist is aware may be also be used for the compounds' synthesis. The claims are not intended to be limited to the structures shown in the Schemes and Processes.

It will also be appreciated that in some of the reactions shown in the Schemes and Processes mentioned herein, it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, *Protective Groups in Organic Synthesis*, published by John Wiley and Sons, (1991)) and as described hereinabove.

The skilled chemist will be able to use and adapt the information contained and referenced within the above references, and accompanying Examples therein and also the Examples and Scheme herein, to obtain necessary starting materials and products.

If not commercially available, the necessary starting materials for the procedures such as those described herein may be made by procedures which are selected from standard organic chemical techniques, techniques which are analogous to the synthesis of known, structurally similar compounds, or techniques which are analogous to the described procedure or the procedures described in the Examples.

It is noted that many of the starting materials for synthetic methods as described herein are commercially available and/or widely reported in the scientific literature, or could be made from commercially available compounds using adaptations of processes reported in the scientific literature. The reader is further referred to *Advanced Organic Chemistry*, 5th Edition, by Jerry March and Michael Smith, published by John Wiley & Sons (2001), for general guidance on reaction conditions and reagents.

General Procedures and Schemes:

In one aspect, compounds of Formulae (I) and (Ia), or pharmaceutically acceptable salts thereof, may be prepared by the process outlined in Scheme 1. From the Weinreb amide, introduction of substituents at the $R^3$ position of Formulae (I) and (Ia) may be done via a Grignard reaction. The ester moieties can be introduced by palladium-catalyzed deallylation followed by alkylation with bromoacetates. Hydrolysis of the esters yield the acids.

Alternatively, other $R^1$ groups could be obtained by modifying the primary alcohol.

SCHEME 1

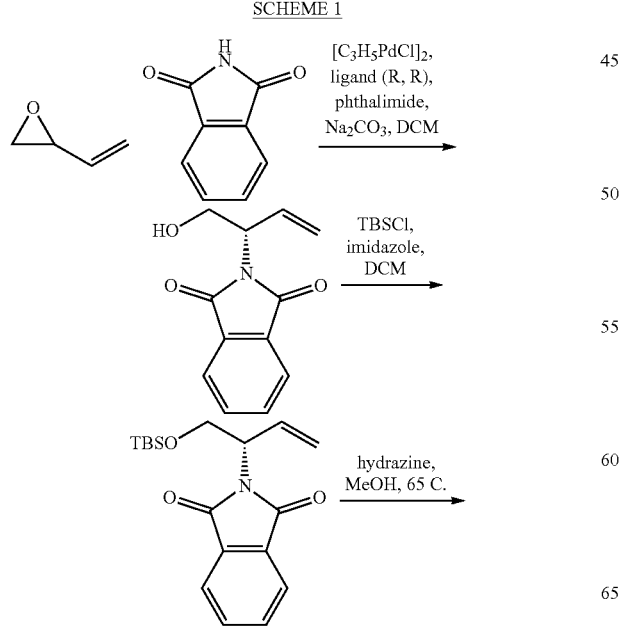

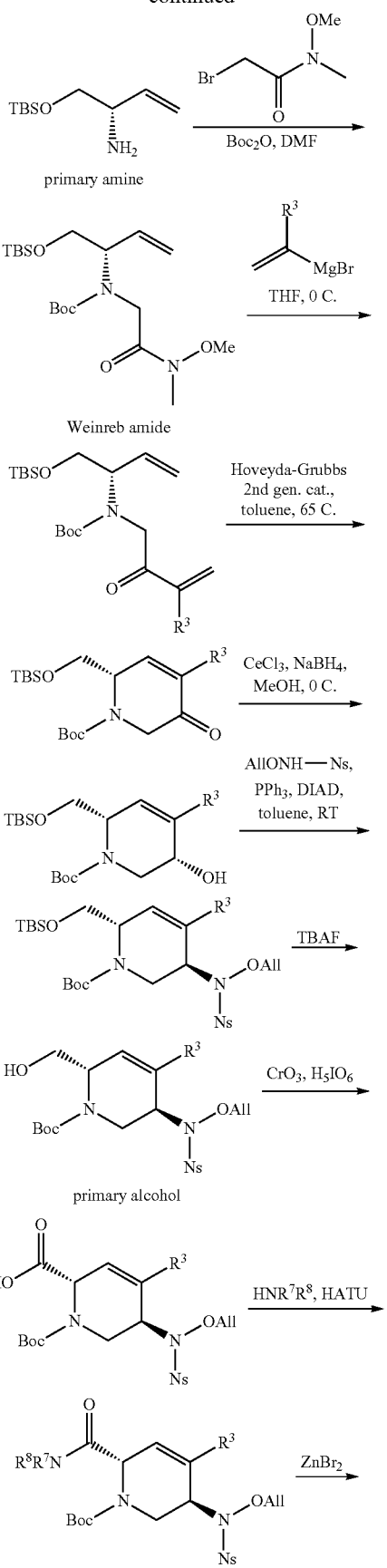

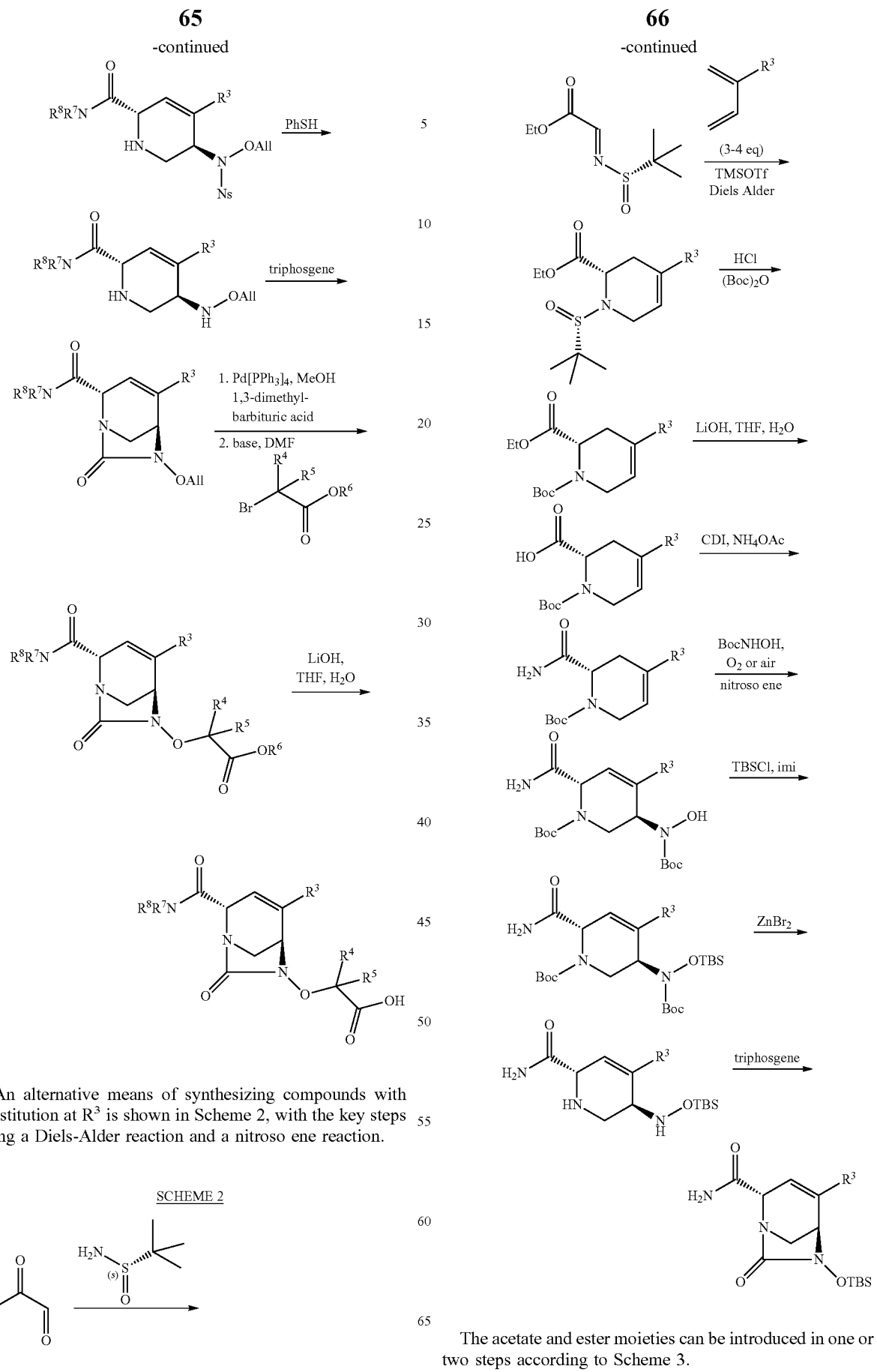
An alternative means of synthesizing compounds with substitution at R³ is shown in Scheme 2, with the key steps being a Diels-Alder reaction and a nitroso ene reaction.
SCHEME 2
The acetate and ester moieties can be introduced in one or two steps according to Scheme 3.

Scheme 3

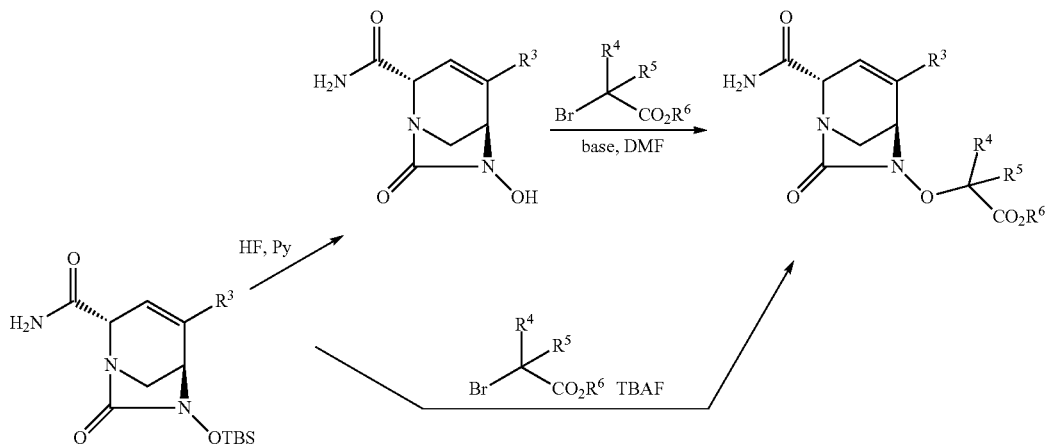

In another aspect, compounds with formulae (I) and (Ia) or pharmaceutically acceptable salts thereof, may be prepared by the process outlined in Scheme 4, where substitution at $R^2$ can be installed via a Michael addition to enone 1, followed by oxidation to afford enone 2, from which the chemistry is similar to that described in Scheme 1.

Scheme 4

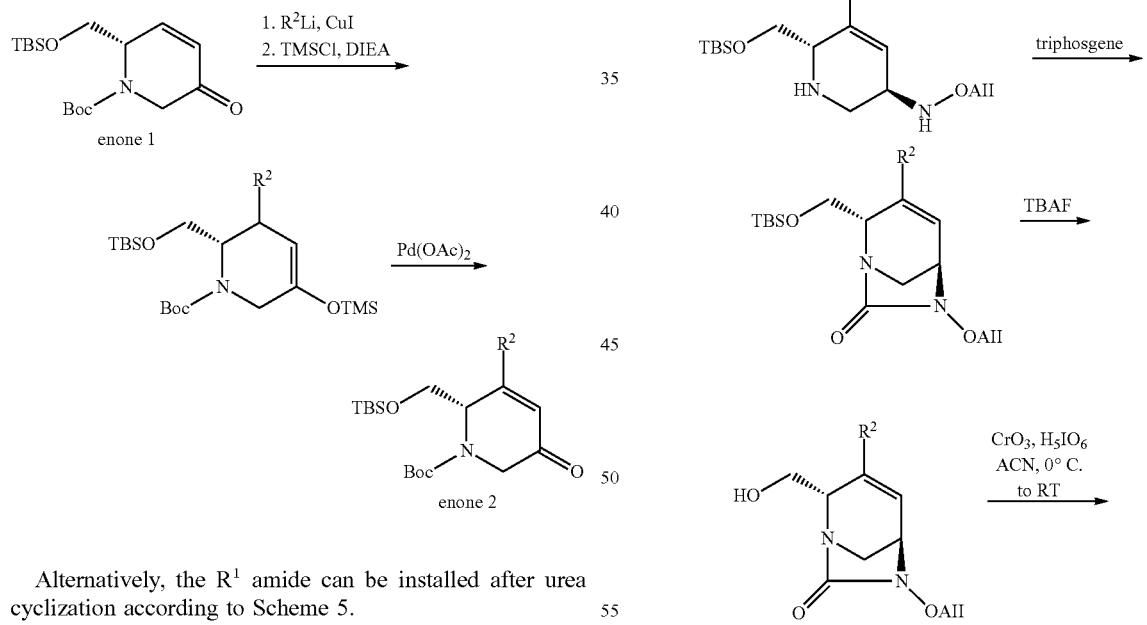

Alternatively, the $R^1$ amide can be installed after urea cyclization according to Scheme 5.

SCHEME 5

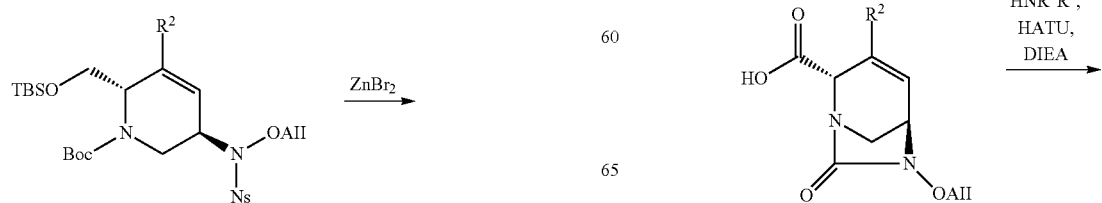

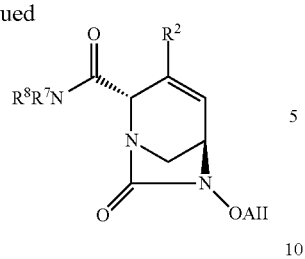

Compounds with substitution at $R^2$ can also be synthesized from Garner's aldehyde as shown in Scheme 6. The route from the primary amine to compounds with formulae (I) or (Ia) is similar to Scheme 1.

Scheme 6

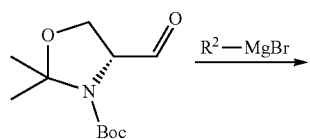

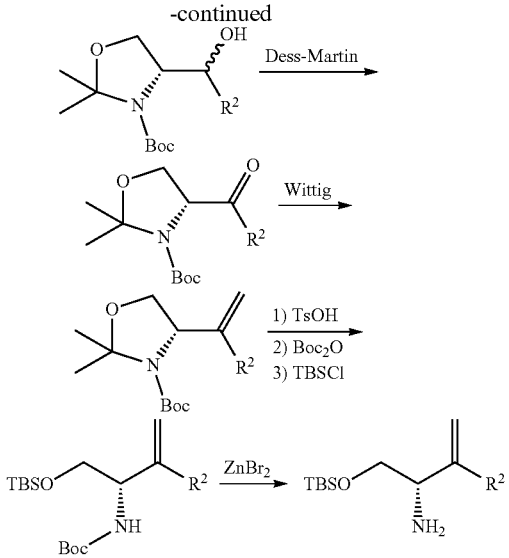

Additionally, compounds with substitution at $R^2$ can be synthesized according to Scheme 7 below, where the key step is a nitroso ene reaction. The amide can also be installed earlier in the synthesis from the carboxylic acid and carried through to the end.

Scheme 7

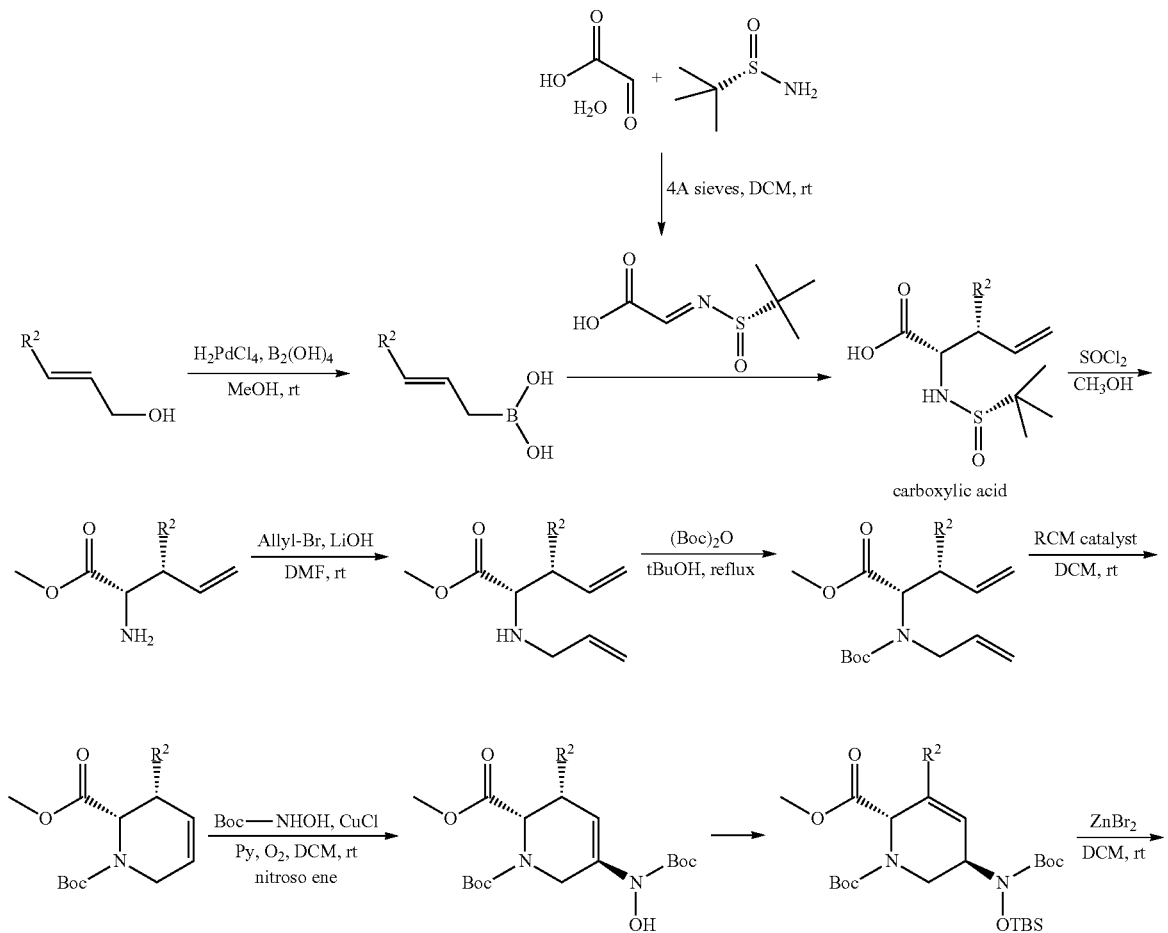

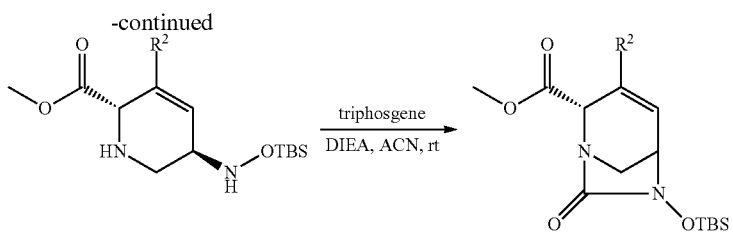

The alkyl bromoacetates for introduction of the carboxylic acid and ester moieties can be prepared by transesterification according to Scheme 8.

Scheme 8

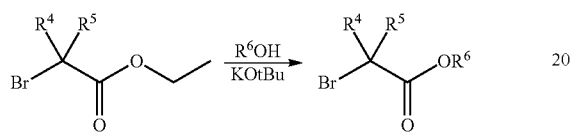

Chiral bromofluoroacetates for introduction of the R and S fluorocarboxylic acid and ester moieties can be prepared by recrystallization of bromofluoroacetic acid with a chiral phenylethanamine followed by esterification according to Scheme 9.

Scheme 9

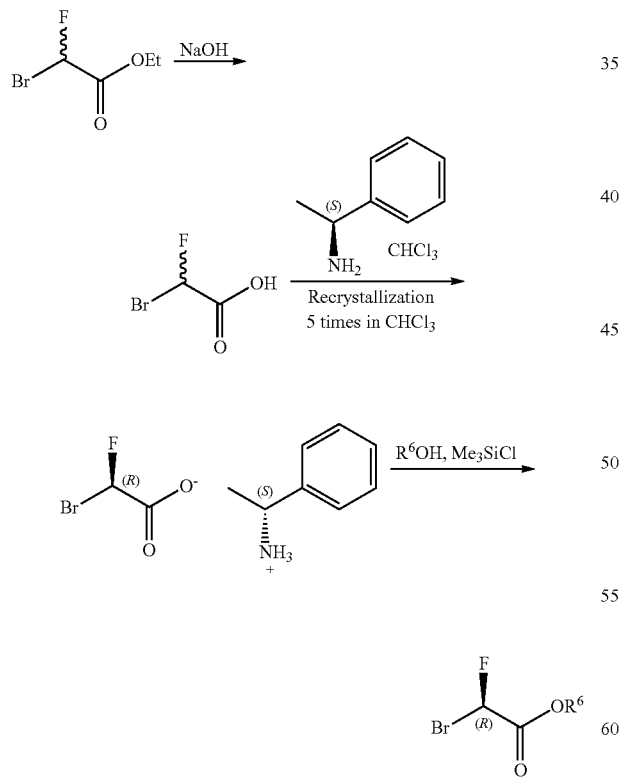

In any of the above-mentioned pharmaceutical compositions, processes, methods, uses, medicaments, and manufacturing features of the instant invention, any of the alternate embodiments of the compounds of the invention described herein also apply. For example, further details and method of performing the nitroso ene reaction on a variety of substrates are as described below in the example section. These details and methods include e.g., a first process for forming a compound of the formula VI:

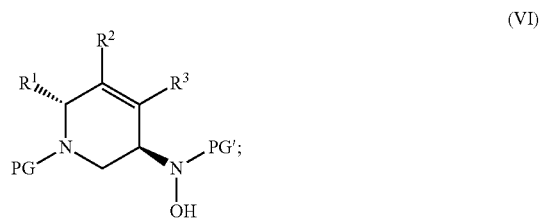

(VI)

or a salt thereof, wherein $R^1$ is —C(O)NR$^7$R$^8$, —C(O)OR$^7$, —CH$_2$OR$^7$, —CN, phenyl, a 5-6 membered heteroaryl, —C(O)NR'NR'C(O)R$^9$, —C(O)NR'OR$^{10}$, or a C$_1$-C$_6$ alkyl group, wherein the alkyl group is substituted with one to three groups consisting of halo, C$_1$-C$_3$ alkoxy, —OH, —CN, —NR$^7$R$^8$, —NR$^7$COR$^9$, a 5-6 membered heteroaryl and a 5-7 membered heterocyclyl, and wherein the phenyl and heteroaryl represented by R$^1$ are optionally and independently substituted with 1-3 groups selected from halo, —OH, C$_1$-C$_3$ alkoxy, —CN, —NR$^7$R$^8$, and —CONR$^7$R$^8$;

$R^2$ and $R^3$ are each independently selected from hydrogen, halo, C$_1$-C$_3$ alkyl, and C$_3$-C$_6$ cycloalkyl, provided that at least one of R$^2$ and R$^3$ is other than hydrogen;

each R$^7$ and R$^8$ are independently hydrogen, C$_1$-C$_3$ alkyl, C$_1$-C$_3$ alkoxy, phenyl, C$_3$-C$_6$ cycloalkyl, 4-7 membered heterocyclyl, or 5-6 membered heteroaryl, wherein the alkyl, alkoxy, phenyl, cycloalkyl, heterocyclyl or heteroaryl represented by R$^7$ or R$^8$ is optionally and independently substituted with 1-6 groups selected from a 5-6 membered heterocyclyl optionally substituted with one or two —F atoms, carboxyl or —CO(OC$_{1-6}$ alkyl), 5-6 membered heteroaryl, —CN, —OH, C$_1$-C$_3$ alkyl optionally substituted with —NH$_2$ or —OH, C$_1$-C$_3$ haloalkyl, C$_1$-C$_3$ haloalkoxy, C$_1$-C$_3$ alkoxy —NHCO(C$_1$-C$_3$alkyl), —NHCO(C$_1$-C$_3$alkoxy), —S(O)$_2$NR'R", —NHS(O)$_2$NR'R", —NHS(O)$_2$(C$_1$-C$_3$alkyl), —NR'R", and —C(O)NR'R";

each R$^9$ is C$_1$-C$_6$ alkyl, C$_1$-C$_6$ haloalkyl, C$_1$-C$_6$ haloalkoxy or C$_1$-C$_6$ alkoxy;

each R' and R" is independently hydrogen, methyl, ethyl or propyl; or R' and R" are taken together with the nitrogen to which they are attached to form a 5-6 membered heterocyclyl; and PG and PG' are each independently an amine protecting group;

the process comprising
reacting a compound of the formula XI:

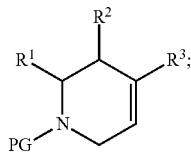
(XI)

or a salt thereof, with PG'NHOH in the presence of an oxidant to form the compound of the Formula VI;

Also provided is a second process for forming a compound of the formula VI:

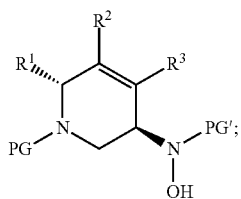
(VI)

or a salt thereof, wherein $R^1$ is —C(O)NR$^7$R$^8$, —C(O)OR$^7$, —CH$_2$OR$^7$, —CN, phenyl, a 5-6 membered heteroaryl, —C(O)NR'NR'C(O)R$^9$, —C(O)NR'OR$^{10}$, or a C$_1$-C$_6$ alkyl group, wherein the alkyl group is substituted with one to three groups consisting of halo, C$_1$-C$_3$ alkoxy, —OH, —CN, —NR$^7$R$^8$, —NR$^7$COR$^9$, a 5-6 membered heteroaryl and a 5-7 membered heterocyclyl, and wherein the phenyl and heteroaryl represented by R$^1$ are optionally and independently substituted with 1-3 groups selected from halo, —OH, C$_1$-C$_3$ alkoxy, —CN, —NR$^7$R$^8$, and —CONR$^7$R$^8$;

$R^2$ and $R^3$ are each independently selected from hydrogen, halo, C$_1$-C$_3$ alkyl, and C$_3$-C$_6$ cycloalkyl, provided that at least one of R$^2$ and R$^3$ is other than hydrogen;

each R$^7$ and R$^8$ are independently hydrogen, C$_1$-C$_3$ alkyl, C$_1$-C$_3$ alkoxy, phenyl, C$_3$-C$_6$ cycloalkyl, 4-7 membered heterocyclyl, or 5-6 membered heteroaryl, wherein the alkyl, alkoxy, phenyl, cycloalkyl, heterocyclyl or heteroaryl represented by R$^7$ or R$^8$ is optionally and independently substituted with 1-6 groups selected from a 5-6 membered heterocyclyl optionally substituted with one or two —F atoms, carboxyl or —CO(OC$_{1-6}$ alkyl), 5-6 membered heteroaryl, —CN, —OH, C$_1$-C$_3$ alkyl optionally substituted with —NH$_2$ or —OH, C$_1$-C$_3$ haloalkyl, C$_1$-C$_3$ haloalkoxy, C$_1$-C$_3$ alkoxy —NHCO(C$_1$-C$_3$alkyl), —NHCO(C$_1$-C$_3$alkoxy), —S(O)$_2$NR'R", —NHS(O)$_2$NR'R", —NHS(O)$_2$(C$_1$-C$_3$alkyl), —NR'R", and —C(O)NR'R";

each R$^9$ is C$_1$-C$_6$ alkyl, C$_1$-C$_6$ haloalkyl, C$_1$-C$_6$ haloalkoxy or C$_1$-C$_6$ alkoxy;

each R' and R" is independently hydrogen, methyl, ethyl or propyl; or R' and R" are taken together with the nitrogen to which they are attached to form a 5-6 membered heterocyclyl; and PG and PG' are each independently an amine protecting group;

the process comprising
reacting a compound of the formula XI:

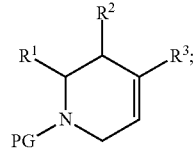
(XI)

or a salt thereof, with PG'N═O to form the compound of the Formula VI.

In a first aspect, the compound of formula XI in the first or second process is of the formula:

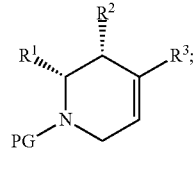

or a salt thereof.

In a second aspect, the compound of the formula VI in the first or second process is of the Formula VII:

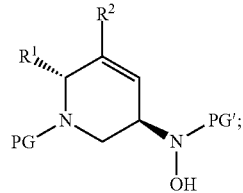
(VII)

or a salt thereof.

In a third aspect, R$^2$ in the first or second process, or formula VII is C$_1$-C$_3$ alkyl, wherein the remaining features are as described in the first or second process and the first or second aspect. Alternatively, R$^2$ in the first or second process, or formula VII is methyl, wherein the remaining features are as described in the first or second process and the first or second aspect.

In a fourth apsect, the compound of the formula VI in the first or second process is of the Formula VIII:

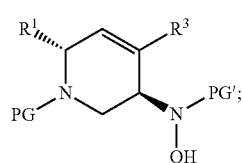
(VIII)

or a salt thereof, wherein the remaining features are as described in the first or second process and the first or second aspect.

In a fifth aspect, R$^3$ in the first or second process, or formula VIII is C$_1$-C$_3$ alkyl, wherein the remaining features are as described in the first or second process and the first or second aspect. Alternatively, R$^3$ in the first or second process, or formula VIII is methyl, wherein the remaining features are as described in the first or second process and the first or second aspect.

In a sixth aspect, $R^1$ in the first or second process is selected from an oxadiazole, —C(O)NHNHC(O)($C_1$-$C_3$ alkyl), —$CH_2NH_2$, —$CH_2$NHCO($C_1$-$C_3$ alkoxy), —$CH_2$NHCO($C_1$-$C_3$ alkyl), or —$CH_2$NHCO($C_1$-$C_3$ haloalkyl), wherein the oxadiazole of $R^1$ is optionally substituted with —OH, $C_1$-$C_3$ alkoxy, —$NR^7R^8$, or —$CONR^7R^8$; and wherein the remaining features are as described in the first or second process and the first, second, third, fourth, or fifth aspect.

In a seventh aspect, $R^1$ in the first or second process is selected from —$CH_2NH_2$,

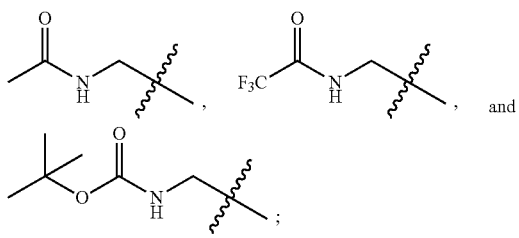

and wherein the remaining features are as described in the first or second process and the first, second, third, fourth, fifth, or sixth aspect.

In an eighth aspect, $R^1$ in the first or second process is: —CN,

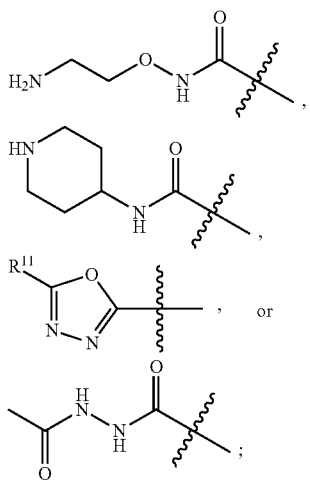

wherein $R^{11}$ is hydrogen or —C(O)$NH_2$; and wherein the remaining features are as described in the first or second process and the first, second, third, fourth, fifth, sixth, or seventh aspect.

In a ninth aspect, $R^1$ in the first or second process is —C(O)$NR^7R^8$, —C(O)$OR^7$, or —CN; and wherein the remaining features are as described in the first or second process and the first, second, third, fourth, fifth, sixth, seventh, or eighth aspect. Alternatively, $R^1$ in the first or second process is —C(O)$NH_2$, —C(O)OH, —CN, or —C(O)O$C_1$-$C_6$ alkyl; wherein the remaining features are as described in the first or second process and the first, second, third, fourth, fifth, sixth, seventh, or eighth aspect. In another alternative, $R^1$ in the first or second process is —CN or —C(O)$NH_2$; wherein the remaining features are as described in the first or second process and the first, second, third, fourth, fifth, sixth, seventh, or eighth aspect. In another alternative, $R^1$ in the first or second process is —CN; wherein the remaining features are as described in the first or second process and the first, second, third, fourth, fifth, sixth, seventh, or eighth aspect. In another alternative, $R^1$ in the first or second process is —C(O)$NR^7R^8$; wherein the remaining features are as described in the first or second process and the first, second, third, fourth, fifth, sixth, seventh, or eighth aspect.

In a tenth aspect, $R^7$ and $R^8$ in the first or second process are both hydrogen; wherein the remaining features are as described in the first or second process and the first, second, third, fourth, fifth, sixth, seventh, eighth, or ninth aspect. Alternatively, $R^7$ in the first or second process is hydrogen and $R^8$ is 1) a phenyl optionally substituted with a $C_1$-$C_3$ alkyl or $C_1$-$C_3$ alkyl-$NH_2$, 2) an $C_1$-$C_3$ alkyl or 3) $C_1$-$C_3$ alkoxy, wherein each alkyl or alkoxy of represented by $R^8$ is optionally and independently substituted with a $C_3$-$C_6$ cycloalkyl, —CN, —OH, —$NH_2$, —$SO_2NH_2$, —$NHSO_2NH_2$, —C(O)$NH_2$, —NHC(O)($C_1$-$C_3$ alkyl), pyrazinyl, oxytanyl, oxazolyl, or a pyrrolidinyl optionally substituted with one or more carboxyl, fluoro, or —C(O)O ($C_1$-$C_6$ alkyl); wherein the remaining features are as described in the first or second process and the first, second, third, fourth, fifth, sixth, seventh, eighth, or ninth aspect. In another alternative, $R^7$ in the first or second process is hydrogen and $R^8$ is selected from the group consisting of:

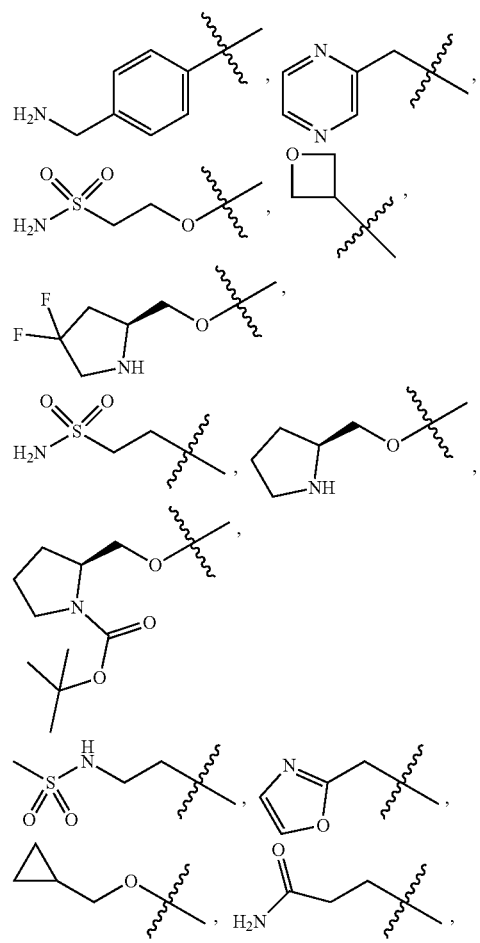

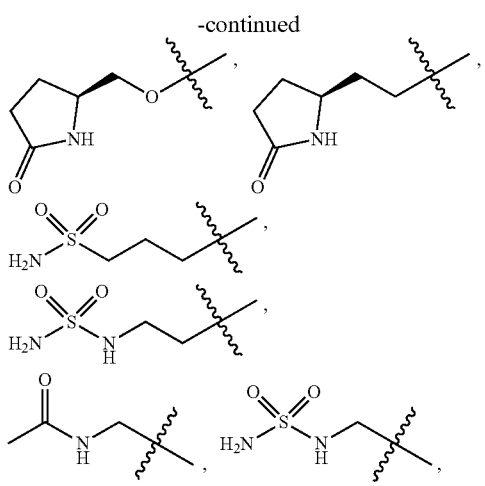

—CH₂CN, and —CH₂OH; wherein the remaining features are as described in the first or second process and the first, second, third, fourth, fifth, sixth, seventh, eighth, or ninth aspect.

In an eleventh aspect, the compound of the formula VI in the first or second process is of the Formula IX:

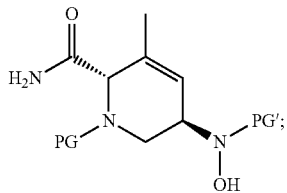

(IX)

or a salt thereof.

In a twelfth aspect, the compound of the formula VI in the first or second process is of the Formula X:

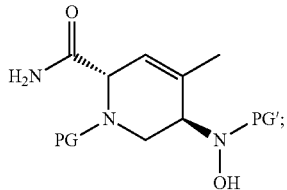

(X)

or a salt thereof.

In a thirteenth aspect, PG and PG' in the first or second process taken together with the nitrogen atom of the amine which they are protecting each independently form a carbamate, an amide, or a N-benzyl or N-aryl; wherein the remaining features are as described in the first or second process and the first, second, third, fourth, fifth, sixth, seventh, eighth, ninth, tenth, eleventh, or twelfth aspect. Alternatively, PG and PG' in the first or second process are each independently selected from t-butyloxycarbonyl (Boc), carboxybenzyl (Cbz),Fluorenylmethyloxycarbonyl (Fmoc), 2,2,2-trichloroethoxycarbonyl (Troc), CF₃CO, acetyl (Ac), p-toluenesulfonamide (Ts), and methanesulfonyl (Ms); wherein the remaining features are as described in the first or second process and the first, second, third, fourth, fifth, sixth, seventh, eighth, ninth, tenth, eleventh, or twelfth aspect. In another alternative, PG and PG' in the first or second process are each the same; wherein the remaining features are as described in the first or second process and the first, second, third, fourth, fifth, sixth, seventh, eighth, ninth, tenth, eleventh, or twelfth aspect. In another alternative, PG and PG' in the first or second process are each a t-butoxycarbonyl; wherein the remaining features are as described in the first or second process and the first, second, third, fourth, fifth, sixth, seventh, eighth, ninth, tenth, eleventh, or twelfth aspect.

In a fourteenth aspect, the first process futher comprises reacting the compound of formula XI with PG'NHOH in the presence of a metal catalyst; wherein the remaining features are as described in the first or second process and the first, second, third, fourth, fifth, sixth, seventh, eighth, ninth, tenth, eleventh, twelfth, or thirteenth aspect. Alternatively, the metal catalyst is selected from CuCl, CuBr, CuI, CuCN, CuSCN, CuBr—Me₂S, Cu(OAc)₂, and CuOTf; wherein the remaining features are as described in the first or second process and the first, second, third, fourth, fifth, sixth, seventh, eighth, ninth, tenth, eleventh, twelfth, or thirteenth aspect. In another alternative, the metal catalyst comprises a copper salt; wherein the remaining features are as described in the first or second process and the first, second, third, fourth, fifth, sixth, seventh, eighth, ninth, tenth, eleventh, twelfth, or thirteenth aspect. In another alternative, the metal catalyst comprises a copper halide salt; wherein the remaining features are as described in the first or second process and the first, second, third, fourth, fifth, sixth, seventh, eighth, ninth, tenth, eleventh, twelfth, or thirteenth aspect. In another alternative, the metal catalyst is CuCl or CuBr—Me₂S; wherein the remaining features are as described in the first or second process and the first, second, third, fourth, fifth, sixth, seventh, eighth, ninth, tenth, eleventh, twelfth, or thirteenth aspect.

In a fifteenth aspect, the first process futher comprises reacting the compound of formula XI with PG'NHOH in the presence of an amine additive; wherein the remaining features are as described in the first or second process and the first, second, third, fourth, fifth, sixth, seventh, eighth, ninth, tenth, eleventh, twelfth, thirteenth, or fourteenth aspect. In one aspect, the amine additive process is pyridine, (1R,2R)-cyclohexane-1,2-diamine, N,N'-dimethylethane-1,2-diamine, 2,6-di-tert-butyl-4-methylpyridine, 1,10-phenanthroline, trans-cyclohexane-1,2-diamine, N1-(2-(diethylamino)ethyl)-N2,N2-diethylethane-1,2-diamine, cis-cyclohexane-1,2-diamine, or N1,N1,N2,N2-tetramethylethane-1,2-diamine; wherein the remaining features are as described in the first or second process and the first, second, third, fourth, fifth, sixth, seventh, eighth, ninth, tenth, eleventh, twelfth, thirteenth, or fourteenth aspect. Alternatively, the amine is selected from pyridine, 2,6-lutidine, 4-dimethylaminopyridine, picoline, 1,8-diazabicyclo[5.4.0]undec-7-ene, and N,N-diisopropylethylamine; wherein the remaining features are as described in the first or second process and the first, second, third, fourth, fifth, sixth, seventh, eighth, ninth, tenth, eleventh, twelfth, thirteenth, or fourteenth aspect. In another alternative, the amine is pyridine; wherein the remaining features are as described in the first or second process and the first, second, third, fourth, fifth, sixth, seventh, eighth, ninth, tenth, eleventh, twelfth, thirteenth, or fourteenth aspect.

In a sixteenth apsect, the oxidant in the first or second process is O₂, air, FeCl₃, MnO₂, meta-chloroperoxybenzoic acid (mCPBA), NaIO₄, 2-iodoxybenzoic acid (IBX), (2,2,6,6-Tetramethylpiperidin-1-yl)oxyl (TEMPO), benzoyl peroxide (BPO), HIO₃, urea-H₂O₂, I₂, N-chlorosuccinimide (NCS), Dess-Martin periodinane (DMP), H₂O₂, or N-methylmorpholine N-oxide (NMMO); wherein the remaining features are as described in the first or second process and the first, second, third, fourth, fifth, sixth, seventh, eighth, ninth, tenth, eleventh, twelfth, thirteenth, fourteenth, or fifteenth aspect. Alternatively, the oxidant is urea-H₂O₂, H₂O₂ or O₂; wherein the remaining features are as described in the first or second process and the first, second, third, fourth, fifth, sixth, seventh, eighth, ninth, tenth, eleventh, twelfth, thirteenth, fourteenth, or fifteenth aspect.

In a seventeenth aspect, the reaction in the first or second process is carried out in a polar solvent; wherein the remaining features are as described in the first or second process and the first, second, third, fourth, fifth, sixth, seventh, eighth, ninth, tenth, eleventh, twelfth, thirteenth, fourteenth, fifteenth, or sixteenth aspect. Alternatively, the reaction is carried out in DCM, THF, MTBE, EtOAc, iPrOAc, MeCN, H₂O, MeOH, EtOH, i-PrOH, t-BuOH, n-BuOH, 2-methyl-2-butanol, DMF, DMSO, ethylene glycol, polyethyleneglycol, sulfolane, sulfolane/H₂O mixture, DMF/H₂O, NMP/H₂O, DCM/H₂O, MeOH/H₂O, EtOH/H₂O, iPrOH/H₂O, or n-BuOH/H₂O; wherein the remaining features are as described in the first or second process and the first, second, third, fourth, fifth, sixth, seventh, eighth, ninth, tenth, eleventh, twelfth, thirteenth, fourteenth, fifteenth, or sixteenth aspect. In another alternative, the reaction is carried out in methylene chloride or sulfolane; wherein the remaining features are as described in the first or second process and the first, second, third, fourth, fifth, sixth, seventh, eighth, ninth, tenth, eleventh, twelfth, thirteenth, fourteenth, fifteenth, or sixteenth aspect.

In an eighteenth aspect, the reaction in the first or second process further comprises the addition of water; wherein the remaining features are as described in the first or second process and the first, second, third, fourth, fifth, sixth, seventh, eighth, ninth, tenth, eleventh, twelfth, thirteenth, fourteenth, fifteenth, sixteenth, or seventeenth aspect.

EXAMPLES

The invention will now be further described with reference to the following illustrative examples in which, unless stated otherwise:
(i) temperatures are given in degrees Celsius (° C.); operations are carried out at room temperature or ambient temperature, that is, in a range of 18-25° C.;
(ii) organic solutions were dried over anhydrous magnesium sulfate; evaporation of organic solvent was carried out using a rotary evaporator under reduced pressure (4.5-30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC or liquid chromatography/mass spectroscopy (LC/MS) and reaction times are given for illustration only;
(v) final products have satisfactory proton nuclear magnetic resonance (NMR) spectra and/or mass spectra data;
(vi) yields are given for illustration only and are not necessarily those which can be obtained by diligent process development; preparations were repeated if more material was required;
(vii) when given, NMR data is in the form of delta values for major diagnostic protons, given in part per million (ppm) relative to tetramethylsilane (TMS) as an internal standard, determined at 300 MHz in DMSO-d₆ unless otherwise stated;
(viii) chemical symbols have their usual meanings;
(ix) solvent ratio was given in volume:volume (v/v) terms;
(x) an ISCO Combiflash refers to flash chromatography on silica gel using Isco Combiflash® separation system: RediSep normal phase flash column, flow rate, 30-40 ml/min;
(xi) the following abbreviations may have been used:
ACN Acetonitrile
BINAP 2,2'-bis(diphenylphosphino)-1,1'-binapthyl
Boc₂O tert-butyloxycarbonyl anhydride
CDI N,N-carbonyldiimidazole
DAST Diethylamino sulfur trifluoride
DCM dichloromethane
DIPEA/DIEA N, N-diisopropylethylamine
DMAc N,N-dimethylacetamide
DMF N,N-dimethylformamide
DMAP 4-dimethylaminopyridine
DMSO dimethylsulfoxide
ee enantiomeric excess
EtOAc/EA ethyl acetate
Et₂O diethyl ether
GC gas chromatography
HATU O-(7-Azabenzotriazol-1-yl)-N,N,N',N'-tetramethyluronium hexafluorophosphate
Hex hexanes
HPLC high-performance liquid chromatography
hr/h hours
KOᵗBu potassium tert-butoxide
LCMS liquid chromatography mass spectrometry
LDA Lithium diisopropylamide
MeCN acetonitrile
MeOH methanol
mins/min minutes
MTBE methyl tert-butyl ether
o/n overnight
Pd₂(dba)₃ Tris(dibenzylideneacetone)dipalladium(0)
PE petroleum ether
iPrOH i-propanol
rac. racemic
TBAF tetra-n-butylammonium fluoride
TEA triethylamine
TFA trifluoroacetic acid
THF tetrahydrofuran
TMS trimethyl silyl
Tosyl, Ts para-toluenesulfonyl
UPLC-MS ultra performance liquid chromatography mass spectrometry Nitroso ene Conditions and Trials In certain aspects, a nitroso ene reaction is used to install the requisite allylic hydroxylamine functionality. (Waldemar Adam and Oliver Krebs, *Chem. Rev.*, 2003, 103, 4131-4146; Charles P. Frazier, Jarred R. Engelking, and Javier Read de Alaniz, *J. Am. Chem. Soc.*, 2011, 133 (27), 10430-10433; Leoni I. Palmer, Charles P. Frazier, Javier Read de Alaniz, *Synthesis* 2014, 46, 269-280). In the presence of an oxidant, hydroxylamines are oxidized to give highly reactive nitroso species, which react with an allylic substrate, as shown in Scheme 10. The oxidant can be an organic oxidant or a combination of an oxidant, a metal catalyst and optionally an amine additive. The nitroso species can be formed in situ (as in the reaction to form a compound of formula VI) from the hydroxylamine or prepared separately and then added to the substrate, e.g., a compound of formula XI. For the 1,2,3,6- tetrahydropyridine scaffold with a N-carbamate functionality, it is believe that the $A^{(1,3)}$ allylic strain exerted by the N-Boc functionality causes the $R^1$ substituent to adopt a pseudo-axial orientation. It is believed to block the approach of the nitroso reactant from that face of the double bond. Therefore, the nitroso reactant reacts regio- and diastereoselectively from the opposite side of $R^1$ to form the desired product in high diastereoselectivity and regioselectivity. The enantioselectivity is measured and has been demonstrated to be uniformly high, >99% ee by chiral HPLC analysis.

Scheme 10

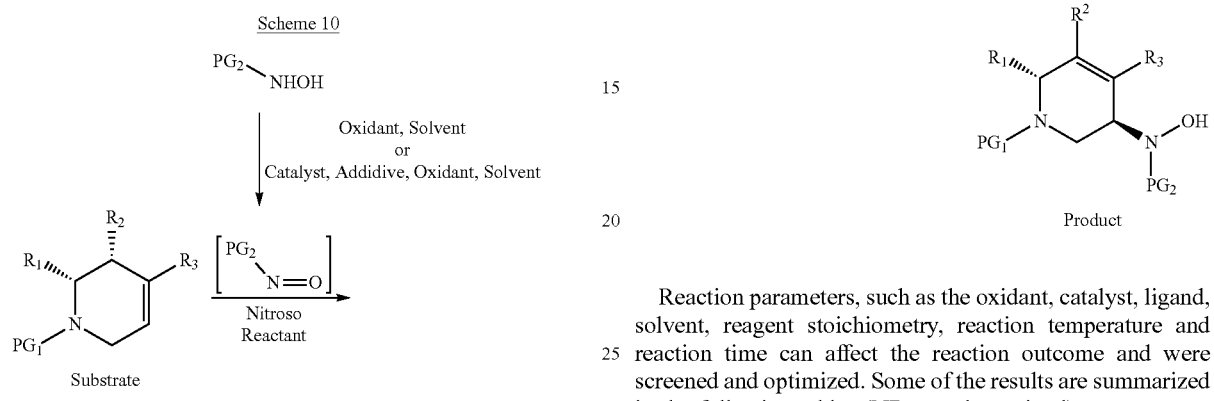

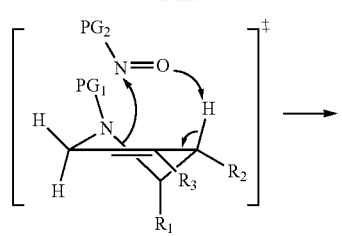

Product

Reaction parameters, such as the oxidant, catalyst, ligand, solvent, reagent stoichiometry, reaction temperature and reaction time can affect the reaction outcome and were screened and optimized. Some of the results are summarized in the following tables (ND=not determined).

| | | | | Oxidant screen | |
|---|---|---|---|---|---|
| | | | | Conversion (by HPLC area %) | |
| Entry | Substrate | Reagents and conditions | Oxidant | Product | SM |
| 1 | $PG_1 = PG_2 = Boc$ | BocNHOH (1.5 eq.) | $O_2$, 1 atm | 84.5 | 5.9 |
| 2 | $R_1 = CONH_2$ | CuCl (0.05 eq.) | $FeCl_3$, 1.2 eq. | 15.3 | 43.2 |
| 3 | $R_2 = Me, R_3 = H$ | Pyridine (0.013 eq.) | $MnO_2$, 1.2 eq. | 48.0 | 10.28 |
| 4 | | DCM | $NaIO_4$, 2.2 eq. | 43.8 | 21.3 |
| 5 | | (10 V), 17~25° C., | m-CPBA, 2.2 eq. | 10.7 | 30.9 |
| 6 | | 20-60 h | BPO, 1.0 eq. TEMPO, 1.5 eq. | 32.3 | 19.6 |
| 7 | | | $HIO_3$, 1.2 eq. | 6.4 | 3.0 |
| 8 | | | $I_2$, 1.2 eq. | 5.8 | 24.6 |
| 9 | | | $H_2O_2$, 3.0 eq. | 78 | 8.9 |
| 10 | | | $MnO_2$, 1.2 eq. $H_2O_2$, 1 drop | 71.6 | 5.0 |
| 11 | | | IBX, 1.2 eq | ND | |
| 12 | | | $PhI(OAc)_2$, 1.2 eq. | ND | |
| 13 | | | urea hydrogen peroxide, 1.2 eq. | 63.9 | 12.1 |
| 14 | | | NCS, 1.0 eq. | 59.9 | 12.5 |
| 15 | | | DMP, 1.0 eq. | ND | |
| 16 | | | 3% $H_2O_2$, 1.2 eq | 70 | 3.1 |
| 17 | | | 1.5% $H_2O_2$, 1.2 eq | 64.4 | 4.1 |
| 18 | | | 6% $H_2O_2$, 1.2 eq | 73.6 | 5.5 |
| 19 | | | NMMO, 1.0 eq. | 37.8 | 38.6 |
| 20 | $PG_1 = PG_2 = Boc$ $R_1 = CO_2Me$ $R_2 = CH_2OPMB,$ $R_3 = H$ | BocNHOH (1.5 eq.) CuCl (0.05 eq.) Pyridine (0.013 eq.) DCM (10 V), 17~25° C., 20-60 h | $O_2$, 1 atm | 36% isolated product | |
| 21 | $PG_1 = PG_2 = Boc$ | BocNHOH (1.5 eq.) | $O_2$, 1 atm | 46.08 | 10.28 |
| 22 | $R_1 = CONH_2$ | CuCl (0.05 eq.) | $FeCl_3$ (1.2 eq.) | 1.33 | 71.43 |
| 23 | $R_2 = H, R_3 = Me$ | Pyridine (0.013 eq.) | $MnO_2$ (1.2 eq.) | 40.79 | 16.85 |
| 24 | | DCM | $NaIO_4$ (1.2 eq.) | 15.2 | 35.58 |
| 25 | | (10 V), 20~30° C., | m-CPBA (1.2 eq.) | 3.04 | 89.1 |
| 26 | | 20-60 h | $HIO_4$ (1.2 eq.) | 0.52 | 46.47 |
| 27 | | | 30% $H_2O_2$ (1.2 eq.) | 4.69 | 7.9 |
| 28 | | | $I_2$ (1.2 eq.) | 1.39 | 52.85 |
| 29 | | | $CaO_2$ (1.2 eq.) | 19.66 | 33.73 |

Oxidant screen

| Entry | Substrate | Reagents and conditions | Oxidant | Conversion (by HPLC area %) Product | SM |
|---|---|---|---|---|---|
| 30 | | BocNHOH (3.0 eq.), CuCl (0.05 eq.), Sulfolane (5 V), H$_2$O (5 V), Py (0.13 eq.), 0~5° C., | H$_2$O$_2$ (3%, 3 eq.), 16 h | 54.3 | 30.5 |
| | | | H$_2$O$_2$ (3%, 3 eq.), 96 h | 38.8 | 0.24 |
| 31 | | BocNHOH (2.0 eq.), CuBr—Me$_2$S (0.05 eq.), Sulfolane (5 V), H$_2$O (0.5 V), Py (0.13 eq.), 25~30° C. | H$_2$O$_2$ (3%, 2 eq.), 64 h | 70.0 | 4.1 |

Solvent screen

| Entry | Substrate | Reagents and conditions | Solvent, time | Conversion (by HPLC area %) Product | SM |
|---|---|---|---|---|---|
| 1 | PG$_1$ = PG$_2$ = Boc R$_1$ = CONH$_2$ | BocNHOH (1.5 eq.) CuCl (0.05 eq.) | 5% THF in DCM (10 V), 90 h | 77.6 | 5.0 |
| 2 | R$_2$ = Me, R$_3$ = H | Pyridine (0.013 eq.), 15° C., air | 10% THF in DCM (10 V), 90 h | 77.5 | 4.7 |
| 3 | | | 20% THF in DCM (10 V), 90 h | 68.8 | 19.4 |
| 4 | | | DCM (10 V), 68 h | 65.8 | 20.4 |
| 5 | | | THF (10 V), 20 h | 81.9 | 7.8 |
| 6 | | | EtOAc (10 V), 68 h | 69.5 | 19.0 |
| 7 | | | Acetone (10 V), 68 h | 87.3 | 3.6 |
| 8 | PG$_1$ = PG$_2$ = Boc | BocNHOH (1.5 eq.) | DCM (10 V) | 35.2 | 20.6 |
| 9 | R$_1$ = CONH$_2$ | CuCl (0.05 eq.) | DCM/H$_2$O 1:1 (10 V) | 38.0 | 18.7 |
| | R$_2$ = H, R$_3$ = Me | Pyridine (0.013 eq.), | | | |
| 10 | | 20-30° C., air, | MeOH (10 V) | 50.0 | 21.8 |
| 11 | | 60 h | MeOH/H$_2$O 1:1 (10 V) | 45.7 | 28.3 |
| 12 | | | EtOH (10 V) | 47.5 | 15.9 |
| 13 | | | i-PrOH (10 V) | 43.3 | 10.0 |
| 14 | | | 2-Methyl-2-butanol (10 V) | 48.0 | 16.6 |
| 15 | | | Ethylene glycol (10 V) | 14.1 | 76.4 |
| 16 | | | Polyethyleneglycol 2000/H$_2$O (5 g/5 V) | 9.3 | 96.9 |
| 17 | | | Sulfolane/H$_2$O 1:1 (10 V) | 57.0 | 14.7 |
| 18 | | | Sulfolane/H$_2$O 9:1 (10 V) | 55.58 | 17.5 |
| 19 | | | Sulfolane/H$_2$O 3:7 (10 V) | 23.3% | 66.7 |
| 20 | | | Sulfolane/H$_2$O 1:1 (5 V) | 62.3 | 5.9 |
| 21 | | BocNHOH (1.5 eq.) CuCl (0.05 eq.) | DMF/H$_2$O 5 V/5 V | 58.11 | 1.71 |
| 22 | | Pyridine (0.013 eq.), 15-30° C., O$_2$ (1 atm), 48 h | NMP/H$_2$O 5 V/5 V | 44.18 | 0.43 |

Catalyst screen

| Entry | Substrate | Reagents and conditions | Catalyst | Conversion (by HPLC area %) Product | SM |
|---|---|---|---|---|---|
| 1 | $PG_1 = PG_2 = Boc$ | BocNHOH (1.5 eq.) | CuCl, 0.05 eq. | 35.2 | 20.6 |
| 2 | $R_1 = CONH_2$ | CuCl (0.05 eq.) | CuBr, 0.05 eq. | 30.7 | 25.2 |
| 3 | $R_2 = H, R_3 = Me$ | Pyridine (0.013 eq.) | CuI, 0.05 eq. | 21.5 | 43.1 |
| 4 | | DCM (10 V), | $Cu(OAc)_2$, 0.05 eq | 33.0 | 28.5 |
| 5 | | 20~30° C., $O_2$ (1 atm), 65 h | Sulfolane/$H_2O$ 5 V/5 V, 24 h | 58.49 | 1.30 |
| 6 | | | Sulfolane/$H_2O$ 5 V/5 V, 96 h | 38.83 | 0.24 |
| 7 | | | HOAc/$H_2O$ 5 V/5 V, 96 h | 7.95 | 71.02 |
| 8 | | BocNHOH (1.5 eq.), | CuCl, 0.05 eq., 24 h | 58.49 | 1.30 |
| 9 | | Pyridine | CuCl, 0.05 eq., 96 h | 38.83 | 0.24 |
| 10 | | (0.013 eq.), | CuBr, 0.05 eq. 72 h | 63.42 | 7.31 |
| 11 | | Sulfolane (5 V), | CuI, 0.05 eq. | 67.49 | 7.35 |
| 12 | | $H_2O$ (5 V), $O_2$, | CuSCN (0.05 eq.), 72 h | 32.98 | 47.05 |
| 13 | | 20~30° C., | $Cu(OAc)_2$ (0.05 eq.), 72 h | 59.69 | 15.94 |
| 14 | | | CuBr—$SMe_2$ (0.05 eq.), 72 h | 68.71 | 3.36 |
| 15 | | | CuCN (0.05 eq.), 84 h | 5.60 | 5.32 |
| 16 | | | $Cu(CH_3CN)_4 PF_6$ (0.05 eq.), 84 h | 61.56 | 14.07 |
| 17 | | | Cu(OTf)-toluene (0.05 eq.), 84 h | 66.24 | 9.31 |
| 18 | | | CuCl (0.05 eq.) 2-ethyloxazoline (0.05 eq.), 84 h | 59.03 | 15.20 |
| 19 | | | CuCl (0.05 eq.) TBAI (0.05 eq.), 89 h | 49.9 | 26.26 |

Additive screen

| Entry | Substrate | Reagents and conditions | Ligand | Conversion (by HPLC area %) Product | SM |
|---|---|---|---|---|---|
| 1 | $PG_1 = PG_2 = Boc$ | BocNHOH (1.5 eq.) CuCl (0.05 eq.) | Pyridine (0.013 eq.) | 35.2 | 20.6 |
| 2 | $R_1 = CONH_2$ | DCM (10 V), 20~30° C., $O_2$ (1 atm), | Ethane-1,2-diamine (0.013 eq.) | 31.8 | 29.0 |
| 3 | $R_2 = H$, $R_3 = Me$ | 65 h | (1R,2R)-cyclohexane-1,2-diamine (0.013 eq.) | 36.3 | 30.1 |
| 4 | | | N1, N1-dimethylethane-1,2-diamine (0.013 eq.) | 35.0 | 21.5 |
| 5 | | | 2,6-di-tert-butyl-4-methylpyridine (0.013 eq.) | 31.5 | 34.0 |
| 6 | | | 1,10-o-Phenanthroline (0.013 eq.) | ND | |
| 7 | | | No ligand | 24.8 | 47.4 |
| 8 | | BocNHOH (1.5 eq.), CuCl (0.05 eq.), Sulfolane (5 V), $H_2O$ (5 V), $O_2$ (1 atm), 20-30° C. | 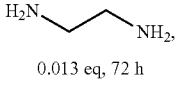 0.013 eq, 72 h | 37.73 | 27.49 |
| 9 | | | 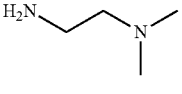 0.013 eq, 72 h | 5.60 | 5.32 |
| 10 | | | 1,10-o-Phenanthroline (0.013 eq.), 72 h | 64.45 | 5.14 |

-continued
| | | | Additive screen | | |
|---|---|---|---|---|---|
| | | | | colspan="2" | Conversion (by HPLC area %) |
| Entry | Substrate | Reagents and conditions | Ligand | Product | SM |
| 11 | | | 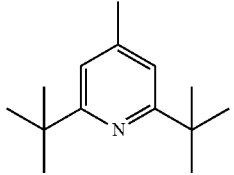\n0.013 eq. 96 h | 69.09 | 0.94 |
| 12 | | | 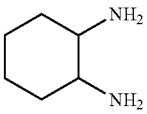\ntrans-\n0.013 eq. 96 h | 69.11 | 0.93 |
| 13 | | | Pyridine (0.013 eq.), 24 h | 58.49 | 1.30 |
| 14 | | | Pyridine (0.013 eq.), 96 h | 38.83 | 0.24 |
| 15 | | | Pyridine (0.065 eq.), 84 h | 74.1 | 7.1 |
| 16 | | | Pyridine (0.13 eq.), 24 h | 73.80 | 5.57 |
| 17 | | | 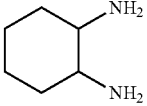\ntrans-\n0.013 eq, 65 h | 66.63 | 5.09 |
| 18 | | | 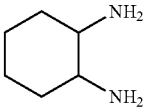\ntrans-\n0.13 eq, 48 h | 9.48 | 86.47 |
| 19 | | | 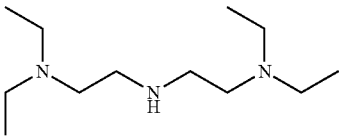\n0.013 eq. 72 h | 62.64 | 10.45 |
| 20 | | | \n0.013 eq., 72 h | 64.43 | 9.24 |
| 21 | | | 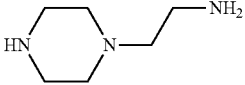\n0.013 eq., 72 h | 66.21 | 7.52 |

-continued

Additive screen

| Entry | Substrate | Reagents and conditions | Ligand | Conversion (by HPLC area %) Product | SM |
|---|---|---|---|---|---|
| 22 | | | 1,2-diaminocyclohexane (Cis-) 0.013 eq., 72 h | 65.09 | 6.79 |
| 23 | | | 2,2,6,6-tetramethylheptane-3,5-dione 0.013 eq., 130 h | 71.2 | 10.0 |
| 24 | | | 2,2':6',2''-terpyridine 0.013 eq., 130 h | 66.3 | 12.0 |
| 25 | | | tris((1-benzyl-1H-1,2,3-triazol-4-yl)methyl)amine 0.013 eq., 130 h | 15.0 | 61.8 |
| 26 | | DMAP, 0.03 eq., 60 h | | 70.88 | 5.91 |
| | | | TMEDA 0.013 eq., 60 h | 71.56 | 4.93 |
| 27 | | | 2,2'-bipyridine 0.013 eq., 89 h | 57.34 | 11.85 |
| 28 | | | 4,4'-dimethoxy-2,2'-bipyridine 0.013 eq., 89 h | 61.04 | 14.65 |
| 29 | | 18-Crown-6 (0.001 eq.), KCl (0.05 eq.), 36 h | | 73.67 | 5.53 |

-continued

| | | Additive screen | | |
|---|---|---|---|---|
| | | | | Conversion (by HPLC area %) |
| Entry | Substrate | Reagents and conditions | Ligand | Product | SM |
| 30 | | | L-sodium ascorbate (0.1 eq.), 36 h | trace | 98.72 |
| 31 | | | 18-Crown-6 (0.001 eq.), KCl (0.05 eq.), Py (0.013 eq.), 86 h | 75.8 | 4.8 |
| 32 | | | 2,2,6,6-tetramethylheptane-3,5-dione 0.013 eq, 18-Crown-6 (0.001 eq.), KCl (0.05 eq.), 86 h | 74.0 | 10.6 |
| 33 | | | 4-ethyl-4,5-dihydrooxazole 0.013 eq, 18-Crown-6 (0.001 eq.), KCl (0.05 eq.), 86 h | 60.6 | 22.5 |
| 34 | | BocNHOH (1.5 eq.), CuCl (0.05 eq.), Sulfolane (5 V), H$_2$O (5 V), air, 20-30° C. | Py (0.013 eq)., 85 h | 46.74 | 24.55 |
| 35 | | | tetraethylenepentamine 0.013 eq., 85 h | 54.08 | 16.81 |
| 36 | | | biuret 0.013 eq., 85 h | 51.32 | 18.78 |
| 37 | | | (1R,2R)-N,N'-dimethylcyclohexane-1,2-diamine 0.013 eq., 85 h | 53.35 | 17.1 |
| 38 | | | 2-(dicyclohexylphosphino)-2'-(dimethylamino)biphenyl 0.013 eq., 85 h | 51.11 | 18.21 |

| | | | | Conversion (by HPLC area %) | |
|---|---|---|---|---|---|
| Entry | Substrate | Reagents and conditions | Ligand | Product | SM |
| 39 | | | 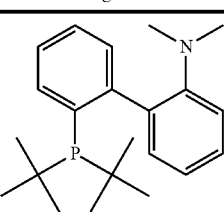<br>0.013 eq., 85 h | 55.61 | 14.39 |
| 40 | | BocNHOH (1.5 eq.), CuBr—Me₂S (0.05 eq.), Sulfolane (5 V), H₂O (5 V), O₂, 20-30° C. | Pyridine (0.013 eq.), 72 h | 68.71 | 3.36 |
| 41 | | | DMAP (0.013 eq.), 86 h | 66.99 | 10.88 |
| 42 | | | 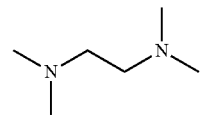<br>0.013 eq., 86 g | 3.01 | 96.57 |
| 43 | | | 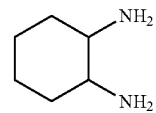<br>trans-<br>0.013 eq., 86 h | 71.53 | 6.53 |
| 44 | | BocNHOH (3 eq.), CuCl (0.05 eq.), Sulfolane (5 V), H₂O (5 V), H₂O₂ (3%, 3 eq.), 0~5° C. | 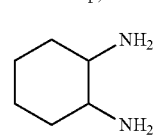<br>trans-<br>0.013 eq, 66 h | 74.3 | 8.7 |

After screening, the best conditions for the substrate with PG₁=PG₂=Boc, R₁=CONH₂, R₂=Me, R₃=H were: BocNHOH (1.5 eq), CuCl (0.05 eq), Py (0.013 eq), DCM (10V), O₂ (1atm), 15-25° C. For the substrate with PG₁=PG₂=Boc, R₁=CONH₂, R₂=H, R₃=Me, the best conditions were: BocNHOH (1.5 eq), CuCl (0.05 eq), Py (0.013 eq), Sulfolane (5 V), H₂O (5 V), O₂(1atm), 15-25° C. or BocNHOH (2 eq), CuBr-Me₂S (0.05 eq), Py (0.13 eq), Sulfolane (5 V), H₂O (0.5 V), H₂O₂ (3% in water, 2-3 eq), 15-25° C.

The following experimental procedures are for illustration purposes.

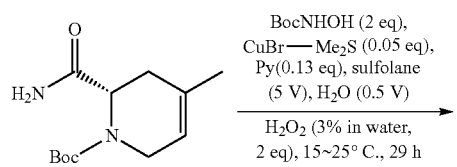

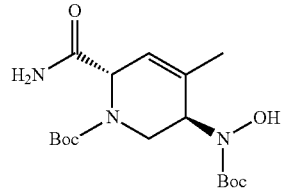

To a mixture of starting material (1 eq), BocNHOH (2 eq), CuBr₂—SMe₂ (0.05 eq) was added sulfolane (5V) and H₂O (0.5V), Pyridine (0.13 eq). The mixture was stirred 30-40 min at 15-25° C. 3% H₂O₂ (2 eq) was added dropwise for 24-30 h. After the reaction is judged as complete, a solution of EDTA-2Na (0.31-0.32 eq. by weight) in water (3-3.2×by weight) and MTBE (7.7× by weight) were added. The resulting mixture was stirred for 20-30 min and settled for 20-30 min. The two phases were separated. The aqueous phase was extracted with MTBE (4× by weight) three times. The combined organic solution was dried with Na₂SO₄ and filtered, concentrated and analyzed by assay. 47.5% yield, 74.12% purity by HPLC % area.

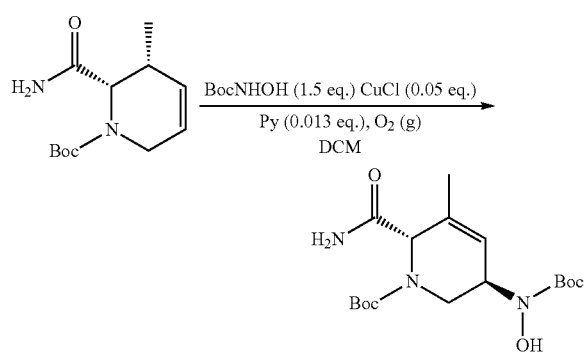

To the crude solution of substrate from previous step in DCM was added CuCl (0.05 eq.), BocNHOH (1.5 eq.) and Py (0.013 eq.). The mixture was stirred under $O_2$ atmosphere at 20±5° C. until the starting material is ≤5% by HPLC % area. EDTA-2Na solution (5.0 vol) was charged and the resulting mixture was stirred for at least 4 hours at 25±5° C. The two phases were separated. The aqueous phase was extracted with DCM (3.0 vol) two times. The organic phases were combined and washed with water (5.0 vol) one time, concentrate under vacuum at <40° C. to ~3.0 vol. i-PrOAc (5.0 V) was charged to the reactor and the mixture was concentrated under vacuum at <40° C. to ~4.0 vol. This process was repeated one more time. n-Heptane (5.0 vol) was added to the reactor at 40±5° C. The resulting mixture was gradually cooled to 20±5° C. Solid was obtained by centrifuge and washed with i-PrOAc/n-Heptane (1:1, 2 vol) and dried under vacuum at 35±5° C. at least for 12 hours. 71.68% yield for 2 steps, 99.7% purity by HPLC % area.

Intermediate 1: (S)-2-(1-hydroxybut-3-en-2-yl)isoindoline-1,3-dione

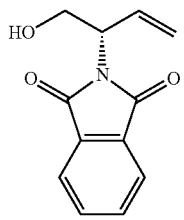 [SMILES: C=C[C@@H](CO)N1C(=O)c2ccccc2C1=O]

A 2-L reaction flask containing a stir bar and sodium carbonate (1.981 g, 18.69 mmol) was placed under high vacuum and dried with a heating gun for ten minutes. Upon cooling, the flask was backfilled with nitrogen. To it was added allylpalladium chloride dimer (0.553 g, 1.53 mmol), (1R,2R)-(+)-1,2-diaminocyclohexane-N,N'-bis(2-diphenylphosphino-1-naphthoyl) (CAS 174810-09-4)(3.36 g, 4.25 mmol), and phthalimide (50 g, 339.83 mmol). The flask was then purged with nitrogen for ten minutes. 1.4 L methylene chloride, previously degassed with a nitrogen line for ten minutes, was then added. This suspension was placed under an atmosphere of nitrogen; it was alternately stirred and sonicated over a ten-minute period to facilitate solvation. At that time, it was a yellow or light orange solution containing white solid. To this mixture was added 2-vinyloxirane (24.06 g, 343.23 mmol).

The resulting mixture was stirred under a nitrogen atmosphere at ambient temperature for approximately 48 hours. Analysis during that time by LCMS and TLC (1:1 hexanes:ethyl acetate) suggested progression of the reaction, and final analyses by those methods suggested complete conversion of starting material to one major product. The reaction mixture was filtered, and the filtrate was concentrated under reduced pressure. The yellow, viscous fluid was injected onto a 330-g silica column: a minimal volume of methylene chloride was used to thin the crude material. Silica gel chromatography (15-75% ethyl acetate in hexanes, 40 minutes, 330 g column) was used to isolate the desired product as a viscous yellow fluid that became a pale yellowish white solid (69.6 g, 94%) over a period of hours under reduced pressure. Optical Rotation: (2.02 g/100 mL, methylene chloride) literature value=−72.2, obtained value=−71.

Intermediate 2: (S)-2-(1-(tert-butyldimethylsilyloxy)but-3-en-2-yl)isoindoline-1,3-dione

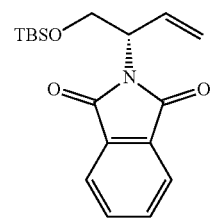 [SMILES: C=C[C@@H](CO[Si](C)(C)C(C)(C)C)N1C(=O)c2ccccc2C1=O]

To a stirred solution of (S)-2-(1-hydroxybut-3-en-2-yl)isoindoline-1,3-dione (Intermediate 1, 69.4 g, 319.49 mmol) and imidazole (26.1 g, 383.39 mmol) in methylene chloride (160 mL), at ambient temperature under an atmosphere of nitrogen, was added tert-butyldimethylchlorosilane (55.4 g, 367.41 mmol) as a solid. This addition was performed over approximately ten minutes. Warming of the mixture was observed during this addition. After two hours stirring, the solution was poured into a saturated solution of aqueous sodium bicarbonate (approximately 150 mL); this biphasic mixture was shaken, and the organic layer was separated. The aqueous layer was back-extracted three times with 200 mL methylene chloride each time. The organic layers were combined, dried over magnesium sulfate, filtered, and concentrated in vacuo. The desired product was obtained as a pale yellow solid after drying overnight under high vacuum (107 g, 101%).

Intermediate 3: (S)-1-(tert-butyldimethylsilyloxy)but-3-en-2-amine

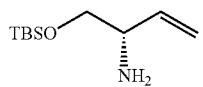

To a stirred solution of (S)-2-(1-(tert-butyldimethylsilyloxy)but-3-en-2-yl)isoindoline-1,3-dione (Intermediate 2, 108.28 g, 326.65 mmol) in methanol (1 L), at ambient temperature under a nitrogen atmosphere, was added hydrazine (35.9 ml, 1143.29 mmol). The yellow solution was heated to 65° C. Within 30 minutes of reaching reaction temperature, a white precipitate was observed in the reaction mixture; this solid quickly became the bulk of the mixture, and at that time water (about 150 mL) was added to the reaction mixture. The reaction continued stirring without interruption and within a few minutes the solid dissolved. Upon complete conversion as indicated by LCMS analysis (both starting material and product give strong UV signals and are easily identified by LCMS), the heat was removed and more water was added (a total water content of 600 mL). The mixture was allowed to come to ambient temperature.

The methanol was removed in vacuo at 35° C. (moderately reduced pressure); vacuum was removed and the aqueous was warmed to about 50° C. and then extracted with 4×200 mL methylene chloride. The organic extracts were combined, washed with saturated sodium bicarbonate (aq), washed with brine, dried over sodium sulfate, filtered, and concentrated in vacuo at not more than 30° C. The desired product was obtained as a yellow liquid (58.5 g, 94%).

Intermediate 4:
2-bromo-N-methoxy-N-methylacetamide

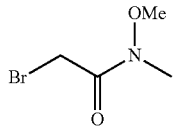

A stirred solution of potassium carbonate (343 g, 2.48 mol) in water (about 800 mL) was prepared and cooled in an ice bath for 15 minutes under nitrogen. To it was added O,N-dimethylhydroxylamine hydrochloride (110 g, 1.13 mol) and diethyl ether (about 800 mL). To this mixture was then added bromoacetyl bromide (273 g, 1.35 mol) by addition funnel over twenty minutes. The ice bath was removed and the mixture was stirred under nitrogen for two hours. The layers were separated and the aqueous layer was extracted with ether (about 350 mL). The organic layers were combined, dried over magnesium sulfate, filtered, and concentrated in vacuo. The desired product was obtained as a yellow liquid (143 g, 70%).

Intermediate 5: (S)-tert-butyl 1-(tert-butyldimethyl-silyloxy)but-3-en-2-yl(2-(methoxy(methyl)amino)-2-oxoethyl)carbamate

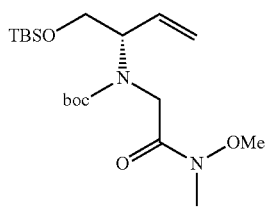

A suspension of (S)-1-(tert-butyldimethylsilyloxy)but-3-en-2-amine (Intermediate 3, 60.4 g, 300 mmol) and cesium carbonate (103 g, 315 mmol) in acetonitrile (about 700 mL) and water (about 120 mL) was prepared and stirred in an ice bath under nitrogen for 5 minutes. The mixture was biphasic and remained so for the duration of the reaction. To this mixture was then added 2-bromo-N-methoxy-N-methylacetamide (Intermediate 4, 57.0 g, 285 mmol) by addition funnel over 10 minutes. The mixture was stirred for two days, with the temperature maintained near 0° C. The mixture was kept in the freezer overnight. Another 0.05 eq of the electrophile was added. To the mixture was added di-tert-butyl dicarbonate (165 mL, 2M solution in THF). The organic layer was separated from the aqueous (TLC indicated that no product remained in the aqueous), and the organic layer was concentrated in vacuo. Silica gel chromatography (5-55% ethyl acetate in hexanes), split into 3 batches, afforded the desired product as a pale yellow oil (80 g, 66%).

Intermediate 6: (S)-tert-butyl 1-(tert-butyldimethyl-silyloxy)but-3-en-2-yl(2-oxopent-3-enyl)carbamate

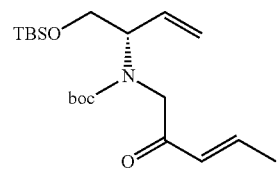

To a solution of (S)-tert-butyl 1-(tert-butyldimethylsilyloxy)but-3-en-2-yl(2-(methoxy-(methyl)amino)-2-oxo-ethyl)carbamate (Intermediate 5, 32.5 g, 80.73 mmol) in THF (400 mL) under nitrogen at 0° C. was added prop-1-enylmagnesium bromide (323 ml, 161.45 mmol) dropwise. The reaction mixture was stirred at 0° C. for 1 hour, then quenched with 400 mL 10% citric acid, diluted further with 100 mL water and extracted with ether. The organics were concentrated and the resulting oil was dissolved in ether and washed with water and brine. The organics were dried over magnesium sulfate, filtered and concentrated. Silica gel chromatography (5%-20% ethyl acetate/hexanes) afforded the desired product as a colorless oil (27 g, 87%).

MS: 384 ES+($C_{20}H_{37}NO_4Si$)

$^1$H NMR (300 MHz, $CDCl_3$) δ: 0.05 (2, 6H); 0.88 (s, 9H); 1.39-1.47 (m, 9H); 1.90 (m, 3H); 3.80 (m, 2H); 4.05-4.18 (m, 2H); 4.43-4.76 (m, 1H); 5.22 (m, 2H); 5.86 (m, 1H); 6.21 (m, 1H); 6.91 (m, 1H).

Intermediate 7: (S)-tert-butyl 2-((tert-butyldimethyl-silyloxy)methyl)-5-oxo-5,6-dihydropyridine-1(2H)-carboxylate

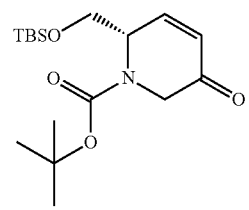 [SMILES: CC(C)(C)OC(=O)N1CC(=O)C=C[C@H]1CO[Si](C)(C)C(C)(C)C]

(S)-tert-butyl 1-(tert-butyldimethylsilyloxy)but-3-en-2-yl (2-oxopent-3-enyl)carbamate (Intermediate 6, 27.0 g, 70.39 mmol) was dissolved in toluene (650 mL). The solution was purged with nitrogen for 15 minutes before the addition of Hoveyda-Grubbs Catalyst 2nd Generation (0.885 g, 1.41 mmol). The reaction mixture was heated under nitrogen at 65° C. The reaction mixture was concentrated under reduced pressure. Silica gel chromatography (10%-35% ethyl acetate/hexanes) afforded the desired product as a solid (17.0 g, 70%). Optical Rotation: 0.1 g/dL, methylene chloride=−175

Intermediate 8: (6S)-tert-butyl 6-(((tert-butyldimethylsilyloxy)methyl)-5-methyl-3-(trimethylsilyloxy)-5,6-dihydropyridine-1(2H)-carboxylate

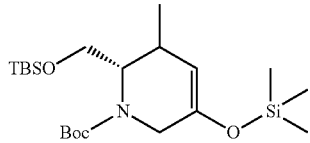 [SMILES: CC1C=C(O[Si](C)(C)C)CN(C(=O)OC(C)(C)C)[C@@H]1CO[Si](C)(C)C(C)(C)C]

To a suspension of copper(I) iodide (22.31 g, 117.12 mmol) in diethyl ether (250 mL) at 0° C. was added methyllithium (1.6M in ether) (146 mL, 234.25 mmol) via cannula. The suspension was stirred for 45 minutes at 0° C. A solution of (S)-tert-butyl 2-(((tert-butyldimethylsilyl)oxy)methyl)-5-oxo-5,6-dihydropyridine-1(2H)-carboxylate (Intermediate 7, 20 g, 58.56 mmol) in diethyl ether (50 mL) was added dropwise to the suspension at 0° C. Once addition was complete, the reaction mixture was stirred for 45 minutes at 0° C. To the reaction mixture was then added chlorotrimethylsilane (1M in THF) (117 mL, 117.12 mmol) dropwise, followed by triethylamine (16.28 mL, 117.12 mmol). The reaction mixture was allowed to warm to room temperature and stir for 2 hours. The reaction mixture was then diluted with ethyl acetate and washed with ice cold saturated sodium bicarbonate solution (added very carefully) three times, followed by brine. The organics were dried over sodium sulfate, filtered and concentrated to afford a brown oil.

Intermediate 9: (S)-tert-butyl 2-((tert-butyldimethylsilyloxy)methyl)-3-methyl-5-oxo-5,6-dihydropyridine-1(2H)-carboxylate

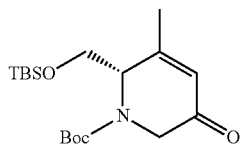 [SMILES: CC1=CC(=O)CN(C(=O)OC(C)(C)C)[C@@H]1CO[Si](C)(C)C(C)(C)C]

To a solution of (6S)-tert-butyl 6-(((tert-butyldimethylsilyl)oxy)methyl)-5-methyl-3-((trimethylsilyl)oxy)-5,6-dihydropyridine-1(2H)-carboxylate (Intermediate 8, 24.1 g, 56.08 mmol) in acetonitrile (280 mL) at room temperature was added palladium (II) acetate (12.59 g, 56.08 mmol). The reaction mixture was stirred at room temperature for ~40 hours, then diluted with ethyl acetate and filtered through celite. The filtrate was concentrated onto silica gel. Silica gel chromatography (0%-20% ethyl acetate/hexanes) afforded (S)-tert-butyl 2-(((tert-butyldimethylsilyl)oxy)methyl)-3-methyl-5-oxo-5,6-dihydropyridine-1(2H)-carboxylate (12.95 g, 65%) as a yellow solid.

Intermediate 10: (2S,5S)-tert-butyl 2-((tert-butyldimethylsilyloxy)methyl)-5-hydroxy-3-methyl-5,6-dihydropyridine-1(2H)-carboxylate

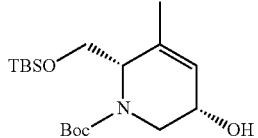 [SMILES: CC1=C[C@H](O)CN(C(=O)OC(C)(C)C)[C@@H]1CO[Si](C)(C)C(C)(C)C]

To a suspension of cerium(III) chloride (8.98 g, 36.42 mmol) and (S)-tert-butyl 2-(((tert-butyldimethylsilyl)oxy)methyl)-3-methyl-5-oxo-5,6-dihydropyridine-1(2H)-carboxylate (Intermediate 9, 12.95 g, 36.42 mmol) in methanol (200 mL) at 0° C. was added sodium borohydride (1.378 g, 36.42 mmol), portionwise. After 15 minutes, the reaction mixture was diluted with saturated ammonium chloride (100 mL) and water (100 mL), then extracted twice with ether. The organic extracts were washed with brine, dried over magnesium sulfate, filtered and concentrated. Silica gel chromatography (0%-20% ethyl acetate/hexanes) afforded (2S,5S)-tert-butyl 2-(((tert-butyldimethylsilyl)oxy)methyl)-5-hydroxy-3-methyl-5,6-dihydropyridine-1(2H)-carboxylate (9.79 g, 75%) as a colorless oil.

Intermediate 11: (2S,5R)-tert-butyl 5-(N-(allyloxy)-2-nitrophenylsulfonamido)-2-((tert-butyldimethylsilyloxy)methyl)-3-methyl-5,6-dihydropyridine-1(2H)-carboxylate

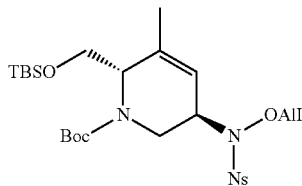

To a solution of (2S,5S)-tert-butyl 2-(((tert-butyldimethylsilyl)oxy)methyl)-5-hydroxy-3-methyl-5,6-dihydropyridine-1(2H)-carboxylate (Intermediate 10, 9.79 g, 27.38 mmol) in toluene (100 mL) at room temperature was added triphenylphosphine (8.58 g, 32.86 mmol), N-(allyloxy)-2-nitrobenzenesulfonamide (7.07 g, 27.38 mmol) and diisopropyl azodicarboxylate (6.47 mL, 32.86 mmol). The reaction mixture was stirred overnight, then filtered and concentrated. The resulting oil was twice triturated with hexanes and filtered. Silica gel chromatography (0%-20% ethyl acetate/hexanes) afforded (2S,5R)-tert-butyl 5-(N-(allyloxy)-2-nitrophenylsulfonamido)-2-(((tert-butyldimethylsilyl)oxy)methyl)-3-methyl-5,6-dihydropyridine-1(2H)-carboxylate (10.75 g, 66%) as a light yellow foam.

Intermediate 12: (2S,5R)-tert-butyl 5-(N-(allyloxy)-2-nitrophenylsulfonamido)-2-(hydroxymethyl)-3-methyl-5,6-dihydropyridine-1(2H)-carboxylate

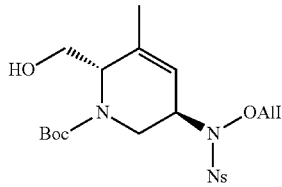

To a solution of (2S,5R)-tert-butyl 5-(N-(allyloxy)-2-nitrophenylsulfonamido)-2-(((tert-butyldimethylsilyl)oxy)methyl)-3-methyl-5,6-dihydropyridine-1(2H)-carboxylate (Intermediate 11, 10.75 g, 17.98 mmol) in THF (100 mL) at 0° C. was added tetrabutylammonium fluoride (1M in THF) (23.38 mL, 23.38 mmol). The reaction mixture turned from yellow to greenish brown. The reaction mixture was stirred for about 2 hours, then concentrated onto silica gel. Silica gel chromatography (0%-70% ethyl acetate/hexanes) afforded (2S,5R)-tert-butyl 5-(N-(allyloxy)-2-nitrophenylsulfonamido)-2-(hydroxymethyl)-3-methyl-5,6-dihydropyridine-1(2H)-carboxylate (7.72 g, 89%) as a tan foam.

Intermediate 13: (2S,5R)-5-(N-(allyloxy)-2-nitrophenylsulfonamido)-1-(tert-butoxycarbonyl)-3-methyl-1,2,5,6-tetrahydropyridine-2-carboxylic acid

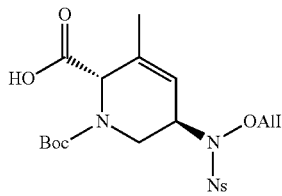

To a solution of periodic acid (1.588 g, 8.27 mmol) in wet acetonitrile (20 mL) (0.75% water by volume) at room temperature was added chromium(VI) oxide (0.019 g, 0.19 mmol). The mixture was stirred until complete dissolution was achieved. To a solution of (2S,5R)-tert-butyl 5-(N-(allyloxy)-2-nitrophenylsulfonamido)-2-(hydroxymethyl)-3-methyl-5,6-dihydropyridine-1(2H)-carboxylate (Intermediate 12, 2 g, 4.14 mmol) in wet acetonitrile (20 mL) (0.75% by volume) at 0° C. was added dropwise the previously formed periodic acid/chromium oxide solution (20 mL, 2 eq.), and stirred for 15 minutes. The reaction mixture was diluted with DCM (100 mL) and washed with 10% citric acid (50 mL) and twice with brine. The organics were dried over sodium sulfate, filtered and concentrated to afford a tan foam (1.9 g, 92%).

Intermediate 14: (2S,5R)-tert-butyl 5-(N-(allyloxy)-2-nitrophenylsulfonamido)-2-carbamoyl-3-methyl-5,6-dihydropyridine-1(2H)-carboxylate

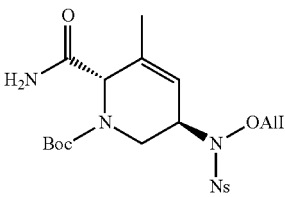

To a solution of (2S,5R)-5-(N-(allyloxy)-2-nitrophenylsulfonamido)-1-(tert-butoxycarbonyl)-3-methyl-1,2,5,6-tetrahydropyridine-2-carboxylic acid (Intermediate 13, 1.9 g, 3.82 mmol) in DMF (9.5 mL) at 0° C. was added HATU (2.178 g, 5.73 mmol), ammonium chloride (0.613 g, 11.46 mmol) and DIEA (2.67 mL, 15.28 mmol) dropwise. The reaction mixture was warmed to room temperature and stirred for 15 minutes. The reaction mixture was diluted with ethyl acetate and washed with saturated sodium bicarbonate and 1:1 brine:water. Silica gel chromatography (0%-70% ethyl acetate/hexanes) afforded (2S,5R)-tert-butyl 5-(N-(allyloxy)-2-nitrophenylsulfonamido)-2-carbamoyl-3-methyl-5,6-dihydropyridine-1(2H)-carboxylate (1.270 g, 67%) as a light orange foam.

Intermediate 15: (2S,5R)-tert-butyl 5-((allyloxy)amino)-2-carbamoyl-3-methyl-5,6-dihydropyridine-1(2H)-carboxylate

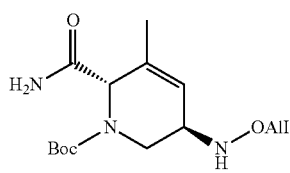

To a solution of (2S,5R)-tert-butyl 5-(N-(allyloxy)-2-nitrophenylsulfonamido)-2-carbamoyl-3-methyl-5,6-dihydropyridine-1(2H)-carboxylate (Intermediate 14, 3.63 g, 7.31 mmol) in acetonitrile (100 mL) at room temperature was added potassium carbonate (5.05 g, 36.55 mmol) and thiophenol (3.75 mL, 36.55 mmol). The reaction mixture was stirred overnight at room temperature. The reaction mixture was concentrated and the resulting residue was triturated with DCM and filtered to remove solids. The filtrate was concentrated onto silica and purified. Silica gel chromatography (0%-90% ethyl acetate/hexanes) afforded (2S,5R)-tert-butyl 5-((allyloxy)amino)-2-carbamoyl-3-methyl-5,6-dihydropyridine-1(2H)-carboxylate (1.49 g, 65%) as a yellow oil.

Intermediate 16: (2S,5R)-tert-butyl 5-(N-(allyloxy)-1H-imidazole-1-carboxamido)-2-carbamoyl-3-methyl-5,6-dihydropyridine-1(2H)-carboxylate

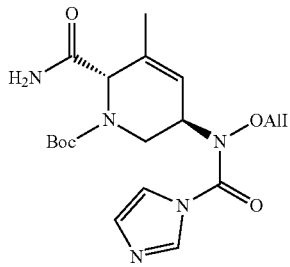

To a solution of (2S,5R)-tert-butyl 5-((allyloxy)amino)-2-carbamoyl-3-methyl-5,6-dihydropyridine-1(2H)-carboxylate (Intermediate 15, 1.49 g, 4.79 mmol) in THF (30 mL) at room temperature was added N,N-diisopropylethylamine (2.5 mL, 14.36 mmol) and N,N-carbonyldiimidazole (2.328 g, 14.36 mmol). The reaction mixture was stirred for ~2 hours at room temperature. Another equivalent of CDI was added, and the reaction mixture stirred at room temperature for 1 hour, then another equivalent of CDI was added and the reaction stirred for another hour. The reaction mixture was diluted with DCM, and washed four times with 1:1 brine:water, then dried over magnesium sulfate, filtered and concentrated to afford an off-white foam, 1.86 g.

Intermediate 17: (2S,5R)-6-(allyloxy)-3-methyl-7-oxo-1,6-diazabicyclo[3.2.1]oct-3-ene-2-carboxamide

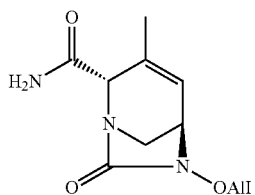

To a solution of (2S,5R)-tert-butyl 5-(N-(allyloxy)-1H-imidazole-1-carboxamido)-2-carbamoyl-3-methyl-5,6-dihydropyridine-1(2H)-carboxylate (Intermediate 16, 1.86 g, 4.59 mmol) in DCM (20 mL) at 0° C. was added trifluoroacetic acid (3.53 mL, 45.88 mmol). The reaction mixture was allowed to warm to room temperature slowly and stir overnight. The reaction mixture was concentrated. The oil was redissolved in DCM and washed with saturated sodium bicarbonate. The aqueous was extracted once with ~10% MeOH/DCM. The organics were dried over magnesium sulfate, filtered and concentrated. Silica gel chromatography (0%-30% acetone/dichloromethane) afforded (2S,5R)-6-(allyloxy)-3-methyl-7-oxo-1,6-diazabicyclo[3.2.1]oct-3-ene-2-carboxamide (0.83 g, 76%) as a light yellow oil.

Example 1

(R)-ethyl 2-((2S,5R)-2-carbamoyl-3-methyl-7-oxo-1,6-diazabicyclo[3.2.1]oct-3-en-6-yloxy)-2-fluoroacetate

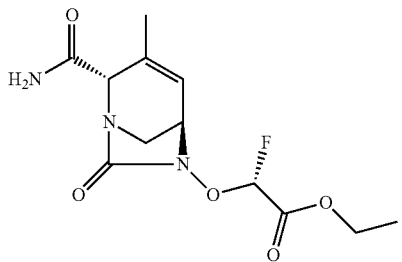

Example 2

(S)-ethyl 2-((2S,5R)-2-carbamoyl-3-methyl-7-oxo-1,6-diazabicyclo[3.2.1]oct-3-en-6-yloxy)-2-fluoroacetate

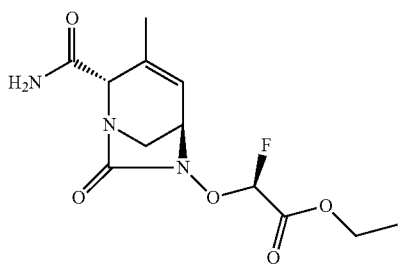 [SMILES: CCOC(=O)[C@H](F)ON1C(=O)N2C[C@H]1C=C(C)[C@H]2C(N)=O]

Example 3

(2S)-{[(2S,5R)-2-carbamoyl-3-methyl-7-oxo-1,6-diazabicyclo[3.2.1]oct-3-en-6-yl]oxy}(fluoro)ethanoic acid lithium salt

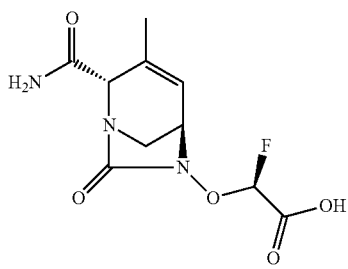 [SMILES: CC1=C[C@@H]2CN(C(=O)N2O[C@@H](F)C(=O)O)[C@@H]1C(N)=O]

Example 4

(2R)-{[(2S,5R)-2-carbamoyl-3-methyl-7-oxo-1,6-diazabicyclo[3.2.1]oct-3-en-6-yl]oxy}(fluoro)ethanoic acid lithium salt

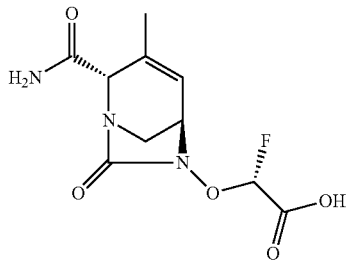

Example 5

{[(2S,5R)-2-carbamoyl-3-methyl-7-oxo-1,6-diazabicyclo[3.2.1]oct-3-en-6-yl]oxy}(fluoro)acetic acid lithium salt (mixture of diastereomers)

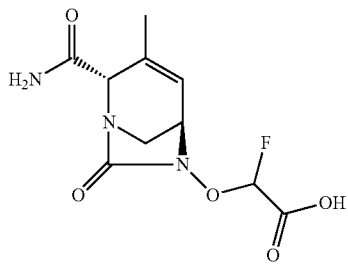

Examples 1-2

To a solution of (2S,5R)-6-(allyloxy)-3-methyl-7-oxo-1,6-diazabicyclo[3.2.1]oct-3-ene-2-carboxamide (Intermediate 17, 100 mg, 0.42 mmol) in methanol (3 mL) at room temperature was added 1,3-dimethylbarbituric acid (132 mg, 0.84 mmol) and tetrakis(triphenylphosphine)palladium(0) (48.7 mg, 0.04 mmol). The reaction was stirred at room temperature for 2 hours. The reaction mixture was concentrated to afford an orange film. The orange film was dissolved in DMF (3 mL) and potassium carbonate (175 mg, 1.26 mmol) and ethyl bromofluoroacetate (0.299 mL, 2.53 mmol) were added. The reaction mixture was stirred overnight at room temperature and was then diluted with ethyl acetate and filtered through a 0.45μ filter to remove solid potassium carbonate. The filtrate was washed twice with 1:1 brine:water. The organics were dried over magnesium sulfate, filtered and concentrated. Silica gel chromatography (0%-70% ethyl acetate/hexanes) afforded ethyl 2-(((2S,5R)-2-carbamoyl-3-methyl-7-oxo-1,6-diazabicyclo[3.2.1]oct-3-en-6-yl)oxy)-2-fluoroacetate (97 mg, 76%) as a mixture of diastereomers of Example 1 and Example 2 as an orange foam.

MS: 198 ES+($C_8H_{11}N_3O_3$)

Examples 3-5

To a solution of ethyl 2-(((2S,5R)-2-carbamoyl-3-methyl-7-oxo-1,6-diazabicyclo[3.2.1]oct-3-en-6-yl)oxy)-2-fluoroacetate (Examples 1-2, 97 mg, 0.32 mmol) in THF (3 mL) and water (1 mL) at −5° C. was added lithium hydroxide (9.25 mg, 0.39 mmol) as a solution in water (0.5 mL). The mixture was stirred at 0° C. for 60 minutes, allowed to warm to room temperature and stirred for 15 minutes. The reaction mixture was adjusted to pH=7 with 0.5M HCl. The THF was evaporated and the remaining aqueous phase was frozen and lyophilized.

Purification of Examples 1-5

The mixture resulting from the reaction described in Examples 3-5 was purified by reversed phase HPLC (Synergi Polar RP 21.2 mm×100 mm, 4 μm coupled with YMC C30 20 mm×150 mm, 5 μm; 0% to 50% acetonitrile in water, 10 min; 20 mL/min) to obtain:

Example 1 ethyl {[(2S,5R)-2-carbamoyl-3-methyl-7-oxo-1,6-diazabicyclo[3.2.1]oct-3-en-6-yl]oxy}(fluoro)acetate (first eluting ester): 4.4 mg, 4.5%

MS: 302 ES+($C_{12}H_{16}FN_3O_5$)

$^1$H NMR (300 MHz, DMSO-$d_6$) δ: 1.21 (t, 3H); 1.62 (s, 3H); 3.05 (m, 1H); 3.75 (m, 1H); 4.03 (m, 1H); 4.20 (m, 3H); 6.01 (m, 1H); 6.13-6.31 (d, 1H); 7.36 (bs, 1H); 7.81 (bs, 1H).

Example 2

(S)-ethyl 2-((2S,5R)-2-carbamoyl-3-methyl-7-oxo-1,6-diazabicyclo[3.2.1]oct-3-en-6-yloxy)-2-fluoroacetate (second eluting ester): 4.2 mg, 4.3%

MS: 302 ES+($C_{12}H_{16}FN_3O_5$)

$^1$H NMR (300 MHz, DMSO-$d_6$) δ: 1.26 (t, 3H); 1.63 (s, 3H); 3.08 (m, 1H); 3.75 (m, 1H); 3.94 (m, 1H); 4.20 (m, 1H); 4.27 (q, 2H); 6.03 (m, 1H); 6.24-6.50 (d, 1H); 7.37 (bs, 1H); 7.83 (bs, 1H).

Example 3

(2S)-{[(2S,5R)-2-carbamoyl-3-methyl-7-oxo-1,6-diazabicyclo[3.2.1]oct-3-en-6-yl]oxy}(fluoro)ethanoic acid (first eluting acid): 7.7 mg, 8.8%

MS: 274 ES+($C_{10}H_{12}FN_3O_5$)

$^1$H NMR (300 MHz, DMSO-$d_6$) δ: 1.61 (s, 3H); 3.05 (m, 1H); 3.68 (m, 1H); 3.96 (m, 1H); 4.13 (m, 1H); 5.12-5.33 (d, 1H); 6.03 (m, 1H); 7.31 (bs, 1H); 7.80 (bs, 1H).

Example 4

(2R)-{[(2S,5R)-2-carbamoyl-3-methyl-7-oxo-1,6-diazabicyclo[3.2.1]oct-3-en-6-yl]oxy}(fluoro)ethanoic acid (second eluting acid): 9.9 mg, 11%

MS: 274 ES+($C_{10}H_{12}FN_3O_5$)

$^1$H NMR (300 MHz, DMSO-$d_6$) δ: 1.61 (s, 3H); 3.05 (m, 1H); 3.70 (m, 1H); 4.00 (m, 1H); 4.13 (m, 1H); 5.15-5.37 (d, 1H); 6.01 (m, 1H); 7.31 (bs, 1H); 7.78 (bs, 1H).

Example 5

{[(2S,5R)-2-carbamoyl-3-methyl-7-oxo-1,6-diazabicyclo[3.2.1]oct-3-en-6-yl]oxy}(fluoro)acetic acid (mixture of diastereomers): 20.4 mg, 23%

MS: 274 ES+($C_{10}H_{12}FN_3O_5$)

$^1$H NMR (300 MHz, DMSO-$d_6$) δ: 1.62 (s, 6H); 3.06 (m, 2H); 3.70 (m, 2H); 4.01 (m, 2H); 4.14 (m, 2H); 5.14-5.35 (d, 1H); 5.18-5.40 (d, 1H); 6.03 (m, 2H); 7.32 (bs, 2H); 7.80 (bs, 2H).

The absolute stereochemistry for all compounds was determined by characterizing the co-crystal structure of example 4 complexed with AmpC. The absolute stereochemistry of the other diastereomer, example 3, was assigned as having the opposite stereochemistry at the fluoroacetate carbon. The stereochemistry of each ester was assigned by hydrolysis of each ester to its corresponding acid and comparison of the UPLC retention times to those of examples 3 and 4.

Example 6 ethyl {[(2S,5R)-2-carbamoyl-3-methyl-7-oxo-1,6-diazabicyclo[3.2.1]oct-3-en-6-yl]oxy}fluoro)acetate (mixture of diastereomers)

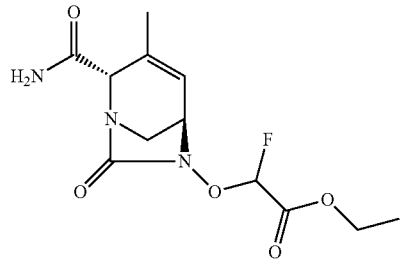 [SMILES: CCOC(=O)C(F)ON1C(=O)N2C[C@H]1C=C(C)[C@H]2C(N)=O]

According to the procedure given for examples 1 and 2, (2S,5R)-6-(allyloxy)-3-methyl-7-oxo-1,6-diazabicyclo[3.2.1]oct-3-ene-2-carboxamide (Intermediate 17, 0.506 g, 2.13 mmol) was converted into 70 mg of Example 6 after HPLC (Synergi Polar RP 21.2 mm×100 mm, 4 μm coupled with YMC C30 20 mm×150 mm, 5 μm; 20% to 60% acetonitrile in water, 10 min; 20 mL/min) and lyophilization.

MS: 302 ES+($C_{12}H_{16}FN_3O_5$)

$^1$H NMR (300 MHz, DMSO-$d_6$) δ: 1.22 (t, 3H); 1.27 (t, 3H); 1.63 (s, 6H); 3.07 (m, 2H); 3.76 (m, 2H); 3.94 (m, 1H); 4.05 (m, 1H); 4.20 (m, 2H); 4.26 (m, 4H); 6.03 (m, 2H); 6.06-6.24 (d, 1H); 6.14-6.32 (d, 1H); 7.37 (bs, 1H); 7.83 (bs, 1H).

Example 7 ethyl {[(2S,5R)-2-carbamoyl-3-methyl-7-oxo-1,6-diazabicyclo[3.2.1]oct-3-en-6-yl]oxy}(difluoro)acetate

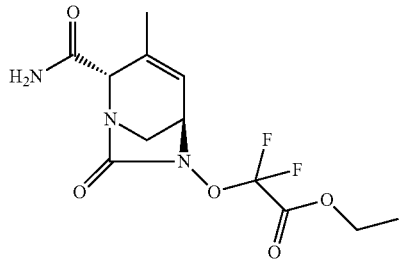 [SMILES: CCOC(=O)C(F)(F)ON1C(=O)N2C[C@H]1C=C(C)[C@H]2C(N)=O]

(2S,5R)-6-(allyloxy)-3-methyl-7-oxo-1,6-diazabicyclo[3.2.1]oct-3-ene-2-carboxamide (Intermediate 17, 204.2 mg, 0.86 mmol) was converted according to the procedure for examples 1 and 2 using ethyl bromodifluoroacetate (0.441 mL, 3.44 mmol) to give 130 mg (47%) of the title compound as an orange foam. Reverse phase chromatography on 40 mg (Synergi Polar RP 21.2 mm×100 mm, 4 μm coupled with YMC C30 20 mm×150 mm, 5 μm; 20% to 40% acetonitrile in water, 10 min; 20 mL/min) afforded the title compound as a white solid (21 mg).

MS: 320 ES+($C_{12}H_{15}F_2N_3O_5$)

$^1$H NMR (300 MHz, DMSO-$d_6$) δ: 1.30 (t, 3H); 1.65 (s, 3H); 3.19 (m, 1H); 3.84 (m, 1H); 4.06 (m, 1H); 4.26 (m, 1H); 4.39 (q, 2H); 6.05 (m, 1H); 7.42 (bs, 1H); 7.87 (bs, 1H).

Example 8

{[(2S,5R)-2-carbamoyl-3-methyl-7-oxo-1,6-diazabicyclo[3.2.1]oct-3-en-6-yl]oxy}(difluoro)acetic acid lithium salt

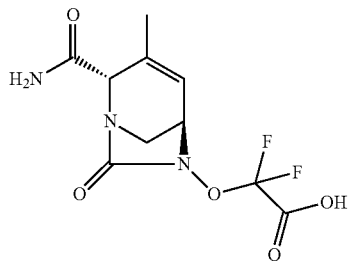 [SMILES: CC1=C[C@@H]2CN(C(=O)N2OC(F)(F)C(=O)O)[C@@H]1C(N)=O]

Ethyl 2-(((2S,5R)-2-carbamoyl-3-methyl-7-oxo-1,6-diazabicyclo[3.2.1]oct-3-en-6-yl)oxy)-2,2-difluoroacetate (Example 7, 113.7 mg, 0.36 mmol) was converted according to the procedure for Examples 3-5. A white solid was obtained after HPLC (Synergi Polar RP 21.2 mm×100 mm, 4 μm coupled with YMC C30 20 mm×150 mm, 5 μm; 100% water, 10 min; 20 mL/min) and lyophilization, 36.7 mg.

MS: 292 ES+($C_{10}H_{11}F_2N_3O_5$)

$^1$H NMR (300 MHz, DMSO-$d_6$) δ: 1.63 (s, 3H); 3.13 (m, 1H); 3.75 (m, 1H); 3.95 (m, 1H); 4.18 (m, 1H); 6.04 (m, 1H); 7.34 (bs, 1H); 7.83 (bs, 1H).

Example 9 ethyl {[(2S,5R)-2-carbamoyl-3-methyl-7-oxo-1,6-diazabicyclo[3.2.1]oct-3-en-6-yl]oxy}acetate

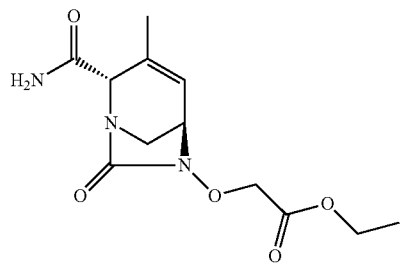 [SMILES: CCOC(=O)CON1C(=O)N2C[C@H]1C=C(C)[C@H]2C(N)=O]

(2S,5R)-6-(allyloxy)-3-methyl-7-oxo-1,6-diazabicyclo[3.2.1]oct-3-ene-2-carboxamide (Intermediate 17, 0.198 g, 0.83 mmol) was converted according to the procedure for Examples 1-2 using ethyl bromoacetate (0.592 mL) to give 147 mg (62%) as an orange solid. Reverse phase chromatography on 41.5 mg (Synergi Polar RP 21.2 mm×100 mm, 4 μm coupled with YMC C30 20 mm×150 mm, 5 μm; 10% to 50% acetonitrile in water, 10 min; 20 mL/min) afforded the title compound as a white solid (32 mg).

MS: 284 ES+($C_{12}H_{17}N_3O_5$)

$^1$H NMR (300 MHz, DMSO-$d_6$) δ: 1.22 (t, 3H); 1.61 (s, 3H); 3.00 (m, 1H); 3.68 (m, 1H); 4.05 (m, 1H); 4.13 (m, 1H); 4.16 (q, 2H); 4.37-4.65 (m, 2H); 6.05 (m, 1H); 7.33 (bs, 1H); 7.77 (bs, 1H).

Example 10

{[(2S,5R)-2-carbamoyl-3-methyl-7-oxo-1,6-diazabicyclo[3.2.1]oct-3-en-6-yl]oxy}acetic acid lithium salt

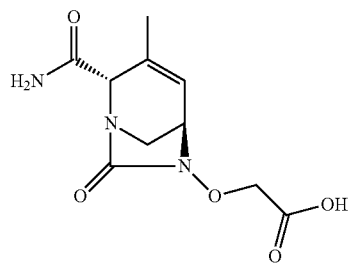

Ethyl 2-(((2S,5R)-2-carbamoyl-3-methyl-7-oxo-1,6-diazabicyclo[3.2.1]oct-3-en-6-yl)oxy)acetate (Example 9, 105.5 mg, 0.37 mmol) was hydrolyzed according to the procedure for Examples 3-5 to give 34 mg (37%) of the title compound after HPLC (Synergi Polar RP 21.2 mm×100 mm, 4 μm; 0% to 20% acetonitrile in water, 10 min; 20 mL/min) and lyophilization.

MS: 256 ES+($C_{10}H_{13}N_3O_5$)

$^1$H NMR (300 MHz, DMSO-$d_6$) δ: 1.60 (s, 3H); 2.96 (m, 1H); 3.58 (m, 1H); 3.87 (m, 2H); 4.05 (m, 1H); 4.27 (m, 1H); 6.08 (m, 1H); 7.27 (bs, 1H); 7.74 (bs, 1H).

Example 11

2-{[(2S,5R)-2-carbamoyl-3-methyl-7-oxo-1,6-diazabicyclo[3.2.1]oct-3-en-6-yl]oxy}-2-fluoropropanoic acid lithium salt (mixture of diastereomers)

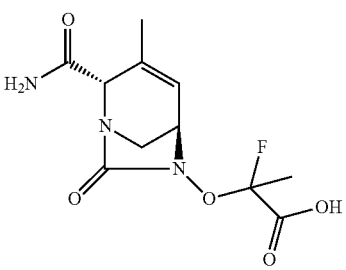

(2S,5R)-6-(allyloxy)-3-methyl-7-oxo-1,6-diazabicyclo[3.2.1]oct-3-ene-2-carboxamide (Intermediate 17, 0.101 g, 0.43 mmol) was converted according to the procedure for Examples 1-2 using methyl 2-bromo-2-fluoropropanoate (0.315 g, 1.70 mmol) to give methyl 2-(((2S,5R)-2-carbamoyl-3-methyl-7-oxo-1,6-diazabicyclo[3.2.1]oct-3-en-6-yl)oxy)-2-fluoropropanoate (0.105 g, 82%) as an orange foam. Reverse phase chromatography (Synergi Polar RP 21.2 mm×100 mm, 4 μm coupled with YMC C30 20 mm×150 mm, 5 μm; 100% water, 10 min; 20 mL/min) afforded the title compound as a white solid (19.1 mg, 19%).

MS: 302 ES+($C_{12}H_{16}FN_3O_5$)

$^1$H NMR (300 MHz, DMSO-$d_6$) δ: 1.67 (m, 6H); 3.04 (m, 1H); 3.72 (m, 4H); 3.80 (m, 1H); 4.17 (m, 1H); 6.02 (m, 1H); 7.36 (bs, 1H); 7.81 (bs, 1H).

Hydrolysis according to the procedure for Example 3-5 afforded 19.1 mg of Example 11 as a white solid after reverse phase purification (Synergi Polar RP 21.2 mm×100 mm, 4 μm coupled with YMC C30 20 mm×150 mm, 5 μm; 100% water, 10 min; 20 mL/min).

MS: 288 ES+($C_{11}H_{14}FN_3O_5$)

$^1$H NMR (300 MHz, DMSO-$d_6$) δ: 1.45 (m, 3H); 1.61 (s, 3H); 3.02 (m, 1H); 3.65 (m, 1H); 3.92-4.09 (m, 1H); 4.11 (m, 1H); 6.04 (m, 1H); 7.32 (m, 1H); 7.80 (m, 1H).

Intermediate 18: isopropyl 2-bromo-2-fluoroacetate

To a solution of ethyl 2-bromo-2-fluoroacetate (0.639 mL, 5.41 mmol) in hexanes (70 mL) and isopropanol (7 mL) at 0° C. was added potassium t-butoxide (0.091 g, 0.81 mmol) in two equal portions, 5 minutes apart. The reaction mixture was stirred for 1 hour at 0° C. The reaction was quenched with concentrated HCl (7 mL) and the layers were separated. The organics were washed twice with water, dried over magnesium sulfate, filtered and concentrated at 0° C. to afford a colorles oil (0.88 g, 4.42 mmol, 82%). NMR confirmed the identity of the product, containing a trace of hexanes. The product was used as is in the next step.

$^1$H NMR (300 MHz, CDCl$_3$-d): δ: 1.34 (m, 6H); 5.18 (m, 1H); 6.45-6.62 (d, 1H).

Reference: Tet. Lett. (2000) 791.

Example 12 propan-2-yl (2R)-{[(2S,5R)-2-carbamoyl-3-methyl-7-oxo-1,6-diazabicyclo[3.2.1]oct-3-en-6-yl]oxy}(fluoro)ethanoate

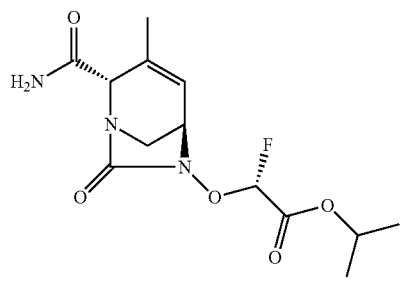 [SMILES: CC1=C[C@@H]2CN(C(=O)N2O[C@H](F)C(=O)OC(C)C)[C@@H]1C(N)=O]

Example 13 propan-2-yl (2S)-{[(2S,5R)-2-carbamoyl-3-methyl-7-oxo-1,6-diazabicyclo[3.2.1]oct-3-en-6-yl]oxy}(fluoro)ethanoate

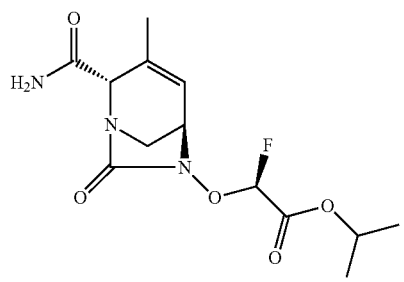 [SMILES: CC1=C[C@@H]2CN(C(=O)N2O[C@@H](F)C(=O)OC(C)C)[C@@H]1C(N)=O]

Example 12-13

(2S,5R)-6-(allyloxy)-3-methyl-7-oxo-1,6-diazabicyclo[3.2.1]oct-3-ene-2-carboxamide (Intermediate 17, 0.103 g, 0.43 mmol) was converted according to the procedure for Examples 1-2 using isopropyl 2-bromo-2-fluoroacetate (Intermediate 18, 0.518 g, 2.60 mmol). 34 mg of each diastereomer was obtained after HPLC (Synergi Polar RP 21.2 mm×100 mm, 4 μm coupled with YMC C30 20 mm×150 mm, 5 μm; 25% to 50% acetonitrile in water, 10 min; 20 mL/min) and lyophilization. The stereochemistry of the ester was assigned by hydrolysis of each ester to its corresponding acid and comparison of the UPLC retention time to those of examples 3 and 4.

Example 12

(First Eluting Ester) 33.4 mg, 24%

MS: 316 ES+(C$_{13}$H$_{18}$FN$_3$O$_5$)

$^1$H NMR (300 MHz, DMSO-d$_6$) δ: 1.22 (m, 6H); 1.63 (s, 3H); 3.03 (m, 1H); 3.75 (m, 1H); 4.01 (m, 1H); 4.19 (m, 1H); 5.00 (m, 1H); 6.01 (m, 1H); 6.11-6.29 (d, 1H); 7.37 (bs, 1H); 7.81 (bs, 1H).

Example 13

(Second Eluting Ester) 33.6 mg, 25%

MS: 316 ES+(C$_{13}$H$_{18}$FN$_3$O$_5$)

$^1$H NMR (300 MHz, DMSO-d$_6$) δ: 1.27 (m, 6H); 1.63 (s, 3H); 3.07 (m, 1H); 3.75 (m, 1H); 3.94 (m, 1H); 4.20 (m, 1H); 5.05 (m, 1H); 6.03 (m, 1H); 6.02-6.21 (d, 1H); 7.37 (bs, 1H); 7.82 (bs, 1H).

Intermediate 19: 2,4-dimethylpentan-3-yl 2-bromo-2-fluoroacetate

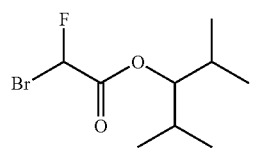

Following the procedure for intermediate 18, using ethyl 2-bromo-2-fluoroacetate (0.639 mL, 5.41 mmol) and 2,4-dimethyl-3-pentanol (7.05 mL, 50.27 mmol) the title compound was obtained as a colorles oil (0.988 g, 3.87 mmol, 71.6%).

$^1$H NMR (300 MHz, CDCl$_3$-d) δ: 0.94 (m, 12H); 2.01 (m, 2H); 4.73 (m, 1H); 6.52-6.69 (d, 1H).

Example 14

2,4-dimethylpentan-3-yl (2S)-{[(2S,5R)-2-carbamoyl-3-methyl-7-oxo-1,6-diazabicyclo[3.2.1]oct-3-en-6-yl]oxy}(fluoro)ethanoate

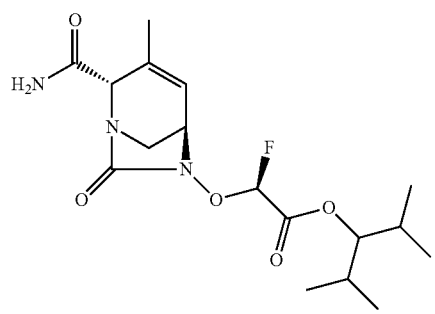 [SMILES: CC1=C[C@@H]2CN(C(=O)N2O[C@@H](F)C(=O)OC(C(C)C)C(C)C)[C@@H]1C(N)=O]

Example 15

2,4-dimethylpentan-3-yl (2R)-{[(2S,5R)-2-carbamoyl-3-methyl-7-oxo-1,6-diazabicyclo[3.2.1]oct-3-en-6-yl]oxy}(fluoro)ethanoate

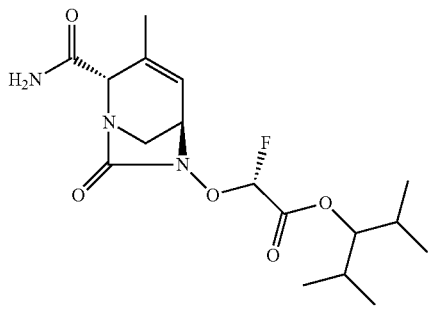 [SMILES: CC1=C[C@@H]2CN(C(=O)N2O[C@H](F)C(=O)OC(C(C)C)C(C)C)[C@@H]1C(N)=O]

Examples 14-15

(2S,5R)-6-(allyloxy)-3-methyl-7-oxo-1,6-diazabicyclo[3.2.1]oct-3-ene-2-carboxamide (Intermediate 17, 0.097 g, 0.41 mmol) was converted according to the procedure for Examples 1-2 using 2,4-dimethylpentan-3-yl 2-bromo-2-fluoroacetate (0.626 g, 2.45 mmol) to give 35 mg of each diastereomer (23% for each, 46% total) after HPLC (Synergi Polar RP 21.2 mm×100 mm, 4 μm coupled with YMC C30 20 mm×150 mm, 5 μm; 40% to 70% acetonitrile in water, 10 min; 20 mL/min) and lyophilization. The stereochemistry of the esters was assigned by hydrolysis of each ester to its corresponding acid and comparison of the UPLC retention time to those of examples 3 and 4.

Example 14

(Second Eluting Peak) 34.5 mg, 23%

MS: 372 ES+($C_{17}H_{26}FN_3O_5$)
$^1$H NMR (300 MHz, DMSO-$d_6$) δ: 0.86 (m, 12H); 1.63 (s, 3H); 1.94 (m, 2H); 3.07 (m, 1H); 3.78 (m, 1H); 3.98 (m, 1H); 4.23 (m, 1H); 4.62 (m, 1H); 6.04 (m, 1H); 6.15-6.34 (d, 1H); 7.38 (bs, 1H); 7.81 (bs, 1H).

Example 15

(First Eluting Peak) 35.2 mg, 23%

MS: 372 ES+($C_{17}H_{26}FN_3O_5$)
$^1$H NMR (300 MHz, DMSO-$d_6$) δ: 0.84 (m, 12H); 1.63 (s, 3H); 1.93 (m, 2H); 3.03 (m, 1H); 3.78 (m, 1H); 4.07 (m, 1H); 4.21 (m, 1H); 4.60 (m, 1H); 5.99 (m, 1H); 6.27-6.45 (d, 1H); 7.37 (bs, 1H); 7.83 (bs, 1H).

Intermediate 20: tetrahydro-2H-pyran-4-yl 2-bromo-2-fluoroacetate

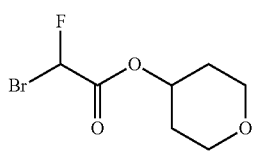 [SMILES: O=C(OC1CCOCC1)C(F)Br]

Following the procedure for Intermediate 18, using ethyl 2-bromo-2-fluoroacetate (0.319 mL, 2.70 mmol) and tetrahydro-2H-pyran-4-ol (2.333 mL, 24.33 mmol), the title compound was obtained as a colorless oil (0.15 g, 0.62 mmol, 29%).

MS: ES+241.2 for C7H10BrFO3

1H NMR (300 MHz, CHLOROFORM-d) δ ppm: 1.47-1.81 (m, 2H) 1.84-2.13 (m, 2H) 3.39-3.68 (m, 2H) 3.75-4.07 (m, 2H) 4.37 (q, J=7.18 Hz, 1H) 6.37-6.74 (m, 1H)

Example 16 tetrahydro-2H-pyran-4-yl {[(2S,5R)-2-carbamoyl-3-methyl-7-oxo-1,6-diazabicyclo[3.2.1]oct-3-en-6-yl]oxy}(fluoro)acetate (mixture of diastereomers)

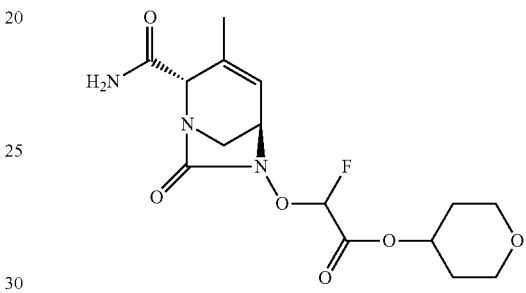

Following the procedure from Examples 1-2, using (2S,5R)-6-(allyloxy)-3-methyl-7-oxo-1,6-diazabicyclo[3.2.1]oct-3-ene-2-carboxamide (Intermediate 17, 40 mg, 0.17 mmol) and tetrahydro-2H-pyran-4-yl 2-bromo-2-fluoroacetate (Intermediate 20, 312 mg, 1.29 mmol), the title compound was obtained after purification by reverse phase ISCO (15.5 g C18 Gold, 0%-80% acetonitrile/water), light orange solid as a mixture of diastereomers. (5.5 mg, 9%)

MS: ES+358.1 for C15H20FN3O6

1H NMR (300 MHz, CHLOROFORM-d) δ ppm 1.15-1.42 (m, 2H) 1.60 (br. s., 2H) 1.92 (s, 3H) 3.14-3.45 (m, 2H) 3.56 (d, J=11.52 Hz, 1H) 3.88-4.13 (m, 2H) 4.20-4.50 (m, 2H) 5.09 (br. s., 1H) 5.35-5.58 (m, 1H) 5.63-5.96 (m, 1H) 6.09 (br. s., 1H)

Intermediate 21: 2-methoxyethyl 2-bromo-2-fluoroacetate

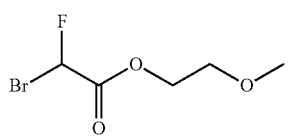

According to the procedure for Intermediate 18, using ethyl 2-bromo-2-fluoroacetate (1.278 mL, 10.81 mmol) and 2-methoxyethanol (13.94 mL, 183.79 mmol) the title compound was obtained as a colorles oil (1.04 g, 4.84 mmol, 44.7%). NMR was consistent with a 3:1 mixture of product: starting material, which was used as is in the next step.

$^1$H NMR (300 MHz, DMSO-$d_6$) δ: 3.27 (s, 3H); 3.57 (m, 2H); 4.35 (m, 2H); 7.22-7.38 (d, 1H).

Example 17

2-methoxyethyl {[(2S,5R)-2-carbamoyl-3-methyl-7-oxo-1,6-diazabicyclo[3.2.1]oct-3-en-6-yl]oxy}(fluoro)acetate (mixture of diastereomers)

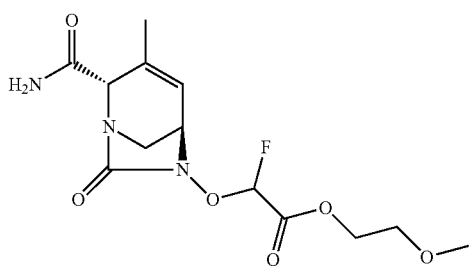 [SMILES: COCCOC(=O)C(F)ON1C(=O)N2C[C@H]1C=C(C)[C@H]2C(N)=O]

Example 18

2-methoxyethyl (2R)-{[(2S,5R)-2-carbamoyl-3-methyl-7-oxo-1,6-diazabicyclo[3.2.1]oct-3-en-6-yl]oxy}(fluoro)ethanoate

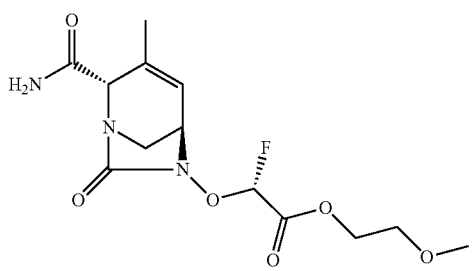

Example 19

2-methoxyethyl (2S)-{[(2S,5R)-2-carbamoyl-3-methyl-7-oxo-1,6-diazabicyclo[3.2.1]oct-3-en-6-yl]oxy}(fluoro)ethanoate

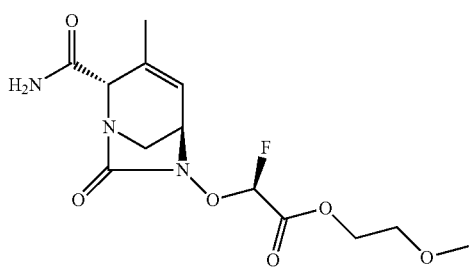 [SMILES: COCCOC(=O)[C@H](F)ON1C(=O)N2C[C@H]1C=C(C)[C@H]2C(N)=O]

Example 17-19

According to the procedure for Examples 1-2, (2S,5R)-6-(allyloxy)-3-methyl-7-oxo-1,6-diazabicyclo[3.2.1]oct-3-ene-2-carboxamide (Intermediate 17, 0.101 g, 0.43 mmol) was converted into the title compound using 2-methoxyethyl 2-bromo-2-fluoroacetate (Intermediate 21, 0.549 g, 2.55 mmol). The following products were obtained after HPLC (Synergi Polar RP 21.2 mm×100 mm, 4 μm coupled with YMC C30 20 mm×150 mm, 5 μm; 30% to 50% acetonitrile in water, 10 min; 20 mL/min) and lyophilization (wherein the stereochemistry of the esters was assigned by hydrolysis of each ester to its corresponding acid and comparison of the UPLC retention time to those of Examples 3 & 4):

Example 17

Mixture of Diastereomers: 14.3 mg, 10.1%

MS: 332 ES+($C_{13}H_{18}FN_3O_5$)
$^1$H NMR (300 MHz, DMSO-$d_6$) δ: 1.63 (s, 6H); 3.07 (m, 2H); 3.26 (s, 3H); 3.27 (s, 3H); 3.54 (m, 2H); 3.59 (m, 2H); 3.73 (m, 1H); 3.77 (m, 1H); 3.98 (m, 1H); 4.03 (m, 1H); 4.19 (m, 1H); 4.32 (m, 4H); 6.02 (m, 2H); 6.11-6.30 (d, 1H); 6.17-6.35 (d, 1H); 7.37 (bs, 2H); 7.81 (bs, 2H).

Example 18

(First Eluting Ester): 22 mg, 15.6%

MS: 332 ES+($C_{13}H_{18}FN_3O_5$)
$^1$H NMR (300 MHz, DMSO-$d_6$) δ: 1.63 (s, 3H); 3.06 (m, 1H); 3.27 (s, 3H); 3.55 (m, 2H); 3.77 (m, 1H); 4.05 (m, 1H); 4.20 (m, 1H); 4.30 (m, 2H); 6.02 (m, 1H); 6.18-6.36 (d, 1H); 7.37 (bs, 1H); 7.82 (bs, 1H).

Example 19

(Second Eluting Ester): 22.8 mg, 16.1%

MS: 332 ES+($C_{13}H_{18}FN_3O_5$)
$^1$H NMR (300 MHz, DMSO-$d_6$) δ: 1.62 (s, 3H); 3.07 (m, 1H); 3.27 (s, 3H); 3.59 (m, 2H); 3.75 (m, 1H); 3.99 (m, 1H); 4.20 (m, 1H); 4.34 (m, 2H); 6.03 (m, 1H); 6.11-6.30 (d, 1H); 7.37 (bs, 1H); 7.83 (bs, 1H).

Intermediate 22: (S)-sec-butyl 2-bromo-2-fluoroacetate

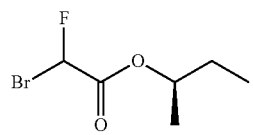

To a solution of ethyl 2-bromo-2-fluoroacetate (0.319 mL, 2.70 mmol) and (S)-butan-2-ol (3.72 mL, 40.54 mmol) in hexane (35 mL) at 0° C. was added potassium t-butoxide (0.061 g, 0.54 mmol) in two equal portions 5 minutes apart. The reaction mixture was stirred for 2 hours at 0° C., then overnight at room temperature. The reaction was quenched with saturated ammonium chloride and the layers were separated. The organics were washed three times with water, dried over magnesium sulfate, filtered and concentrated at 0° C. to afford a colorless oil, 0.550 g, 96%.

$^1$H NMR (300 MHz, DMSO-$d_6$) δ: 0.88 (m, 3H); 1.25 (m, 3H); 1.61 (m, 2H); 4.91 (m, 1H); 7.16-7.33 (m, 1H).

Intermediate 23: (R)-sec-butyl 2-bromo-2-fluoroacetate

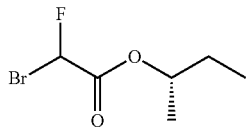

To a solution of ethyl 2-bromo-2-fluoroacetate (0.319 mL, 2.70 mmol) and (R)-butan-2-ol (3.72 mL, 40.54 mmol) in hexane (35 mL) at 0° C. was added potassium t-butoxide (0.061 g, 0.54 mmol) in two equal portions 5 minutes apart. The reaction mixture was stirred for 2 hours at 0° C., then at room temperature for 2 hours. Then, more (R)-butan-2-ol (3.72 mL, 40.54 mmol) was added followed by another 0.1 eq of potassium t-butoxide. The reaction mixture was stirred at room temperature overnight. 0.1 eq of potassium t-butoxide was added every 2 hours for 6 hours. The reaction was quenched with saturated ammonium chloride and the layers were separated. The organics were washed four times with water, dried over magnesium sulfate, filtered and concentrated at 0° C. to afford a colorles oil, 422 mg, 73%.

$^1$H NMR (300 MHz, DMSO-$d_6$) δ: 0.88 (m, 3H); 1.25 (m, 3H); 1.61 (m, 2H); 4.91 (m, 1H); 7.16-7.33 (m, 1H).

Example 20

(2R)-(S)-sec-butyl 2-(((2S,5R)-2-carbamoyl-3-methyl-7-oxo-1,6-diazabicyclo[3.2.1]oct-3-en-6-yl)oxy)-2-fluoroacetate

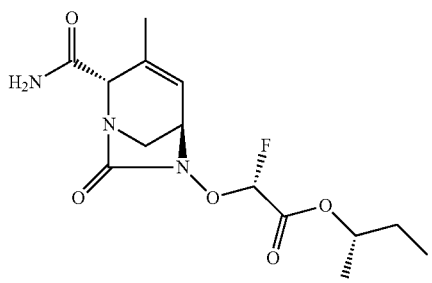

Example 21

(2S)-(S)-sec-butyl 2-(((2S,5R)-2-carbamoyl-3-methyl-7-oxo-1,6-diazabicyclo[3.2.1]oct-3-en-6-yl)oxy)-2-fluoroacetate

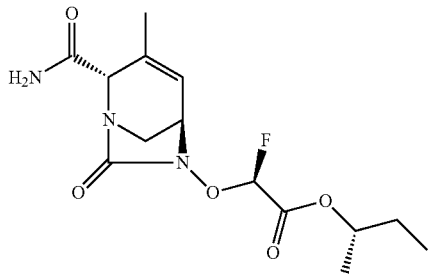

Example 20-21

Prepared according to the procedure for Examples 1-2. To a solution of (2S,5R)-6-(allyloxy)-3-methyl-7-oxo-1,6-diazabicyclo[3.2.1]oct-3-ene-2-carboxamide (Intermediate 17, 0.196 g, 0.83 mmol) in methanol (5 mL) at room temperature was added 1,3-dimethylbarbituric acid (0.258 g, 1.65 mmol) and tetrakis(triphenylphosphine)palladium(0) (0.095 g, 0.08 mmol). The reaction was stirred at room temperature for 2 hours then concentrated to afford an orange film. The orange film was dissolved in DMF (5 mL), and potassium carbonate (0.343 g, 2.48 mmol) and (S)-sec-butyl 2-bromo-2-fluoroacetate (Intermediate 22, 0.528 g, 2.48 mmol) were added. The reaction mixture was stirred for ~5 hours at room temperature then diluted with ethyl acetate and filtered through a 0.45 μm filter to remove solid potassium carbonate. The filtrate was washed three times with 1:1 brine:water. The organics were dried over magnesium sulfate, filtered and concentrated. Silica gel chromatography (0%-65% ethyl acetate/hexanes) afforded (S)-sec-butyl 2-(((2S,5R)-2-carbamoyl-3-methyl-7-oxo-1,6-diazabicyclo[3.2.1]oct-3-en-6-yl)oxy)-2-fluoroacetate (0.218 g, 80%) as a light yellow foam, ~1:1 mixture of diastereomers. Separation of diastereomers was done on reverse phase HPLC (Atlantis T3 19 mm×150 mm, 30-50% acetonitrile in water, 20 mL/min, 15 min). The stereochemistry of the esters was assigned by hydrolysis of each ester to its corresponding acid and comparison of the UPLC retention time to those of examples 3 and 4.

Example 20

(First Eluting Peak) 84 mg, 31%

MS: 330 ES+($C_{14}H_{20}FN_3O_5$)
$^1$H NMR (300 MHz, DMSO-$d_6$) δ: 0.84 (t, 3H); 1.22 (d, 3H); 1.55 (m, 2H); 1.63 (s, 3H); 3.03 (m, 1H); 3.76 (d, 1H); 4.04 (m, 1H); 4.19 (s, 1H); 4.86 (m, 1H); 6.01 (m, 1H); 6.13-6.31 (m, 1H); 7.37 (bs, 1H); 7.82 (bs, 1H).

Example 21

(Second Eluting Peak) 85 mg, 31%

MS: 330 ES+($C_{14}H_{20}FN_3O_5$)
$^1$H NMR (300 MHz, DMSO-$d_6$) δ: 0.84 (t, 3H); 1.22 (d, 3H); 1.55 (m, 2H); 1.63 (s, 3H); 3.03 (m, 1H); 3.76 (d, 1H); 4.04 (m, 1H); 4.19 (s, 1H); 4.86 (m, 1H); 6.01 (m, 1H); 6.13-6.31 (m, 1H); 7.37 (bs, 1H); 7.82 (bs, 1H).

Example 22

(2R)-(R)-sec-butyl 2-(((2S,5R)-2-carbamoyl-3-methyl-7-oxo-1,6-diazabicyclo[3.2.1]oct-3-en-6-yl)oxy)-2-fluoroacetate

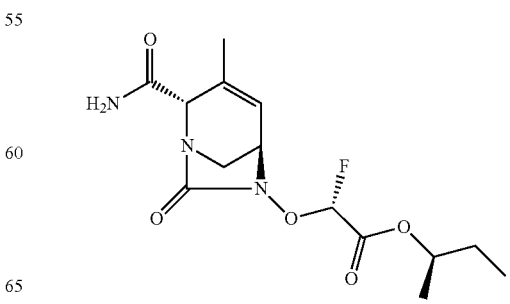

Example 23

(2S)-(R)-sec-butyl 2-(((2S,5R)-2-carbamoyl-3-methyl-7-oxo-1,6-diazabicyclo[3.2.1]oct-3-en-6-yl)oxy)-2-fluoroacetate

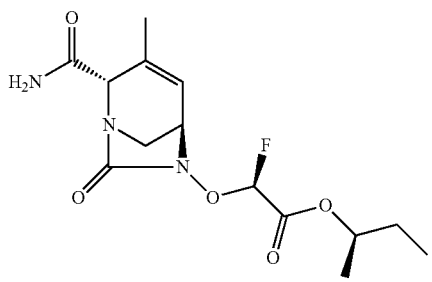 [SMILES: CC[C@@H](C)OC(=O)[C@H](F)ON1C(=O)N2C[C@H]1C=C(C)[C@H]2C(N)=O]

Example 22-23

Examples 22-23 were prepared according to the procedure for Examples 1-2. To a solution of (2S,5R)-6-(allyloxy)-3-methyl-7-oxo-1,6-diazabicyclo[3.2.1]oct-3-ene-2-carboxamide (Intermediate 17, 0.202 g, 0.85 mmol) in methanol (5 mL) at room temperature was added 1,3-dimethylbarbituric acid (0.266 g, 1.70 mmol) and tetrakis(triphenylphosphine)-palladium(0) (0.098 g, 0.09 mmol). The reaction was stirred at room temperature for 2 hours. The reaction mixture was concentrated to afford an orange film. The orange film was dissolved in DMF (5 mL), and potassium carbonate (0.353 g, 2.55 mmol) and (R)-sec-butyl 2-bromo-2-fluoroacetate (Intermediate 23, 0.421 g, 1.98 mmol) were added. The reaction mixture was stirred for 3 hours at room temperature then diluted with ethyl acetate and filtered through a 0.45 μm filter to remove solid potassium carbonate. The filtrate was washed three times with 1:1 brine:water. The organics were dried over magnesium sulfate, filtered and concentrated. Silica gel chromatography (0%-65% ethyl acetate/hexanes) afforded (R)-sec-butyl 2-(((2S,5 R)-2-carbamoyl-3-methyl-7-oxo-1,6-diazabicyclo[3.2.1]oct-3-en-6-yl)oxy)-2-fluoroacetate (0.220 g, 78%) as an orange foam, 1:1 mixture of diastereomers. Separation of diastereomers was done on reverse phase HPLC (Atlantis T3 19 mm×150 mm, 30-50% acetonitrile in water, 20 mL/min, 15 min). The stereochemistry of the esters was assigned by hydrolysis of each ester to its corresponding acid and comparison of the UPLC retention time to those of examples 3 and 4.

Example 22

(First Eluting Peak) 90 mg, 32%

MS: 330 ES+($C_{14}H_{20}FN_3O_5$)
$^1$H NMR (300 MHz, DMSO-$d_6$) δ: 0.87 (t, 3H); 1.17 (d, 3H); 1.59 (m, 2H); 1.63 (s, 3H); 3.03 (m, 1H); 3.76 (d, 1H); 4.02 (m, 1H); 4.19 (s, 1H); 4.86 (m, 1H); 6.02 (m, 1H); 6.16-6.34 (m, 1H); 7.37 (bs, 1H); 7.82 (bs, 1H).

Example 23

(Second Eluting Peak) 87 mg, 31%

MS: 330 ES+($C_{14}H_{20}FN_3O_5$)
$^1$H NMR (300 MHz, DMSO-$d_6$) δ: 0.88 (t, 3H); 1.24 (d, 3H); 1.61 (m, 2H); 1.63 (s, 3H); 3.08 (m, 1H); 3.76 (d, 1H); 3.94 (m, 1H); 4.21 (s, 1H); 4.89 (m, 1H); 6.04 (m, 1H); 6.03-6.22 (m, 1H); 7.38 (bs, 1H); 7.82 (bs, 1H).

Intermediate 24: pentan-3-yl 2-bromo-2-fluoroacetate

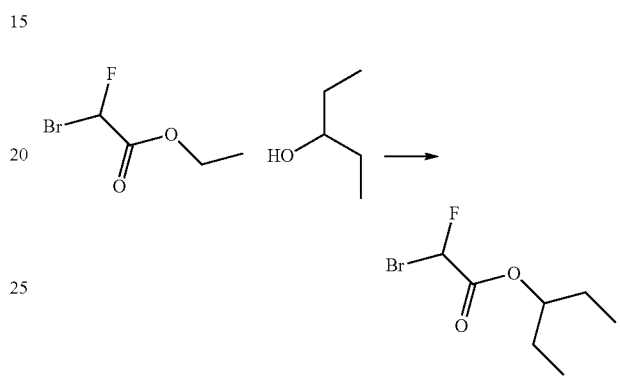

Ethyl 2-bromo-2-fluoroacetate (0.639 ml, 5.41 mmol) was added to a mixture of dry pentan-3-ol (4.68 ml, 43.25 mmol) and hexane (20 ml). The resulting mixture was cooled to 0° C. KOtBu (0.091 g, 0.81 mmol) was added and the mixture was allowed to stir for 16 h at 25° C. The reaction was then quenched with 1N HCl (30 mL), washed with water (50 mL) and brine (50 mL), dried with $Na_2SO_4$, and concentrated. The crude material was purified by flash chromatography (20 g silica gel, 0-100% $Et_2O$ in hexane, 25 min) to give pentan-3-yl 2-bromo-2-fluoroacetate (0.754 g, 61.4%) as a colorless oil.

$^1$H NMR (300 MHz, CHLOROFORM-d) δ ppm 0.96 (td, J=7.46, 2.08 Hz, 6H) 1.60-1.76 (m, 4H) 4.93 (dt, J=12.28, 6.33 Hz, 1H) 6.50 (s, 0.5 H) 6.67 (s, 0.5 H)

Example 24

(R)-pentan-3-yl 2-((2S,5R)-2-carbamoyl-3-methyl-7-oxo-1,6-diazabicyclo[3.2.1]oct-3-en-6-yloxy)-2-fluoroacetate

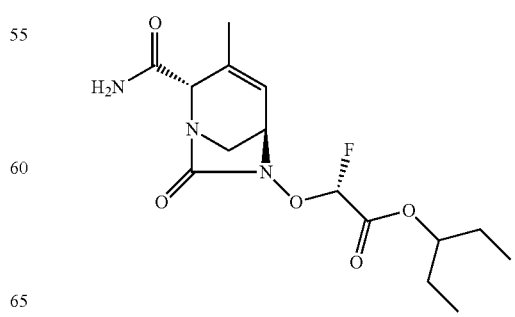

Example 25

(S)-pentan-3-yl 2-((2S,5R)-2-carbamoyl-3-methyl-7-oxo-1,6-diazabicyclo[3.2.1]oct-3-en-6-yloxy)-2-fluoroacetate

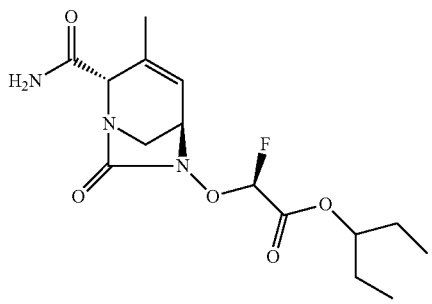

Example 24-25

Examples 24-25 were prepared according to the procedure for Examples 1-2. To a solution of (2S,5R)-6-(allyloxy)-3-methyl-7-oxo-1,6-diazabicyclo[3.2.1]oct-3-ene-2-carboxamide (Intermediate 17, 272 mg, 1.15 mmol) in methanol (5 mL) at room temperature was added 1,3-dimethylbarbituric acid (358 mg, 2.29 mmol) and Pd(Ph$_3$P)$_4$ (132 mg, 0.11 mmol). The reaction was stirred at room temperature for 2 hours. The mass of the desired product was observed and no starting material was seen by LCMS. The reaction mixture was concentrated to afford an orange film. The orange film was dissolved in DMF (5 mL), and K$_2$CO$_3$ (475 mg, 3.44 mmol) and pentan-3-yl 2-bromo-2-fluoroacetate (Intermediate 24, 751 mg, 3.31 mmol) were added. The reaction mixture was stirred overnight at room temperature then diluted with ethyl acetate and filtered through a 0.45μ filter to remove solid potassium carbonate. The filtrate was washed twice with 1:1 brine:water. The organics were dried over magnesium sulfate, filtered and concentrated. Silica gel chromatography (0%-70% ethyl acetate/hexanes) afforded pentan-3-yl 2-(((2S,5R)-2-carbamoyl-3-methyl-7-oxo-1,6-diazabicyclo[3.2.1]oct-3-en-6-yl)oxy)-2-fluoroacetate (320 mg, 81%) as a light yellow foam. LCMS and NMR confirm it is a 1:1 mixture of diastereomers. The diastereomers were separated on reverse phase HPLC (Atlantis T3 4.6 mm×50 mm 5 μm column, from 30 to 50% ACN in water in 5 min, flow rate 1 ml/min).

Example 24

125 mg, 32%

UPLC LCMS 2min_Acid_CV10 method acid condition retention time: 0.86 min, 344 (M+H)$^+$ $^1$H NMR (300 MHz, CHLOROFORM-d) δ ppm 0.92 (td, J=7.46, 3.21 Hz, 6H) 1.61-1.75 (m, 4H) 1.93 (s, 3H) 3.21-3.35 (m, 2H) 4.07 (dd, J=4.91, 2.64 Hz, 1H) 4.36 (s, 1H) 4.91 (quin, J=6.18 Hz, 1H) 5.47 (br. s., 1H) 5.77 (s, 0.5 H) 5.94 (s, 0.5 H) 6.07-6.12 (m, 1H) 6.59 (br. s., 1H)

Example 25

125 mg, 32%

UPLC LCMS 2min_Acid_CV10 method acid condition retention time: 0.91 min, 344 (M+H)+

$^1$H NMR (300 MHz, CHLOROFORM-d) δ ppm 0.93 (t, J=7.46 Hz, 3H) 0.95 (t, J=7.46 Hz, 3 H) 1.63-1.74 (m, 4H) 1.93 (s, 3H) 3.20-3.38 (m, 2H) 4.02 (dd, J=5.00, 2.55 Hz, 1H) 4.35 (s, 1H) 4.92 (quin, J=6.18 Hz, 1H) 5.56 (br. s., 1H) 5.69 (s, 0.5 H) 5.89 (s, 0.5 H) 6.07-6.14 (m, 1H) 6.64 (br. s., 1H)

Intermediate 25: N-[(3R,6S)-6-[[(tert-butyldimethylsilyl)oxy]methyl]-5-methyl-1,2,3,6-tetrahydropyridin-3-yl]-2-nitro-N-(prop-2-en-1-yloxy)benzene-1-sulfonamide

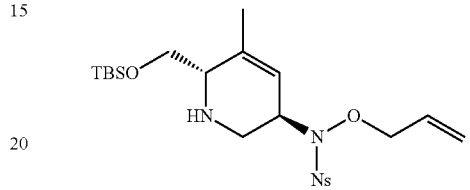

Into a 250-mL round-bottom flask purged and maintained with an inert atmosphere of nitrogen, was placed a solution of tert-butyl (3R,6S)-6-tert-butyldimethylsilyl)-oxy]methyl]-5-methyl-3-[N-(prop-2-en-1-yloxy)(2-nitrobenzene)sulfonamido]-1,2,3,6-tetrahydropyridine-1-carboxylate (Intermediate 11, 13.6 g, 22.75 mmol, 1 eq.) in dichloromethane (100 mL). This was followed by the addition of ZnBr$_2$ (10.2 g, 45.29 mmol, 2 eq.) in several batches. The resulting solution was stirred overnight at room temperature. The resulting solution was diluted with 500 mL of dichloromethane. The resulting mixture was washed with 2×200 mL of sodium bicarbonate (aq) and 2×200 mL of NH$_4$Cl (aq). The mixture was dried over anhydrous sodium sulfate and concentrated under vacuum. This resulted in 12 g (crude product) of the title compound as yellow oil.

MS: 498 ES+(C$_{22}$H$_{35}$N$_3$O$_6$SSi)

Intermediate 26: (3R,6S)-6-[[(tert-butyldimethylsilyl)oxy]methyl]-5-methyl-N-(prop-2-en-1-yloxy)-1,2,3,6-tetrahydropyridin-3-amine

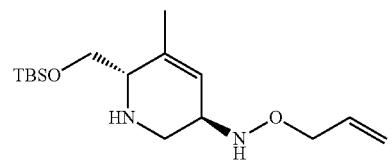 [SMILES: C=CCON[C@@H]1C=C(C)[C@@H](CO[Si](C)(C)C(C)(C)C)NC1]

Into a 250-mL round-bottom flask, purged and maintained with an inert atmosphere of nitrogen, was placed a solution of N—R3R,6S)-6-[[(tert-butyldimethylsilyl)oxy]methyl]-5-methyl-1,2,3,6-tetrahydropyridin-3-yl]-2-nitro-N-(prop-2-en-1-yloxy)benzene-1-sulfonamide (Intermediate 25, 12 g, 24.11 mmol, 1 eq.) in N,N-dimethylformamide (100 mL), 2-sulfanylacetic acid (4.4 g, 47.77 mmol, 2 eq.). This was followed by the addition of LiOH (5.8 g, 242.17 mmol, 10 eq.), in portions. The resulting solution was stirred for 2 h at room temperature, then diluted with 500 mL of water, and extracted with 5×200 mL of ethyl acetate, and the organic layers combined. The organic mixture was washed with 3×200 mL of brine and 2×200 mL of sodium bicarbonate (aq.). The mixture was dried over anhydrous sodium sulfate and concentrated under vacuum. This resulted in 8.4 g (crude product) of the title compound as yellow oil.
MS: 313 ES+($C_{16}H_{32}N_2O_2Si$)

Intermediate 27: (2S,5R)-2-[[(tert-butyldimethylsilyl)oxy]methyl]-3-methyl-6-(prop-2-en-1-yloxy)-1,6-diazabicyclo[3.2.1]oct-3-en-7-one

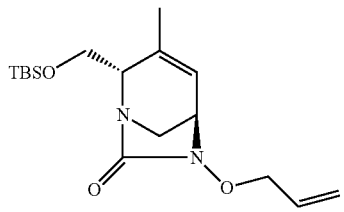 [SMILES: C=CCON1C(=O)N2C[C@H]1C=C(C)[C@H]2CO[Si](C)(C)C(C)(C)C]

Into a 2 L 3-necked round-bottom flask, purged and maintained with an inert atmosphere of nitrogen, was placed a solution of (3R,6S)-6-[[(tert-butyldimethylsilyl)oxy]methyl]-5-methyl-N-(prop-2-en-1-yloxy)-1,2,3,6-tetrahydropyridin-3-amine (Intermediate 26, 8.4 g, 26.88 mmol, 1 eq.) in acetonitrile (1.6 L) and N,N-diisopropylethylamine (14.2 g, 109.87 mmol, 4 eq.). This was followed by the addition of a solution of ditrichloromethyl carbonate (2.9 g, 9.77 mmol, 0.4 eq.) in acetonitrile (100 mL) dropwise with stirring at −15° C. over 3 hr. The resulting solution was stirred overnight at room temperature. The resulting mixture was concentrated under vacuum. The crude product was diluted with 500 mL of ethyl acetate. The resulting mixture was washed with 2×400 mL of $NH_4Cl$ (aq.) and 2×400 mL of brine, then concentrated under vacuum. The residue was applied onto a silica gel column with ethyl acetate/petroleum ether (1:10). This resulted in 3.9 g (43%) of the title compound as yellow oil.
MS: 339 ES+($C_{17}H_{30}N_2O_3Si$)

Intermediate 28: (2S,5R)-2-(hydroxymethyl)-3-methyl-6-(prop-2-en-1-yloxy)-1,6-diazabicyclo[3.2.1]oct-3-en-7-one

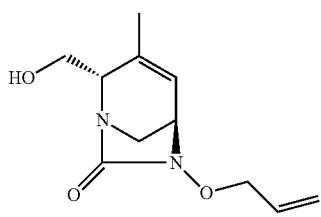 [SMILES: C=CCON1C(=O)N2C[C@H]1C=C(C)[C@H]2CO]

Into a 100 mL round-bottom flask was placed tetrahydrofuran (30 mL) and (2S,5R)-2-[[(tert-butyldimethylsilyl)oxy]methyl]-3-methyl-6-(prop-2-en-1-yloxy)-1,6-diazabicyclo[3.2.1]oct-3-en-7-one (Intermediate 27, 3.2 g, 9.45 mmol, 1 eq.) and the solution was cooled to 0° C., then TBAF (14.2 mL 1N in THF, 1.5 eq.) was added dropwise. The reaction mixture was stirred for 1 h at 0° C. in a water/ice bath. The resulting mixture was concentrated under vacuum. The residue was applied onto a silica gel column with ethyl acetate/petroleum ether (1:5-1:2). This resulted in 1.6 g (75%) of the title compound as a light yellow solid.
MS: 225 ES+($C_{11}H_{16}N_2O_3$)

$^1H$ NMR (300 MHz, $CDCl_3$) δ 1.63 (3H, d), 3.20 (2H, d), 3.62-3.84 (2H, m), 3.85-3.90 (2H, m), 4.35-4.48 (2H, m), 5.28-5.39 (2H, m), 5.95-6.08 (2H, m).

Intermediate 29: 2S,5R)-3-methyl-7-oxo-6-(prop-2-en-1-yloxy)-1,6-diazabicyclo[3.2.1]oct-3-ene-2-carboxylic acid

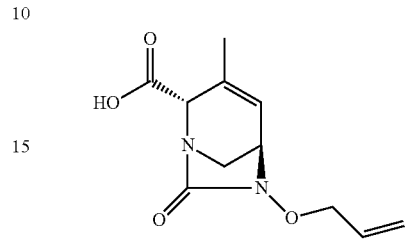

To a solution of $H_5IO_6$(12.93 g,56.71 mmol) in wet $CH_3CN$ (150 mL, 0.75% $H_2O$ v/v) at RT was added $CrO_3$ (128 mg, 1.28 mmol). The mixture was stirred until it was completely dissolved. Into a 100 mL round-bottom flask, was placed wet acetonitrile (35 mL) and (2S,5R)-2-(hydroxymethyl)-3-methyl-6-(prop-2-en-1-yloxy)-1,6-diazabicyclo[3.2.1]oct-3-en-7-one (Intermediate 28, 740 mg, 3.30 mmol, 1 eq.) and it was cooled to 0° C. Then, the above oxidation solution (35 mL, 3 eq.) was added dropwise over the course of 30 min at 0° C. The resulting solution was stirred for 1 h at 0° C. in a water/ice bath. The reaction mixture was then diluted with 200 mL of chloroform and 50 mL of citric acid solution (25%). The organic layer was isolated and then washed by 3×50 mL of brine, dried over anhydrous sodium sulfate and concentrated under vacuum. This resulted in 0.70 g crude of the title compound as yellow oil.
MS: 239 ES+($C_{11}H_{16}N_2O_4$)

Intermediate 30: (2S,5R)—N'-acetyl-6-(allyloxy)-3-methyl-7-oxo-1,6-diazabicyclo[3.2.1]oct-3-ene-2-carbohydrazide

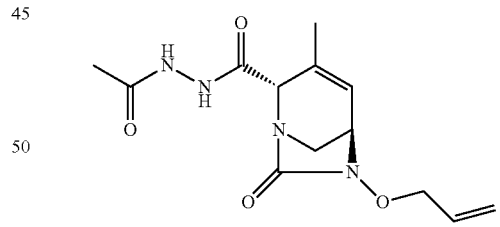

To a solution of (2S,5R)-6-(allyloxy)-3-methyl-7-oxo-1,6-diazabicyclo[3.2.1]oct-3-ene-2-carboxylic acid (Intermediate 29, 195.7 mg, 0.82 mmol) in DCM (10 mL) at room temperature was added 1-(3-dimethylaminopropyl)-3-ethylcarbodiimide hydrochloride (236 mg, 1.23 mmol), 1-hydroxybenzotriazole hydrate (219 mg, 1.23 mmol) and monoacetyl hydrazine (101 mg, 1.23 mmol). The mixture was cooled to 0° C. and DIEA (0.715 mL, 4.11 mmol) was added. The reaction mixture was allowed to warm to rt and stirred at room temperature overnight, then diluted with ethyl acetate and washed twice with 1:1 brine:water. The aqueous washes contained some product and were back extracted twice with ethyl acetate and once with ~5% methanol in dichloromethane. The combined organics were dried over magnesium sulfate, filtered and concentrated. Silica gel chromatography (0%-5% methanol/dichloromethane) afforded the title compound as a white foam (45.5 mg, 19%, ~50% purity).

MS: 295 ES+($C_{13}H_{18}N_4O_4$)

$^1$H NMR (300 MHz, DMSO-$d_6$) δ: 1.62 (s, 3H); 1.86 (m, 3H); 2.88 (m, 1H); 3.40 (m, 1H); 3.81 (m, 1H); 3.95 (m, 1H); 4.38 (m, 2H); 5.32 (m, 2H); 5.94 (m, 1H); 6.11 (m, 1H); 9.86 (s, 1H); 10.24 (bs, 1H).

Example 26 ethyl 2-(((2S,5R)-2-(2-acetylhydrazinecarbonyl)-3-methyl-7-oxo-1,6-diazabicyclo[3.2.1]oct-3-en-6-yl)oxy)-2-fluoroacetate

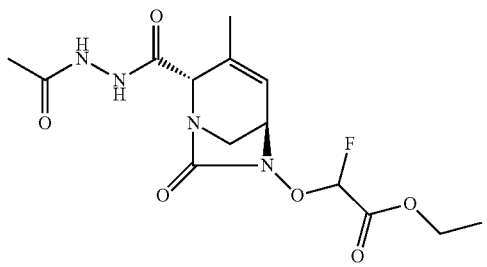 [SMILES: CCOC(=O)C(F)ON1C(=O)N2C[C@H]1C=C(C)[C@H]2C(=O)NNC(C)=O]

To a solution of (2S,5R)—N'-acetyl-6-(allyloxy)-3-methyl-7-oxo-1,6-diazabicyclo[3.2.1]oct-3-ene-2-carbohydrazide (Intermediate 30, 22.75 mg, 0.08 mmol,) in methanol (3 mL) at room temperature was added 1,3-dimethylbarbituric acid (48.3 mg, 0.31 mmol) and tetrakis(triphenylphosphine)palladium(0) (17.87 mg, 0.02 mmol). The reaction was stirred at room temperature for 2 hours then concentrated to afford an orange film. The orange film was dissolved in DMF (3 mL). Potassium carbonate (64.1 mg, 0.46 mmol) and ethyl 2-bromo-2-fluoroacetate (0.055 mL, 0.46 mmol) were added. The reaction mixture was stirred for ~5 hours at room temperature then diluted with ethyl acetate and filtered through a 0.45 μm filter to remove solid potassium carbonate. The filtrate was washed three times with 1:1 brine:water. The organics were dried over magnesium sulfate, filtered and concentrated. Silica gel chromatography (0%-65% ethyl acetate/hexanes) afforded the title compound as an orange foam (25.9 mg, 94%). The two diastereomers were present in a 1:1 ratio. The material was dissolved in ethyl acetate and washed three times with 1:1 brine:water. The organics were dried over magnesium sulfate, filtered and concetrated. Another silica gel column was run (0%-30% acetone/dichloromethane) to afford pure title compound (16.6 mg, 60%).

MS: 359 ES+($C_{14}H_{19}FN_4O_6$)

$^1$H NMR (300 MHz, DMSO-$d_6$) δ: 1.24 (m, 3H); 1.65 (s, 3H); 1.86 (m, 3H); 3.09 (m, 1H); 3.89 (d, 1H); 4.01 (m, 1H); 4.25 (m, 3H); 6.09 (m, 1H); 6.20 (m, 1H); 9.90 (s, 1H); 10.30 (d, 1H).

Example 27

2-(((2S,5R)-2-(2-acetylhydrazinecarbonyl)-3-methyl-7-oxo-1,6-diazabicyclo[3.2.1]oct-3-en-6-yl)oxy)-2-fluoroacetic acid lithium salt

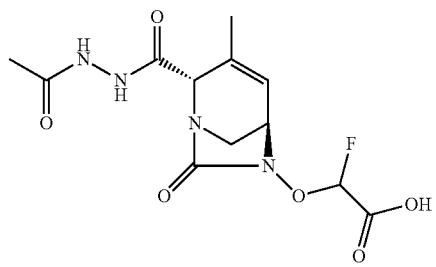 [SMILES: CC(=O)NNC(=O)[C@@H]1C(C)=C[C@@H]2CN1C(=O)N2OC(F)C(=O)O]

To a solution of ethyl 2-(((2S,5R)-2-(2-acetylhydrazinecarbonyl)-3-methyl-7-oxo-1,6-diazabicyclo[3.2.1]oct-3-en-6-yl)oxy)-2-fluoroacetate (Example 26, 16.6 mg, 0.05 mmol) in THF (1 mL) and water (0.33 mL) at 0° C. was added lithium hydroxide (1M) (0.05 mL, 0.05 mmol), and stirred for 10 minutes at 0° C. Another 0.2 eq of lithium hydroxide was added. After 30 minutes another 0.2 equivalents of lithium hydroxide were added. The reaction mixture was stirred for an additional 30 minutes. HCl (0.5M) (0.046 mL, 0.02 mmol) was added to adjust the pH to ~4-5. The reaction mixture was extracted with ethyl acetate twice. The aqueous layer was frozen and lyophilized. 15 mg of the title compound was obtained as an orange solid. The 2 diastereomers were present in a 1:1 ratio.

MS: 331 ES+($C_{12}H_{15}FN_4O_6$)

$^1$H NMR (300 MHz, DMSO-$d_6$) δ: 1.65 (s, 3H); 1.87 (m, 3H); 3.08 (m, 1H); 3.84 (m, 1H); 4.03 (m, 1H); 4.23 (s, 1H); 5.23 (m, 1H); 6.10 (m, 1H); 9.88 (s, 1H); 10.26 (bs, 1H).

Intermediate 31: tert-butyl 4-((2S,5R)-6-(allyloxy)-3-methyl-7-oxo-1,6-diazabicyclo[3.2.1]oct-3-enecarboxamido)benzylcarbamate

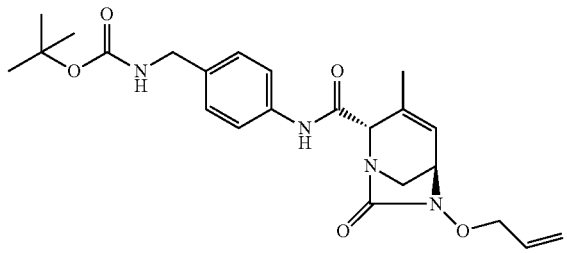 [SMILES: C=CCON1C(=O)N2C[C@H]1C=C(C)[C@H]2C(=O)Nc1ccc(CNC(=O)OC(C)(C)C)cc1]

To a solution of (2S,5R)-6-(allyloxy)-3-methyl-7-oxo-1,6-diazabicyclo[3.2.1]oct-3-ene-2-carboxylic acid (Intermediate 29, 130.5 mg, 0.55 mmol) in DMF (5 mL) at room temperature was added tert-butyl 4-aminobenzylcarbamate (146 mg, 0.66 mmol), Hunig's Base (0.287 mL, 1.64 mmol) and 1-propanephosphonic acid cyclic anhydride (50 wt % in DMF) (0.326 mL, 1.10 mmol). The mixture was stirred at room temperature for 1 h. Water (10 mL) and 10% MeOH in DCM (20 mL) were added. The organic layer was separated, and concentrated to give the crude product. Purification by flash chromatography (20 g silica gel, 0%-10% MeOH in DCM, 20 min) afforded the title compound (178 mg, 73.4% yield, ~50% purity) as a yellow oil.

MS: 443 ES+($C_{23}H_{30}N_4O_5$)

$^1$H NMR (300 MHz, CHLOROFORM-d) δ ppm 1.47 (m, 12H) 3.10-3.23 (m, 1H) 3.25-3.39 (m, 1H) 4.34-4.54 (m, 3H) 4.36-4.49 (m, 3H) 5.25-5.45 (m, 2H) 6.03 (d, J=6.61 Hz, 1H) 6.09-6.17 (m, 1H) 7.24-7.29 (m, 2H) 7.42-7.62 (m, 2H) 8.64 (s, 1H)

Intermediate 32: (R)-ethyl 2-((2S,5R)-2-(4-((tert-butoxycarbonylamino)methyl)phenyl-carbamoyl)-3-methyl-7-oxo-1,6-diazabicyclo[3.2.1]oct-3-en-6-yloxy)-2-fluoroacetate

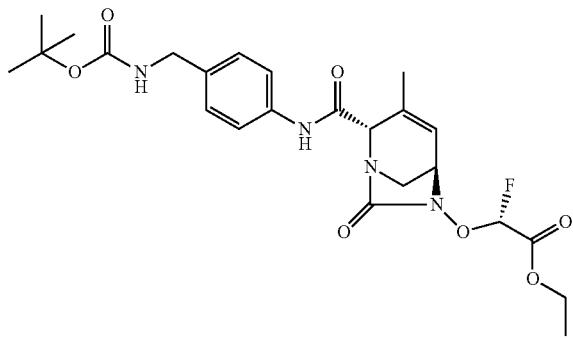 [SMILES: CCOC(=O)[C@@H](F)ON1C(=O)N2C[C@H]1C=C(C)[C@H]2C(=O)Nc1ccc(CNC(=O)OC(C)(C)C)cc1]

To a solution of tert-butyl 4-((2S,5R)-6-(allyloxy)-3-methyl-7-oxo-1,6-diazabicyclo-[3.2.1]oct-3-ene-2-carboxamido)benzylcarbamate (Intermediate 31, 178 mg, 0.40 mmol) in methanol (10 mL) at room temperature was added Pd(Ph$_3$P)$_4$ (465 mg, 0.40 mmol). The reaction was stirred at room temperature for 16 hours. The reaction mixture was concentrated to afford crude intermediate tert-butyl 4-((2S,5R)-6-hydroxy-3-methyl-7-oxo-1,6-diazabicyclo[3.2.1]oct-3-enecarboxamido)benzylcarbamate as an orange film. The crude material was dissolved in DMF (1 mL). K$_2$CO$_3$ (167 mg, 1.21 mmol) and ethyl 2-bromo-2-fluoroacetate (0.052 mL, 0.44 mmol) were added. The reaction mixture was stirred overnight at room temperature. EtOAC (20 mL) was added, and the reaction mixture was washed with water (10 mL). The organic layer was concentrated to give the crude product which was purified by flash chromatography (12 g silca gel, 0-100% EtOAc in Hexane, 20 min; then 5% MeOH in DCM, 10 min) to afford the title compound (11 mg, 5.4% yield) as an orange solid.

MS: 507 ES+ ($C_{24}H_{31}FN_4O_7$)

$^1$H NMR (300 MHz, CHLOROFORM-d) δ ppm 1.36 (t, 3H) 1.48 (s, 9H) 2.00 (s, 3H) 3.21-3.27 (m, 1H) 3.36 (d, J=1.70 Hz, 1H) 4.08 (dd, J=5.00, 2.74 Hz, 1H) 4.24-4.42 (m, 5H) 4.47 (s, 1H) 5.78-5.95 (m, 1H) 6.12-6.17 (m, 1H) 7.38-7.55 (m, 4H) 8.47 (s, 1H)

Intermediate 33: (R)-2-((2S,5R)-2-(4-((tert-butoxycarbonylamino)methyl)phenyl-carbamoyl)-3-methyl-7-oxo-1,6-diazabicyclo[3.2.1]oct-3-en-6-yloxy)-2-fluoroacetic acid lithium salt

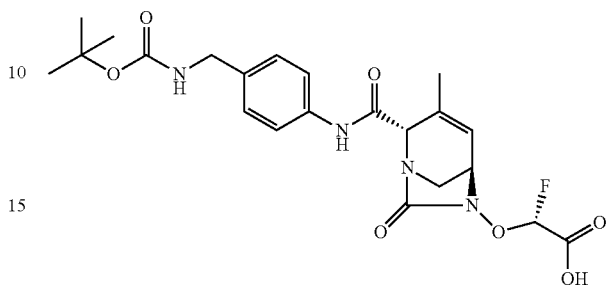

To a solution of (2R)-ethyl 2-(((2S,5R)-2-((4-(((tert-butoxycarbonyl)amino)methyl)phenyl)-carbamoyl)-3-methyl-7-oxo-1,6-diazabicyclo[3.2.1]oct-3-en-6-yl)oxy)-2-fluoroacetate (Intermediate 32, 11 mg, 0.02 mmol) in THF (1 mL) and water (0.5 mL) at 0° C. was added lithium hydroxide (1M) (0.02 mL, 0.02 mmol). The mixture was stirred for 5 minutes at 0° C. and DCM (10 mL) was added. Hydrochloric acid (0.5N) was carefully added to adjust the pH to ~5-6. The organic layer was separated and concentrated to give the title compound (8 mg, 77%) as a yellow solid.

UPLC acid condition retention time: 0.80 min, 479 (M+H)+

$^1$H NMR (300 MHz, CHLOROFORM-d) δ ppm 1.47 (s, 9H) 1.98 (s, 3H) 3.19-3.44 (m, 1 H) 4.03-4.55 (m, 6H) 5.68-6.05 (m, 1H) 7.44-7.56 (m, 4H) 8.49 (br. s., 1H)

Example 28

(R)-2-((2S,5R)-2-(4-(aminomethyl)phenylcarbamoyl)-3-methyl-7-oxo-1,6-diazabicyclo[3.2.1]oct-3-en-6-yloxy)-2-fluoroacetic acid TFA salt

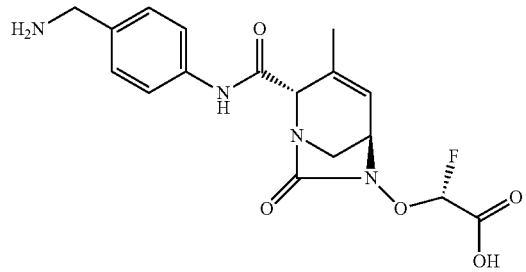 [SMILES: CC1=C[C@@H]2CN(C(=O)N2O[C@H](F)C(=O)O)[C@@H]1C(=O)Nc1ccc(CN)cc1]

To a solution of (2R)-2-(((2S,5R)-2-((4-(((tert-butoxycarbonyl)amino)methyl)phenyl)-carbamoyl)-3-methyl-7-oxo-1,6-diazabicyclo[3.2.1]oct-3-en-6-yl)oxy)-2-fluoroacetic acid lithium salt (Intermediate 33, 8 mg, 0.02 mmol) in DCM (2 mL) at 0° C. was added TFA (0.128 mL, 1.67 mmol). The reaction mixture was stirred at 0° C. for 6 hours and solvent was removed. Toluene (2×1 mL) was added and concentrated to remove excess TFA. Et$_2$O (2 mL) was added and the precipitation formed was filtered, washed with Et$_2$O and dried to give the title compound (8 mg, 97%) as a TFA salt.

MS: 379 ES+ ($C_{17}H_{19}FN_4O_5$)

$^1$H NMR (300 MHz, D2O) δ ppm 1.75 (s, 3H) 3.23-3.61 (m, 2H) 4.12-4.25 (m, 3H) 4.51-4.60 (m, 1H) 5.53-5.98 (m, 1H) 6.29 (br. s., 1H) 7.45-7.57 (m, 4H)

Intermediate 34: (2S,5R)-6-(allyloxy)-3-methyl-7-oxo-N-(pyrazin-2-ylmethyl)-1,6-diazabicyclo[3.2.1]oct-3-ene-2-carboxamide

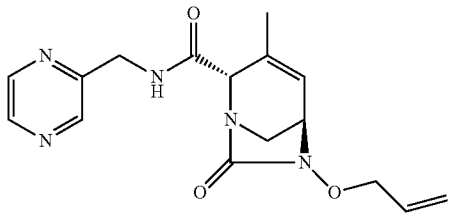 [SMILES: C=CCON1C(=O)N2C[C@H]1C=C(C)[C@H]2C(=O)NCc1cnccn1]

To a solution of (2S,5R)-6-(allyloxy)-3-methyl-7-oxo-1,6-diazabicyclo[3.2.1]oct-3-ene-2-carboxylic acid (Intermediate 29, 199 mg, 0.84 mmol) in DMF (5 mL) at 0° C. was added pyrazin-2-ylmethanamine (91 mg, 0.84 mmol), O-(7-azabenzotriazol-1-yl)-N,N,N',N'-tetramethyluronium hexafluorophosphate (635 mg, 1.67 mmol) and DIEA (0.582 mL, 3.34 mmol). The reaction mixture was stirred for 30 minutes at room temperature, then diluted with ethyl acetate and washed with saturated sodium bicarbonate once and 1:1 brine:water three times. The organics were dried over magnesium sulfate, filtered and concentrated. Silica gel chromatography (0%-2.5% methanol/dichloromethane) afforded the title compound (147 mg, 53.5%) as an orange oil.

MS: 330 ES+($C_{16}H_{19}N_5O_3$)

$^1$H NMR (300 MHz, DMSO-$d_6$) δ: 1.60 (s, 3H); 3.14 (m, 2H); 3.64 (m, 1H); 3.94 (m, 1H); 4.35 (m, 2H); 4.46 (m, 2H); 5.29 (m, 2H); 5.96 (m, 1H); 6.07 (m, 1H); 8.56 (m, 3H); 9.05 (m, 1H).

Example 29 ethyl 2-fluoro-2-(((2S,5R)-3-methyl-7-oxo-2-((pyrazin-2-ylmethyl)carbamoyl)-1,6-diazabicyclo[3.2.1]oct-3-en-6-yl)oxy)acetate

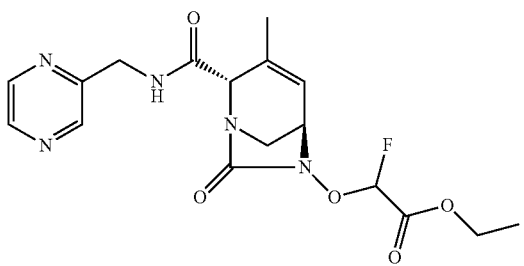 [SMILES: CCOC(=O)C(F)ON1C(=O)N2C[C@H]1C=C(C)[C@H]2C(=O)NCc1cnccn1]

To a solution of (2S,5R)-6-(allyloxy)-3-methyl-7-oxo-N-(pyrazin-2-ylmethyl)-1,6-diazabicyclo[3.2.1]oct-3-ene-2-carboxamide (Intermediate 34, 153.8 mg, 0.47 mmol) in methanol (3 mL) at room temperature was added 1,3-dimethylbarbituric acid (146 mg, 0.93 mmol) and tetrakis(triphenylphosphine)palladium(0) (54.0 mg, 0.05 mmol). The reaction was stirred at room temperature for 2 hours. More tetrakis(triphenylphosphine)palladium(0) (54.0 mg, 0.05 mmol) was added as well as 2 mL of methanol, and the mixture was stirred at room temperature for another 2 hours. The reaction mixture was concentrated to afford an orange oil. The oil was dissolved in DMF (3 mL) and potassium carbonate (194 mg, 1.40 mmol) and ethyl 2-bromo-2-fluoroacetate (0.166 mL, 1.40 mmol) were added. The reaction mixture was stirred overnight at room temperature then diluted with ethyl acetate and filtered through a 0.45 μm filter to remove solid potassium carbonate. The filtrate was washed three times with 1:1 brine:water. The organics were dried over magnesium sulfate, filtered and concentrated. Silica gel chromatography (0%-100% ethyl acetate/hexanes) afforded the title compound (95 mg, 52%) as a light orange foam. The compound is a 1:1 mixture of diastereomers.

MS: 394 ES+ ($C_{17}H_{20}FN_5O_5$)

$^1$H NMR (300 MHz, DMSO-$d_6$) δ: 1.22 (m, 3H); 1.63 (s, 3H); 2.71 (m, 1H); 3.10 (m, 1H); 3.98 (d, 1H); 4.02 (m, 1H); 4.26 (m, 2H); 4.47 (m, 2H); 6.05 (m, 1H); 6.20 (m, 1H); 8.56 (m, 3H); 9.10 (m, 1H).

Example 30

2-fluoro-2-(((2S,5R)-3-methyl-7-oxo-2-((pyrazin-2-ylmethyl)carbamoyl)-1,6-diazabicyclo[3.2.1]oct-3-en-6-yl)oxy)acetic acid lithium salt

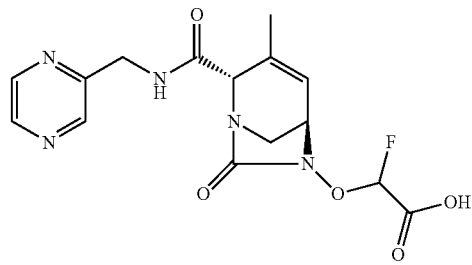 [SMILES: CC1=C[C@@H]2CN(C(=O)N2OC(F)C(=O)O)[C@@H]1C(=O)NCc1cnccn1]

To a solution of ethyl 2-fluoro-2-(((2S,5R)-3-methyl-7-oxo-2-((pyrazin-2-ylmethyl)-carbamoyl)-1,6-diazabicyclo[3.2.1]oct-3-en-6-yl)oxy)acetate (Example 29, 95.3 mg, 0.24 mmol) in THF (2 mL) and water (0.66 mL) at 0° C. was added lithium hydroxide (1M) (0.254 mL, 0.25 mmol), and stirred for 25 minutes at 0° C. Another 0.1 eq of lithium hydroxide was added. After 15 minutes hydrochloric acid (0.5N) (0.242 mL, 0.12 mmol) was added to adjust the pH to ~5-6. The reaction mixture was frozen and lyophilized. 90 mg of a pale yellow solid were purified by reverse phase HPLC (YMC Carotenoid C30, 21.2 mm×150 mm, 4 μm coupled with Synergi Polar RP, 21.2 mm×100 mm, 4 μm, 0%-30% acetonitrile in water, 20 mL/min, 15 min). 23.6 mg (27%) of the title compound was obtained as a white solid. The compound is a 1:1 mixture of diastereomers.

MS: 366 ES+($C_{15}H_{16}FN_5O_5$)

$^1$H NMR (300 MHz, DMSO-$d_6$) δ: 1.63 (s, 3H); 3.09 (m, 1H); 3.68 (m, 1H); 4.02 (m, 1H); 4.29 (s, 1H); 4.48 (d, 2H); 5.22 (m, 1H); 6.05 (m, 1H); 8.57 (m, 3H); 9.07 (m, 1H).

Intermediate 35: (S)-tert-butyl 1-(tert-butyldimethylsilyloxy)but-3-en-2-yl(3-methyl-2-oxobut-3-enyl)carbamate

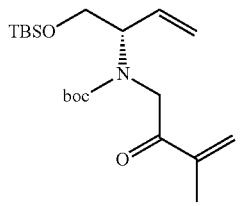

To a solution of (S)-tert-butyl 1-(tert-butyldimethylsilyloxy)but-3-en-2-yl(2-(methoxy(methyl)amino)-2-oxoethyl)carbamate (Intermediate 5, 30.79 g, 76.48 mmol) in THF (200 mL) at 0° C. was added prop-1-en-2-ylmagnesium bromide (0.5M in THF) (300 mL, 149.90 mmol), and stirred at 0° C. for 1 hour. The reaction mixture was quenched with 200 mL 10% citric acid, diluted further with 100 mL water and extracted with ether. The organics were concentrated and the resulting oil was dissolved in ether and washed with water and brine. The organics were dried over magnesium sulfate, filtered and concentrated. Silica gel chromatography (0%-20% ethyl acetate/hexanes) afforded the desired product (26.2 g, 89%) as a colorless oil.

MS: 384 ES+($C_{20}H_{37}NO_4Si$)

$^1$H NMR (300 MHz, DMSO-$d_6$) δ: 0.02 (d, 6H); 0.83 (s, 9H); 1.27-1.38 (m, 9H); 1.80 (m, 3H); 3.71 (m, 2H); 4.34 (m, 2H); 4.61 (m, 1H); 5.17 (m, 2H); 5.77 (m, 1H); 5.85 (m, 1H); 6.03 (m, 1H).

Intermediate 36: (S)-tert-butyl 2-((tert-butyldimethylsilyloxy)methyl)-4-methyl-5-oxo-5,6-dihydropyridine-1(2H)-carboxylate

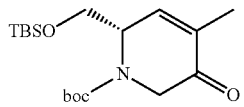

A solution of (S)-tert-butyl 1-(tert-butyldimethylsilyloxy)but-3-en-2-yl(3-methyl-2-oxobut-3-enyl)carbamate (Intermediate 35, 26.18 g, 68.25 mmol) in toluene (600 mL) was purged with nitrogen for 15 minutes. (1,3-Bis-(2,4,6-trimethylphenyl)-2-imidazolidinylidene)-dichloro(o-isopropoxyphenylmethylene)ruthenium (0.987 g, 1.57 mmol) was then added. The reaction mixture was heated at 65° C. for 1.5 hours. The reaction mixture was concentrated onto silica gel. Silica gel chromatography (0%-15% ethyl acetate/hexanes) afforded the desired product (21.18 g, 87%) as a colorless oil.

MS: 356 ES+($C_{18}H_{33}NO_4Si$)

$^1$H NMR (300 MHz, DMSO-$d_6$) δ: 0.01 (d, 6H); 0.81 (s, 9H); 1.42 (s, 9H); 1.75 (m, 3H); 3.74-3.89 (m, 3H); 4.04-4.32 (m, 1H); 4.67 (m, 1H); 6.88 (m, 1H).

Intermediate 37: (2S,5S)-tert-butyl 2-((tert-butyldimethylsilyloxy)methyl)-5-hydroxy-4-methyl-5,6-dihydropyridine-1(2H)-carboxylate

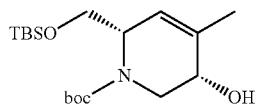

To a solution of cerium(III) chloride (14.68 g, 59.57 mmol) and (S)-tert-butyl 2-((tert-butyldimethylsilyloxy)methyl)-4-methyl-5-oxo-5,6-dihydropyridine-1(2H)-carboxylate (Intermediate 36, 21.18 g, 59.57 mmol) in methanol (300 mL) at 0° C. was added sodium borohydride (2.254 g, 59.57 mmol) portionwise. After 15 minutes, the reaction mixture was diluted with saturated ammonium chloride (100 mL) and water (100 mL), then extracted twice with diethyl ether. The organic extracts were washed with brine, dried over magnesium sulfate, filtered and concentrated. Silica gel chromatography (0%-20% ethyl acetate/hexanes) afforded the desired product (19.45 g, 91%) as a colorless oil.

MS: 358 ES+($C_{18}H_{35}NO_4Si$)

$^1$H NMR (300 MHz, DMSO-$d_6$) δ: 0.02 (s, 6H); 0.86 (s, 9H); 1.39 (s, 9H); 1.69 (m, 3H); 2.63-2.72 (m, 1H); 3.59 (m, 2H); 3.82 (m, 1H); 4.03 (m, 1H); 4.21 (m, 1H); 5.04 (d, 1H); 5.38 (m, 1H).

Intermediate 38: N-(allyloxy)-2-nitrobenzenesulfonamide

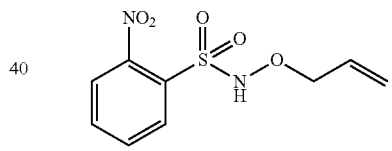

To a stirred solution of O-allylhydroxylamine hydrochloride (147.05 g, 1341.59 mmol) in DCM (2.5 L) at 0° C., pyridine (318 mL, 3948 mmol) was added followed by the addition of 2-nitrobenzene-1-sulfonyl chloride (250 g, 1128.05 mmol) portionwise as a solid. The reaction mixture was then stirred at the same temperature for 1 h. Completion of the reaction was monitored by TLC. The reaction mixture was quenched with 1.5 N HCl (1 L). The organic layer was separated, washed with water (250 mL), brine (250 mL), dried over anhydrous $Na_2SO_4$, filtered and concentrated under vacuum to yield the residue. The crude was purified by crystallization using EtOAc:petroleum ether (1:3) (800 mL) and afforded 202 g of the title compound as a light brown solid. The mother liquor was concentrated and purified by silica gel column chromatography (mesh 60-120) using petroleum ether:EtOAc (7:3) to yield another 19.1 g of the title compound as a yellow solid. The total yield was 76%.

UPLC: 257 (M-1) for $C_9H_{10}N_2O_5S$ $^1$HNMR (400 MHz, DMSO-$d_6$): δ 4.36-4.38 (m, 2H), 5.22-5.32 (m, 2H), 5.84-5.91 (m, 1H), 7.92-7.96 (m, 2H), 8.02-8.05 (m, 2H), 11.07 (s, 1H).

Intermediate 39: (2S,5R)-tert-butyl 5-(N-(allyloxy)-2-nitrophenylsulfonamido)-2-((tert-butyldimethylsilyloxy)methyl)-4-methyl-5,6-dihydropyridine-1(2H)-carboxylate

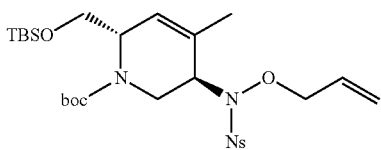

To a solution of (2S,5S)-tert-butyl 2-((tert-butyldimethylsilyloxy)methyl)-5-hydroxy-4-methyl-5,6-dihydropyridine-1(2H)-carboxylate (Intermediate 37, 19.45 g, 54.40 mmol) in toluene (300 mL) at room temperature was added triphenylphosphine (17.06 g, 65.28 mmol), N-(allyloxy)-2-nitrobenzenesulfonamide (Intermediate 38, 14.05 g, 54.40 mmol) and diisopropyl azodicarboxylate (12.85 mL, 65.28 mmol). After 2 hours, the reaction mixture was concentrated onto silica gel and purified. Silica gel chromatography (0%-50% ethyl acetate/hexanes) afforded the desired product (25.2 g, 78%) as a yellow oil.

MS: 598 ES+($C_{27}H_{43}N_3O_8SSi$)

$^1$H NMR (300 MHz, DMSO-$d_6$) δ: 0.00 (s, 6H); 0.83 (s, 9H); 1.31 (m, 9H); 1.34 (m, 3H); 3.10-3.25 (m, 1H); 3.59 (m, 2H); 3.99-4.41 (m, 5H); 5.17 (m, 2H); 5.72 (m, 2H); 7.93-8.16 (m, 4H).

Intermediate 40: (2S,5R)-tert-butyl 5-(N-(allyloxy)-2-nitrophenylsulfonamido)-2-(hydroxymethyl)-4-methyl-5,6-dihydropyridine-1(2H)-carboxylate

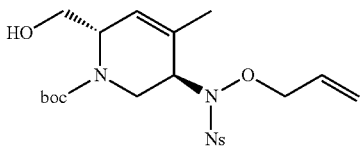

To a solution of (2S,5R)-tert-butyl 5-(N-(allyloxy)-2-nitrophenylsulfonamido)-2-((tert-butyldimethylsilyloxy)methyl)-4-methyl-5,6-dihydropyridine-1(2H)-carboxylate (Intermediate 39, 1 g, 1.67 mmol) in THF (11 mL) at 0° C. was added tetrabutylammonium fluoride (1M in THF) (2.175 mL, 2.17 mmol). After 90 minutes, the reaction mixture was concentrated onto silica gel. Silica gel chromatography (0%-70% ethyl acetate/hexanes) afforded the desired product (0.732 g, 90%) as a tan foam.

MS: 484 ES+($C_{21}H_{29}N_3O_8S$)

$^1$H NMR (300 MHz, DMSO-$d_6$) δ: 1.31 (m, 9H); 1.35 (m, 3H); 3.20 (m, 1H); 3.41 (m, 2H); 3.96-4.37 (m, 5H); 4.76 (m, 1H); 5.19 (m, 2H); 5.66-5.84 (m, 2H); 7.94-8.18 (m, 4H).

Intermediate 41: (2S,5R)-5-(N-(allyloxy)-2-nitrophenylsulfonamido)-1-(tert-butoxycarbonyl)-4-methyl-1,2,5,6-tetrahydropyridine-2-carboxylic acid

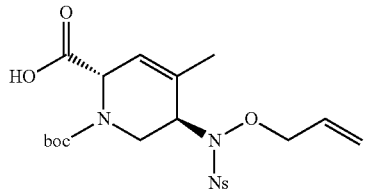

To a solution of periodic acid (6 g, 31.26 mmol) in wet acetonitrile (60 mL) (0.75% water by volume) at room temperature was added chromium(VI) oxide (10 mg, 0.10 mmol). The mixture was stirred until complete dissolution was achieved. To a solution of (2S,5R)-tert-butyl 5-(N-(allyloxy)-2-nitrophenylsulfonamido)-2-(hydroxymethyl)-4-methyl-5,6-dihydropyridine-1(2H)-carboxylate (Intermediate 40, 5 g, 10.34 mmol) in wet acetonitrile (60 mL) (0.75% by volume) at 0° C. was added dropwise the previously formed periodic acid/chromium oxide solution (60 mL, 3 eq). After 30 minutes, the reaction mixture was diluted with ether and washed with 10% citric acid, sat. sodium bicarbonate and brine. The organics were dried over magnesium sulfate, filtered and concentrated to afford an orange foam (4.16 g, 81%).

MS: 498 ES+($C_{21}H_{27}N_3O_9S$)

$^1$H NMR (300 MHz, DMSO-$d_6$) δ: 1.26 (m, 9H); 1.31 (m, 3H); 3.02-3.25 (m, 1H); 3.90 (m, 1H); 4.17 (m, 3H); 4.65-4.77 (m, 1H); 5.12-5.21 (m, 2H); 5.68 (m, 1H); 5.88 (m, 1H); 7.92-8.17 (m, 4H).

Intermediate 42: (2S,5R)-tert-butyl 5-(N-(allyloxy)-2-nitrophenylsulfonamido)-2-carbamoyl-4-methyl-5,6-dihydropyridine-1(2H)-carboxylate

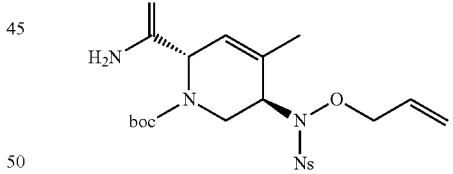

To a solution of (2S,5R)-5-(N-(allyloxy)-2-nitrophenylsulfonamido)-1-(tert-butoxycarbonyl)-4-methyl-1,2,5,6-tetrahydropyridine-2-carboxylic acid (Intermediate 41, 4.16 g, 8.36 mmol) in DMF (35 mL) at room temperature was added ammonium chloride (0.895 g, 16.72 mmol), HATU (4.77 g, 12.54 mmol) and DIEA (5.84 mL, 33.45 mmol). After 15 minutes, the reaction mixture was diluted with ethyl acetate, washed with saturated sodium bicarbonate and twice with 1:1 brine:water. The organics were dried over magnesium sulfate, filtered and concentrated. Silica gel chromatography (0%-80% ethyl acetate/hexanes) was run twice to afforded the desired product (2.16 g, 52%) as a yellow foam.

MS: 497 ES+($C_{21}H_{28}N_4O_8S$)

$^1$H NMR (300 MHz, DMSO-$d_6$) δ: 1.26 (m, 9H); 1.37 (m, 3H); 3.12-3.35 (m, 1H); 3.80 (m, 1H); 4.18 (m, 3H);

4.64-4.79 (m, 1H); 5.13-5.22 (m, 2H); 5.68 (m, 1H); 5.88 (m, 1H); 7.04 (m, 1H); 7.45 (bs, 1H); 7.90-8.18 (m, 4H).

Intermediate 43: (2S,5R)-5-(N-(allyloxy)-2-nitrophenylsulfonamido)-4-methyl-1,2,5,6-tetrahydropyridine-2-carboxamide

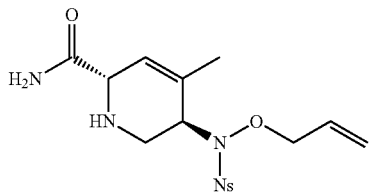

To a solution of (2S,5R)-tert-butyl 5-(N-(allyloxy)-2-nitrophenylsulfonamido)-2-carbamoyl-4-methyl-5,6-dihydropyridine-1(2H)-carboxylate (Intermediate 42, 2.16 g, 4.35 mmol) in DCM (20 mL) at room temperature was added zinc bromide (0.700 mL, 13.05 mmol). After stirring overnight at room temperature, the reaction mixture was diluted with dichloromethane and washed with saturated sodium bicarbonate and brine. The organics were dried over magnesium sulfate, filtered and concentrated to afford the desired product (1.450 g, 84%) as a yellow foam.

MS: 397 ES+($C_{16}H_{20}N_4O_6S$)

$^1$H NMR (300 MHz, DMSO-$d_6$) δ: 1.65 (m, 3H); 2.71 (m, 3H); 3.76 (m, 1H); 3.95 (m, 1H); 4.18-4.42 (m, 2H); 5.23 (m, 2H); 5.82 (m, 1H); 6.02 (m, 1H); 7.05 (bs, 1H); 7.30 (bs, 1H); 7.93-8.18 (m, 4H).

Intermediate 44: (2S,5R)-5-(allyloxyamino)-4-methyl-1,2,5,6-tetrahydropyridine-2-carboxamide and (2R,5R)-5-(allyloxyamino)-4-methyl-1,2,5,6-tetrahydropyridine-2-carboxamide

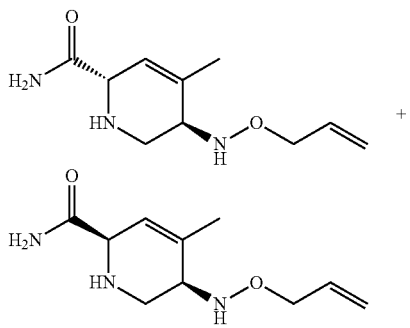

To a solution of (2S,5R)-5-(N-(allyloxy)-2-nitrophenylsulfonamido)-4-methyl-1,2,5,6-tetrahydropyridine-2-carboxamide (Intermediate 43, 1.4 g, 3.53 mmol) and cesium carbonate (9.21 g, 28.25 mmol) in THF (100 mL) at room temperature was added PS-thiophenol (3-(3-mercaptophenyl)propanamidomethylpolystyrene) (1.55 mmol/g) (9.12 g, 14.13 mmol). After stirring overnight at room temperature, the reaction mixture was filtered through a fritted funnel and the resin was washed twice with DCM. The filtrate was concentrated to afford a yellow oil. Silica gel chromatography (0%-5% methanol/dichloromethane) afforded a 3 to 1 mixture of trans and cis isomers (0.473 g, 63.4%) as a light yellow oil. The mixture was taken forward without separation.

MS: 212 ES+($C_{10}H_{17}N_3O_2$)

$^1$H NMR (300 MHz, DMSO-$d_6$) δ: 1.73 (m, 3H); 2.63 (m, 1H); 2.97 (m, 1H); 3.01 (m, 1H); 3.60 (m, 1H); 4.12 (m, 2H); 5.11-5.26 (m, 2H); 5.92 (m, 1H); 6.45 (m, 1H); 7.00 (m, 1H); 7.33 (bs, 1H).

Intermediate 45: (2S,5R)-6-(allyloxy)-4-methyl-7-oxo-1,6-diazabicyclo[3.2.1]oct-3-ene-2-carboxamide

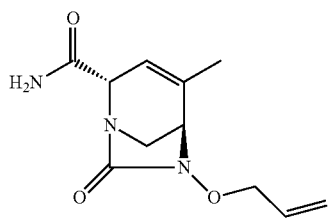 [SMILES: C=CCON1C(=O)N2C[C@H]1C(C)=C[C@H]2C(N)=O]

To a solution of (2S,5R)-5-(allyloxyamino)-4-methyl-1,2,5,6-tetrahydropyridine-2-carboxamide and (2R,5R)-5-(allyloxyamino)-4-methyl-1,2,5,6-tetrahydropyridine-2-carboxamide (Intermediate 44, 0.429 g, 2.03 mmol) and DIEA (1.415 mL, 8.12 mmol) in acetonitrile (170 mL) at 0° C. was added triphosgene (0.241 g, 0.81 mmol) as a solution in acetonitrile (1.5 mL) at a rate of 0.1 mL/min. Once addition was complete, the reaction was warmed to room temperature and stirred two days. The reaction mixture was diluted with ethyl acetate, washed with saturated sodium bicarbonate and brine, dried over magnesium sulfate, filtered and concentrated. Silica gel chromatography (0%-20% ethyl acetate/hexanes) afforded the product (0.312 g, 64.8%) as a light yellow oil.

MS: 238 ES+($C_{11}H_{15}N_3O_3$)

$^1$H NMR (300 MHz, DMSO-$d_6$) δ: 1.79 (m, 3H); 3.19 (m, 2H); 3.81 (m, 1H); 4.12 (m, 1H); 4.36 (m, 2H); 5.24-5.45 (m, 3H); 5.89-6.00 (m, 1H); 7.28 (bs, 1H); 7.49 (bs, 1H).

Example 31

(2R)-ethyl 2-(((2S,5R)-2-carbamoyl-4-methyl-7-oxo-1,6-diazabicyclo[3.2.1]oct-3-en-6-yl)oxy)-2-fluoroacetate

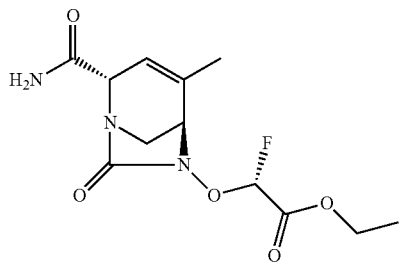 [SMILES: CCOC(=O)[C@@H](F)ON1C(=O)N2C[C@H]1C(C)=C[C@H]2C(N)=O]

Example 32

(2S)-ethyl 2-(((2S,5R)-2-carbamoyl-4-methyl-7-oxo-1,6-diazabicyclo[3.2.1]oct-3-en-6-yl)oxy)-2-fluoroacetate

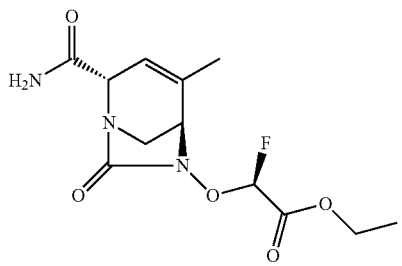 [SMILES: CCOC(=O)[C@H](F)ON1C(=O)N2C[C@H]1C(C)=C[C@H]2C(N)=O]

Examples 31-32

To a solution of (2S,5R)-6-(allyloxy)-4-methyl-7-oxo-1,6-diazabicyclo[3.2.1]oct-3-ene-2-carboxamide (Intermediate 45, 0.2972 g, 1.25 mmol) in methanol (6 mL) at room temperature was added 1,3-dimethylbarbituric acid (0.391 g, 2.51 mmol) and tetrakis(triphenylphosphine)palladium(0) (0.145 g, 0.13 mmol). The reaction was stirred at room temperature for 2 hours, then concentrated to afford an orange film. The orange film was dissolved in DMF (6 mL). Potassium carbonate (0.519 g, 3.76 mmol) and ethyl bromofluoroacetate (0.592 mL, 5.01 mmol) were added. The reaction mixture was stirred overnight at room temperature, then diluted with ethyl acetate and filtered through a 0.45 µm filter to remove solid potassium carbonate. The filtrate was washed twice with 1:1 brine:water. The organics were dried over magnesium sulfate, filtered and concentrated. Silica gel chromatography (0%-65% ethyl acetate/hexanes) afforded a 1:1 mixture of diastereomers, 372 mg, 99%. Separation of diastereomers was done on reverse phase HPLC (Atlantis T3, 19 mm×150 mm, 5 µm, 20%-40% acetonitrile in water, 20 mL/min, 15 min). Both diastereomers were obtained as white solids after lyophilization.

The following products were obtained:

Example 31

(First Eluting Diastereomer): 108.8 mg, 29%

MS: 302 ES+($C_{12}H_{16}FN_3O_5$)
$^1$H NMR (300 MHz, DMSO-$d_6$) δ: 1.23 (t, 3H); 1.82 (m, 3H); 3.19 (m, 1H); 3.29 (m, 1H); 3.96 (m, 1H); 4.23 (m, 1H); 4.24 (q, 2H); 5.52 (m, 1H); 6.28 (m, 1H); 7.32 (br s, 1H); 7.56 (br s, 1H).

Example 32

(Second Eluting Diastereomer): 103.3 mg, 27%

MS: 302 ES+($C_{12}H_{16}FN_3O_5$)
$^1$H NMR (300 MHz, DMSO-$d_6$) δ: 1.27 (t, 3H); 1.81 (m, 3H); 3.21 (m, 1H); 3.31 (m, 1H); 3.82 (m, 1H); 4.24 (m, 1H); 4.28 (q, 2H); 5.52 (m, 1H); 6.17 (m, 1H); 7.32 (br s, 1H); 7.55 (br s, 1H).

The stereochemistry of the two diastereomers were assigned based on order of elution as well as based on the inhibitory activity of the corresponding carboxylic acids (examples 33 and 34): the more active acid, coming from the first eluting diastereomer, was assigned as the R-isomer.

Example 33

(2R)-2-(((2S,5R)-2-carbamoyl-4-methyl-7-oxo-1,6-diazabicyclo[3.2.1]oct-3-en-6-yl)oxy)-2-fluoroacetic acid lithium salt

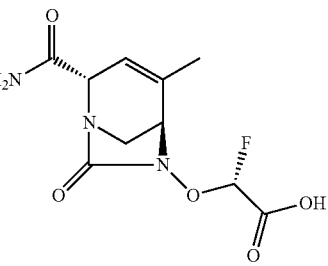

To a solution of (2R)-ethyl 2-(((2S,5R)-2-carbamoyl-4-methyl-7-oxo-1,6-diazabicyclo-[3.2.1]oct-3-en-6-yl)oxy)-2-fluoroacetate (Example 31, 96.6 mg, 0.32 mmol) in THF (3 mL) and water (1 mL) at 0° C. was added lithium hydroxide (0.337 mL, 0.34 mmol). The reaction mixture was kept in ice bath and stirred for 15 minutes. Another 0.2 eq of lithium hydroxide was added. After 15 minutes, the reaction mixture was adjusted to pH=7 with 0.5N HCl. The THF was evaporated and the remaining aqueous was frozen and lyophilized to afford a pale yellow solid. Reverse phase HPLC (YMC Carotenoid C30, 19 mm×150 mm, 5 µm coupled with Synergi Polar RP 21.2 mm×100 mm, 4 µm, 0%-40% acetonitrile in water, 20 mL/min, 15 min) afforded the title compound as a white solid after lyophilization, 34.8 mg, 40%.

MS: 274 ES+($C_{10}H_{12}FN_3O_5$)
$^1$H NMR (300 MHz, DMSO-$d_6$) δ: 1.83 (m, 3H); 3.21 (m, 2H); 3.91 (m, 1H); 4.16 (m, 1H); 5.33 (m, 1H); 5.44 (m, 1H); 7.27 (br s, 1H); 7.53 (br s, 1H).

Example 34

(2S)-2-(((2S,5R)-2-carbamoyl-4-methyl-7-oxo-1,6-diazabicyclo[3.2.1]oct-3-en-6-yl)oxy)-2-fluoroacetic acid lithium salt

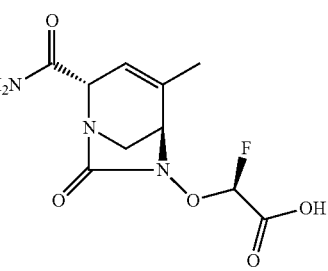

The title compound was prepared from (2S)-ethyl 2-(((2S,5R)-2-carbamoyl-4-methyl-7-oxo-1,6-diazabicyclo[3.2.1]oct-3-en-6-yl)oxy)-2-fluoroacetate (Example 32, 91.8 mg, 0.30 mmol) according to the procedure for Example 33.

Purification conditions were the same to afford an off-white solid after lyophilization, 11.7 mg, 14%.

MS: 274 ES+($C_{10}H_{12}FN_3O_5$)

$^1$H NMR (300 MHz, DMSO-$d_6$) δ: 1.81 (m, 3H); 3.21 (m, 2H); 3.87 (m, 1H); 4.16 (m, 1H); 5.25 (m, 1H); 5.45 (m, 1H); 7.28 (br s, 1H); 7.54 (br s, 1H).

Example 35

(2R)-isopropyl 2-(((2S,5R)-2-carbamoyl-4-methyl-7-oxo-1,6-diazabicyclo[3.2.1]oct-3-en-6-yl)oxy)-2-fluoroacetate

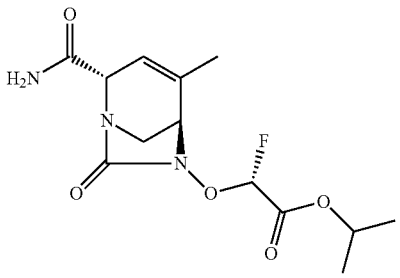 [SMILES: CC1=C[C@@H](C(N)=O)N2C[C@@H]1N(O[C@H](F)C(=O)OC(C)C)C2=O]

Example 36

(2S)-isopropyl 2-(((2S,5R)-2-carbamoyl-4-methyl-7-oxo-1,6-diazabicyclo[3.2.1]oct-3-en-6-yl)oxy)-2-fluoroacetate

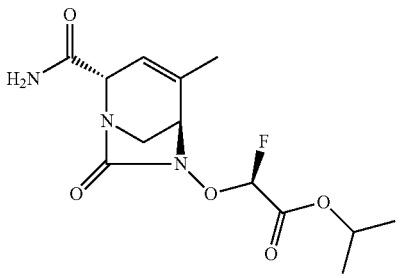 [SMILES: CC1=C[C@@H](C(N)=O)N2C[C@@H]1N(O[C@@H](F)C(=O)OC(C)C)C2=O]

To a solution of (2S,5R)-6-(allyloxy)-4-methyl-7-oxo-1,6-diazabicyclo[3.2.1]oct-3-ene-2-carboxamide (Intermediate 45, 0.15 g, 0.63 mmol) in methanol (3 mL) at room temperature was added 1,3-dimethylbarbituric acid (0.197 g, 1.26 mmol) and tetrakis(triphenyl-phosphine)palladium(0) (0.073 g, 0.06 mmol). The reaction was stirred at room temperature for 2 hours, then concentrated to afford an orange film. The orange film was dissolved in DMF (4 mL). Potassium carbonate (0.175 g, 1.26 mmol) and isopropyl 2-bromo-2-fluoroacetate (Intermediate 18, 0.377 g, 1.90 mmol) were added. The reaction mixture was stirred at room temperature for 4.5 hours then diluted with ethyl acetate and filtered through a 0.45 μm filter to remove solid potassium carbonate. The filtrate was washed twice with 1:1 brine: water. The organics were dried over magnesium sulfate, filtered and concentrated. Silica gel chromatography (0%-65% ethyl acetate/hexanes) afforded a 1:1 mixture of diastereomers, 196 mg, 98%. Separation of diastereomers was done on reverse phase HPLC (Atlantis T3, 19 mm×150 mm, 5 μm, 20%-40% acetonitrile in water, 20 mL/min, 15 min). Both diastereomers were obtained as white solids after lyophilization.

Example 35

(First Eluting Diastereomer): 58.6 mg, 31%

MS: 316 ES+($C_{13}H_{18}FN_3O_5$)

$^1$H NMR (300 MHz, DMSO-$d_6$) δ: 1.22 (m, 6H); 1.81 (m, 3H); 3.17 (m, 1H); 3.34 (m, 1H); 3.93 (m, 1H); 4.22 (m, 1H); 5.01 (q, 2H); 5.51 (m, 1H); 6.23 (m, 1H); 7.31 (br s, 1H); 7.54 (br s, 1H).

Example 36

(2nd Eluting Diastereomer): 53.8 mg, 29%

MS: 316 ES+($C_{13}H_{18}FN_3O_5$)

$^1$H NMR (300 MHz, DMSO-$d_6$) δ: 1.28 (m, 6H); 1.81 (m, 3H); 3.19 (m, 1H); 3.29 (m, 1H); 3.82 (m, 1H); 4.24 (m, 1H); 5.06 (m, 1H); 5.52 (m, 1H); 6.14 (m, 1H); 7.32 (br s, 1H); 7.55 (br s, 1H).

Intermediates 46-50 were intentionally omitted.

Intermediate 51: (R)-tert-butyl 4-(cyclopropyl(hydroxy)methyl)-2,2-dimethyloxazolidine-3-carboxylate

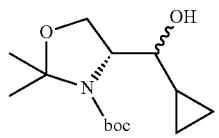

To a solution of (R)-tert-butyl 4-formyl-2,2-dimethyloxazolidine-3-carboxylate (Aldrich, 12.44 g, 54.26 mmol) in THF (150 mL) at −78° C. was added cyclopropylmagnesium bromide (217 mL, 108.52 mmol), dropwise. The reaction mixture was allowed to warm to room temperature and stir overnight. The reaction was quenched with water and diluted with ethyl acetate and brine. The resulting emulsion was filtered through celite and the layers separated. The organics were dried over magnesium sulfate, filtered and concentrated. Silica gel chromatography (0%-20% ethyl acetate/hexanes) afforded the title compound as a light yellow oil (12.47 g, 85%).

$^1$H NMR (300 MHz, DMSO-$d_6$) δ: 0.16 (m, 2H); 0.37 (m, 2H); 0.82 (m, 1H); 1.45 (m, 15H); 2.87 (m, 1H); 3.86 (m, 2H); 3.97 (m, 1H); 4.74 (m, 1H).

Intermediate 52: (R)-tert-butyl 4-(cyclopropanecarbonyl)-2,2-dimethyloxazolidine-3-carboxylate

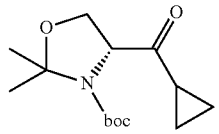

To a solution of (R)-tert-butyl 4-(cyclopropyl(hydroxy) methyl)-2,2-dimethyloxazolidine-3-carboxylate (Intermediate 51, 12.47 g, 45.95 mmol) in DCM (300 mL) at room temperature was added Dess-Martin periodinane (29.2 g, 68.93 mmol). The reaction mixture was stirred overnight then diluted with ethyl acetate and washed with saturated sodium bicarbonate. An emulsion formed and was filtered through celite. The layers were separated and the organics washed with brine. The organics were dried over magnesium sulfate, filtered and concentrated. Silica gel chromatography (0%-20% ethyl acetate/hexanes) afforded the title compound as a colorless oil (11.15 g, 90%).

$^1$H NMR (300 MHz, DMSO-d$_6$) δ: 0.90 (m, 4H); 1.38 (m, 12H); 1.54 (m, 3H); 2.12 (m, 1H); 3.94 (m, 1H); 4.18 (m, 1H); 4.56 (m, 1H).

Intermediate 53: (S)-tert-butyl 4-(1-cyclopropylvinyl)-2,2-dimethyloxazolidine-3-carboxylate

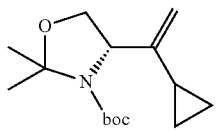

To a suspension of potassium tert-butoxide (9.29 g, 82.80 mmol) in ether (250 mL) at room temperature was added methyltriphenylphosphonium bromide (29.6 g, 82.80 mmol). The mixture turned bright yellow and was heated to 40° C. for 1 hour. The mixture was cooled to room temperature and a solution of (R)-tert-butyl 4-(cyclopropanecarbonyl)-2,2-dimethyloxazolidine-3-carboxylate (Intermediate 52, 11.15 g, 41.40 mmol) in ether (30 mL) was added and the reaction mixture was stirred for 2 hours. The reaction was quenched with water (10 mL) and the layers were separated. The aqueous was extracted once with ether. The combined organic extracts were dried over magnesium sulfate, filtered and concentrated. Silica gel chromatography (0%-15% ethyl acetate/hexanes) afforded the title compound as a colorless oil (9.84 g, 89%).

$^1$H NMR (300 MHz, DMSO-d$_6$) δ: 0.42 (m, 2H); 0.65 (m, 2H); 1.43 (m, 16H); 3.76 (m, 1H); 4.09 (m, 1H); 4.27 (m, 1H); 4.66 (m, 2H).

Intermediate 54: (S)-tert-butyl 1-(tert-butyldimethylsilyloxy)-3-cyclopropylbut-3-en-2-ylcarbamate

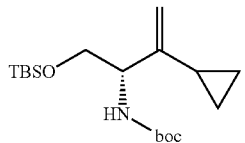

To a solution of (S)-tert-butyl 4-(1-cyclopropylvinyl)-2,2-dimethyloxazolidine-3-carboxylate (Intermediate 53, 8.25 g, 30.86 mmol) in methanol (100 mL) at room temperature was added p-toluenesulfonic acid monohydrate (1.174 g, 6.17 mmol). The reaction mixture was heated to 80° C. overnight. Another 0.2 eq of p-toluenesulfonic acid monohydrate was added and heated at 80° C. for another 2 hours. The reaction mixture was cooled to room temperature. Triethylamine (4.29 mL, 30.86 mmol) and di-tert-butyl dicarbonate (3.37 g, 15.43 mmol) were added. The reaction mixture was stirred two days then concentrated. The residue was dissolved in ethyl acetate and washed once with saturated sodium bicarbonate. The combined organic extracts were dried over magnesium sulfate, filtered and concentrated. The resulting oil was dissolved in DCM (100 mL). Imidazole (2.73 g, 40.11 mmol), 4-dimethylaminopyridine (0.754 g, 6.17 mmol) and tert-butyldimethylsilyl chloride (4.65 g, 30.86 mmol) were added and the reaction mixture was stirred overnight at room temperature. The reaction mixture was filtered to remove solids and washed with brine twice. The organic layer was dried over magnesium sulfate, filtered and concentrated. Silica gel chromatography (0%-10% ethyl acetate/hexanes) afforded the title compound as a colorless oil (6.77 g, 64%).

MS: 342 ES+(C$_{18}$H$_{35}$NO$_3$Si)

$^1$H NMR (300 MHz, DMSO-d$_6$) δ: 0.04 (s, 6H); 0.39 (m, 2H); 0.63 (m, 2H); 0.85 (s, 9H); 1.32 (m, 1H); 1.37 (m, 9H); 3.55 (m, 1H); 3.67 (m, 1H); 3.99 (m, 1H); 4.63 (s, 1H); 4.78 (s, 1H); 6.80 (m, 1H).

Intermediate 55: (S)-1-(tert-butyldimethylsilyloxy)-3-cyclopropylbut-3-en-2-amine

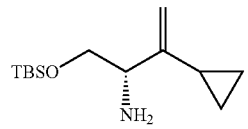

To a solution of (S)-tert-butyl 1-(tert-butyldimethylsilyloxy)-3-cyclopropylbut-3-en-2-ylcarbamate (Intermediate 54, 6.77 g, 19.82 mmol) in DCM (100 mL) at room temperature was added zinc bromide (17.86 g, 79.28 mmol). The reaction mixture was stirred overnight at room temperature. Another 1 eq of zinc bromide was added. After several hours the reaction mixture was filtered and washed with saturated sodium bicarbonate. The resulting emulsion was filtered through a nylon filter and the layers were separated. The organics were dried over magnesium sulfate, filtered and concentrated to afford the title compound as a yellow oil (4.61 g, 96%).

$^1$H NMR (300 MHz, DMSO-d$_6$) δ: 0.04 (s, 6H); 0.39 (m, 2H); 0.63 (m, 2H); 0.87 (s, 9H); 1.35 (m, 1H); 1.81 (m, 2H); 3.33 (m, 1H); 3.45 (m, 1H); 3.67 (m, 1H); 4.59 (s, 1H); 4.83 (m, 1H).

Intermediate 56: (S)-tert-butyl 1-(tert-butyldimethylsilyloxy)-3-cyclopropylbut-3-en-2-yl(2-(methoxy(methyl)amino)-2-oxoethyl)carbamate

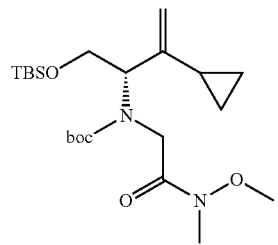

The title compound was prepared from (S)-1-(tert-butyldimethylsilyloxy)-3-cyclopropylbut-3-en-2-amine (Intermediate 55, 4.61 g, 19.09 mmol) and 2-bromo-N-methoxy-N-methylacetamide (Intermediate 4, 3.16 g, 17.36 mmol)

following the procedure described for Intermediate 5. The desired product was obtained as a light yellow oil (4.94 g, 64%).

MS: 443 ES+($C_{22}H_{42}N_2O_5Si$)

$^1$H NMR (300 MHz, DMSO-$d_6$) δ: 0.03 (m, 6H); 0.35 (m, 1H); 0.48 (m, 1H); 0.61 (m, 2H); 0.83 (m, 9H); 1.35 (m, 9H); 3.07 (m, 3H); 3.65 (m, 3H); 3.84 (m, 2H); 4.02 (m, 2H); 4.54 (m, 1H); 4.83 (m, 2H).

Intermediate 57: (S)-tert-butyl 1-(tert-butyldimethylsilyloxy)-3-cyclopropylbut-3-en-2-yl(2-oxopent-3-enyl)carbamate

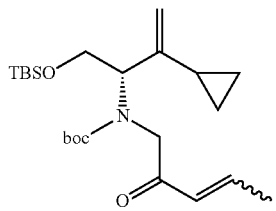

A suspension of cerium (III) chloride (27.8 g, 112.95 mmol) in THF (100 mL) at room temperature was stirred vigorously for 2 hours. The suspension was cooled to −78° C. and (E)-prop-1-enylmagnesium bromide (0.5 M in THF) (226 mL, 112.95 mmol) was added dropwise. The mixture was stirred at −78° C. for 1.5 hours. (S)-tert-butyl 1-(tert-butyldimethylsilyloxy)-3-cyclopropylbut-3-en-2-yl(2-(methoxy(methyl)amino)-2-oxoethyl)carbamate (Intermediate 56, 5 g, 11.30 mmol) in THF (20 mL) was then added dropwise at −78° C. The reaction was stirred at −78° C. for 30 minutes and then warmed to 0° C. for 15 minutes. The reaction was quenched with 10% citric acid, diluted further with water and extracted twice with ether. The organics were washed once with brine, dried over magnesium sulfate, filtered and concentrated. Silica gel chromatography (0%-20% ethyl acetate/hexanes) afforded the title compound as a light yellow oil (4.0 g, 84%).

MS: 424 ES+($C_{23}H_{41}NO_4Si$)

$^1$H NMR (300 MHz, DMSO-$d_6$) δ: 0.03 (m, 6H); 0.43 (m, 2H); 0.61 (m, 2H); 0.83 (m, 9H); 1.34 (m, 10H); 1.84 (m, 2H); 2.04 (m, 1H); 3.74 (m, 1H); 3.84 (m, 2H); 4.03 (m, 1H); 4.57 (m, 1H); 4.79 (m, 2H); 6.28 (m, 1H); 6.84 (m, 1H).

Intermediate 58: (S)-tert-butyl 2-((tert-butyldimethylsilyloxy)methyl)-3-cyclopropyl-5-oxo-5,6-dihydropyridine-1(2H)-carboxylate

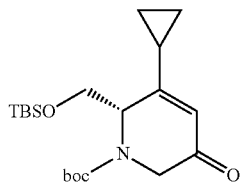

The title compound was prepared from (S)-tert-butyl 1-(tert-butyldimethylsilyloxy)-3-cyclopropylbut-3-en-2-yl (2-oxopent-3-enyl)carbamate (Intermediate 57, 4 g, 9.44 mmol) following the procedure described for Intermediate 7, except the reaction mixture was heated at 110° C. overnight. The desired product was obtained as a light brown oil (2.97 g, 82%).

MS: 382 ES+($C_{20}H_{35}NO_4Si$)

$^1$H NMR (300 MHz, DMSO-$d_6$) δ: 0.01 (m, 6H); 0.62 (m, 1H); 0.80 (s, 9H); 1.00 (m, 3H); 1.42 (s, 9H); 1.61 (m, 1H); 3.80 (m, 1H); 3.95 (m, 2H); 4.19 (m, 1H); 4.75 (m, 1H); 5.72 (s, 1H).

Intermediate 59: (2S,5S)-tert-butyl 2-((tert-butyldimethylsilyloxy)methyl)-3-cyclopropyl-5-hydroxy-5,6-dihydropyridine-1(2H)-carboxylate

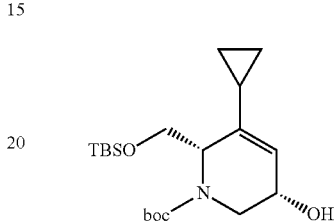

The title compound was prepared from (S)-tert-butyl 2-((tert-butyldimethylsilyloxy)methyl)-3-cyclopropyl-5-oxo-5,6-dihydropyridine-1(2H)-carboxylate (Intermediate 58, 2.97 g, 7.78 mmol) following the procedure described for Intermediate 10. The desired product was obtained as a tan oil (2.74 g, 92%).

MS: 384 ES+($C_{20}H_{37}NO_4Si$)

$^1$H NMR (300 MHz, DMSO-$d_6$) δ: 0.02 (m, 6H); 0.34 (m, 1H); 0.47 (m, 1H); 0.64 (m, 2H); 0.85 (m, 9H); 1.26 (m, 1H); 1.39 (s, 9H); 2.65 (m, 1H); 3.89 (m, 3H); 4.05 (m, 1H); 4.95 (m, 1H); 5.34 (m, 1H).

Intermediate 60: (2S,5R)-tert-butyl 5-(N-(allyloxy)-2-nitrophenylsulfonamido)-2-((tert-butyldimethylsilyloxy)methyl)-3-cyclopropyl-5,6-dihydropyridine-1(2H)-carboxylate

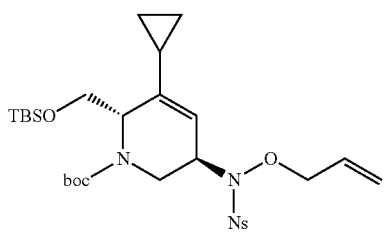

The title compound was prepared from (2S,5S)-tert-butyl 2-((tert-butyldimethylsilyloxy)-methyl)-3-cyclopropyl-5-hydroxy-5,6-dihydropyridine-1(2H)-carboxylate (Intermediate 59, 2.74 g, 7.14 mmol) and N-(allyloxy)-2-nitrobenzenesulfonamide (1.85 g, 7.14 mmol) following the procedure described for Intermediate 11. The desired product was obtained as a light yellow oil (3.19 g, 71%).

MS: 624 ES+($C_{29}H_{45}N_3O_8SSi$)

$^1$H NMR (300 MHz, DMSO-$d_6$) δ: 0.00 (m, 6H); 0.34 (m, 1H); 0.63 (m, 2H); 0.83 (m, 9H); 1.37 (m, 9H); 3.30 (m, 1H); 3.84 (m, 2H); 4.30 (m, 4H); 5.18 (m, 2H); 5.75 (m, 1H); 8.04 (m, 4H).

Intermediate 61: (2S,5R)-tert-butyl 5-(N-(allyloxy)-2-nitrophenylsulfonamido)-3-cyclopropyl-2-(hydroxymethyl)-5,6-dihydropyridine-1(2H)-carboxylate

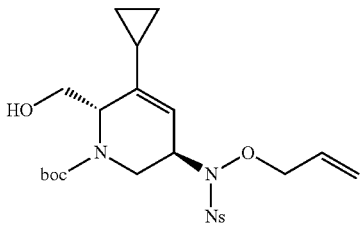

The title compound was prepared from (2S,5R)-tert-butyl 5-(N-(allyloxy)-2-nitrophenylsulfonamido)-2-((tert-butyldimethylsilyloxy)methyl)-3-cyclopropyl-5,6-dihydropyridine-1(2H)-carboxylate (Intermediate 60, 3.19 g, 5.11 mmol) following the procedure described for Intermediate 12. The desired product was obtained as a tan foam (2.35 g, 90%).

MS: 510 ES+($C_{23}H_{31}N_3O_8S$)

$^1$H NMR (300 MHz, DMSO-$d_6$) δ: 0.32 (m, 2H); 0.62 (m, 2H); 1.35 (m, 9H); 3.30 (m, 1H); 3.67 (m, 2H); 4.27 (m, 4H); 4.71 (m, 1H); 5.19 (m, 2H); 5.71 (m, 1H); 8.04 (m, 4H).

Intermediate 62: (2S,5R)-5-(N-(allyloxy)-2-nitrophenylsulfonamido)-1-(tert-butoxycarbonyl)-3-cyclopropyl-1,2,5,6-tetrahydropyridine-2-carboxylic acid

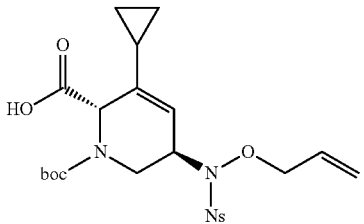

The title compound was prepared from (2S,5R)-tert-butyl 5-(N-(allyloxy)-2-nitrophenylsulfonamido)-3-cyclopropyl-2-(hydroxymethyl)-5,6-dihydropyridine-1(2H)-carboxylate (Intermediate 61, 2.35 g, 4.61 mmol) following the procedure described for Intermediate 13. The desired product was obtained as an orange foam (2.28 g, 94%).

MS: 524 ES+($C_{23}H_{29}N_3O_9S$)

Intermediate 63: (2S,5R)-tert-butyl 5-(N-(allyloxy)-2-nitrophenylsulfonamido)-2-carbamoyl-3-cyclopropyl-5,6-dihydropyridine-1(2H)-carboxylate

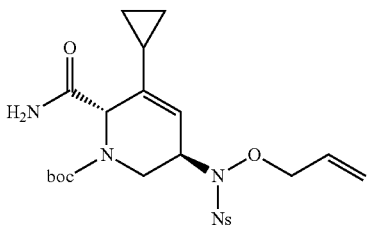

The title compound was prepared from (2S,5R)-5-(N-(allyloxy)-2-nitrophenylsulfonamido)-1-(tert-butoxycarbonyl)-3-cyclopropyl-1,2,5,6-tetrahydropyridine-2-carboxylic acid (Intermediate 62, 2.28 g, 4.35 mmol) following the procedure described for Intermediate 14. The desired product was obtained as an orange foam (1.07 g, 47%).

MS: 523 ES+($C_{23}H_{30}N_4O_8S$)

$^1$H NMR (300 MHz, DMSO-$d_6$) δ: 0.23 (m, 2H); 0.59 (m, 2H); 1.35 (m, 9H); 3.58 (m, 1H); 4.23 (m, 3H); 4.72 (m, 1H); 5.19 (m, 2H); 5.71 (m, 1H); 7.18 (m, 1H); 7.59 (m, 1H); 8.04 (m, 4H).

Intermediate 64: (2S,5R)-5-(N-(allyloxy)-2-nitrophenylsulfonamido)-3-cyclopropyl-1,2,5,6-tetrahydropyridine-2-carboxamide

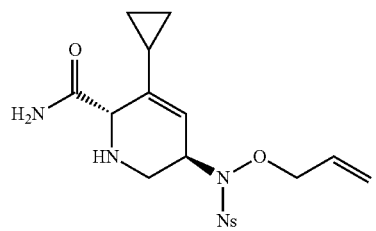

The title compound was prepared from (2S,5R)-tert-butyl 5-(N-(allyloxy)-2-nitrophenylsulfonamido)-2-carbamoyl-3-cyclopropyl-5,6-dihydropyridine-1(2H)-carboxylate (Intermediate 63, 0.932 g, 1.78 mmol) following the procedure described for Intermediate 25. The desired product was obtained as an orange foam (0.518 g, 68%).

MS: 423 ES+($C_{18}H_{22}N_4O_6S$)

$^1$H NMR (300 MHz, DMSO-$d_6$) δ: 0.18 (m, 2H); 0.53 (m, 2H); 1.29 (m, 1H); 2.30 (m, 1H); 2.58 (m, 1H); 2.95 (m, 1H); 3.72 (m, 1H); 4.22 (m, 1H); 4.36 (m, 2H); 4.96 (m, 1H); 5.24 (m, 2H); 5.80 (m, 1H); 7.07 (bs, 1H); 7.39 (bs, 1H); 8.04 (m, 4H).

Intermediate 65: (R)-5-(allyloxyamino)-3-cyclopropyl-1,2,5,6-tetrahydropyridine-2-carboxamide

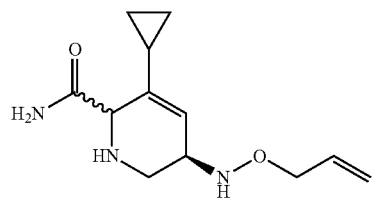 [SMILES: C=CCON[C@@H]1C=C(C2CC2)C(C(N)=O)NC1]

The title compound was prepared from (2S,5R)-5-(N-(allyloxy)-2-nitrophenylsulfonamido)-3-cyclopropyl-1,2,5,6-tetrahydropyridine-2-carboxamide (Intermediate 64, 0.518 g, 1.23 mmol) following the procedure described for Intermediate 26. The desired product was obtained as a light yellow oil (0.171 g, 59%). The product is a mixture of diastereomers.

MS: 238 ES+($C_{12}H_{19}N_3O_2$)

$^1$H NMR (300 MHz, DMSO-$d_6$) δ: 0.28 (m, 2H); 0.41 (m, 2H); 0.54 (m, 2H); 1.33 (m, 1H); 2.49 (m, 1H); 2.64 (m, 1H); 2.93 (m, 1H); 3.23 (m, 1H); 3.65 (m, 1H); 4.07 (m, 2H); 5.19 (m, 3H); 5.89 (m, 1H); 6.26 (m, 1H); 6.97 (bs, 1H); 7.34 (bs, 1H).

Intermediate 66: (2S,5R)-6-(allyloxy)-3-cyclopropyl-7-oxo-1,6-diazabicyclo[3.2.1]oct-3-ene-2-carboxamide

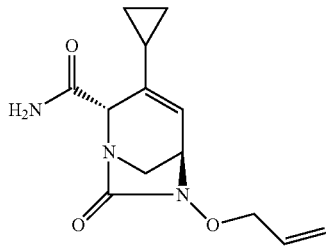 [SMILES: C=CCON1C(=O)N2C[C@H]1C=C(C1CC1)[C@H]2C(N)=O]

The title compound was prepared from (R)-5-(allyloxyamino)-3-cyclopropyl-1,2,5,6-tetrahydropyridine-2-carboxamide (Intermediate 65, 0.316 g, 1.33 mmol) following the procedure described for Intermediate 27. The desired product was obtained as a colorless oil (0.261 g, 74%).

MS: 264 ES+($C_{13}H_{17}N_3O_3$)

$^1$H NMR (300 MHz, DMSO-$d_6$) δ: 0.37 (m, 2H); 0.60 (m, 2H); 1.20 (m, 1H); 2.98 (m, 1H); 3.79 (m, 1H); 3.92 (m, 1H); 4.20 (m, 1H); 4.33 (m, 2H); 5.28 (m, 2H); 5.93 (m, 2H); 7.30 (bs, 1H); 7.86 (bs, 1H).

Example 37

(2R)-isopropyl 2-(((2S,5R)-2-carbamoyl-3-cyclopropyl-7-oxo-1,6-diazabicyclo[3.2.1]oct-3-en-6-yl)oxy)-2-fluoroacetate

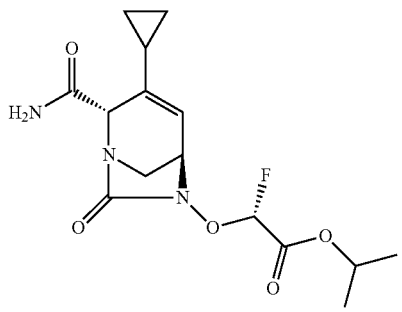 [SMILES: CC(C)OC(=O)[C@@H](F)ON1C(=O)N2C[C@H]1C=C(C1CC1)[C@H]2C(N)=O]

To a solution of (2S,5R)-6-(allyloxy)-3-cyclopropyl-7-oxo-1,6-diazabicyclo[3.2.1]oct-3-ene-2-carboxamide (Intermediate 66, 0.15 g, 0.57 mmol) in methanol (3 mL) at room temperature was added 1,3-dimethylbarbituric acid (0.178 g, 1.14 mmol) and tetrakis(triphenylphosphine)palladium(0) (0.066 g, 0.06 mmol). The reaction was stirred at room temperature for 2 hours, then concentrated to afford an orange film. The orange film was dissolved in DMF (4 mL). Potassium carbonate (0.157 g, 1.14 mmol) and isopropyl 2-bromo-2-fluoroacetate (Intermediate 18, 0.340 g, 1.71 mmol) were added. The reaction mixture was stirred at room temperature overnight then diluted with ethyl acetate and filtered through a 0.45 μm filter to remove solid potassium carbonate. The filtrate was washed twice with 1:1 brine:water. The organics were dried over magnesium sulfate, filtered and concentrated. Silica gel chromatography (0%-65% ethyl acetate/hexanes) afforded a 1:1 mixture of diastereomers, 166.3 mg, 86%. Separation of diastereomers was done on reverse phase HPLC (Atlantis T3, 19 mm×150 mm, 5 μm, 20%-40% acetonitrile in water, 20 mL/min, 15 min). Both diastereomers were obtained as white solids after lyophilization.

Example 37

(First Eluting Diastereomer): 47.3 mg, 24%

MS: 342 ES+($C_{15}H_{20}FN_3O_5$)

$^1$H NMR (300 MHz, DMSO-$d_6$) δ: 0.39 (m, 2H); 0.61 (m, 1H); 1.19 (d, 3H); 1.21 (m, 1H); 1.24 (d, 3H); 2.99 (m, 1H); 3.88 (m, 1H); 4.01 (m, 1H); 4.29 (m, 1H), 5.00 (m, 1H); 5.87 (m, 1H); 6.20 (m, 1H); 7.36 (br s, 1H); 7.90 (br s, 1H).

Example 38

(Second Eluting Diastereomer): 49.8 mg, 26%

MS: 342 ES+($C_{15}H_{20}FN_3O_5$)

$^1$H NMR (300 MHz, DMSO-$d_6$) δ: 0.41 (m, 2H); 0.62 (m, 1H); 1.22 (m, 1H); 1.27 (d, 3H); 1.29 (d, 3H); 3.03 (m, 1H); 3.91 (m, 1H); 3.94 (m, 1H); 4.31 (m, 1H), 5.05 (m, 1H); 5.91 (m, 1H); 6.12 (m, 1H); 7.37 (br s, 1H); 7.93 (br s, 1H).

Example 38

(2S)-isopropyl 2-(((2S,5R)-2-carbamoyl-3-cyclopropyl-7-oxo-1,6-diazabicyclo[3.2.1]oct-3-en-6-yl)oxy)-2-fluoroacetate

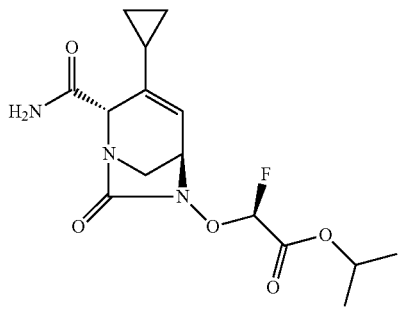 [SMILES: CC(C)OC(=O)[C@H](F)ON1C(=O)N2C[C@H]1C=C(C1CC1)[C@H]2C(N)=O]

Example 39

(2R)-ethyl 2-(((2S,5R)-2-carbamoyl-3-cyclopropyl-7-oxo-1,6-diazabicyclo[3.2.1]oct-3-en-6-yl)oxy)-2-fluoroacetate

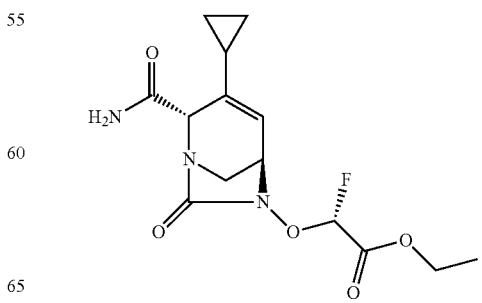

Example 40

(2S)-ethyl 2-(((2S,5R)-2-carbamoyl-3-cyclopropyl-7-oxo-1,6-diazabicyclo[3.2.1]oct-3-en-6-yl)oxy)-2-fluoroacetate

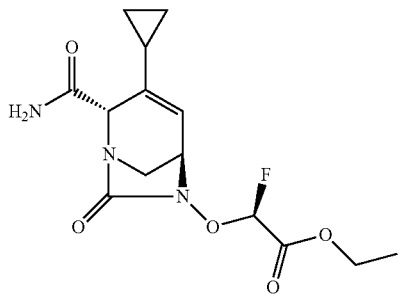

To a solution of (2S,5R)-6-(allyloxy)-3-cyclopropyl-7-oxo-1,6-diazabicyclo[3.2.1]oct-3-ene-2-carboxamide (Intermediate 66, 0.2972 g, 1.13 mmol) in methanol (6 mL) at room temperature was added 1,3-dimethylbarbituric acid (0.352 g, 2.26 mmol) and tetrakis(triphenylphosphine)palladium(0) (0.130 g, 0.11 mmol). The reaction was stirred at room temperature for 2 hours, then concentrated to afford an orange film. The orange film was dissolved in DMF (6 mL). Potassium carbonate (0.468 g, 3.39 mmol) and ethyl bromofluoroacetate (0.534 mL, 4.52 mmol) were added. The reaction mixture was stirred overnight at room temperature then diluted with ethyl acetate and filtered through a 0.45 μm filter to remove solid potassium carbonate. The filtrate was washed twice with 1:1 brine:water. The organics were dried over magnesium sulfate, filtered and concentrated. Silica gel chromatography (0%-65% ethyl acetate/hexanes) afforded a 1:1 mixture of diastereomers, 303.7 mg, 82%. Separation of diastereomers was done on reverse phase HPLC (Atlantis T3, 19 mm×150 mm, 5 μm, 20%-40% acetonitrile in water, 20 mL/min, 15 min). Both diastereomers were obtained as white solids after lyophilization.

Example 39

(First Eluting Diastereomer): 107 mg, 29%

MS: 328 ES+($C_{14}H_{18}FN_3O_5$)

$^1$H NMR (300 MHz, DMSO-$d_6$) δ: 0.39 (m, 2H); 0.61 (m, 2H); 1.21 (m, 4H); 3.01 (m, 1H); 3.89 (m, 1H); 4.02 (m, 1H); 4.19 (m, 2H); 4.29 (s, 1H); 5.88 (m, 1H); 6.22 (m, 1H); 7.36 (br s, 1H); 7.91 (br s, 1H).

Example 40

(Second Eluting Diastereomer): 110.9 mg, 30%

MS: 328 ES+($C_{14}H_{18}FN_3O_5$)

$^1$H NMR (300 MHz, DMSO-$d_6$) δ: 0.40 (m, 2H); 0.61 (m, 2H); 1.26 (m, 4H); 3.04 (m, 1H); 3.90 (m, 1H); 3.94 (m, 1H); 4.26 (m, 3H); 5.90 (m, 1H); 6.24 (m, 1H); 7.36 (br s, 1H); 7.92 (br s, 1H).

Example 41

(2R)-2-(((2S,5R)-2-carbamoyl-3-cyclopropyl-7-oxo-1,6-diazabicyclo[3.2.1]oct-3-en-6-yl)oxy)-2-fluoroacetic acid lithium salt

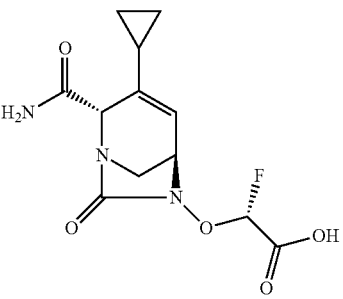

To a solution of (2R)-ethyl 2-(((2S,5R)-2-carbamoyl-3-cyclopropyl-7-oxo-1,6-diazabicyclo[3.2.1]oct-3-en-6-yl)oxy)-2-fluoroacetate (Example 39, 96.6 mg, 0.30 mmol) in THF (3 mL) and water (1 mL) at 0° C. was added lithium hydroxide (1M) (0.310 mL, 0.31 mmol). The reaction mixture was kept in an ice bath and stirred for 15 minutes. Another 0.2 eq of lithium hydroxide was added. After 15 minutes the reaction mixture was adjusted to pH=7 with 0.5N HCl. The mixture was frozen and lyophilized to afford a pale yellow solid, 90.4 mg. Reverse phase HPLC (YMC Carotenoid 30, 19 mm×150 mm, 5 μm coupled with Synergi Polar RP, 21.2 mm×100 mm, 4 μm, 0%-25% acetonitrile in water, 20 mL/min, 5 min) afforded the title copound as awhite solid, 45.9 mg, 52%.

MS: 300 ES+($C_{12}H_{14}FN_3O_5$)

$^1$H NMR (300 MHz, DMSO-$d_6$) δ: 0.38 (m, 2H); 0.59 (m, 2H); 1.20 (m, 1H); 3.02 (m, 1H); 3.83 (m, 1H); 4.00 (m, 1H); 4.25 (m, 1H); 5.24 (m, 1H); 5.89 (m, 1H); 7.30 (br s, 1H); 7.88 (br s, 1H).

Example 42

(2R)-2-(((2S,5R)-2-carbamoyl-3-cyclopropyl-7-oxo-1,6-diazabicyclo[3.2.1]oct-3-en-6-yl)oxy)-2-fluoroacetic acid lithium salt

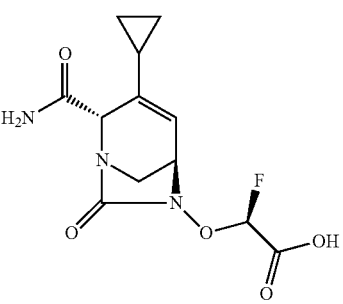 [SMILES: NC(=O)[C@@H]1C(C2CC2)=C[C@@H]2CN1C(=O)N2O[C@@H](F)C(=O)O]

To a solution of (2S)-2-(((2S,5R)-2-carbamoyl-3-cyclopropyl-7-oxo-1,6-diazabicyclo[3.2.1]oct-3-en-6-yl)oxy)-2-fluoroacetic acid (Example 40, 96.6 mg, 0.30 mmol) in THF (3 mL) and water (1) at 0° C. was added lithium hydroxide (1M) (0.310 mL, 0.31 mmol). The reaction mixture was kept in ice bath and stirred for 15 minutes. Another 0.2 eq of lithium hydroxide was added. After 15 minutes the reaction mixture was adjusted to pH=7 with 0.5N HCl. The mixture was frozen and lyophilized to afford a pale yellow solid, 90.6 mg. Reverse phase HPLC (YMC Carotenoid 30, 19 mm×150 mm, 5 µm coupled with Synergi Polar RP, 21.2 mm×100 mm, 4 µm, 0%-25% acetonitrile in water, 20 mL/min, 5 min) afforded the title copound as awhite solid, 41.2 mg, 45%.

MS: 300 ES+($C_{12}H_{14}FN_3O_5$)

$^1$H NMR (300 MHz, DMSO-$d_6$) δ: 0.39 (m, 2H); 0.59 (m, 2H); 1.20 (m, 1H); 3.02 (m, 1H); 3.82 (m, 1H); 3.98 (m, 1H); 4.24 (m, 1H); 5.24 (m, 1H); 5.90 (m, 1H); 7.31 (br s, 1H); 7.90 (br s, 1H).

Example 43

2-(((2S,5R)-2-carbamoyl-3-cyclopropyl-7-oxo-1,6-diazabicyclo[3.2.1]oct-3-en-6-yl)oxy)-2-fluoroacetic acid lithium salt

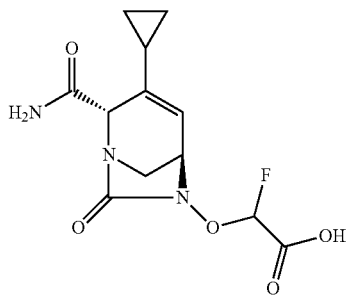

(2R)-2-(((2S,5R)-2-carbamoyl-3-cyclopropyl-7-oxo-1,6-diazabicyclo[3.2.1]oct-3-en-6-yl)oxy)-2-fluoroacetic acid (Example 41, 8 mg, 0.03 mmol) and (2S)-2-(((2S,5R)-2-carbamoyl-3-cyclopropyl-7-oxo-1,6-diazabicyclo [3.2.1] oct-3-en-6-yl)oxy)-2-fluoroacetic acid (Example 42, 8 mg, 0.03 mmol) were combined in an amber vial. Water (1.5 mL) was added. The mixture was frozen and lyophilized to afford a white solid, 16 mg.

MS: 300 ES+($C_{12}H_{14}FN_3O_5$)

$^1$H NMR (300 MHz, DMSO-$d_6$) δ: 0.39 (m, 2H); 0.58 (m, 2H); 1.19 (m, 1H); 3.00 (m, 1H); 3.81 (m, 1H); 3.98 (m, 1H); 4.24 (m, 1H); 5.19 (m, 1H); 5.89 (m, 1H); 7.29 (br s, 1H); 7.88 (br s, 1H).

Intermediate 67: (1-isopropyl-2-methyl-propyl) 2-bromo-2,2-difluoro-acetate

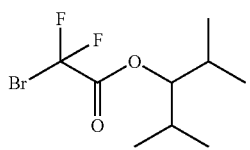

To a solution of 2,4-dimethylpentan-3-ol (0.72 mL, 5.17 mmol) and N,N-diisopropylethylamine (1.81 mL, 10.34 mmol) in DCM (20 mL) at 0° C. was added 2-bromo-2,2-difluoro-acetyl chloride (0.49 mL, 5.17 mmol) dropwise. The reaction mixture was stirred at 35° C. overnight. The reaction was quenched with 10 mL of 1N hydrochloric acid. The layers were separated. The organics were washed twice with water, once with brine, then dried over magnesium sulfate, filtered and concentrated to afford the title compound as a dark orange oil, 1.95 g, quant. Crude used in next step.

$^1$H NMR (300 MHz, CDCl$_3$-d) δ: 0.95 (m, 12H); 2.06 (m, 2H); 4.74 (m, 1H).

Example 44

(1-isopropyl-2-methyl-propyl) 2-[[(2S,5R)-2-carbamoyl-3-methyl-7-oxo-1,6-diazabicyclo[3.2.1]oct-3-en-6-yl]oxy]-2,2-difluoro-acetate

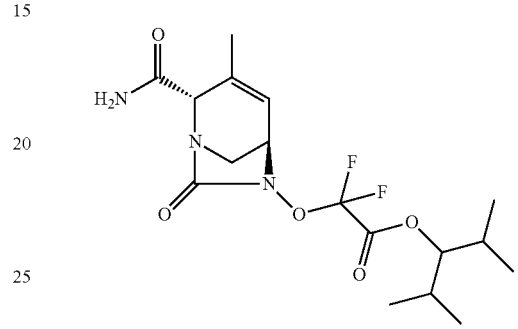

To a solution of (2S,5R)-6-hydroxy-3-methyl-7-oxo-1,6-diazabicyclo[3.2.1]oct-3-ene-2-carboxamide (Intermediate 193, 150 mg, 0.76 mmol) in DMF (5 mL) at room temperature was added potassium carbonate (210.27 mg, 1.52 mmol) and (1-isopropyl-2-methyl-propyl) 2-bromo-2,2-difluoro-acetate (Intermediate 67, 623.28 mg, 2.28 mmol). The reaction mixture was stirred for 4 hours at room temperature. Another two equivalents of (1-isopropyl-2-methyl-propyl) 2-bromo-2,2-difluoro-acetate were added, and the reaction mixture was stirred overnight at room temperature. The reaction mixture was diluted with ethyl acetate and filtered to remove the potassium carbonate. The filtrate was washed three times with 1:1 brine:water. The organics were dried over magnesium sulfate, filtered and concentrated. Silica gel chromatography (0%-15% acetone/dichloromethane) afforded the title compound as a light orange sticky film after lyophilization, 44.6 mg, 13%.

MS: 390 ES+($C_{17}H_{25}FN_3O_5$)

$^1$H NMR (300 MHz, DMSO-$d_6$) δ: 0.86 (m, 12H); 1.64 (s, 3H); 1.99 (m, 2H); 3.15 (m, 1H); 3.85 (m, 1H); 4.07 (m, 1H); 4.28 (s, 1H); 4.69 (m, 1H); 6.03 (m, 1H); 7.42 (s, 1H); 7.85 (s, 1H).

Intermediate 68: octyl (2R)-2-bromo-2-fluoro-acetate

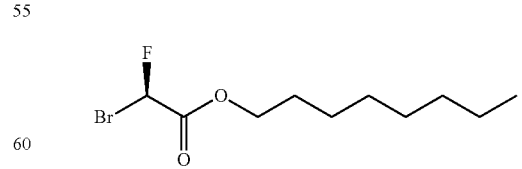

To a suspension of (2R)-2-bromo-2-fluoro-acetic acid; (1S)-1-phenylethanamine (Intermediate 168, 642.8 mg, 2.31 mmol) and 1-octanol (554 mg, 5.78 mmol) in DCM (9 mL) at room temperature was added chlorotrimethylsilane (1.19 mL, 9.39 mmol) dropwise. The suspension became a solution and was stirred overnight at room temperature. The reaction mixture was washed with water three times. The organics were dried over magnesium sulfate, filtered and concentrated. Silica gel chromatography (0%-10% ethyl acetate/hexanes) afforded the title compound as a colorless liquid, 554.9 mg, 89%.

$^1$H NMR (300 MHz, CDCl$_3$-d) δ: 0.84 (m, 3H); 1.24 (m, 10H); 1.61 (m, 2H); 4.22 (m, 2H); 7.25 (d, 1H).

Example 45 octyl (2R)-2-[[(2S,5R)-2-carbamoyl-3-methyl-7-oxo-1,6-diazabicyclo[3.2.1]oct-3-en-6-yl]oxy]-2-fluoro-acetate

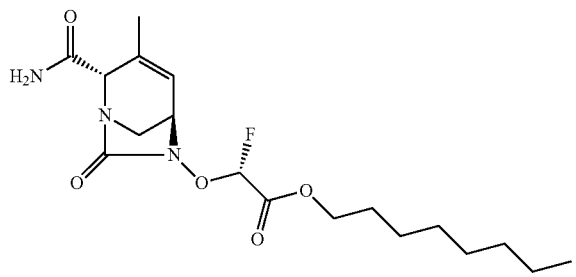 [SMILES: CCCCCCCCOC(=O)[C@@H](F)ON1C(=O)N2C[C@H]1C=C(C)[C@H]2C(N)=O]

To a solution of (2S,5R)-6-hydroxy-3-methyl-7-oxo-1,6-diazabicyclo[3.2.1]oct-3-ene-2-carboxamide (Intermediate 193, 150 mg, 0.76 mmol) in 1,4-dioxane (4 mL) and DMF (0.5 mL) was added octyl (2R)-2-bromo-2-fluoro-acetate (Intermediate 68, 0.09 mL, 2.06 mmol). The reaction mixture was cooled to 0° C. and DBU (0.11 mL, 0.76 mmol) was added dropwise. The reaction mixture was stirred for 10 minutes, then diluted with ethyl acetate and washed three times with 1:1 brine:water. The organics were dried over magnesium sulfate, filtered and concentrated to afford an orange oil. Silica gel chromatography (0%-60% ethyl acetate/hexanes) afforded the title compound as a white solid, 247.9 mg, 84%.

MS: 386 ES+(C$_{18}$H$_{28}$FN$_3$O$_5$)

$^1$H NMR (300 MHz, DMSO-d$_6$) δ: 0.86 (m, 3H); 1.25 (m, 10H); 1.59 (m, 5H); 3.04 (m, 1H); 3.78 (m, 1H); 4.04 (m, 1H); 4.16 (m, 3H); 6.00 (m, 1H); 6.24 (d, 1H); 7.37 (s, 1H); 7.81 (s, 1H).

Intermediate 69: octyl (2R)-2-bromo-2-fluoro-acetate

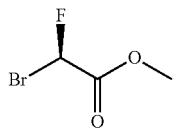

The title compound was prepared from (2R)-2-bromo-2-fluoro-acetic acid; (1S)-1-phenylethanamine (Intermediate 168, 526.2 mg, 1.89 mmol) and methanol (260 mg, 5.68 mmol) according to the procedure for Intermediate 68 to afford a white oily/solid, 260 mg, 80%.

$^1$H NMR (300 MHz, CDCl$_3$-d) δ: 3.84 (s, 3H); 6.52 (d, 1H).

Example 46 methyl (2R)-2-[[(2S,5R)-2-carbamoyl-3-methyl-7-oxo-1,6-diazabicyclo[3.2.1]oct-3-en-6-yl]oxy]-2-fluoro-acetate

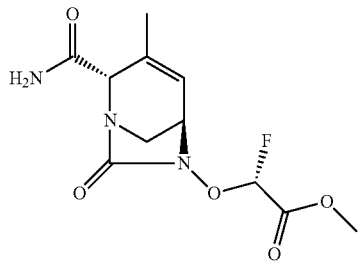 [SMILES: COC(=O)[C@@H](F)ON1C(=O)N2C[C@H]1C=C(C)[C@H]2C(N)=O]

The title compound was prepared from (2S,5R)-6-hydroxy-3-methyl-7-oxo-1,6-diazabicyclo[3.2.1]oct-3-ene-2-carboxamide (Intermediate 193, 120 mg, 0.61 mmol) and methyl (2R)-2-bromo-2-fluoro-acetate (Intermediate 69, 0.09 mL, 1.52 mmol) according to the procedure for Example 45 to a white foam, 81.2 mg, 46%.

MS: 288 ES+(C$_{11}$H$_{14}$FN$_3$O$_5$)

$^1$H NMR (300 MHz, DMSO-d$_6$) δ: 1.63 (s, 3H); 3.07 (m, 1H); 3.75 (m, 1H); 3.78 (s, 3H); 4.05 (m, 1H); 4.19 (s, 1H); 6.02 (m, 1H); 6.24 (m, 1H); 7.37 (s, 1H); 7.81 (s, 1H).

Intermediate 70: allyl (2R)-2-bromo-2-fluoro-acetate

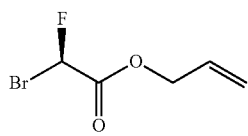

The title compound was prepared from (2R)-2-bromo-2-fluoro-acetic acid; (1S)-1-phenylethanamine (Intermediate 168, 510 mg, 1.83 mmol) and allyl alcohol (0.37 mL, 5.5 mmol) according to the procedure for Intermediate 68 to afford a colorless liquid, 100 mg, 28%.

$^1$H NMR (300 MHz, CDCl$_3$-d) δ: 4.71 (m, 2H); 5.31 (m, 2H); 5.86 (m, 1H); 6.55 (d, 1H).

Example 47 allyl (2R)-2-[[(2S,5R)-2-carbamoyl-3-methyl-7-oxo-1,6-diazabicyclo[3.2.1]oct-3-en-6-yl]oxy]-2-fluoro-acetate

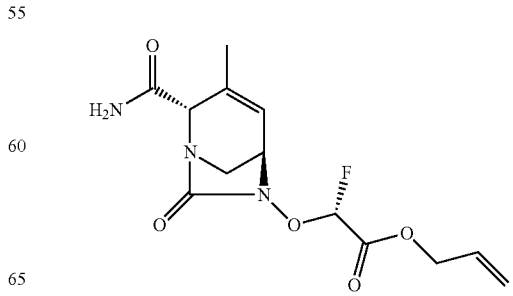

The title compound was prepared from (2S,5R)-6-hydroxy-3-methyl-7-oxo-1,6-diazabicyclo[3.2.1]oct-3-ene-2-carboxamide (Intermediate 193, 50 mg, 0.25 mmol) and allyl (2R)-2-bromo-2-fluoro-acetate (Intermediate 70, 100 mg, 0.51 mmol) according to the procedure for Example 45 to afford a white foam, 61.3 mg, 77%.

MS: 314 ES+($C_{13}H_{16}FN_3O_5$)

$^1$H NMR (300 MHz, DMSO-$d_6$) δ: 1.63 (s, 3H); 3.55 (m, 1H); 3.76 (m, 1H); 4.05 (m, 1H); 4.19 (s, 1H); 4.70 (m, 2H); 5.36 (m, 2H); 5.90 (m, 1H); 6.01 (m, 1H); 6.28 (d, 1H); 7.37 (s, 1H); 7.82 (s, 1H).

Intermediate 71: propyl (2R)-2-bromo-2-fluoro-acetate

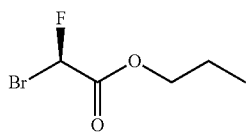

The title compound was prepared from (2R)-2-bromo-2-fluoro-acetic acid; (1S)-1-phenylethanamine (Intermediate 168, 444.9 mg, 1.6 mmol) and 1-propanol (0.3 mL, 4 mmol) according to the procedure for Intermediate 68 to afford a colorless liquid, 318 mg, 100%.

$^1$H NMR (300 MHz, CDCl$_3$-d) δ: 0.92 (t, 3H); 1.67 (m, 2H); 4.19 (m, 2H); 6.51 (d, 1H).

Example 48 propyl (2R)-2-[[(2S,5R)-2-carbamoyl-3-methyl-7-oxo-1,6-diazabicyclo[3.2.1]oct-3-en-6-yl]oxy]-2-fluoro-acetate

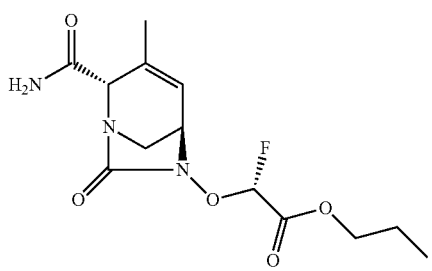 [SMILES: CCCOC(=O)[C@@H](F)ON1C(=O)N2C[C@H]1C=C(C)[C@H]2C(N)=O]

The title compound was prepared from (2S,5R)-6-hydroxy-3-methyl-7-oxo-1,6-diazabicyclo[3.2.1]oct-3-ene-2-carboxamide (Intermediate 193, 150 mg, 0.76 mmol) and propyl (2R)-2-bromo-2-fluoro-acetate (Intermediate 71, 302.78 mg, 1.52 mmol) according to the procedure for Example 45 to afford a white sticky foam, 156 mg, 65%.

MS: 316 ES+($C_{13}H_{18}FN_3O_5$)

$^1$H NMR (300 MHz, DMSO-$d_6$) δ: 0.89 (t, 3H); 1.61 (m, 5H); 3.05 (m, 1H); 3.76 (m, 1H); 4.04 (m, 1H); 4.13 (m, 2H); 4.19 (m, 1H); 6.01 (m, 1H); 6.25 (d, 1H); 7.37 (s, 1H); 7.82 (s, 1H).

Intermediate 72: isobutyl (2R)-2-bromo-2-fluoro-acetate

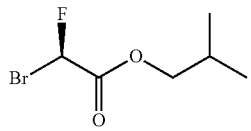

The title compound was prepared from (2R)-2-bromo-2-fluoro-acetic acid; (1S)-1-phenylethanamine (Intermediate 168, 487.5 mg, 1.75 mmol) and 2-methyl-1-propanol (0.4 mL, 4.38 mmol) according to the procedure for Intermediate 68 to afford a colorless liquid, 373 mg, 100%.

$^1$H NMR (300 MHz, CDCl$_3$-d) δ: 0.91 (d, 6H); 1.97 (m, 1H); 4.00 (m, 2H); 6.51 (d, 1H).

Example 49 isobutyl (2R)-2-[[(2S,5R)-2-carbamoyl-3-methyl-7-oxo-1,6-diazabicyclo[3.2.1]oct-3-en-6-yl]oxy]-2-fluoro-acetate

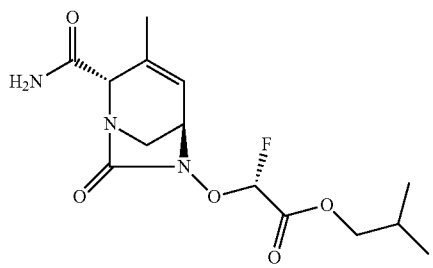 [SMILES: CC1=C[C@@H]2CN(C(=O)N2O[C@H](F)C(=O)OCC(C)C)[C@@H]1C(N)=O]

The title compound was prepared from (2S,5R)-6-hydroxy-3-methyl-7-oxo-1,6-diazabicyclo[3.2.1]oct-3-ene-2-carboxamide (Intermediate 193, 150 mg, 0.76 mmol) and isobutyl (2R)-2-bromo-2-fluoro-acetate (Intermediate 72, 372.73 mg, 1.75 mmol) according to the procedure for Example 45 to afford a sticky white foam, 161 mg, 64%.

MS: 330 ES+($C_{14}H_{20}FN_3O_5$)

$^1$H NMR (300 MHz, DMSO-$d_6$) δ: 0.90 (d, 6H); 1.63 (s, 3H); 1.90 (m, 1H); 3.05 (m, 1H); 3.76 (m, 1H); 3.97 (m, 2H); 4.04 (m, 1H); 4.20 (s, 1H); 6.00 (m, 1H); 6.27 (d, 1H); 7.37 (s, 1H); 7.82 (s, 1H).

Intermediate 73: butyl (2R)-2-bromo-2-fluoro-acetate

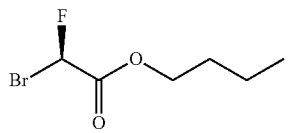

The title compound was prepared from (2R)-2-bromo-2-fluoro-acetic acid; (1S)-1-phenylethanamine (Intermediate 168, 400 mg, 1.44 mmol) and 1-butanol (0.33 mL, 3.6 mmol) according to the procedure for Intermediate 68 to afford a colorless liquid, 322 mg, quant.

$^1$H NMR (300 MHz, CDCl$_3$-d) δ: 0.88 (t, 3H); 1.33 (m, 2H); 1.65 (m, 2H); 4.23 (m, 2H); 6.50 (d, 1H).

Example 50 butyl (2R)-2-[[(2S,5R)-2-carbamoyl-3-methyl-7-oxo-1,6-diazabicyclo[3.2.1]oct-3-en-6-yl]oxy]-2-fluoro-acetate

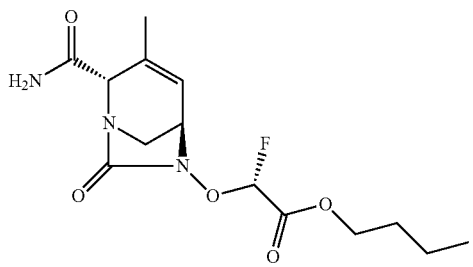

The title compound was prepared from (2S,5R)-6-hydroxy-3-methyl-7-oxo-1,6-diazabicyclo[3.2.1]oct-3-ene-2-carboxamide (Intermediate 193, 150 mg, 0.76 mmol) and butyl (2R)-2-bromo-2-fluoro-acetate (Intermediate 73, 322.49 mg, 1.51 mmol) according to the procedure for Example 45 to afford a sticky white foam, 198 mg, 79%.

MS: 330 ES+($C_{14}H_{20}FN_3O_5$)

$^1$H NMR (300 MHz, DMSO-$d_6$) δ: 0.88 (t, 3H); 1.35 (m, 2H); 1.59 (m, 2H); 1.63 (s, 3H); 3.06 (m, 1H); 3.77 (m, 1H); 4.04 (m, 1H); 4.20 (m, 2H); 4.21 (s, 1H); 6.00 (m, 1H); 6.24 (d, 1H); 7.37 (s, 1H); 7.82 (s, 1H).

Intermediate 74: pentyl (2R)-2-bromo-2-fluoro-acetate

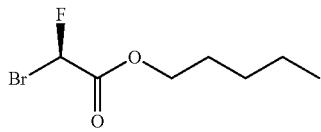

The title compound was prepared from (2R)-2-bromo-2-fluoro-acetic acid; (1S)-1-phenylethanamine (Intermediate 168, 474.2 mg, 1.71 mmol) and 1-pentanol (0.46 mL, 4.26 mmol) according to the procedure for Intermediate 68 to afford a colorless liquid, 363 mg, 93%.

$^1$H NMR (300 MHz, CDCl$_3$-d) δ: 0.88 (m, 3H); 1.28 (m, 4H); 1.60 (m, 2H); 4.17 (m, 2H); 6.45 (d, 1H).

Example 51 pentyl (2R)-2-[[(2S,5R)-2-carbamoyl-3-methyl-7-oxo-1,6-diazabicyclo[3.2.1]oct-3-en-6-yl]oxy]-2-fluoro-acetate

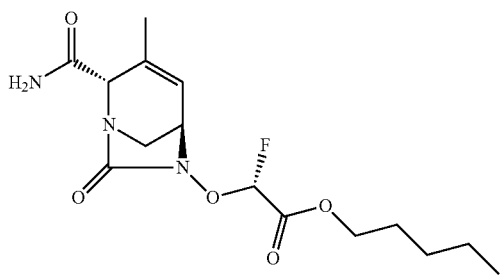 [SMILES: CCCCCOC(=O)[C@@H](F)ON1C(=O)N2C[C@H]1C=C(C)[C@H]2C(N)=O]

The title compound was prepared from (2S,5R)-6-hydroxy-3-methyl-7-oxo-1,6-diazabicyclo[3.2.1]oct-3-ene-2-carboxamide (Intermediate 193, 150 mg, 0.76 mmol) and pentyl (2R)-2-bromo-2-fluoro-acetate (Intermediate 74, 362.73 mg, 1.6 mmol) according to the procedure for Example 45 to afford a sticky white foam, 225 mg, 86%.

MS: 344 ES+($C_{15}H_{22}FN_3O_5$)

$^1$H NMR (300 MHz, DMSO-$d_6$) δ: 0.87 (m, 3H); 1.30 (m, 4H); 1.58 (m, 2H); 1.63 (s, 3H); 3.04 (m, 1H); 3.77 (m, 1H); 4.04 (m, 1H); 4.20 (m, 2H); 4.21 (s, 1H); 6.00 (m, 1H); 6.24 (d, 1H); 7.37 (s, 1H); 7.82 (s, 1H).

Intermediate 75: hexyl (2R)-2-bromo-2-fluoro-acetate

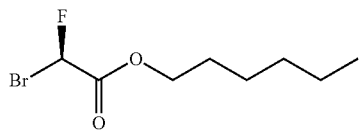

The title compound was prepared from (2R)-2-bromo-2-fluoro-acetic acid; (1S)-1-phenylethanamine (Intermediate 168, 400 mg, 1.44 mmol) and hexyl alcohol (0.45 mL, 3.6 mmol) according to the procedure for Intermediate 68 to afford a colorless liquid, 313 mg, 90%.

$^1$H NMR (300 MHz, CDCl$_3$-d) δ: 0.86 (m, 3H); 1.22 (m, 6H); 1.59 (m, 2H); 4.17 (m, 2H); 6.45 (d, 1H).

Example 52 hexyl (2R)-2-[[(2S,5R)-2-carbamoyl-3-methyl-7-oxo-1,6-diazabicyclo[3.2.1]oct-3-en-6-yl]oxy]-2-fluoro-acetate

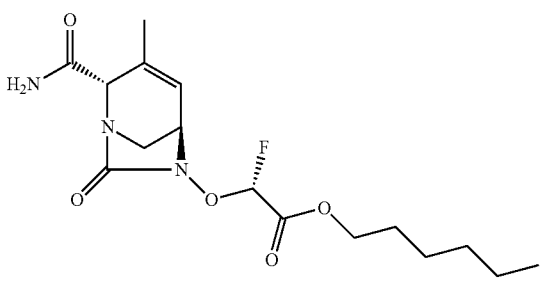 [SMILES: CCCCCCOC(=O)[C@@H](F)ON1C(=O)N2C[C@H]1C=C(C)[C@H]2C(N)=O]

The title compound was prepared from (2S,5R)-6-hydroxy-3-methyl-7-oxo-1,6-diazabicyclo[3.2.1]oct-3-ene-2-carboxamide (Intermediate 193, 150 mg, 0.76 mmol) and hexyl (2R)-2-bromo-2-fluoro-acetate (Intermediate 75, 313.62 mg, 1.3 mmol) according to the procedure for Example 45 to afford a sticky white foam, 224 mg, 82%.

MS: 358 ES+($C_{16}H_{24}FN_3O_5$)

$^1$H NMR (300 MHz, DMSO-$d_6$) δ: 0.87 (m, 3H); 1.30 (m, 6H); 1.57 (m, 2H); 1.62 (s, 3H); 3.04 (m, 1H); 3.77 (m, 1H); 4.04 (m, 1H); 4.19 (m, 2H); 4.20 (s, 1H); 6.00 (m, 1H); 6.24 (d, 1H); 7.37 (s, 1H); 7.82 (s, 1H).

Intermediate 76: 1-chloroethyl isopropyl carbonate

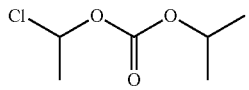

To a solution of 2-propanol (0.64 mL, 8.39 mmol) and pyridine (0.79 mL, 9.79 mmol) at −78° C. was added 1-chloroethyl chloroformate (0.76 mL, 6.99 mmol) dropwise. The reaction mixture was allowed to slowly warm to room temperature and stir overnight. The reaction mixture became a solid white clump and was sonicated in dichloromethane. The resulting suspension was concentrated and the white solid was dissolved in ethyl acetate and washed with water and brine. The organics were dried over magnesium sulfate, filtered and concentrated to afford the title compound as a colorless liquid, 1.29 g, 99%.

$^1$H NMR (300 MHz, CDCl$_3$-d) δ: 1.35 (m, 6H); 1.84 (d, 3H); 4.96 (m, 1H); 4.44 (m, 1H).

Example 53

1-isopropoxycarbonyloxyethyl (2R)-2-[[(2S,5R)-2-carbamoyl-3-methyl-7-oxo-1,6-diazabicyclo[3.2.1]oct-3-en-6-yl]oxy]-2-fluoro-acetate

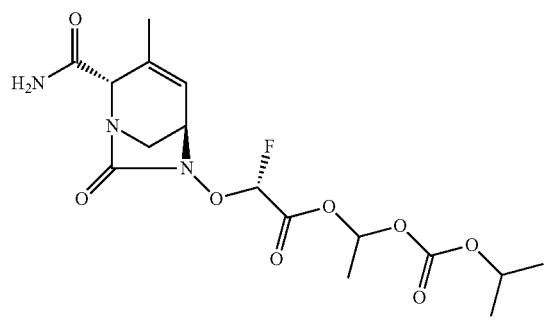 [SMILES: CC1=C[C@@H]2CN(C(=O)N2O[C@H](F)C(=O)OC(C)OC(=O)OC(C)C)[C@@H]1C(N)=O]

To a solution of (2R)-2-[[(2S,5R)-2-carbamoyl-3-methyl-7-oxo-1,6-diazabicyclo[3.2.1]oct-3-en-6-yl]oxy]-2-fluoro-acetic acid (Example 4, 194.46 mg, 0.71 mmol), N,N-diisopropylethylamine (0.12 mL, 0.71 mmol) and 1-chloroethyl isopropyl carbonate (Intermediate 76, 237.15 mg, 1.42 mmol) in DMF (5 mL) at room temperature was added tetrabutylammonium chloride (162.22 mg, 0.71 mmol). The reaction mixture was heated at 40° C. for ~4 hours, then diluted with ethyl acetate and washed twice with 1:1 brine:water. The organics were dried over magnesium sulfate, filtered and concentrated to afford an orange oil. Silica gel chromatography (0%-50% ethyl acetate/hexanes) afforded the title compound as a 1:1 mixture of diastereomers, white foam, 33.2 mg, 11%.

MS: 404 ES+(C$_{16}$H$_{22}$FN$_3$O$_8$)

$^1$H NMR (300 MHz, DMSO-d$_6$) δ: 1.23 (m, 6H); 1.46 (m, 3H); 1.62 (m, 3H); 3.05 (m, 1H); 3.79 (m, 1H); 4.00 (m, 1H); 4.19 (s, 1H); 4.80 (m, 1H); 6.00 (m, 1H); 6.33 (dd, 1H); 7.37 (s, 1H); 7.80 (d, 1H).

Example 54

(2R)-benzyl 2-(((2S,5R)-2-carbamoyl-3-methyl-7-oxo-1,6-diazabicyclo[3.2.1]oct-3-en-6-yl)oxy)-2-fluoroacetate

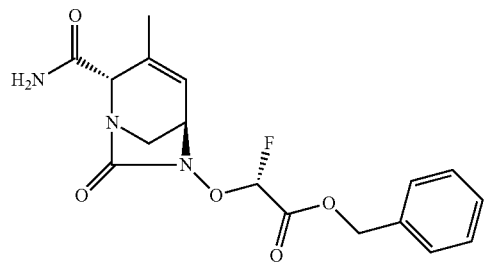 [SMILES: CC1=C[C@@H]2CN(C(=O)N2O[C@H](F)C(=O)OCc2ccccc2)[C@@H]1C(N)=O]

DBU (8.83 mL, 58.57 mmol) in DMF (30 mL) was added dropwise to a solution of (2S,5R)-6-hydroxy-3-methyl-7-oxo-1,6-diazabicyclo[3.2.1]oct-3-ene-2-carboxamide (Intermediate 193, 10.5 g, 53.25 mmol) and (R)-benzyl 2-bromo-2-fluoroacetate (Intermediate 171, 14.47 g, 58.57 mmol) in DMF (100 mL) at −40° C. over a period of 30 minutes under nitrogen. The resulting solution was stirred at −40° C. for 30 minutes, then quenched with water (15 mL). The reaction mixture was extracted with ethyl acetate (3×20 mL). The combined organics were washed with brine (3×20 mL), dried over sodium sulfate, filtered and concentrated. Silica chromatography (0% to 40% ethyl acetate/petroleum ether) afforded the title compound as a white solid, 8.8 g, 45%.

MS: 364 ES+(C$_{17}$H$_{18}$FN$_3$O$_5$)

$^1$H NMR (400 MHz, DMSO-d$_6$) δ: 1.62 (s, 3H); 2.92 (d, 1H); 3.75 (d, 1H); 3.99 (m, 1H); 4.02 (s, 1H); 5.25 (s, 2H); 5.76 (s, 1H); 6.33 (d, 1H); 7.38 (m, 5H); 7.39 (s, 1H); 7.85 (s, 1H).

Intermediate 77: (2S,5R)-6-[tert-butyl(dimethyl)silyl]oxy-3-methyl-7-oxo-1,6-diazabicyclo[3.2.1]oct-3-ene-2-carboxylic acid

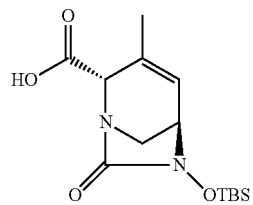 [SMILES: CC1=C[C@@H]2CN(C(=O)N2O[Si](C)(C)C(C)(C)C)[C@@H]1C(=O)O]

To a solution of methyl (2S,5R)-6-[tert-butyl(dimethyl)silyl]oxy-3-methyl-7-oxo-1,6-diazabicyclo[3.2.1]oct-3-ene-2-carboxylate (Intermediate 185, 538.5 mg, 1.65 mmol) in DCE (3 mL) in a 20 mL microwave vial was added trimethyltin hydroxide (477.17 mg, 2.64 mmol). The reaction was run in the microwave for 2 hours at 80° C. The solvent was removed and the resulting residue was dissolved in ethyl acetate and washed three times with 0.01N potassium bisulfate and once with brine. The organics were dried over sodium sulfate, filtered and concentrated to afford an orange foam, 649 mg, 100%.

MS: 313 ES+(C$_{14}$H$_{24}$N$_2$O$_4$Si)

¹H NMR (300 MHz, DMSO-d₆) δ: 0.00 (s, 6H); 0.78 (s, 9H); 1.50 (s, 3H); 2.92 (m, 1H); 3.47 (m, 1H); 3.53 (m, 1H); 3.77 (m, 1H); 5.85 (m, 1H).

Intermediate 78: 2-[2-[(2S,5R)-6-[tert-butyl(dimethyl)silyl]oxy-3-methyl-7-oxo-1,6-diazabicyclo[3.2.1]oct-3-ene-2-carbonyl]hydrazino]-2-oxo-acetamide

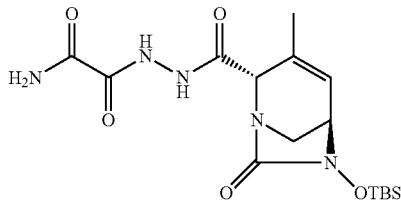 [SMILES: CC1=C[C@@H]2CN(C(=O)N2O[Si](C)(C)C(C)(C)C)[C@@H]1C(=O)NNC(=O)C(N)=O]

To a solution of (2S,5R)-6-[tert-butyl(dimethyl)silyl]oxy-3-methyl-7-oxo-1,6-diazabicyclo[3.2.1]oct-3-ene-2-carboxylic acid (Intermediate 77, 397.5 mg, 1.02 mmol) in DMF (6 mL) at 0° C. was added oxamic hydrazide (209.83 mg, 2.04 mmol), HATU (387 mg, 1.02 mmol) and N,N-diisopropylethylamine (0.57 mL, 3.26 mmol). The reaction mixture was stirred for 1 hour, then diluted with ethyl acetate and washed once with saturated sodium bicarbonate. The aqueous contained some product and was extracted once with ethyl acetate. The combined organics were dried over magnesium sulfate, filtered and concentrated to afford a yellow oil. Silica gel chromatography (0%-5% methanol) afforded the title compound as a light yellow solid, 142 mg, 35%.

MS: 398 ES+(C₁₆H₂₇N₅O₅Si)

¹H NMR (300 MHz, DMSO-d₆) δ: 0.00 (s, 6H); 0.78 (s, 9H); 1.53 (s, 3H); 2.95 (m, 1H); 3.60 (m, 1H); 3.67 (m, 1H); 4.04 (s, 1H); 5.98 (m, 1H); 7.75 (s, 1H); 8.07 (s, 1H); 10.30 (s, 1H); 10.48 (s, 1H).

Intermediate 79: 5-[(2 S,5R)-6-[tert-butyl(dimethyl)silyl]oxy-3-methyl-7-oxo-1,6-diazabicyclo[3.2.1]oct-3-en-2-yl]-1,3,4-oxadiazole-2-carboxamide

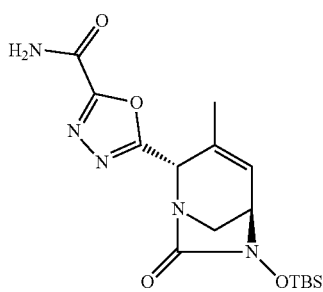 [SMILES: CC1=C[C@@H]2CN(C(=O)N2O[Si](C)(C)C(C)(C)C)[C@@H]1c1nnc(C(N)=O)o1]

To a solution of 2-[2-[(2S,5R)-6-[tert-butyl(dimethyl)silyl]oxy-3-methyl-7-oxo-1,6-diazabicyclo[3.2.1]oct-3-ene-2-carbonyl]hydrazino]-2-oxo-acetamide (Intermediate 78, 142 mg, 0.36 mmol) in DCM (6 mL) at room temperature was added 4-nitrobenzenesulfonyl chloride (79.17 mg, 0.36 mmol) and N,N-diisopropylethylamine (0.19 mL, 1.07 mmol). The reaction mixture became yellow and was stirred for 30 minutes, then was diluted with dichloromethane and washed with brine. The organics were dried over magnesium sulfate, filtered and concentrated to afford an orange oil. Silica gel chromatography (0%-5% methanol/dichloromethane) afforded the title compound as an orange foam, 93.8 mg, 69%.

MS: 380 ES+(C₁₆H₂₅N₅O₄Si)

¹H NMR (300 MHz, DMSO-d₆) δ: 0.00 (s, 6H); 0.77 (s, 9H); 1.53 (s, 3H); 3.02 (m, 2H); 3.70 (m, 1H); 5.01 (s, 1H); 6.14 (m, 1H); 8.13 (s, 1H); 8.53 (s, 1H).

Intermediate 80: 5-[(2S,5R)-6-hydroxy-3-methyl-7-oxo-1,6-diazabicyclo[3.2.1]oct-3-en-2-yl]-1,3,4-oxadiazole-2-carboxamide

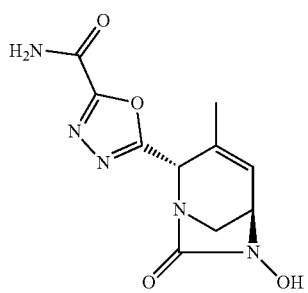 [SMILES: CC1=C[C@@H]2CN(C(=O)N2O)[C@@H]1c1nnc(C(N)=O)o1]

To a solution of 5-[(2S,5R)-6-[tert-butyl(dimethyl)silyl]oxy-3-methyl-7-oxo-1,6-diazabicyclo[3.2.1]oct-3-en-2-yl]-1,3,4-oxadiazole-2-carboxamide (Intermediate 79, 267.6 mg, 0.71 mmol) in ethyl acetate (6 mL) was added HF-pyridine (0.04 mL, 1.41 mmol). The reaction mixture was stirred for 2.5 hours, then another 2 eq of HF-pyridine was added and the reaction stirred for another hour. The reaction mixture was concentrated to afford the title compound as a tan solid, 245 mg, 99%.

MS: 266 ES+(C₁₀H₁₁N₅O₄)

¹H NMR (300 MHz, DMSO-d₆) δ: 1.52 (s, 3H); 3.01 (m, 2H); 3.66 (m, 1H); 4.95 (s, 1H); 6.18 (m, 1H); 8.09 (s, 1H); 8.45 (m, 1H).

Intermediate 81: ethyl (2S)-2-[[(2S,5R)-2-(5-carbamoyl-1,3,4-oxadiazol-2-yl)-3-methyl-7-oxo-1,6-diazabicyclo[3.2.1]oct-3-en-6-yl]oxy]-2-fluoro-acetate

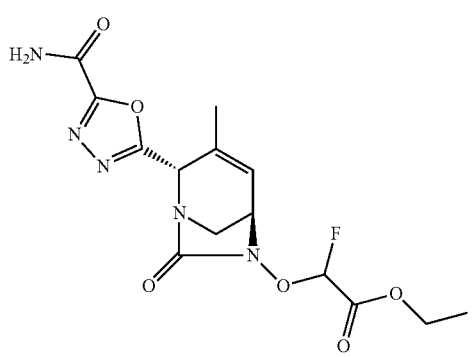 [SMILES: CCOC(=O)C(F)ON1C(=O)N2C[C@H]1C=C(C)[C@H]2c1nnc(C(N)=O)o1]

To a solution of 5-[(2S,5R)-6-hydroxy-3-methyl-7-oxo-1,6-diazabicyclo[3.2.1]oct-3-en-2-yl]-1,3,4-oxadiazole-2-carboxamide (Intermediate 80, 176.8 mg, 0.67 mmol) in DMF (5 mL) was added ethyl (2S)-2-bromo-2-fluoro-acetate (0.16 mL, 1.33 mmol) and potassium carbonate (276.39 mg, 2 mmol). The reaction mixture was stirred for 2 hours, then diluted with ethyl acetate, filtered and washed three times with 1:1 brine:water. The organics were dried over magnesium sulfate, filtered and concentrated to afford a yellow oil. Silica gel chromatography (0%-70% ethyl acetate/hexanes) afforded the title compound as a light yellow film, 66.8 mg, 27%. The compound is a 7:3 mixture of diastereomers.

MS: 370 ES+($C_{14}H_{16}FN_5O_6$)

$^1$H NMR (300 MHz, DMSO-$d_6$) δ: 1.25 (m, 3H); 1.72 (s, 3H); 3.20 (m, 2H); 4.19 (m, 1H); 5.30 (m, 1H); 6.25 (m, 1H); 6.26 (m, 1H); 8.26 (s, 1H); 8.65 (s, 1H).

Example 55

2-[[(2S,5R)-2-(5-carbamoyl-1,3,4-oxadiazol-2-yl)-3-methyl-7-oxo-1,6-diazabicyclo[3.2.1]oct-3-en-6-yl]oxy]-2-fluoro-acetic acid lithium salt

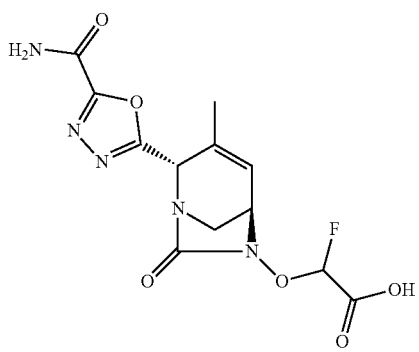 [SMILES: CC1=C[C@@H]2CN(C(=O)N2OC(F)C(=O)O)[C@@H]1c1nnc(C(N)=O)o1]

To a solution of ethyl (2S)-2-[[(2S,5R)-2-(5-carbamoyl-1,3,4-oxadiazol-2-yl)-3-methyl-7-oxo-1,6-diazabicyclo[3.2.1]oct-3-en-6-yl]oxy]-2-fluoro-acetate (Intermediate 81, 66.8 mg, 0.18 mmol) in THF (1 mL) and water (0.5 mL) at 0° C. was added lithium hydroxide (0.18 mL, 0.18 mmol). The reaction mixture was stirred for 10 minutes. Another 0.5 equivalents of lithium hydroxide added. After 10 minutes, the reaction mixture was treated with an additional 0.5 equivalents of lithium hydroxide. The reaction mixture was stirred for 20 minutes, neutralized with 0.5N HCl, frozen and lyophilized to afford a yellow solid. Reverse phase ISCO (50 g RediSep Gold C18, 100% water, 4 min; then 0%-50% acetonitrile/water) afforded the title compound as an off-white solid, 26 mg, 36%. The compound is a 7:3 mixture of diastereomers.

MS: 342 ES+($C_{12}H_{12}FN_5O_6$)

$^1$H NMR (300 MHz, DMSO-$d_6$) δ: 1.70 (s, 3H); 3.20 (m, 2H); 4.15 (m, 1H); 5.20 (s, 1H); 5.28 (m, 1H); 6.27 (m, 1H); 8.25 (s, 1H); 8.65 (s, 1H).

Intermediate 82: 2-(1,3-dioxoisoindolin-2-yl)oxyethanesulfonamide

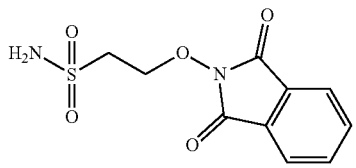 [SMILES: NS(=O)(=O)CCON1C(=O)c2ccccc2C1=O]

To a suspension of 2-hydroxyethanesulfonamide (Enamine, 1.92 mL, 7.19 mmol), N-hydroxyphthalimide (1.41 g, 8.63 mmol) and triphenylphosphine (2.26 g, 8.63 mmol) at 0° C. was added diisopropylazodicarboxylate (1.7 mL, 8.63 mmol) dropwise. The reaction mixture became dark orange then turned pale yellow. After stirring for ~3 hours the reaction mixture was concentrated to afford a sticky pale yellow oil, which was triturated with ethyl acetate/hexanes. The white solid was collected by filtration and is the title compound, 1.8 g, 70%.

MS: 271 ES+($C_{10}H_{10}N_2O_5S$)

$^1$H NMR (300 MHz, DMSO-$d_6$) δ: 3.52 (m, 2H); 4.50 (m, 2H); 6.96 (s, 2H); 7.87 (s, 4H).

Intermediate 83: 2-aminooxyethanesulfonamide

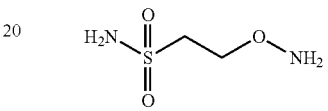

To a solution of 2-(1,3-dioxoisoindolin-2-yl)oxyethanesulfonamide (Intermediate 82, 740 mg, 2.05 mmol) in DCM (20 mL) at room temperature was added methylhydrazine (0.11 mL, 2.05 mmol). A precipitate immediately formed. The suspension was stirred at room temperature for ~2 hours, then concentrated. The solid was triturated with DCM and collected by filtration. The solid was triturated with methanol and the resulting white solid was filtered off. NMR of the solid indicates byproduct. The filtrate was concentrated to afford the title compound as an off-white solid, 228.2 mg, 58%. NMR indicates 73% desired product.

$^1$H NMR (300 MHz, DMSO-$d_6$) δ: 3.27 (m, 2H); 3.85 (m, 2H); 6.11 (bs, 2H); 6.79 (s, 2H).

Intermediate 84: (2S,5R)-6-[tert-butyl(dimethyl)silyl]oxy-3-methyl-7-oxo-N-(2-sulfamoylethoxy)-1,6-diazabicyclo[3.2.1]oct-3-ene-2-carboxamide

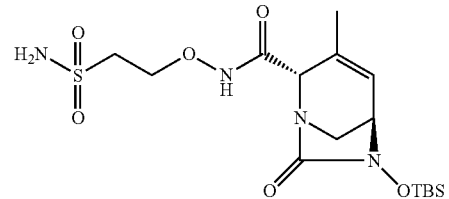 [SMILES: CC1=C[C@@H]2CN(C(=O)N2O[Si](C)(C)C(C)(C)C)[C@@H]1C(=O)NOCCS(N)(=O)=O]

To a solution of (2S,5R)-6-[tert-butyl(dimethyl)silyl]oxy-3-7-oxo-1,6-diazabicyclo[3.2.1]oct-3-ene-2-carboxylic acid (Intermediate 77, 465.74 mg, 1.19 mmol) in DMF (8 mL) at 0° C. was added 2-aminooxyethanesulfonamide (Intermediate 83, 228.96 mg, 1.19 mmol), HATU (453.43 mg, 1.19 mmol) and N,N-diisopropylethylamine (0.57 mL, 3.26 mmol). The reaction mixture was then stirred for 1 hour at 0° C., then diluted with ethyl acetate and washed twice with 1:1 brine:water. The organics were dried over magnesium sulfate, filtered and concentrated to afford a yellow oil. Silica gel chromatography (0%-80% ethyl acetate/hexanes) afforded the title compound as a colorless oil, 343 mg, 66%.

MS: 435 ES+($C_{16}H_{30}N_4O_6SiS$)

¹H NMR (300 MHz, DMSO-d₆) δ: 0.00 (s, 6H); 0.78 (s, 9H); 1.45 (s, 3H); 2.97 (m, 1H); 3.20 (m, 2H); 3.57 (m, 2H); 3.84 (m, 1H); 4.02 (m, 2H); 6.01 (m, 1H); 6.80 (s, 2H); 11.74 (s, 1H).

Intermediate 85: (2S,5R)-6-hydroxy-3-methyl-7-oxo-N-(2-sulfamoylethoxy)-1,6-diazabicyclo[3.2.1]oct-3-ene-2-carboxamide

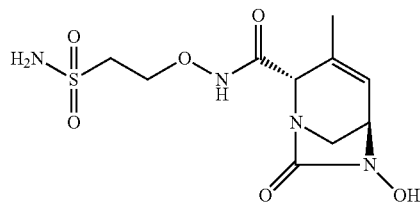 [SMILES: CC1=C[C@@H]2CN(C(=O)N2O)[C@@H]1C(=O)NOCCS(N)(=O)=O]

To a solution of (2S,5R)-6-[tert-butyl(dimethyl)silyl]oxy-3-methyl-7-oxo-N-(2-sulfamoylethoxy)-1,6-diazabicyclo[3.2.1]oct-3-ene-2-carboxamide (Intermediate 84, 343 mg, 0.79 mmol) in ethyl acetate (4 mL) was added HF-pyridine (0.04 mL, 1.58 mmol). The reaction mixture was stirred for 30 minutes. Another 2 eq. of HF-pyridine were added and the reaction stirred for another hour. After 6 hours, and a total of 7 eq of HF-pyridine, the reaction was complete. The reaction mixture was filtered to collect an off-white solid. The solid became gummy and stuck in the filter. Ethyl acetate and a small amount of methanol was used to rinse the filter and transfer the solid to a flask. The solvent was removed under vacuum to afford the title compound as an off-white solid, 337 mg, 100%.

MS: 321 ES+($C_{10}H_{16}N_4O_6S$)

Intermediate 86: ethyl (2S)-2-fluoro-2-[[(2S,5R)-3-methyl-7-oxo-2-(2-sulfamoylethoxycarbamoyl)-1,6-diazabicyclo[3.2.1]oct-3-en-6-yl]oxy]acetate

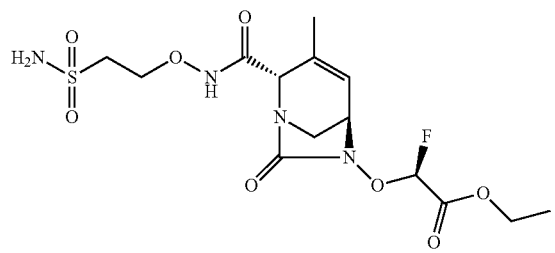 [SMILES: CCOC(=O)[C@H](F)ON1C(=O)N2C[C@H]1C=C(C)[C@H]2C(=O)NOCCS(N)(=O)=O]

The title compound was prepared from (2S,5R)-6-hydroxy-3-methyl-7-oxo-N-(2-sulfamoylethoxy)-1,6-diazabicyclo[3.2.1]oct-3-ene-2-carboxamide (Intermediate 85, 279.32 mg, 0.65 mmol) and ethyl (2S)-2-bromo-2-fluoroacetate (Intermediate 174, 0.08 mL, 0.65 mmol) according to the procedure for Example 45 to afford a light yellow oil, 26.7 mg, 10%.

MS: 425 ES+($C_{14}H_{21}FN_4O_8S$)

¹H NMR (300 MHz, DMSO-d₆) δ: 1.25 (m, 3H); 1.60 (m, 3H); 3.15 (m, 1H); 3.36 (m, 1H); 3.78 (m, 1H); 4.02 (m, 3H); 4.07 (m, 2H); 4.28 (m, 2H); 6.13 (m, 1H); 6.16 (d, 1H); 6.95 (s, 2H); 11.91 (s, 1H).

Example 56

(2S)-2-fluoro-2-[[(2S,5R)-3-methyl-7-oxo-2-(2-sulfamoylethoxycarbamoyl)-1,6-diazabicyclo[3.2.1]oct-3-en-6-yl]oxy]acetic acid lithium salt

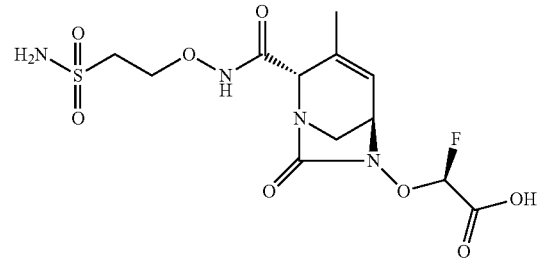 [SMILES: CC1=C[C@@H]2CN(C(=O)N2O[C@@H](F)C(=O)O)[C@@H]1C(=O)NOCCS(N)(=O)=O]

To a solution of ethyl (2S)-2-fluoro-2-[[(2S,5R)-3-methyl-7-oxo-2-(2-sulfamoylethoxy-carbamoyl)-1,6-diazabicyclo[3.2.1]oct-3-en-6-yl]oxy]acetate (Intermediate 86, 26.7 mg, 0.06 mmol) in THF (1 mL) and water (0.5 mL) at 0° C. was added LiOH (0.06 mL, 0.06 mmol). The reaction mixture was stirred for 15 minutes, and another 0.5 equivalents of lithium hydroxide was added. After 15 minutes, another 0.5 eq of lithium hydroxide was added. After 30 minutes, and warming the temperature slightly, the reaction was complete. The reaction mixture was neutralized with 0.5N HCl, frozen and lyophilized to afford a yellow oil. The compound was purified by reverse phase ISCO (5.5 g RediSep Gold C18, 100% water). The title compound was obtained as an off-white solid, 11.3 mg, 29%.

MS: 397 ES+($C_{12}H_{17}FN_4O_8S$)

¹H NMR (300 MHz, DMSO-d₆) δ: 1.56 (s, 3H); 3.02 (m, 1H); 3.26 (m, 1H); 3.98 (m, 5H); 5.20 (d, 1H); 6.03 (m, 1H); 7.06 (s, 2H).

Intermediate 87: (2S,5R)-6-allyloxy-3-methyl-7-oxo-N-(2-sulfamoylethyl)-1,6-diazabicyclo[3.2.1]oct-3-ene-2-carboxamide

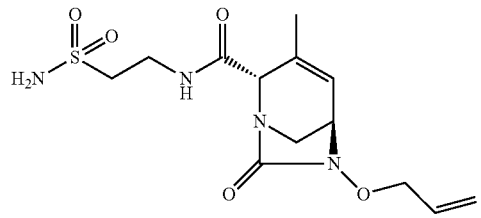 [SMILES: C=CCON1C(=O)N2C[C@H]1C=C(C)[C@H]2C(=O)NCCS(N)(=O)=O]

The title compound was prepared from (2S,5R)-6-allyloxy-3-methyl-7-oxo-1,6-diazabicyclo[3.2.1]oct-3-ene-2-carboxylic acid (Intermediate 29, 208.5 mg, 0.88 mmol) and 2-amino-ethanesulfonamide hydrochloride (281.1 mg, 1.75 mmol) according to the procedure for Intermediate 84 to afford a pale yellow oil, 86.6, 29%.

MS: 345 ES+($C_{13}H_{20}N_4O_5S$)

¹H NMR (300 MHz, DMSO-d₆) δ: 1.63 (s, 3H); 3.04 (m, 1H); 3.14 (m, 2H); 3.26 (m, 1H); 3.51 (m, 2H); 3.94 (m, 1H); 4.09 (m, 1H); 4.36 (m, 2H); 5.27 (m, 2H); 5.95 (m, 1H); 6.07 (m, 1H); 6.89 (s, 2H); 8.52 (m, 1H).

Intermediate 88: (2S,5R)-6-hydroxy-3-methyl-7-oxo-N-(2-sulfamoylethyl)-1,6-diazabicyclo[3.2.1]oct-3-ene-2-carboxamide

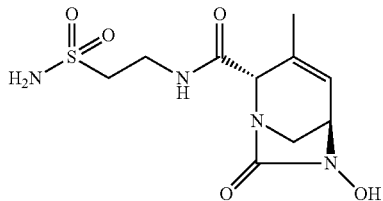

To a solution of (2S,5R)-6-allyloxy-3-methyl-7-oxo-N-(2-sulfamoylethyl)-1,6-diazabicyclo[3.2.1]oct-3-ene-2-carboxamide (Intermediate 87, 86.6 mg, 0.25 mmol) in methanol (3 mL) at room temperature was added 1,3-dimethylbarbituric acid (78.53 mg, 0.5 mmol) and tetrakis(triphenylphosphine)palladium(0) (58.12 mg, 0.05 mmol). The reaction mixture was stirred for 1 hour at room temperature, then concentrated to afford a dark orange oil, 76.5 mg, 100%.

MS: 305 ES+($C_{10}H_{16}N_4O_5S$)

Intermediate 89: ethyl (2S)-2-fluoro-2-[[(2S,5R)-3-methyl-7-oxo-2-(2-sulfamoylethylcarbamoyl)-1,6-diazabicyclo[3.2.1]oct-3-en-6-yl]oxy]acetate

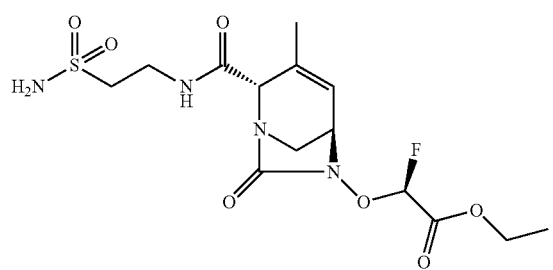 [SMILES: CCOC(=O)[C@H](F)ON1C(=O)N2C[C@H]1C=C(C)[C@H]2C(=O)NCCS(N)(=O)=O]

To a solution of (2S,5R)-6-hydroxy-3-methyl-7-oxo-N-(2-sulfamoylethyl)-1,6-diazabicyclo[3.2.1]oct-3-ene-2-carboxamide (Intermediate 88, 76.5 mg, 0.25 mmol) in 1,4-dioxane (2 mL) and DMF (0.25 mL) was added ethyl (2S)-2-bromo-2-fluoro-acetate (Intermediate 174, 0.09 mL, 0.75 mmol). The reaction mixture was cooled to 0° C. and DBU (0.04 mL, 0.25 mmol) was added dropwise. More ethyl (2S)-2-bromo-2-fluoro-acetate (0.09 mL, 0.75 mmol) was added. Then, more DBU (0.04 mL, 0.25 mmol) was added. After another 15 minutes at 0° C., with occasional warming, another 0.5 eq. of DBU was added. The reaction mixture was stirred for another 15 minutes at room temperature. The reaction mixture was diluted with ethyl acetate and washed three times with 1:1 brine:water. The organics were dried over magnesium sulfate, filtered and concentrated to afford an orange oil. Silica gel chromatography (0%-25% acetone/dichloromethane) afforded the title compound and with some triphenylphosphine oxide as an orange film, 77.3 mg, 75%.

MS: 409 ES+($C_{14}H_{21}FN_4O_7S$)

Example 57

(2S)-2-fluoro-2-[[(2S,5R)-3-methyl-7-oxo-2-(2-sulfamoylethylcarbamoyl)-1,6-diazabicyclo[3.2.1]oct-3-en-6-yl]oxy]acetic acid lithium salt

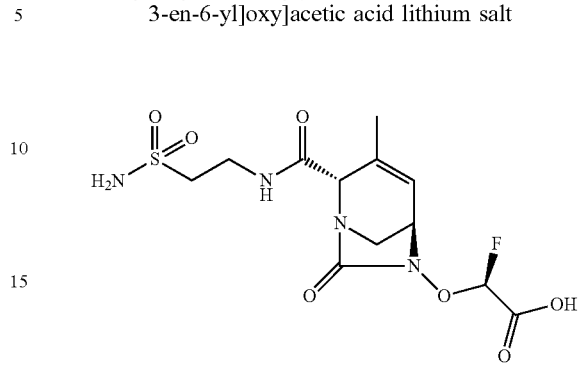

T a solution of ethyl (2S)-2-fluoro-2-[[(2S,5R)-3-methyl-7-oxo-2-(2-sulfamoylethyl-carbamoyl)-1,6-diazabicyclo[3.2.1]oct-3-en-6-yl]oxy]acetate (Intermediate 89, 72.3 mg, 0.18 mmol) in THF (2 mL) and water (1 mL) at 0° C. was added 1M lithium hydroxide (0.18 mL, 0.18 mmol). The reaction mixture was stirred for 10 minutes at 0° C., then neutralized with 0.5N hydrochloric acid, frozen and lyophilized to afford a yellow solid. Reverse phase ISCO (100% water) afforded the title compound as a pale yellow solid, 14.3 mg, 21%.

MS: 381 ES+($C_{12}H_{17}FN_4O_7S$)

$^1$H NMR (300 MHz, DMSO-$d_6$) δ: 1.64 (s, 3H); 3.13 (m, 3H); 3.52 (m, 3H); 3.99 (m, 1H); 4.14 (m, 1H); 5.24 (d, 1H); 6.04 (m, 1H); 6.90 (m, 2H); 8.57 (m, 1H).

Example 58 ethyl 2-[[(2R)-2-[[(2S,5R)-2-carbamoyl-3-methyl-7-oxo-1,6-diazabicyclo[3.2.1]oct-3-en-6-yl]oxy]-2-fluoro-acetyl]oxymethoxycarbonylamino]-3-methyl-butanoate

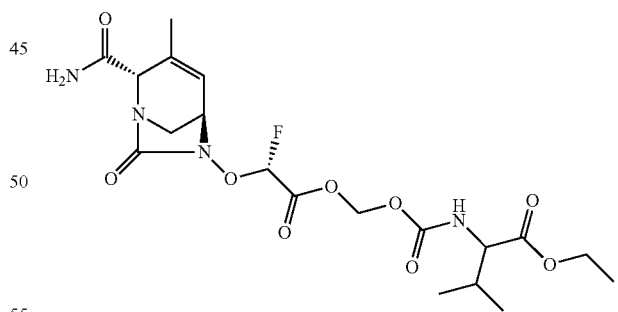

To a solution of (2R)-2-[[(2S,5R)-2-carbamoyl-3-methyl-7-oxo-1,6-diazabicyclo[3.2.1]oct-3-en-6-yl]oxy]-2-fluoro-acetic acid (Example 4, 100 mg, 0.37 mmol), Hunig's base (0.06 mL, 0.37 mmol) and ethyl 2-(chloromethoxycarbonylamino)-3-methyl-butanoate (0.05 mL, 0.73 mmol) in DMF (1.5 mL) at room temperature was added tetrabutylammonium chloride (83.42 mg, 0.37 mmol). The reaction mixture was stirred at 40° C. for 2 hours. It was then diluted with ethyl acetate and washed twice with brine/water (1:1). The organics were dried over anhydrous magnesium sulfate, filtered and concentrated to afford an orange oil. Silica gel chromatography (0%-80% ethyl acetate/hexanes) afforded the title compound (7 mg, 3.63%) as a white solid.

MS: 475 ES+($C_{19}H_{27}FN_4O_9$)

$^1$H NMR (300 MHz, DMSO-$d_6$) δ: 0.90 (m, 6H); 1.21 (m, 3H); 1.61 (s, 3H); 2.15 (m, 1H); 3.78 (m, 1H); 3.95 (m, 1H); 4.01 (m, 1H); 4.15 (m, 2H); 4.22 (m, 1H); 5.80 (m, 2H); 5.95 (m, 1H); 6.30 (d, 1H); 7.40 (s, 1H); 7.80 (s, 1H); 8.10 (d, 1H).

Intermediate 90: tert-butyl (2S)-2-[(1,3-dioxoisoindolin-2-yl)oxymethyl]pyrrolidine-1-carboxylate

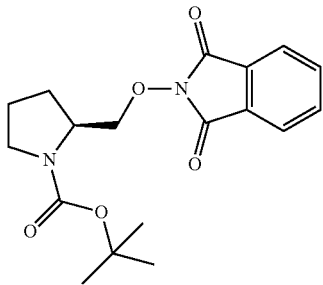 [SMILES: CC(C)(C)OC(=O)N1CCC[C@H]1CON1C(=O)c2ccccc2C1=O]

To a solution of diethylazodicarboxylate (14.21 mL, 12.48 mmol) in THF (10 mL) at <10° C. was added dropwise a solution of triphenylphosphine (3273.22 mg, 12.48 mmol) in THF (20 mL). The suspension was stirred at −10° C. After 20 minutes the suspension became a solid and another 40 mL of THF was added. After 1 hour, a solution of Boc-L-prolinol (448.18 mL, 5.94 mmol) in THF (10 mL) was added, followed by a solution of N-Hydroxyphthalimide (969.41 mg, 5.94 mmol) in THF (10 mL). The reaction mixture was allowed to warm to room temperature and stir overnight. It was concentrated and the resulting oil was triturated with ethyl acetate/hexanes. The precipitate was removed by filtration and the filtrate was concentrated onto silica gel. Silica gel chromatography (0%-40% EtOAc/Hexanes) afforded the title compound (2.37 g, quant.) as a pale yellow solid.

MS: 347 ES+($C_{18}H_{22}N_2O_5$)

Intermediate 91: tert-butyl (2S)-2-(aminooxymethyl)pyrrolidine-1-carboxylate

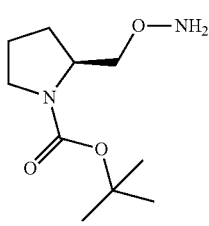

To a solution of tert-butyl (2S)-2-[(1,3-dioxoisoindolin-2-yl)oxymethyl]pyrrolidine-1-carboxylate (Intermediate 90, 2.06 g, 5.95 mmol) in DCM (20 mL) at room temperature was added hydrazine monohydrate (2.14 mL, 17.84 mmol). A white precipitate immediately formed. The suspension was stirred at room temperature for 1 hour, then filtered through Celite. The filtrate was washed twice with brine/water (1:1), dried over anhydrous magnesium sulfate, filtered and concentrated to afford the title compound (1.35 g, quant.) as a sticky oil.

$^1$H NMR (300 MHz, CDCl$_3$) δ: 1.50 (s, 9H); 1.85 (m, 4H); 3.32 (m, 2H); 3.63 (m, 1H); 4.25 (m, 2H).

Intermediate 92: tert-butyl (2S)-2-[[[(2S,5R)-6-[tert-butyl(dimethyl)silyl]oxy-3-methyl-7-oxo-1,6-diazabicyclo[3.2.1]oct-3-ene-2-carbonyl]amino]oxymethyl]pyrrolidine-1-carboxylate

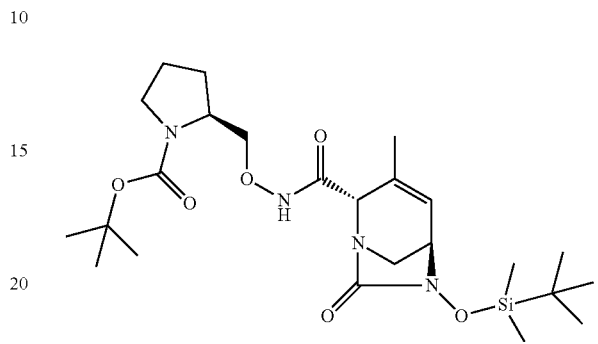

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 1.85 g, 5.92 mmol) and tert-butyl (2S)-2-(aminooxymethyl)pyrrolidine-1-carboxylate (Intermediate 91, 1.28 g, 5.92 mmol) according to the procedure for Intermediate 84 to afford (585 mg, 19%) a white sticky foam.

MS: 511 ES+($C_{24}H_{42}N_4O_6Si$)

Intermediate 93: tert-butyl (2S)-2-[[[(2S,5R)-6-hydroxy-3-methyl-7-oxo-1,6-diazabicyclo[3.2.1]oct-3-ene-2-carbonyl]amino]oxymethyl]pyrrolidine-1-carboxylate

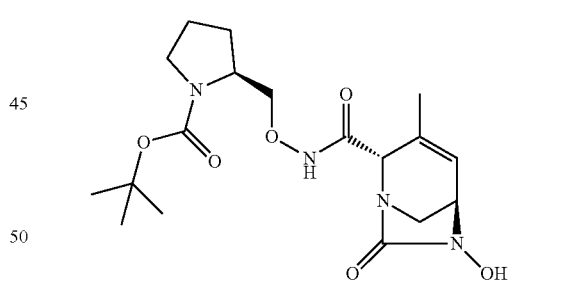

To a solution of tert-butyl (2S)-2-[[[(2S,5R)-6-[tert-butyl(dimethyl)silyl]oxy-3-methyl-7-oxo-1,6-diazabicyclo[3.2.1]oct-3-ene-2-carbonyl]amino]oxymethyl]pyrrolidine-1-carboxylate (Intermediate 92, 401 mg, 0.79 mmol) in ethyl acetate (20 mL) at 0° C. under nitrogen atmosphere was added HF Pyridine (24 µL, 0.94 mmol). The reaction mixture was stirred at room temperature for 3 hours, then concentrated. The crude material was partitioned between DCM (100 mL) and brine (50 mL). The organic layer was dried over anhydrous sodium sulfate, and concentrated to give the title compound (309 mg, 84%) as a white sticky solid.

MS: 396 ES+($C_{18}H_{28}N_4O_6$)

Example 59 tert-butyl (2S)-2-((((2S,5R)-6-((S)-2-ethoxy-1-fluoro-2-oxoethoxy)-3-methyl-7-oxo-1,6-diazabicyclo[3.2.1]oct-3-ene-2-carboxamido)oxy)methyl)pyrrolidine-1-carboxylate

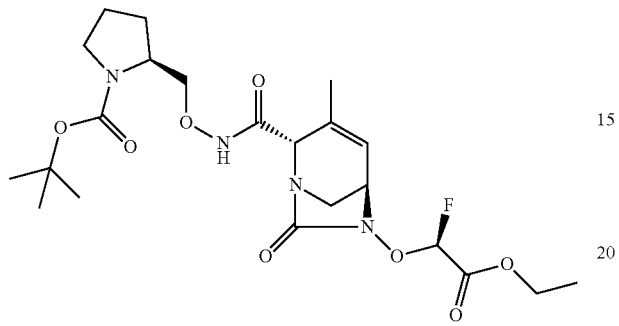

To a suspension of tert-butyl (2S)-2-[[[(2S,5R)-6-hydroxy-3-methyl-7-oxo-1,6-diazabicyclo[3.2.1]oct-3-ene-2-carbonyl]amino]oxymethyl]pyrrolidine-1-carboxylate (Intermediate 93, 309 mg, 0.78 mmol) and cesium carbonate (304.75 mg, 0.94 mmol) in THF (15 mL) at 0° C. was added ethyl (2S)-2-bromo-2-fluoro-acetate (Intermediate 174, 0.14 mL, 1.17 mmol). The reaction was stirred at 0° C. for 8 hours. Water (50 mL) and EtOAc (100 mL) were added. The organic layer was dried over anhydrous sodium sulfate, concentrated, and purified by flash chromatography (20 g silica gel, 0-100% EtOAc/Hexanes) to afford the title compound (164 mg, 40%) as a sticky solid.

MS: 501 ES+($C_{22}H_{33}FN_4O_8$)

$^1$H NMR (300 MHz, CDCl$_3$) δ: 1.38 (m, 3H); 1.45 (s, 9H); 1.80 (s, 3H); 1.95 (m, 4H); 3.35 (m, 3H); 3.60 (m, 2H); 3.95 (m, 1H); 4.01 (m, 1H); 4.28 (m, 2H); 4.35 (m, 2H); 5.75 (d, 1H); 6.10 (s, 1H).

Example 60 ethyl (2S)-2-fluoro-2-(((2S,5R)-3-methyl-7-oxo-2-((((S)-pyrrolidin-2-yl)methoxy)carbamoyl)-1,6-diazabicyclo[3.2.1]oct-3-en-6-yl)oxy)acetate TFA salt

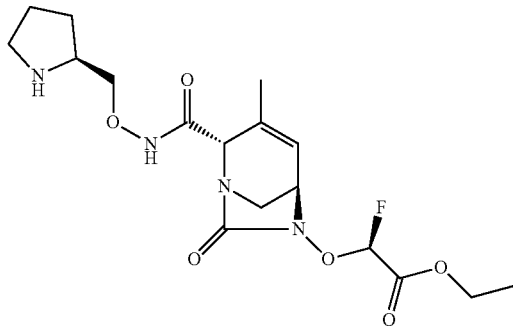 [SMILES: CCOC(=O)[C@H](F)ON1C(=O)N2C[C@H]1C=C(C)[C@H]2C(=O)NOC[C@@H]1CCCN1]

To a solution of tert-butyl (2S)-2-((((2S,5R)-6-((S)-2-ethoxy-1-fluoro-2-oxoethoxy)-3-methyl-7-oxo-1,6-diazabicyclo[3.2.1]oct-3-ene-2-carboxamido)oxy)methyl)pyrrolidine-1-carboxylate (Example 59, 76 mg, 0.15 mmol) in DCM (10 mL) at 0° C. was added TFA (0.58 mL, 7.59 mmol) dropwise. The reaction mixture was stirred at 0° C. for 2 hours then concentrated. The residue was triturated with diethyl ether to afford the title compound (53 mg, 83%) as a TFA salt.

MS: 401 ES+($C_{17}H_{25}FN_4O_6$)

$^1$H NMR (300 MHz, CDCl$_3$) δ: 1.45 (m, 3H); 1.86 (m, 4H); 2.15 (m, 3H); 3.55 (m, 4H); 4.01 (m, 2H); 4.32 (m, 5H); 5.85 (d, 1H); 6.13 (s, 1H).

Intermediate 94: tert-butyl (S)-2-(((1,3-dioxoisoindolin-2-yl)oxy)methyl)-4,4-difluoropyrrolidine-1-carboxylate

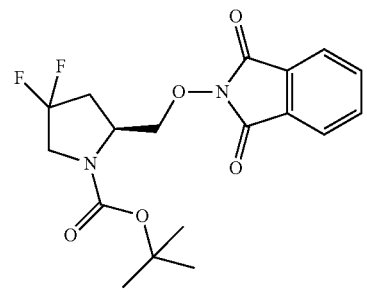 [SMILES: CC(C)(C)OC(=O)N1CC(F)(F)C[C@H]1CON1C(=O)c2ccccc2C1=O]

The title compound was prepared from tert-butyl (S)-4,4-difluoro-2-(hydroxymethyl)-pyrrolidine-1-carboxylate (2.8 g, 11.8 mmol) according to the procedure for Intermediate 90 to afford (4.3 g, 95%) a pale yellow sticky solid.

MS: 383 ES+($C_{18}H_{20}F_2N_2O_5$)

Intermediate 95: tert-butyl (S)-2-((aminooxy)methyl)-4,4-difluoropyrrolidine-1-carboxylate

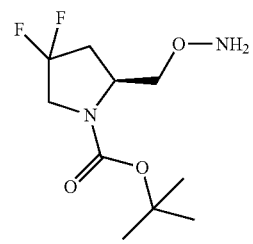 [SMILES: CC(C)(C)OC(=O)N1CC(F)(F)C[C@H]1CON]

The title compound was prepared from tert-butyl (S)-2-(((1,3-dioxoisoindolin-2-yl)oxy)methyl)-4,4-difluoropyrrolidine-1-carboxylate (Intermediate 94, 1.9 g, 4.97 mmol) according to the procedure for Intermediate 91 to afford (1.25 g, 99%) an orange sticky oil.

$^1$H NMR (300 MHz, CDCl$_3$) δ: 1.51 (s, 9H); 2.42 (m, 2H); 3.63 (m, 2H); 3.85 (m, 2H); 4.97 (m, 1H).

Intermediate 96: tert-butyl (2S)-2-((((2S,5R)-6-((tert-butyldimethylsilyl)oxy)-3-methyl-7-oxo-1,6-diazabicyclo[3.2.1]oct-3-ene-2-carboxamido)oxy)methyl)-4,4-difluoropyrrolidine-1-carboxylate

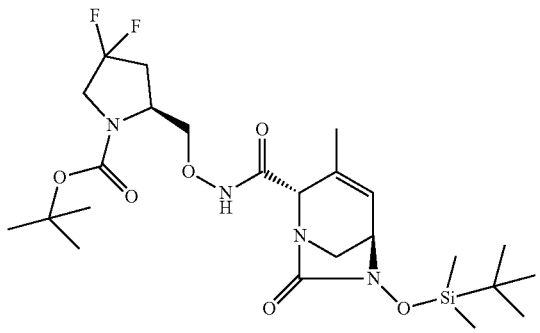 [SMILES: CC1=C[C@@H]2CN(C(=O)N2O[Si](C)(C)C(C)(C)C)[C@@H]1C(=O)NOC[C@@H]1CC(F)(F)CN1C(=O)OC(C)(C)C]

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 1.3 g, 4.16 mmol) and tert-butyl (S)-2-((aminooxy)methyl)-4,4-difluoropyrrolidine-1-carboxylate (Intermediate 95, 1.26 g, 4.99 mmol) according to the procedure for Intermediate 84 to afford (489 mg, 18%) a sticky white foam.

MS: 547 ES+($C_{24}H_{40}F_2N_4O_6Si$)

Intermediate 97: tert-butyl (2S)-4,4-difluoro-2-((((2S,5R)-6-hydroxy-3-methyl-7-oxo-1,6-diazabicyclo[3.2.1]oct-3-ene-2-carboxamido)oxy)methyl)pyrrolidine-1-carboxylate

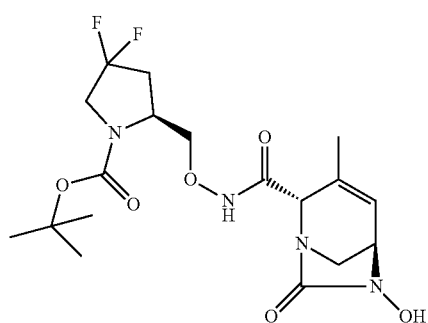 [SMILES: CC1=C[C@@H]2CN(C(=O)N2O)[C@@H]1C(=O)NOC[C@@H]1CC(F)(F)CN1C(=O)OC(C)(C)C]

The title compound was prepared from tert-butyl (2S)-2-((((2S,5R)-6-((tert-butyldimethylsilyl)oxy)-3-methyl-7-oxo-1,6-diazabicyclo[3.2.1]oct-3-ene-2-carboxamido)oxy)methyl)-4,4-difluoropyrrolidine-1-carboxylate (Intermediate 96, 489 mg, 0.89 mmol) according to the procedure for Intermediate 93 to afford (330 mg, 72%) as a white sticky solid.

MS: 433 ES+($C_{18}H_{26}F_2N_4O_6$)

Intermediate 98: tert-butyl (2S)-2-((((2S,5R)-6-(S)-2-ethoxy-1-fluoro-2-oxoethoxy)-3-methyl-7-oxo-1,6-diazabicyclo[3.2.1]oct-3-ene-2-carboxamido)oxy)methyl)-4,4-difluoropyrrolidine-1-carboxylate

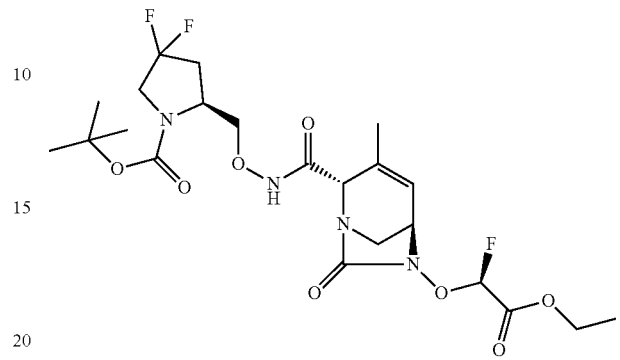

To a suspension of tert-butyl (2S)-4,4-difluoro-2-((((2S,5R)-6-hydroxy-3-methyl-7-oxo-1,6-diazabicyclo[3.2.1]oct-3-ene-2-carboxamido)oxy)methyl)pyrrolidine-1-carboxylate (Intermediate 97, 300 mg, 0.69 mmol) and cesium carbonate (339 mg, 1.04 mmol) in ethyl acetate (15 mL) at 0° C. was added ethyl (2S)-2-bromo-2-fluoro-acetate (Intermediate 174, 0.1 mL, 0.83 mmol). The reaction was stirred at 10° C. for 1 hour. Water (50 mL) and EtOAc (100 mL) were added. The organic layer was separated, concentrated and purified by silica gel flash chromatography (0-100%, EtOAc/Hexane) to afford the title compound (70 mg, 18%) as a sticky white foam.

MS: 537 ES+($C_{22}H_{31}F_3N_4O_8$)

Example 61 ethyl (2S)-2-(((2S,5R)-2-((((S)-4,4-difluoropyrrolidin-2-yl)methoxy)carbamoyl)-3-methyl-7-oxo-1,6-diazabicyclo[3.2.1]oct-3-en-6-yl)oxy)-2-fluoroacetate TFA salt

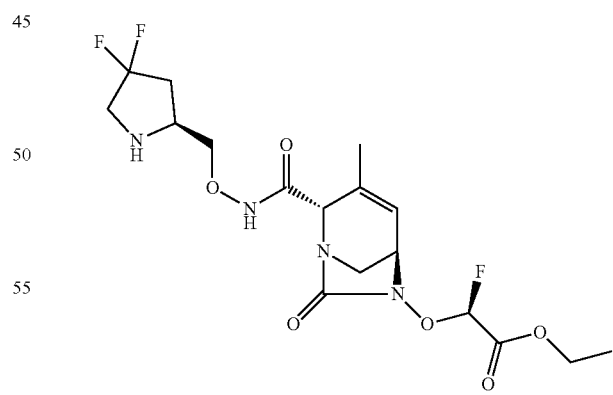

The title compound was prepared from tert-butyl (2S)-2-((((2S,5R)-6-((S)-2-ethoxy-1-fluoro-2-oxoethoxy)-3-methyl-7-oxo-1,6-diazabicyclo [3.2.1]oct-3-ene-2-carboxamido)oxy)methyl)-4,4-difluoropyrrolidine-1-carboxylate (Intermediate 98, 26 mg, 0.05 mmol) according to the procedure for Example 60 to afford (20 mg, 85%) as a TFA salt.

MS: 437 ES+(C$_{17}$H$_{23}$F$_3$N$_4$O$_6$)

$^1$H NMR (300 MHz, CDCl$_3$) δ: 1.42 (m, 3H); 1.80 (s, 3H); 2.65 (m, 2H); 3.45 (m, 2H); 3.82 (m, 2H); 4.10 (m, 1H); 4.38 (m, 6H); 5.80 (d, 1H); 6.18 (s, 1H).

Intermediate 99: (2S)-2-[[(2S,5R)-2-[[(2S)-1-tert-butoxycarbonylpyrrolidin-2-yl]methoxycarbamoyl]-3-methyl-7-oxo-1,6-diazabicyclo[3.2.1]oct-3-en-6-yl]oxy]-2-fluoro-acetic acid

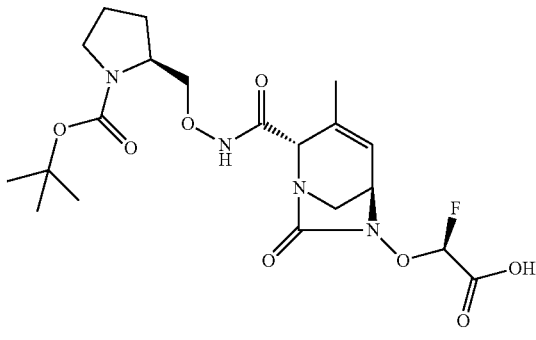 [SMILES: CC1=C[C@@H]2CN(C(=O)N2O[C@@H](F)C(=O)O)[C@@H]1C(=O)NOC[C@@H]1CCCN1C(=O)OC(C)(C)C]

To a solution of tert-butyl (2S)-2-((((2S,5R)-6-((S)-2-ethoxy-1-fluoro-2-oxoethoxy)-3-methyl-7-oxo-1,6-diazabicyclo[3.2.1]oct-3-ene-2-carboxamido)oxy)methyl)pyrrolidine-1-carboxylate (Example 59, 81 mg, 0.16 mmol) in THF (1 mL) and water (0.50 mL) at 0° C. was added lithium hydroxide (1N, 0.01 mL, 0.40 mmol). The reaction mixture was stirred for 30 min. Dilute HCl solution (0.5N) was added to adjust the pH to 2. The reaction mixture was extracted with EtOAc (20 mL). The organic layer was dried over anhydrous sodium sulfate and concentrated to afford the title compound (50 mg, 65%) as a gum.

MS: 471 ES–(C$_{20}$H$_{29}$FN$_4$O$_8$)

Example 62

(2S)-2-fluoro-2-[[(2S,5R)-3-methyl-7-oxo-2-[[(2S)-pyrrolidin-2-yl]methoxycarbamoyl]-1,6-diazabicyclo[3.2.1]oct-3-en-6-yl]oxy]acetic acid TFA salt

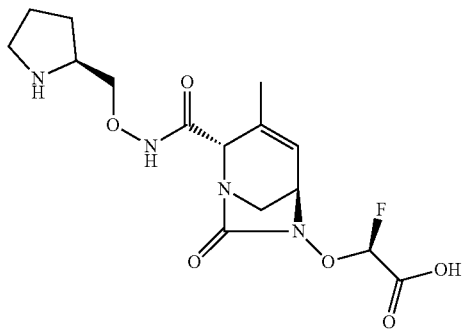 [SMILES: CC1=C[C@@H]2CN(C(=O)N2O[C@@H](F)C(=O)O)[C@@H]1C(=O)NOC[C@@H]1CCCN1]

The title compound was prepared from (2S)-2-[[(2S,5R)-2-[[(2S)-1-tert-butoxycarbonyl-pyrrolidin-2-yl]methoxycarbamoyl]-3-methyl-7-oxo-1,6-diazabicyclo[3.2.1]oct-3-en-6-yl]oxy]-2-fluoro-acetic acid (Intermediate 99, 65 mg, 0.14 mmol) according to the procedure for Example 60 to afford (40 mg, 70%) as a TFA salt.

MS: 473 ES+(C$_{20}$H$_{29}$FN$_4$O$_8$)

$^1$H NMR (300 MHz, D$_2$O) δ: 1.65 (s, 3H); 1.82 (m, 1H); 2.23 (m, 2H); 2.35 (m, 1H); 3.40 (m, 3H); 3.58 (m, 1H); 3.82 (m, 1H); 4.02 (m, 1H); 4.18 (m, 1H); 4.33 (m, 2H); 5.70 (d, 1H); 6.28 (s, 1H).

Intermediate 100: (2S)-2-(((2S,5R)-2-((((S)-1-(tert-butoxycarbonyl)-4,4-difluoropyrrolidin-2-yl)methoxy)carbamoyl)-3-methyl-7-oxo-1,6-diazabicyclo[3.2.1]oct-3-en-6-yl)oxy)-2-fluoroacetic acid

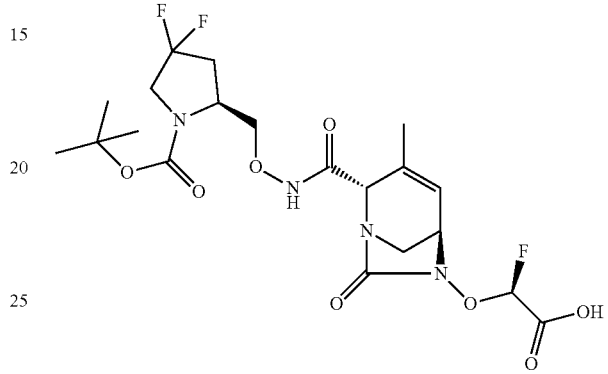

The title compound was prepared from tert-butyl (2S)-2-((((2S,5R)-6-((S)-2-ethoxy-1-fluoro-2-oxoethoxy)-3-methyl-7-oxo-1,6-diazabicyclo[3.2.1]oct-3-ene-2-carboxamido)oxy)methyl)-4,4-difluoropyrrolidine-1-carboxylate (Intermediate 98, 37 mg, 0.07 mmol) according to the procedure for Intermediate 99 to afford (35 mg, 90%) as a gum.

MS: 507 ES–(C$_{20}$H$_{27}$F$_3$N$_4$O$_8$)

Example 63

(2S)-2-(((2S,5R)-2-((((S)-4,4-difluoropyrrolidin-2-yl)methoxy)carbamoyl)-3-methyl-7-oxo-1,6-diazabicyclo[3.2.1]oct-3-en-6-yl)oxy)-2-fluoroacetic acid TFA salt

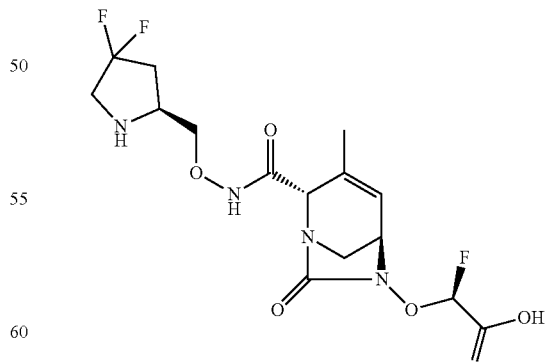

The title compound was prepared from (2S)-2-(((2S,5R)-2-((((S)-1-(tert-butoxycarbonyl)-4,4-difluoropyrrolidin-2-yl)methoxy)carbamoyl)-3-methyl-7-oxo-1,6-diazabicyclo[3.2.1]oct-3-en-6-yl)oxy)-2-fluoroacetic acid (Intermediate 100, 35 mg, 0.07 mmol) according to the procedure for Example 60 to afford (22 mg, 70%) as a TFA salt.

MS: 409 ES+($C_{15}H_{19}F_3N_4O_6$)

$^1$H NMR (300 MHz, D$_2$O) δ: 1.78 (s, 3H); 2.62 (m, 1H); 2.95 (m, 1H); 3.13 (m, 1H); 3.42 (m, 1H); 3.58 (m, 1H); 3.96 (m, 2H); 4.61 (m, 1H); 4.40 (m, 3H); 5.82 (d, 1H); 6.33 (s, 1H).

Example 64

[(2R)-2-[[(2S,5R)-2-carbamoyl-3-methyl-7-oxo-1,6-diazabicyclo[3.2.1]oct-3-en-6-yl]oxy]-2-fluoro-acetyl]oxymethyl 2,2-dimethylpropanoate

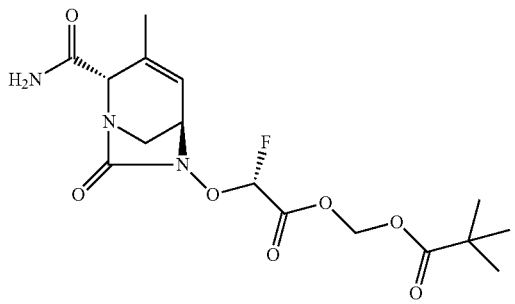 [SMILES: CC1=C[C@@H]2CN(C(=O)N2O[C@H](F)C(=O)OCOC(=O)C(C)(C)C)[C@@H]1C(N)=O]

The title compound was prepared from (2R)-2-[[(2S,5R)-2-carbamoyl-3-methyl-7-oxo-1,6-diazabicyclo[3.2.1]oct-3-en-6-yl]oxy]-2-fluoro-acetic acid (Example 4, 47 mg, 0.17 mmol) and chloromethyl pivalate (0.05 mL, 0.34 mmol) according to the procedure for Example 53 to afford (33.2 mg, 49.8%) as a white solid.

MS: 388 ES+($C_{16}H_{22}FN_3O_7$)

$^1$H NMR (300 MHz, DMSO-d$_6$) δ: 1.12 (s, 9H); 1.62 (s, 3H); 3.01 (m, 1H); 3.82 (m, 1H); 4.02 (m, 1H); 4.19 (m, 1H); 5.76 (m, 1H); 5.87 (m, 1H); 5.91 (m, 1H); 6.25-6.43 (d, 1H); 7.41 (bs, 1H); 7.86 (bs, 1H).

Example 65 indan-5-yl (2R)-2-[[(2S,5R)-2-carbamoyl-3-methyl-7-oxo-1,6-diazabicyclo[3.2.1]oct-3-en-6-yl]oxy]-2-fluoro-acetate

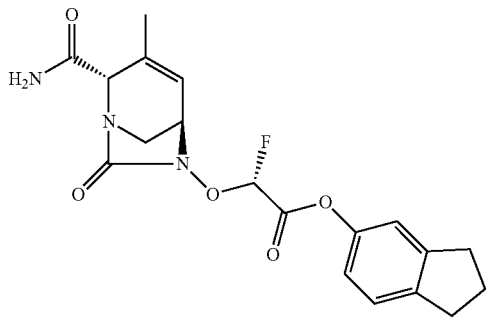 [SMILES: CC1=C[C@@H]2CN(C(=O)N2O[C@H](F)C(=O)Oc2ccc3c(c2)CCC3)[C@@H]1C(N)=O]

To a solution of (2R)-2-[[(2S,5R)-2-carbamoyl-3-methyl-7-oxo-1,6-diazabicyclo[3.2.1]oct-3-en-6-yl]oxy]-2-fluoro-acetic acid (Example 4, 100 mg, 0.37 mmol) and 5-indanol (58.9 mg, 0.44 mmol) in DCM (3 mL) and THF (3 mL) at 0° C. was added N,N'-dicyclohexyl-carbodiimide (113.3 mg, 0.55 mmol) and DMAP (5.0 mg). The reaction mixture was stirred at RT for 1 hour. The reaction was concentrated, then dissolved in EtOAC. The white solid formed was filtered off. The filtrate was concentrated. Silica gel chromatography (0-80% ethyl acetate/hexanes) afforded the title compound (72 mg, 48%) as a white solid.

MS: 390 ES+($C_{19}H_{20}FN_3O_5$)

$^1$H NMR (300 MHz, DMSO-d$_6$) δ: 1.64 (s, 3H); 2.05 (m, 2H); 2.85 (m, 4H); 3.10 (m, 1H); 3.79 (m, 1H); 4.06 (m, 1H); 4.22 (m, 1H); 6.06 (m, 1H); 6.44-6.51 (d, 1H); 6.86 (m, 1H); 6.97 (m, 1H); 7.28 (m, 1H); 7.43 (bs, 1H); 7.87 (bs, 1H).

Intermediate 101: (2S,5R)-6-[tert-butyl(dimethyl)silyl]oxy-3-methyl-N-(oxetan-3-yl)-7-oxo-1,6-diazabicyclo[3.2.1]oct-3-ene-2-carboxamide

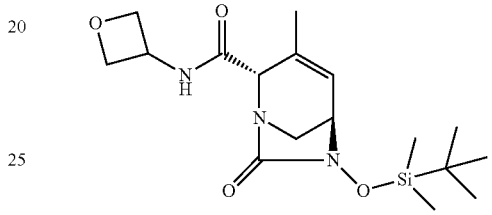

To a solution of (2S,5R)-6-[tert-butyl(dimethyl)silyl]oxy-3-methyl-7-oxo-1,6-diazabicyclo[3.2.1]oct-3-ene-2-carboxylic acid (Intermediate 77, 100 mg, 0.32 mmol) in DMF (1.5 mL) at 0° C. was added HATU (35 mg, 0.48 mmol) and N,N'-diisopropylethylamine (0.167 mL, 0.96 mmol). The reaction mixture was stirred for 30 minutes at room temperature, then diluted with ethyl acetate and washed with saturated sodium bicarbonate once and 1:1 brine:water three times. The organics were dried over magnesium sulfate, filtered and concentrated. Silica gel chromatography (0-2.5% methanol/dichloromethane) afforded the title compound (80 mg, 68%) as a yellow oil.

MS: 368 ES+($C_{17}H_{29}N_3O_4Si$)

Intermediate 102: (2S,5R)-6-hydroxy-3-methyl-N-(oxetan-3-yl)-7-oxo-1,6-diazabicyclo[3.2.1]oct-3-ene-2-carboxamide

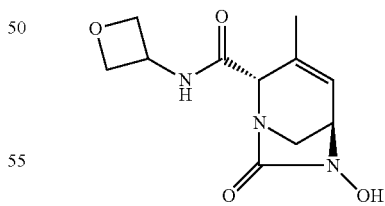

A 25 mL round bottom flask was charged with (2S,5R)-6-[tert-butyl(dimethyl)silyl]oxy-3-methyl-N-(oxetan-3-yl)-7-oxo-1,6-diazabicyclo[3.2.1]oct-3-ene-2-carboxamide (Intermediate 101, 0.10 g, 0.22 mmol) in ethyl acetate (0.5 mL) at room temperature under nitrogen. HF.Pyridine (0.015 mL, 0.33 mmol) was added and the reaction mixture was stirred at room temperature for 1 hour. The solvent was removed.

MS: 254 ES+($C_{11}H_{15}N_3O_4$)

Intermediate 103: ethyl (2S)-2-fluoro-2-[[(2S,5R)-3-methyl-2-(oxetan-3-ylcarbamoyl)-7-oxo-1,6-diazabicyclo[3.2.1]oct-3-en-6-yl]oxy]acetate

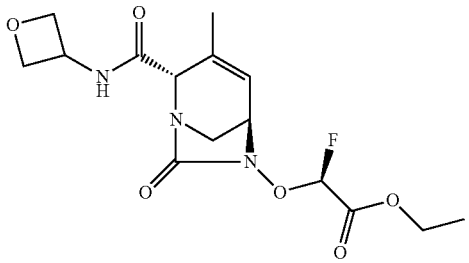 [SMILES: CCOC(=O)[C@H](F)ON1C(=O)N2C[C@H]1C=C(C)[C@H]2C(=O)NC1COC1]

To a solution of (2S,5R)-6-hydroxy-3-methyl-N-(oxetan-3-yl)-7-oxo-1,6-diazabicyclo[3.2.1]oct-3-ene-2-carboxamide (Intermediate 102, 50 mg, 0.20 mmol) in 1,4-dioxane (2 mL) and DMF (0.25 mL) was added ethyl (2S)-2-bromo-2-fluoro-acetate (Intermediate 174, 0.047 mL, 0.39 mmol). The reaction mixture was cooled to 0° C. and DBU (0.089 mL, 0.59 mmol) was added dropwise. The reaction mixture was stirred at 0° C. for 15 minutes, then diluted with ethyl acetate and washed three times with 1:1 brine:water. The organics were dried over magnesium sulfate, filtered and concentrated. Silica gel chromatography (0-80% EtOAc/Hexane) afforded the title compound (58 mg, 82.2%) as colorless oil. The compound is a 2:8 mixture of diastereomers.
MS: 358 ES+($C_{15}H_{20}FN_3O_6$)

Example 66

(2S)-2-fluoro-2-[[(2S,5R)-3-methyl-2-(oxetan-3-ylcarbamoyl)-7-oxo-1,6-diazabicyclo[3.2.1]oct-3-en-6-yl]oxy]acetic acid lithium salt

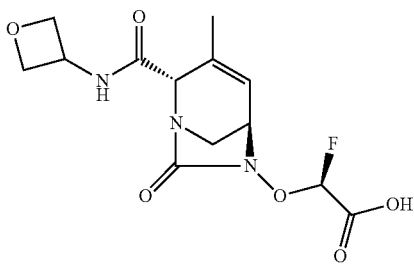 [SMILES: CC1=C[C@@H]2CN(C(=O)N2O[C@@H](F)C(=O)O)[C@@H]1C(=O)NC1COC1]

To a solution of ethyl (2S)-2-fluoro-2-[[(2S,5R)-3-methyl-2-(oxetan-3-ylcarbamoyl)-7-oxo-1,6-diazabicyclo[3.2.1]oct-3-en-6-yl]oxy]acetate (Intermediate 103, 56.3 mg, 0.16 mmol) in THF (1.0 mL) and water (0.5 mL) at 0° C. was added lithium hydroxide (1M) (0.50 mL, 0.50 mmol). The reaction mixture was stirred for 1 hour. HCl (1N) solution was added to adjust pH to ~5-6. The solvent was removed. A sepabead column (saturated with water first, then ACN, then washed with water) eluting with water (0%-5% ACN/water) afforded the title compound (10 mg, 17.3%) as a white solid after lyophilization.
MS: 330 ES+($C_{13}H_{16}FN_3O_6$) $^1$H NMR (300 MHz, $D_2O$) δ: 1.63 (s, 3H); 3.22 (m, 1H); 3.37 (m, 1H); 4.04 (m, 1H); 4.30 (s, 1H); 4.58 (m, 2H); 4.86 (m, 3H); 5.15-5.56 (d, 1H); 6.15 (m, 1H).

Intermediate 104: (2S,5R)-6-[tert-butyl(dimethyl)silyl]oxy-N-[2-(methanesulfonamido)ethyl]-3-methyl-7-oxo-1,6-diazabicyclo[3.2.1]oct-3-ene-2-carboxamide

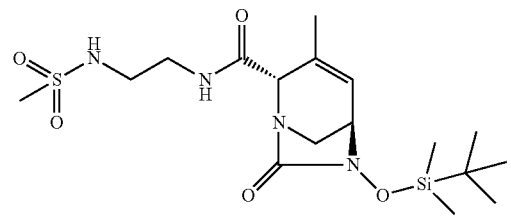 [SMILES: CC1=C[C@@H]2CN(C(=O)N2O[Si](C)(C)C(C)(C)C)[C@@H]1C(=O)NCCNS(C)(=O)=O]

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 300 mg, 0.96 mmol) in DMF (1.5 mL) and N-(2-Amino-ethyl)-methanesulfonamide hydrochloride salt (251.5 mg, 1.44 mmol) according to the procedure for Intermediate 101 to afford (220 mg, 53%) as a white solid.
MS: 433 ES+($C_{17}H_{32}N_4O_5SiS$)

Intermediate 105: (2S,5R)-6-hydroxy-N-[2-(methanesulfonamido)ethyl]-3-methyl-7-oxo-1,6-diazabicyclo[3.2.1]oct-3-ene-2-carboxamide

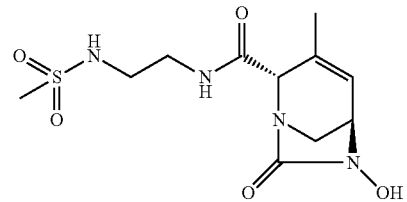 [SMILES: CC1=C[C@@H]2CN(C(=O)N2O)[C@@H]1C(=O)NCCNS(C)(=O)=O]

The title compound was prepared from (2S,5R)-6-[tert-butyl(dimethyl)silyl]oxy-N-[2-(methanesulfonamido)ethyl]-3-methyl-7-oxo-1,6-diazabicyclo[3.2.1]oct-3-ene-2-carboxamide (Intermediate 104, 0.12 g, 0.28 mmol) according to the procedure for Intermediate 102 to afford a tan residue.
MS: 319 ES+($C_{11}H_{18}N_4O_5S$)

Intermediate 106: ethyl (2S)-2-fluoro-2-[[(2S,5R)-2-[2-(methanesulfonamido)ethyl-carbamoyl]-3-methyl-7-oxo-1,6-diazabicyclo[3.2.1]oct-3-en-6-yl]oxy]acetate

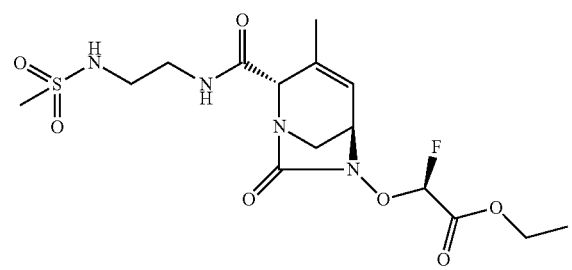 [SMILES: CCOC(=O)[C@H](F)ON1C(=O)N2C[C@H]1C=C(C)[C@H]2C(=O)NCCNS(C)(=O)=O]

The title compound was prepared from (2S,5R)-6-hydroxy-N-[2-(methanesulfonamido)-ethyl]-3-methyl-7-oxo-1,6-diazabicyclo[3.2.1]oct-3-ene-2-carboxamide (Intermediate 105, 80 mg, 0.25 mmol) and ethyl (2S)-2-bromo-2-fluoro-acetate (Intermediate 174, 0.089 mL, 0.75 mmol) according to the procedure for Intermediate 103 to afford (25 mg, 18.8%) as a white solid. The compound is a 1:4 mixture of diastereomers.

MS: 423 ES+($C_{15}H_{23}FN_4O_7S$)

Example 67

(2S)-2-fluoro-2-[[(2S,5R)-2-[2-(methanesulfonamido)ethylcarbamoyl]-3-methyl-7-oxo-1,6-diazabicyclo[3.2.1]oct-3-en-6-yl]oxy]acetic acid lithium salt

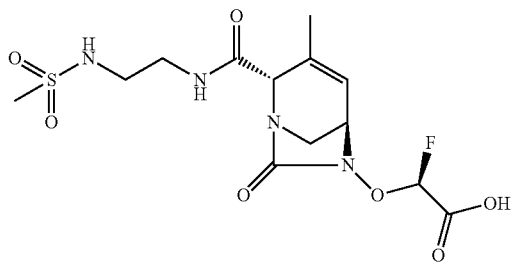 [SMILES: CC1=C[C@@H]2CN(C(=O)N2O[C@@H](F)C(=O)O)[C@@H]1C(=O)NCCNS(C)(=O)=O]

The title compound was prepared from ethyl (2S)-2-fluoro-2-[[(2S,5R)-3-methyl-2-(3-methylsulfonylpropylcarbamoyl)-7-oxo-1,6-diazabicyclo[3.2.1]oct-3-en-6-yl]oxy]acetate (Intermediate 106, 25 mg, 0.06 mmol) according to the procedure for Example 66 to afford (4.0 mg, 15.4%) as a white solid after lyophilization.

MS: 395 ES+($C_{13}H_{19}FN_4O_7S$)

$^1$H NMR (300 MHz, $D_2O$) δ: 1.63 (s, 3H); 2.95 (s, 3H); 3.18-3.38 (m, 6H); 4.02 (m, 1H); 4.27 (s, 1H); 5.56-5.74 (d, 1H); 6.13 (m, 1H).

Intermediate 107: (2S,5R)-6-[tert-butyl(dimethyl)silyl]oxy-3-methyl-N-(oxazol-2-ylmethyl)-7-oxo-1,6-diazabicyclo[3.2.1]oct-3-ene-2-carboxamide

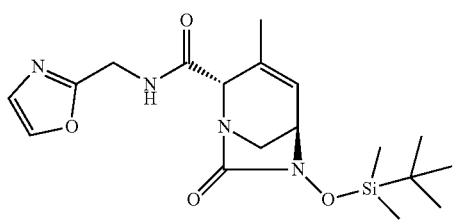 [SMILES: CC1=C[C@@H]2CN(C(=O)N2O[Si](C)(C)C(C)(C)C)[C@@H]1C(=O)NCc1ncco1]

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 400 mg, 1.28 mmol) and oxazol-2-yl-methylamine hydrochloride (258.4 mg, 1.92 mmol) according to the procedure for Intermediate 101 to afford (120 mg, 23.9%) as a white solid.

MS: 393 ES+($C_{18}H_{28}N_4O_4Si$)

Intermediate 108: (2S,5R)-6-hydroxy-3-methyl-N-(oxazol-2-ylmethyl)-7-oxo-1,6-diazabicyclo[3.2.1]oct-3-ene-2-carboxamide

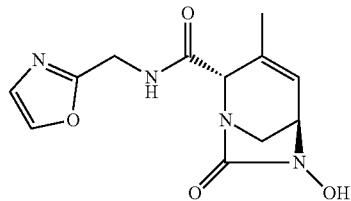 [SMILES: CC1=C[C@@H]2CN(C(=O)N2O)[C@@H]1C(=O)NCc1ncco1]

The title compound was prepared from (2S,5R)-6-[tert-butyl(dimethyl)silyl[oxy-3-methyl-N-(oxazol-2-ylmethyl)-7-oxo-1,6-diazabicyclo[3.2.1]oct-3-ene-2-carboxamide (Intermediate 107, 0.12 g, 0.31 mmol) according to the procedure for Intermediate 102 to afford a residue.

MS: 279 ES+($C_{12}H_{14}N_4O_4$)

Intermediate 109: ethyl (2S)-2-fluoro-2-[[(2S,5R)-3-methyl-2-(oxazol-2-ylmethylcarbamoyl)-7-oxo-1,6-diazabicyclo[3.2.1]oct-3-en-6-yl]oxy]acetate

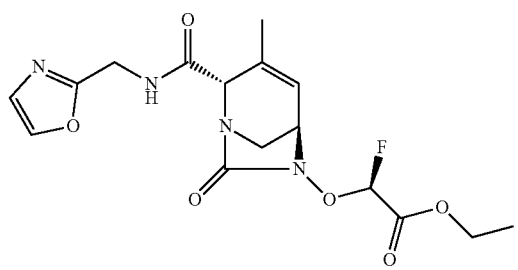 [SMILES: CCOC(=O)[C@H](F)ON1C(=O)N2C[C@H]1C=C(C)[C@H]2C(=O)NCc1ncco1]

The title compound was prepared from (2S,5R)-6-hydroxy-3-methyl-N-(oxazol-2-ylmethyl)-7-oxo-1,6-diazabicyclo[3.2.1]oct-3-ene-2-carboxamide (Intermediate 108, 80 mg, 0.29 mmol) and ethyl (2S)-2-bromo-2-fluoro-acetate (Intermediate 174, 0.10 mL, 0.86 mmol) according to the procedure for Intermediate 103 to afford (15 mg, 13.6%) a colorless oil. The compound is a 15:85 mixture of diastereomers.

MS: 383 ES+($C_{16}H_{19}FN_4O_6$)

Example 68

(2S)-2-fluoro-2-[[(2S,5R)-3-methyl-2-(oxazol-2-ylmethylcarbamoyl)-7-oxo-1,6-diazabicyclo[3.2.1]oct-3-en-6-yl]oxy]acetic acid lithium salt

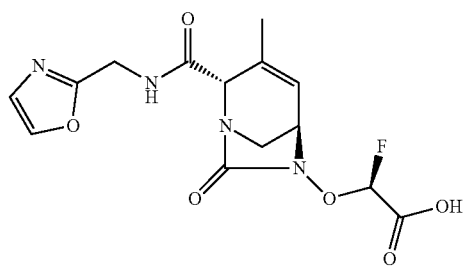 [SMILES: CC1=C[C@@H]2CN(C(=O)N2O[C@@H](F)C(=O)O)[C@@H]1C(=O)NCc1ncco1]

The title compound was prepared from ethyl (2S)-2-fluoro-2-[[(2S,5R)-3-methyl-2-(oxazol-2-ylmethylcarbamoyl)-7-oxo-1,6-diazabicyclo[3.2.1]oct-3-en-6-yl]oxy]acetate (Intermediate 109, 15 mg, 0.039 mmol) according to the procedure for Example 66 to afford (4.0 mg, 25.9%) as a white solid after lyophilization.

MS: 355 ES+($C_{14}H_{15}FN_4O_6$)

$^1$H NMR (300 MHz, $D_2O$) δ: 1.62 (s, 3H); 3.28 (m, 2H); 4.03 (m, 1H); 4.36 (s, 1H); 4.47 (m, 2H); 5.56-5.74 (d, 1H); 6.13 (m, 1H); 7.01 (d, 1H); 7.71 (d, 1H).

Intermediate 110: (2S,5R)-6-[tert-butyl(dimethyl)silyl]oxy-3-methyl-7-oxo-N-(pyrazin-2-ylmethyl)-1,6-diazabicyclo[3.2.1]oct-3-ene-2-carboxamide

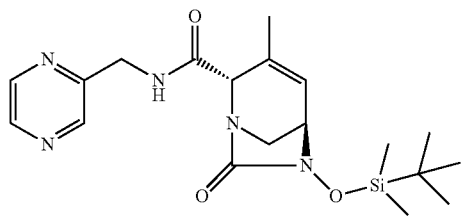 [SMILES: CC1=C[C@@H]2CN(C(=O)N2O[Si](C)(C)C(C)(C)C)[C@@H]1C(=O)NCc1cnccn1]

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 200 mg, 0.64 mmol) and pyrazin-2-yl-methylamine oxalate (191.2 mg, 0.96 mmol) according to the procedure for Intermediate 101 to afforded (120 mg, 46.4%) a white solid.

MS: 404 ES+($C_{19}H_{29}N_5O_3Si$)

Intermediate 111: (2S,5R)-6-hydroxy-3-methyl-7-oxo-N-(pyrazin-2-ylmethyl)-1,6-diazabicyclo[3.2.1]oct-3-ene-2-carboxamide

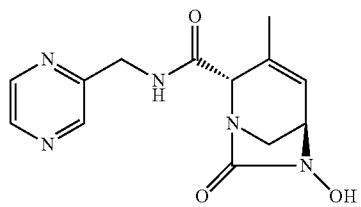 [SMILES: CC1=C[C@@H]2CN(C(=O)N2O)[C@@H]1C(=O)NCc1cnccn1]

The title compound was prepared from (2S,5R)-6-[tert-butyl(dimethyl)silyl]oxy-3-methyl-7-oxo-N-(pyrazin-2-ylmethyl)-1,6-diazabicyclo[3.2.1]oct-3-ene-2-carboxamide (Intermediate 110, 0.10 g, 0.26 mmol) according to the procedure for Intermediate 102 to afford a residue.

MS: 290 ES+($C_{13}H_{15}N_5O_3$)

Intermediate 112: ethyl (2S)-2-fluoro-2-[[(2S,5R)-3-methyl-7-oxo-2-(pyrazin-2-ylmethylcarbamoyl)-1,6-diazabicyclo[3.2.1]oct-3-en-6-yl]oxy]acetate

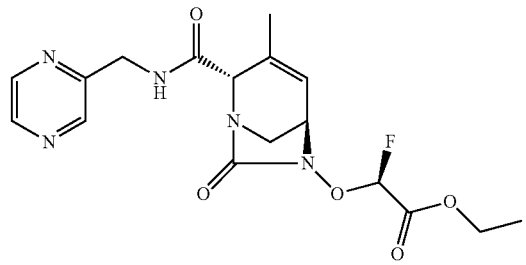 [SMILES: CCOC(=O)[C@H](F)ON1C(=O)N2C[C@H]1C=C(C)[C@H]2C(=O)NCc1cnccn1]

The title compound was prepared from (2S,5R)-6-hydroxy-3-methyl-7-oxo-N-(pyrazin-2-ylmethyl)-1,6-diazabicyclo[3.2.1]oct-3-ene-2-carboxamide (Intermediate 111, 70 mg, 0.24 mmol) and ethyl (2S)-2-bromo-2-fluoro-acetate (Intermediate 174, 0.086 mL, 0.73 mmol) according to the procedure for Intermediate 103 to afford (50 mg, 52.5%) a colorless oil. The compound is a 15:85 mixture of diastereomers.

MS: 394 ES+($C_{17}H_{20}FN_5O_5$)

Example 69

(2S)-2-fluoro-2-[[(2S,5R)-3-methyl-7-oxo-2-(pyrazin-2-ylmethyl-carbamoyl)-1,6-diazabicyclo[3.2.1]oct-3-en-6-yl]oxy]acetic acid lithium salt

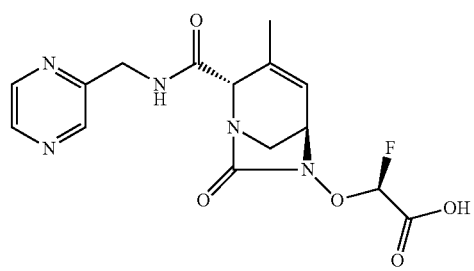 [SMILES: CC1=C[C@@H]2CN(C(=O)N2O[C@@H](F)C(=O)O)[C@@H]1C(=O)NCc1cnccn1]

The title compound was prepared from ethyl (2S)-2-fluoro-2-[[(2S,5R)-3-methyl-7-oxo-2-(pyrazin-2-ylmethyl-carbamoyl)-1,6-diazabicyclo[3.2.1]oct-3-en-6-yl]oxy]acetate (Intermediate 112, 50 mg, 0.13 mmol) according to the procedure for Example 66 to afford (4.0 mg, 8.2%) a white solid after lyophilization.

MS: 366 ES+($C_{15}H_{16}FN_5O_5$)

$^1$H NMR (300 MHz, $D_2O$) δ: 1.62 (s, 3H); 3.28 (m, 2H); 4.03 (m, 1H); 4.36 (s, 1H); 4.53 (m, 2H); 5.56-5.75 (d, 1H); 6.13 (m, 1H); 8.49 (m, 3H).

Intermediate 113: (2S,5R)-6-[tert-butyl(dimethyl)silyl]oxy-N-(cyclopropylmethoxy)-3-methyl-7-oxo-1,6-diazabicyclo[3.2.1]oct-3-ene-2-carboxamide

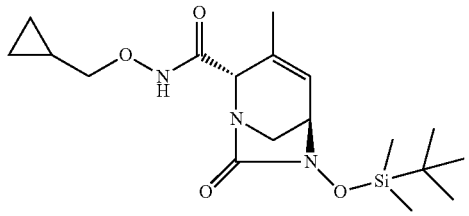 [SMILES: CC1=C[C@@H]2CN(C(=O)N2O[Si](C)(C)C(C)(C)C)[C@@H]1C(=O)NOCC1CC1]

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 200 mg, 0.64 mmol) and O-(cyclopropylmethyl) hydroxylamine (83.6 mg, 0.96 mmol) according to the procedure for Intermediate 101 to afford (100 mg, 40.9%) a colorless oil.
MS: 382 ES+($C_{18}H_{31}N_3O_4Si$)

Intermediate 114: (2S,5R)—N-(cyclopropylmethoxy)-6-hydroxy-3-methyl-7-oxo-1,6-diazabicyclo[3.2.1]oct-3-ene-2-carboxamide

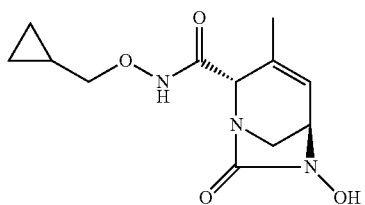 [SMILES: CC1=C[C@@H]2CN(C(=O)N2O)[C@@H]1C(=O)NOCC1CC1]

The title compound was prepared from (2S,5R)-6-[tert-butyl(dimethyl)silyl]oxy-N-(cyclopropylmethoxy)-3-methyl-7-oxo-1,6-diazabicyclo[3.2.1]oct-3-ene-2-carboxamide (Intermediate 113, 0.1 g, 0.26 mmol) according to the procedure for Intermediate 102 to afford a residue.
MS: 268 ES+($C_{12}H_{17}N_3O_4$)

Intermediate 115: ethyl (2S)-2-[[(2S,5R)-2-(cyclopropylmethoxycarbamoyl)-3-methyl-7-oxo-1,6-diazabicyclo[3.2.1]oct-3-en-6-yl]oxy]-2-fluoro-acetate

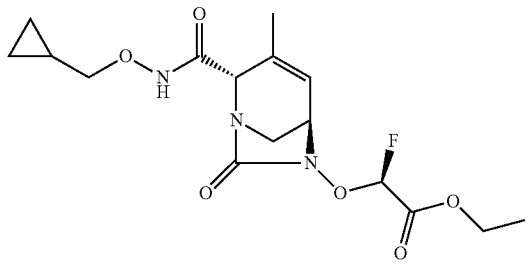 [SMILES: CCOC(=O)[C@H](F)ON1C(=O)N2C[C@H]1C=C(C)[C@H]2C(=O)NOCC1CC1]

The title compound was prepared from (2S,5R)—N-(cyclopropylmethoxy)-6-hydroxy-3-methyl-7-oxo-1,6-diazabicyclo[3.2.1]oct-3-ene-2-carboxamide (Intermediate 114, 60 mg, 0.22 mmol) and ethyl (2S)-2-bromo-2-fluoro-acetate (Intermediate 174, 0.08 mL, 0.67 mmol) according to the procedure for Intermediate 103 to afford (15 mg, 18%) a colorless oil. The compound is a 1:9 mixture of diastereomers.
MS: 372 ES+($C_{16}H_{22}FN_3O_6$)

Example 70

(2S)-2-[[(2S,5R)-2-(cyclopropylmethoxycarbamoyl)-3-methyl-7-oxo-1,6-diazabicyclo[3.2.1]oct-3-en-6-yl]oxy]-2-fluoro-acetic acid lithium salt

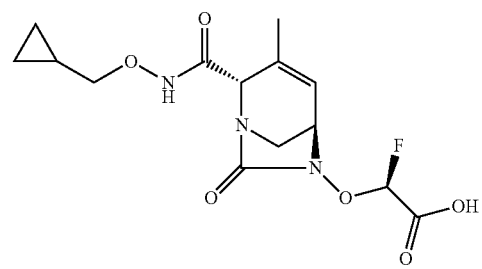 [SMILES: CC1=C[C@@H]2CN(C(=O)N2O[C@@H](F)C(=O)O)[C@@H]1C(=O)NOCC1CC1]

The title compound was prepared from ethyl (2S)-2-[[(2S,5R)-2-(cyclopropylmethoxy-carbamoyl)-3-methyl-7-oxo-1,6-diazabicyclo[3.2.1]oct-3-en-6-yl]oxy]-2-fluoro-acetate (Intermediate 115, 15 mg, 0.04 mmol) according to the procedure for Example 66 to afford (4.5 mg, 32.5%) as a white solid after lyophilization MS: 344 ES+($C_{14}H_{18}FN_3O_6$)
$^1$H NMR (300 MHz, $D_2O$) δ: 0.00 (m, 2H); 0.28 (m, 2H); 0.81 (m, 1H); 1.38 (s, 3H); 3.02 (m, 1H); 3.35 (m, 1H); 3.42 (m, 2H); 3.82 (m, 1H); 3.92 (s, 1H); 5.37-5.55 (d, 1H); 5.95 (m, 1H).

Intermediate 116: (2S,5R)—N-(3-amino-3-oxo-propyl)-6-[tert-butyl(dimethyl)silyl]oxy-3-methyl-7-oxo-1,6-diazabicyclo[3.2.1]oct-3-ene-2-carboxamide

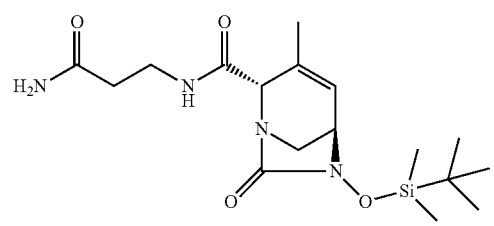 [SMILES: CC1=C[C@@H]2CN(C(=O)N2O[Si](C)(C)C(C)(C)C)[C@@H]1C(=O)NCCC(N)=O]

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 200 mg, 0.64 mmol) and alaninamide hydrochloride (119.6 mg, 0.96 mmol) according to the procedure for Intermediate 101 to afford (140 mg, 57.2%) as a white solid.
MS: 383 ES+($C_{17}H_{30}N_4O_4Si$)

Intermediate 117: (2S,5R)—N-(3-amino-3-oxo-propyl)-6-hydroxy-3-methyl-7-oxo-1,6-diazabicyclo[3.2.1]oct-3-ene-2-carboxamide

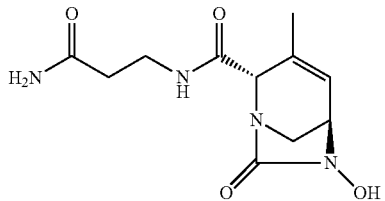 [SMILES: CC1=C[C@@H]2CN(C(=O)N2O)[C@@H]1C(=O)NCCC(N)=O]

The title compound was prepared from (2S,5R)—N-(3-amino-3-oxo-propyl)-6-[tert-butyl(dimethyl)silyl]oxy-3-methyl-7-oxo-1,6-diazabicyclo[3.2.1]oct-3-ene-2-carboxamide (Intermediate 116, 140 mg, 0.37 mmol) according to the procedure for Intermediate 102 to afford a residue.
MS: 269 ES+($C_{11}H_{16}N_4O_4$)

Intermediate 118: ethyl (2S)-2-[[(2S,5R)-2-[(3-amino-3-oxo-propyl)carbamoyl]-3-methyl-7-oxo-1,6-diazabicyclo[3.2.1]oct-3-en-6-yl]oxy]-2-fluoro-acetate

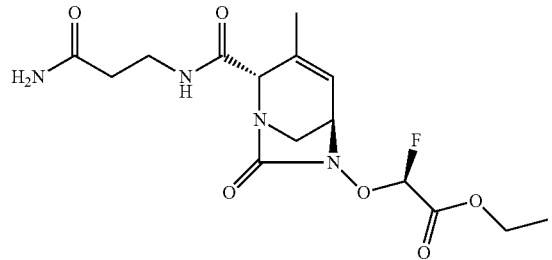 [SMILES: CCOC(=O)[C@H](F)ON1C(=O)N2C[C@H]1C=C(C)[C@H]2C(=O)NCCC(N)=O]

The title compound was prepared from (2S,5R)—N-(3-amino-3-oxo-propyl)-6-hydroxy-3-methyl-7-oxo-1,6-diazabicyclo[3.2.1]oct-3-ene-2-carboxamide (Intermediate 117, 90 mg, 0.34 mmol), $K_2CO_3$ (139.1 mg, 1.01 mmol) and ethyl (2S)-2-bromo-2-fluoro-acetate (Intermediate 174, 0.12 mL, 1.01 mmol) according to the procedure for Intermediate 103 to afford (26.0 mg, 20.8%) as a white solid. The compound is a 1:9 mixture of diastereomers.
MS: 373 ES+($C_{15}H_{21}FN_4O_6$)

Example 71

(2S)-2-[[(2S,5R)-2-[(3-amino-3-oxo-propyl)carbamoyl]-3-methyl-7-oxo-1,6-diazabicyclo[3.2.1]oct-3-en-6-yl]oxy]-2-fluoro-acetic acid lithium salt

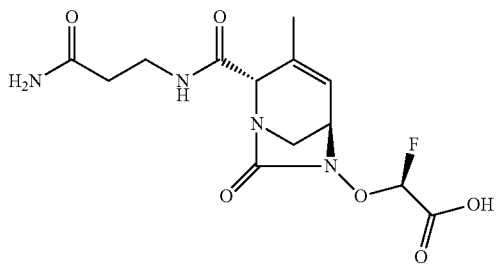

The title compound was prepared from ethyl (2S)-2-[[(2S,5R)-2-[(3-amino-3-oxo-propyl)carbamoyl]-3-methyl-7-oxo-1,6-diazabicyclo[3.2.1]oct-3-en-6-yl]oxy]-2-fluoro-acetate (Intermediate 118, 25 mg, 0.07 mmol) according to the procedure for Example 66 to afford (8 mg, 34.6%) a white solid after lyophilization.
MS: 345 ES+($C_{13}H_{17}FN_4O_6$).
$^1$H NMR (300 MHz, $D_2O$) δ: 1.62 (s, 3H); 2.49 (m, 2H); 3.29 (M, 1H); 3.42 (m, 1H); 3.50 (m, 2H); 4.10 (m, 1H); 4.30 (s, 1H); 5.65-5.82 (d, 1H); 6.22 (m, 1H).

Intermediate 119: 2-[[(2S)-5-oxopyrrolidin-2-yl]methoxy]isoindoline-1,3-dione

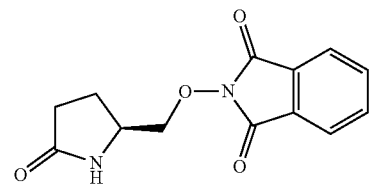 [SMILES: O=C1CC[C@@H](CON2C(=O)c3ccccc3C2=O)N1]

To a solution of diethylazodicarboxylate (16.6 mL, 14.6 mmol, 40% wt) in THF (10 mL) at −10° C. was added dropwise a solution of triphenylphosphine (3.83 g, 14.6 mmol) in THF (20 mL). The suspension was stirred at −10° C. After 1 hour, a solution of (S)-(+)-5-(hydroxymethyl)-2-pyrrolidinone) (0.80 g, 6.95 mmol) in THF (10 mL) was added dropwise, followed by a solution of N-hydroxyphthalimide (1.13 g, 6.95 mmol) in THF (10 mL). The reaction mixture was allowed to warm to room temperature and stir for 2 days. The reaction mixture was concentrated. Silica gel chromatography (0-100% EtOAc/Hexane, then 10% MeOH/DCM) afforded the title compound (1.5 g, 83%) as a pale yelllow solid.
MS: 261 ES+($C_{13}H_{12}N_2O_4$)

Intermediate 120:
(5S)-5-(aminooxymethyl)pyrrolidin-2-one

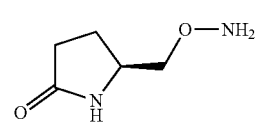

To a solution of 2-[[(2S)-5-oxopyrrolidin-2-yl]methoxy]isoindoline-1,3-dione (Intermediate 119, 1.5 g, 5.76 mmol) in DCM (70 mL) at room temperature was added hydrazine monohydrate (0.84 mL, 17.3 mmol). The reaction mixture was stirred at room temperature for 1 hour, then washed with water (3×20 mL). The aqueous layer was concentrated. A sepabead column afforded the title compound (0.60 g, 79.9%) as a white solid.
MS: 163 ES+($C_8H_6N_2O_2$)

189

Intermediate 121: (2S,5R)-6-[tert-butyl(dimethyl)silyl]oxy-3-methyl-7-oxo-N-[5-oxopyrrolidin-2-yl)methoxy]-1,6-diazabicyclo[3.2.1]oct-3-ene-2-carboxamide

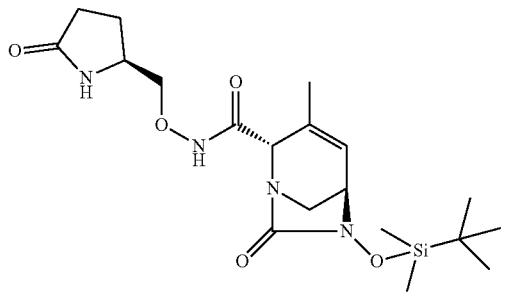 [SMILES: CC1=C[C@@H]2CN(C(=O)N2O[Si](C)(C)C(C)(C)C)[C@@H]1C(=O)NOC[C@@H]1CCC(=O)N1]

The title compound was prepared from (2S,5 R)-6-[tert-butyl(dimethyl)silyl]oxy-3-methyl-7-oxo-1,6-diazabicyclo[3.2.1]oct-3-ene-2-carboxylic acid (Intermediate 77, 250 mg, 0.80 mmol) and 5-(aminooxymethyl) pyrrolidin-2-one (Intermediate 120, 156.2 mg, 1.2 mmol) according to the procedure for Intermediate 101 to afford (55 mg, 16.2%) as a white solid.

MS: 425 ES+($C_{19}H_{32}N_4O_5Si$)

Intermediate 122: (2S,5R)-6-hydroxy-3-methyl-7-oxo-N—R5-oxopyrrolidin-2-yl)methoxy]-1,6-diazabicyclo[3.2.1]oct-3-ene-2-carboxamide

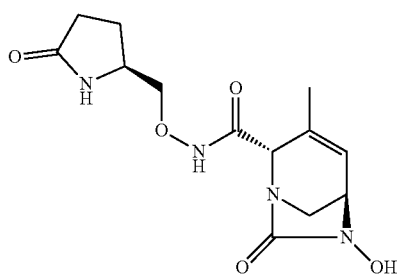 [SMILES: CC1=C[C@@H]2CN(C(=O)N2O)[C@@H]1C(=O)NOC[C@@H]1CCC(=O)N1]

The title compound was prepared from (2S,5R)-6-[tert-butyl(dimethyl)silyl]oxy-3-methyl-7-oxo-N-[[(2S)-5-oxopyrrolidin-2-yl]methoxy]-1,6-diazabicyclo[3.2.1]oct-3-ene-2-carboxamide (Intermediate 121, 55 mg, 0.13 mmol) according to the procedure for Intermediate 102 to afford a light yellow gum.

MS: 311 ES+($C_{13}H_{18}N_4O_5$)

190

Intermediate 123: ethyl (2S)-2-fluoro-2-[[(2S,5R)-3-methyl-7-oxo-2-[(5-oxopyrrolidin-2-yl)methoxycarbamoyl]-1,6-diazabicyclo[3.2.1]oct-3-en-6-yl]oxy]acetate

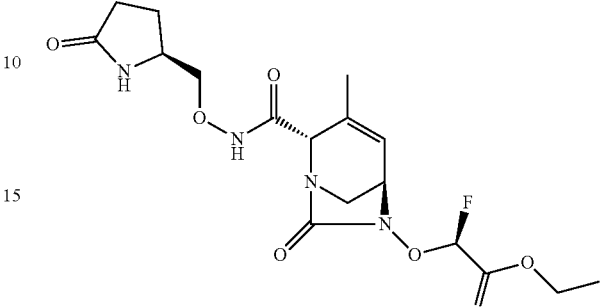

The title compound was prepared from (2S,5R)-6-hydroxy-3-methyl-7-oxo-N-[(5-oxopyrrolidin-2-yl)methoxy]-1,6-diazabicyclo[3.2.1]oct-3-ene-2-carboxamide (Intermediate 122, 35 mg, 0.11 mmol) and ethyl (2S)-2-bromo-2-fluoro-acetate (Intermediate 174, 0.04 mL, 0.34 mmol) according to the procedure for Intermediate 103 to afford (15 mg, 32.1%) as a sticky solid. The compound is a 1:4 mixture of diastereomers.

MS: 415 ES+($C_{17}H_{23}FN_4O_7$)

Example 72

(2S)-2-fluoro-2-[[(2S,5R)-3-methyl-7-oxo-2-[(5-oxopyrrolidin-2-yl)methoxycarbamoyl]-1,6-diazabicyclo[3.2.1]oct-3-en-6-yl]oxy]acetic acid lithium salt

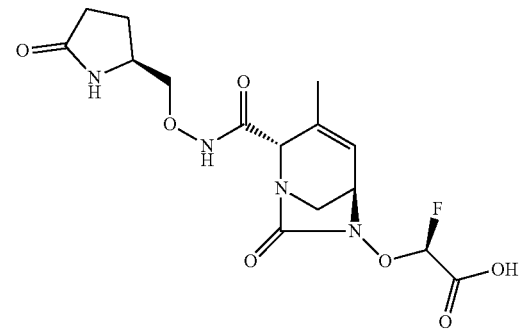

The title compound was prepared from ethyl (2S)-2-fluoro-2-[[(2S,5R)-3-methyl-7-oxo-2-[(5-oxopyrrolidin-2-yl)methoxycarbamoyl]-1,6-diazabicyclo[3.2.1]oct-3-en-6-yl]oxy]acetate (Intermediate 123, 15 mg, 0.036 mmol) according to the procedure for Example 66 to afford (7.0 mg, 40%) a white solid after lyophilization.

MS: 387 ES+($C_{15}H_{19}FN_4O_7$).

$^1$H NMR (300 MHz, $D_2O$) δ: 1.64 (s, 3H); 1.82 (m, 1H); 2.25 (m, 1H); 2.38 (m, 2H); 3.24 (m, 1H); 3.76 (m, 2H); 3.96 (m, 2H); 4.09 (m, 2H); 5.63-5.82 (d, 1H); 6.17 (m, 1H).

Intermediate 124: [(2S)-5-oxopyrrolidin-2-yl]methyl 4-methylbenzenesulfonate

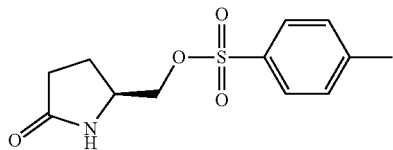 [SMILES: Cc1ccc(S(=O)(=O)OC[C@@H]2CCC(=O)N2)cc1]

To a stirred solution of (S)-(+)-5-(hydroxymethyl)-2-pyrrolinone (2.0 g, 17.4 mmol) and P-toluenesulfonyl chloride (4.17 g, 21.9 mmol) in $CH_2Cl_2$ (50 mL) at 0° C. were added dimethylaminopyridine (111.4 mg, 0.91 mmol) and triethylamine (3.05 mL, 21.9 mmol). The resulting mixture was allowed to warm to RT and stir for 12 hours. The reaction was then quenched with water, and the aqueous layer was extracted with $CH_2Cl_2$. The combined organic extracts were washed with 1N HCl solution and dried over anhydrous $Na_2SO_4$. Removal of solvent under reduced pressure followed by flash chromatography (2.5% MeOH in DCM) afforded the title compound (4.58 g, 93.2%) as a white solid.

MS: 270 ES+($C_{12}H_{15}NO_4S$).

Intermediate 125: 2-[(2S)-5-oxopyrrolidin-2-yl]acetonitrile

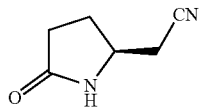

To a solution of [(2S)-5-oxopyrrolidin-2-yl]methyl 4-methylbenzenesulfonate (Intermediate 124, 4.5 g, 16.7 mmol) in acetonitrile (50 mL) was added KCN (2.76 g, 41.8 mmol). The solution was heated at 85° C. for 18 hours. The solution was then diluted with acetonitrile (200 mL), filtered through celite, and concentrated in vacuo. The residue was purified by silica gel flash chromatography (9:1 DCM/MeOH) to afford the title compound (1.8 g, 86.8%) as a white solid.

MS: 125 ES+($C_6H_8N_2O$).

Intermediate 126: tert-butyl N-[2-[(2S)-5-oxopyrrolidin-2-yl]ethyl]carbamate

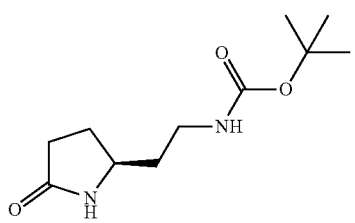 [SMILES: CC(C)(C)OC(=O)NCC[C@@H]1CCC(=O)N1]

To a stirred solution of 2-[(2S)-5-oxopyrrolidin-2-yl]acetonitrile (Intermediate 125, 300 mg, 2.42 mmol) in methanol (15 mL) at 0° C. was added di-tert-butyl dicarbonate (1.05 g, 4.83 mmol) and $NiCl_2.6 H_2O$ (57.4 mg, 0.24 mmol). Then $NaBH_4$ (0.64 g, 16.9 mmol) was added over 30 minutes. The reaction mixture was warmed up to RT and stirred for 1 hour. Hunig's base (0.42 mL, 2.42 mmol) was added, then stirred for 30 minutes. The solvent was removed. The residue was dissolved in EtOAc and washed with sat. $NaHCO_3$ solution, brine, dried over $MgSO_4$, filtered and concentrated to afford the title compound (0.50 g, 90.6%) as a white solid.

MS: 229 ES+($C_{11}H_{20}N_2O_3$)

Intermediate 127: (5S)-5-(2-aminoethyl)pyrrolidin-2-one

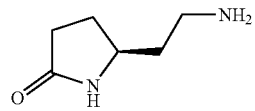

To a solution of tert-butyl N-[2-[(2S)-5-oxopyrrolidin-2-yl]ethyl]carbamate (Intermediate 126, 500 mg, 2.19 mmol) in DCM (2.5 mL) was added trifluoroacetic acid (1.15 g, 10.9 mmol). The reaction was then stirred at RT for 2 hours. The solvent was removed to afford the title compound as a TFA salt.

MS: 129 ES+($C_6H_{12}N_2O$)

Intermediate 128: (2S,5R)-6-[tert-butyl(dimethyl)silyl]oxy-3-methyl-7-oxo-N-[2-(5-oxopyrrolidin-2-yl)ethyl]-1,6-diazabicyclo[3.2.1]oct-3-ene-2-carboxamide

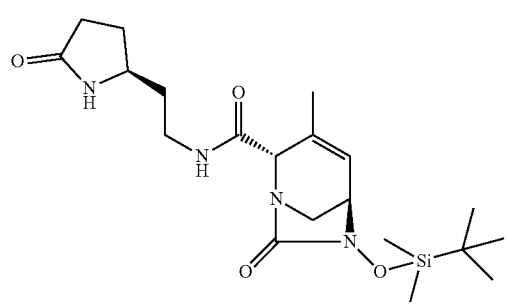 [SMILES: CC1=C[C@@H]2CN(C(=O)N2O[Si](C)(C)C(C)(C)C)[C@@H]1C(=O)NCC[C@@H]1CCC(=O)N1]

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 300 mg, 0.96 mmol) and 5-(2-aminoethyl)pyrrolidin-2-one TFA salt (Intermediate 127, 0.35 g, 1.44 mmol) according to the procedure for Intermediate 101 to afford (120 mg, 29.6%) as a white solid.

MS: 423 ES+($C_{20}H_{34}N_4O_4Si$)

Intermediate 129: (2S,5R)-6-hydroxy-3-methyl-7-oxo-N-[2-(5-oxopyrrolidin-2-yl)ethyl]-1,6-diazabicyclo[3.2.1]oct-3-ene-2-carboxamide

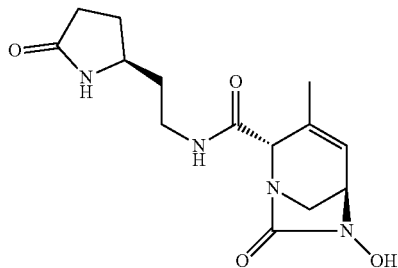 [SMILES: CC1=C[C@@H]2CN(C(=O)N2O)[C@@H]1C(=O)NCC[C@@H]1CCC(=O)N1]

The title compound was prepared from (2S,5R)-6-[tert-butyl(dimethyl)silyl]oxy-3-methyl-7-oxo-N-[2-(5-oxopyrrolidin-2-yl)ethyl]-1,6-diazabicyclo[3.2.1]oct-3-ene-2-carboxamide (Intermediate 128, 120 mg, 0.28 mmol) according to the procedure for Intermediate 102 to afford a white gum.

MS: 309 ES+($C_{14}H_{20}N_4O_4$)

Intermediate 130: ethyl (2S)-2-fluoro-2-[[(2S,5R)-3-methyl-7-oxo-2-[(5-oxopyrrolidin-2-yl)methoxycarbamoyl]-1,6-diazabicyclo[3.2.1]oct-3-en-6-yl]oxy]acetate

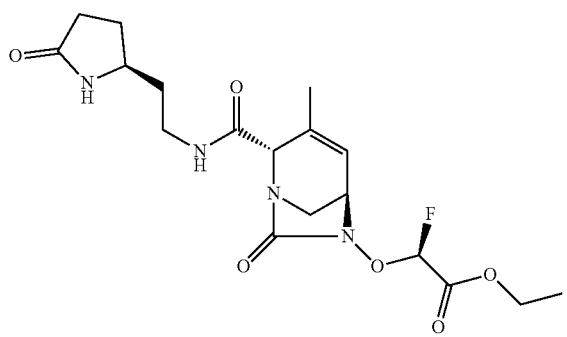 [SMILES: CCOC(=O)[C@H](F)ON1C(=O)N2C[C@H]1C=C(C)[C@H]2C(=O)NCC[C@@H]1CCC(=O)N1]

The title compound was prepared from (2S,5R)-6-hydroxy-3-methyl-7-oxo-N-[2-(5-oxopyrrolidin-2-yl)ethyl]-1,6-diazabicyclo[3.2.1]oct-3-ene-2-carboxamide (Intermediate 129, 80 mg, 0.26 mmol), $K_2CO_3$ (179.3 mg, 1.3 mmol) and ethyl (2S)-2-bromo-2-fluoro-acetate (Intermediate 174, 0.12 mL, 0.78 mmol) according to the procedure for Intermediate 103 to afford (30 mg, 28%) as a white solid. The compound is a 1:4 mixture of diastereomers.

MS: 413 ES+($C_{18}H_{25}FN_4O_6$)

Example 73

(2S)-2-fluoro-2-[[(2S,5R)-3-methyl-7-oxo-2-[2-(5-oxopyrrolidin-2-yl)ethylcarbamoyl]-1,6-diazabicyclo[3.2.1]oct-3-en-6-yl]oxy]acetic acid lithium salt

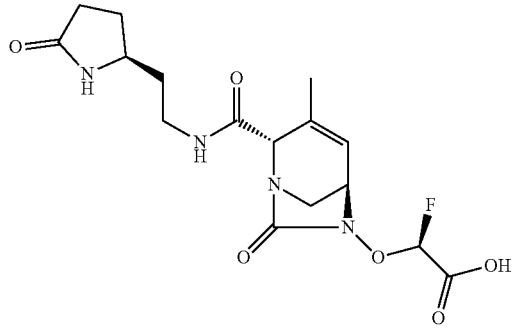

The title compound was prepared from ethyl (2S)-2-fluoro-2-[[(2S,5R)-3-methyl-7-oxo-2-[2-(5-oxopyrrolidin-2-yl)ethylcarbamoyl]-1,6-diazabicyclo[3.2.1]oct-3-en-6-yl]oxy]acetate (Intermediate 130, 30 mg, 0.07 mmol) according to the procedure for Example 66 to afford (8.0 mg, 25.8%) as a white solid after lyophilization.

MS: 385 ES+($C_{16}H_{21}FN_4O_6$)

$^1$H NMR (300 MHz, $D_2O$) δ: 1.69 (s, 3H); 1.77 (m, 3H); 2.36 (m, 2H); 3.30 (m, 3H); 3.44 (m, 1H); 3.76 (m, 2H); 4.11 (m, 1H); 4.31 (m, 1H); 5.63-5.82 (d, 1H); 6.23 (m, 1H).

Intermediate 131: ((2S,5R)-6-[tert-butyl(dimethyl)silyl]oxy-3-methyl-7-oxo-N-(3-sulfamoylpropyl)-1,6-diazabicyclo[3.2.1]oct-3-ene-2-carboxamide

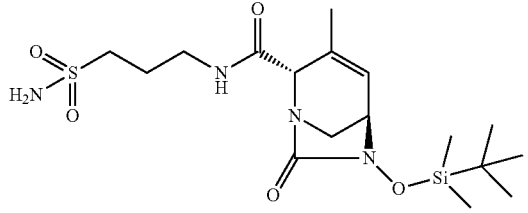 [SMILES: CC1=C[C@@H]2CN(C(=O)N2O[Si](C)(C)C(C)(C)C)[C@@H]1C(=O)NCCCS(N)(=O)=O]

The title compound was prepared from (2S,5R)-6-[tert-butyl(dimethyl)silyl[oxy-3-methyl-7-oxo-1,6-diazabicyclo[3.2.1]oct-3-ene-2-carboxylic acid (Intermediate 174, 300 mg, 0.96 mmol) and 3-aminopropane-1-sulfonamide hydrochloride (251 mg, 1.44 mmol) according to the procedure for Intermediate 101 to afford (198 mg, 47.7%) as a white solid.

MS: 433 ES+($C_{17}H_{32}N_4O_5SiS$)

Intermediate 132: (2S,5R)-6-hydroxy-3-methyl-7-oxo-N-(3-sulfamoylpropyl)-1,6-diazabicyclo[3.2.1]oct-3-ene-2-carboxamide

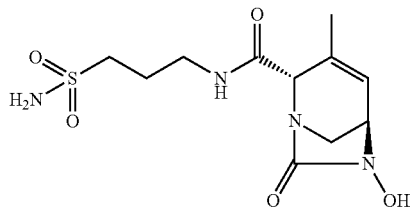 [SMILES: CC1=C[C@@H]2CN(C(=O)N2O)[C@@H]1C(=O)NCCCS(N)(=O)=O]

The title compound was prepared from (2S,5R)-6-[tert-butyl(dimethyl)silyl[oxy-3-methyl-7-oxo-N-(3-sulfamoylpropyl)-1,6-diazabicyclo[3.2.1]oct-3-ene-2-carboxamide (Intermediate 131, 200 mg, 0.46 mmol) according to the procedure for Intermediate 102 to afford a white gum.
MS: 319 ES+($C_{11}H_{18}N_4O_5S$)

Intermediate 133: ethyl (2S)-2-fluoro-2-[[(2S,5R)-3-methyl-7-oxo-2-(3-sulfamoylpropylcarbamoyl)-1,6-diazabicyclo[3.2.1]oct-3-en-6-yl]oxy]acetate

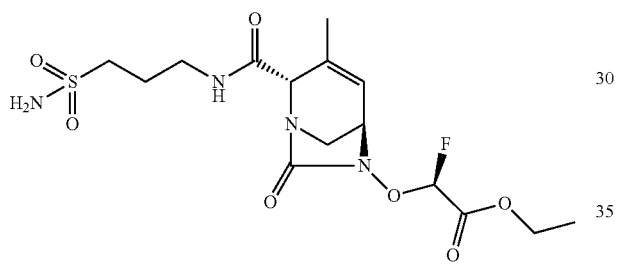

The title compound was prepared from (2S,5R)-6-hydroxy-3-methyl-7-oxo-N-(3-sulfamoylpropyl)-1,6-diazabicyclo[3.2.1]oct-3-ene-2-carboxamide (Intermediate 132, 100 mg, 0.31 mmol) and ethyl (2S)-2-bromo-2-fluoro-acetate (Intermediate 174, 0.11 mL, 0.94 mmol) according to the procedure for Intermediate 103 to afford (22 mg, 16.7%) as a white solid. The compound is a 1:4 mixture of diastereomers.
MS: 423 ES+($C_{15}H_{23}FN_4O_7S$)

Example 74

(2S)-2-fluoro-2-[[(2S,5R)-3-methyl-7-oxo-2-(3-sulfamoylpropylcarbamoyl)-1,6-diazabicyclo[3.2.1]oct-3-en-6-yl]oxy]acetic acid lithium salt

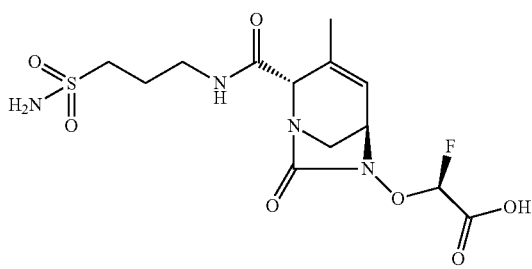 [SMILES: CC1=C[C@@H]2CN(C(=O)N2O[C@@H](F)C(=O)O)[C@@H]1C(=O)NCCCS(N)(=O)=O]

The title compound was prepared from ethyl (2S)-2-fluoro-2-[[(2S,5R)-3-methyl-7-oxo-2-(3-sulfamoylpropylcarbamoyl)-1,6-diazabicyclo[3.2.1]oct-3-en-6-yl]oxy]acetate (Intermediate 133, 22 mg, 0.05 mmol) according to the procedure for Example 66 to afford (8.0 mg, 37%) a white solid after lyophilization.
MS: 395 ES+($C_{13}H_{19}FN_4O_7S$)
$^1$H NMR (300 MHz, $D_2O$) δ: 1.69 (s, 3H); 2.04 (m, 2H); 3.35 (m, 6H); 4.11 (m, 1H); 4.34 (m, 1H); 5.65-5.83 (d, 1H); 6.22 (m, 1H).

Intermediate 134: tert-butyl N-[2-(sulfamoylamino)ethyl]carbamate

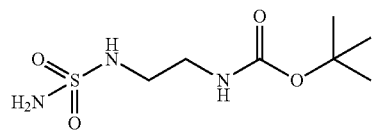

A solution of tert-butyl N-(2-aminoethyl) carbamate (2.0 g, 12.5 mmol) and sulfamide (2.0 g, 24.9 mmol) in dioxane (10 mL) was stirred at 90° C. for 5 hours. The mixture was then filtered to remove the insoluble material and the filtrate was concentrated under reduced pressure. The residue was then dissolved in EtOAc, washed with dilute HCl solution three times, then brine, dried over $MgSO_4$, filtered and concentrated to afford the title compound (1.2 g, 40.2%) as a yellow oil.
$^1$H NMR (300 MHz, DMSO-$d_6$) δ: 1.39 (s, 9H); 2.92 (m, 2H); 3.04 (m, 6H); 6.50 (m, 3H); 6.75 (m, 1H).

Intermediate 135: 1-amino-2-(sulfamoylamino) ethane TFA salt

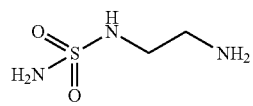

To a solution of tert-butyl N-[2-(sulfamoylamino)ethyl] carbamate (Intermediate 134, 1.2 g, 5.01 mmol) in DCM (5 mL) was added trifluoroacetic acid (5.72 g, 50.1 mmol). The reaction mixture was stirred at room temperature for 2 hours. The solvent was removed to afford the title compound as a yellow TFA salt.
MS: 140 ES+($C_2H_9N_3O_2S$)

Intermediate 136: (2S,5R)-6-[tert-butyl(dimethyl) silyl]oxy-3-methyl-7-oxo-N-[2-(sulfamoylamino) ethyl]-1,6-diazabicyclo[3.2.1]oct-3-ene-2-carboxamide

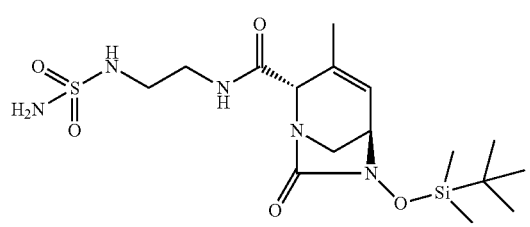 [SMILES: CC1=C[C@@H]2CN(C(=O)N2O[Si](C)(C)C(C)(C)C)[C@@H]1C(=O)NCCNS(N)(=O)=O]

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 300 mg, 0.96 mmol) and 1-amino-2-(sulfamoylamino) ethane TFA salt (Intermediate 135, 365 mg, 1.44 mmol) according to the procedure for Intermediate 101 to afford (117 mg, 28.1%) a white solid.

MS: 434 ES+($C_{16}H_{31}N_5O_5SiS$)

Intermediate 137: (2S,5R)-6-hydroxy-3-methyl-7-oxo-N-[2-(sulfamoylamino)ethyl]-1,6-diazabicyclo[3.2.1]oct-3-ene-2-carboxamide

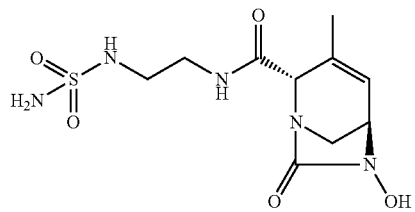 [SMILES: CC1=C[C@@H]2CN(C(=O)N2O)[C@@H]1C(=O)NCCNS(N)(=O)=O]

The title compound was prepared from (2S,5R)-6-[tert-butyl(dimethyl)silyl]oxy-3-methyl-7-oxo-N-[2-(sulfamoylamino)ethyl]-1,6-diazabicyclo[3.2.1]oct-3-ene-2-carboxamide (Intermediate 136, 117 mg, 0.27 mmol) according to the procedure for Intermediate 102 to afford the title compound as a white gum.

MS: 320 ES+($C_{10}H_{17}N_5O_5S$)

Intermediate 138: ethyl (2S)-2-fluoro-2-[[(2S,5R)-3-methyl-7-oxo-2-[2-(sulfamoylamino)ethylcarbamoyl]-1,6-diazabicyclo[3.2.1]oct-3-en-6-yl]oxy]acetate

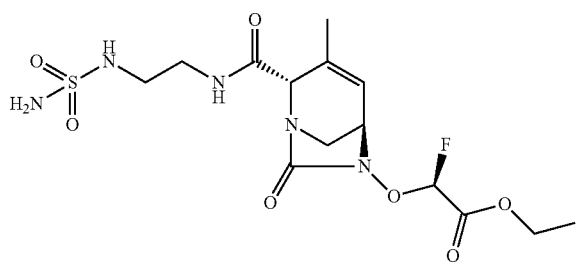 [SMILES: CCOC(=O)[C@H](F)ON1C(=O)N2C[C@H]1C=C(C)[C@H]2C(=O)NCCNS(N)(=O)=O]

The title compound was prepared from (2S,5R)-6-hydroxy-3-methyl-7-oxo-N-[2-(sulfamoylamino)ethyl]-1,6-diazabicyclo[3.2.1]oct-3-ene-2-carboxamide (Intermediate 137, 80 mg, 0.25 mmol) and ethyl (2S)-2-bromo-2-fluoroacetate (Intermediate 174, 0.089 mL, 0.75 mmol) according to the procedure for Intermediate 103 to afford (22.0 mg, 16.5%) as a white solid. The compound is a 3:7 mixture of diastereomers.

MS: 424 ES+($C_{14}H_{22}FN_5O_7$)

Example 75

(2S)-2-fluoro-2-[[(2S,5R)-3-methyl-7-oxo-2-[2-(sulfamoylamino)ethyl-carbamoyl]-1,6-diazabicyclo[3.2.1]oct-3-en-6-yl]oxy]acetic acid lithium salt

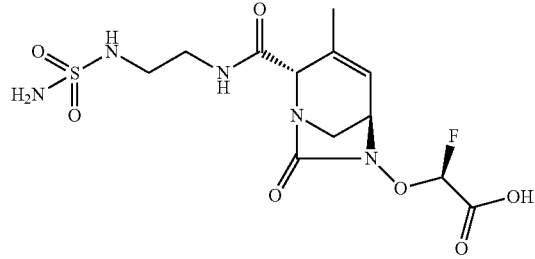 [SMILES: CC1=C[C@@H]2CN(C(=O)N2O[C@@H](F)C(=O)O)[C@@H]1C(=O)NCCNS(N)(=O)=O]

The title compound was prepared from ethyl (2S)-2-fluoro-2-[[(2S,5R)-3-methyl-7-oxo-2-[2-(sulfamoylamino)ethylcarbamoyl]-1,6-diazabicyclo[3.2.1]oct-3-en-6-yl]oxy]acetate (Intermediate 138, 30 mg, 0.071 mmol) according to the procedure for Example 66 to afford (13.0 mg, 44.1%) as a white solid.

MS: 396 ES+($C_{12}H_{18}FN_5O_7S$)

$^1$H NMR (300 MHz, D$_2$O) δ: 1.71 (s, 3H); 3.21-3.47 (m, 6H); 4.11 (m, 1H); 4.35 (m, 1H); 5.64-5.84 (d, 1H); 6.22 (m, 1H).

Intermediate 139: (2S,5R)-6-[tert-butyl(dimethyl)silyl]oxy-3-methyl-7-oxo-1,6-diazabicyclo[3.2.1]oct-3-ene-2-carbonitrile

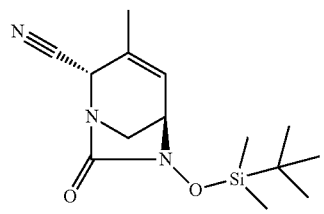

To a solution of (2S,5R)-6-[tert-butyl(dimethyl)silyl]oxy-3-methyl-7-oxo-1,6-diazabicyclo[3.2.1]oct-3-ene-2-carboxamide (Intermediate 192, 3.0 g, 9.63 mmol) in DCM (50 mL) at room temperature was added Burgess Reagent (3.44 g, 14.4 mmol) portionwise over 2 hours. The reaction mixture was stirred for an additional 16 hours, then washed with 1:1 brine:water twice. The organics were dried over magnesium sulfate, filtered and concentrated. Silica gel chromatography (0-25% ethyl acetate/hexanes) afforded the title compound (2.3 g, 81.3%) as a white solid.

MS: 294 ES+($C_{14}H_{23}N_3O_2Si$)

Intermediate 140: tert-butyl N-[[(2S)-6-[tert-butyl(dimethyl)silyl]oxy-3-methyl-7-oxo-1,6-diazabicyclo[3.2.1]oct-3-en-2-yl]methyl]carbamate

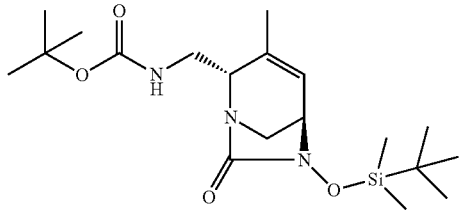 [SMILES: CC1=C[C@@H]2CN(C(=O)N2O[Si](C)(C)C(C)(C)C)[C@@H]1CNC(=O)OC(C)(C)C]

To a stirred solution of (2S)-6-[tert-butyl(dimethyl)silyl]oxy-3-methyl-7-oxo-1,6-diazabicyclo[3.2.1]oct-3-ene-2-carbonitrile (Intermediate 139, 1.2 g, 4.09 mmol) in methanol (100 mL) at 0° C. was added di-tert-butyl dicarbonate (1.78 g, 8.18 mmol) and NiCl$_2$.6 H$_2$O (97.2 mg, 0.41 mmol). Then NaBH$_4$ (1.08 g, 28.6 mmol) was added over 30 minutes. The reaction mixture was then warmed to RT and stirred for 1 hour. Hunig's base (0.71 mL, 4.09 mmol) was added, then stirred for 30 minutes. The solvent was removed. The residue was dissolved in EtOAc and washed with sat. NaHCO$_3$ solution, brine, dried over MgSO$_4$, filtered and concentrated. The residue was purified with silica gel chromatography (40 g, 0%-35% EtOAc/Hexane) to afford the title compound (0.58 g, 35.7%) as a white solid.

MS: 398 ES+(C$_{19}$H$_{35}$N$_3$O$_4$Si)

Intermediate 141: tert-butyl N-[[(2S,5R)-6-hydroxy-3-methyl-7-oxo-1,6-diazabicyclo[3.2.1]oct-3-en-2-yl]methyl]carbamate

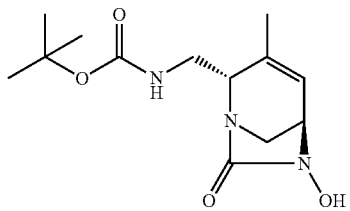 [SMILES: CC1=C[C@@H]2CN(C(=O)N2O)[C@@H]1CNC(=O)OC(C)(C)C]

The title compound was prepared from tert-butyl N-[[(2S,5 R)-6-[tert-butyl(dimethyl)-silyl]oxy-3-methyl-7-oxo-1,6-diazabicyclo[3.2.1]oct-3-en-2-yl]methyl]carbamate (Intermediate 140, 80 mg, 0.20 mmol) according to the procedure for Intermediate 102 to afford a white gum.

MS: 284 ES+(C$_{13}$H$_{21}$N$_3$O$_4$)

Intermediate 142: ethyl (2S)-2-(((2S,5R)-2-(((tert-butoxycarbonyl)amino)methyl)-3-methyl-7-oxo-1,6-diazabicyclo[3.2.1]oct-3-en-6-yl)oxy)-2-fluoroacetate

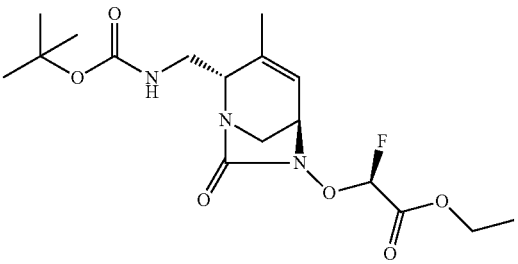 [SMILES: CCOC(=O)[C@H](F)ON1C(=O)N2C[C@H]1C=C(C)[C@H]2CNC(=O)OC(C)(C)C]

The title compound was prepared from tert-butyl N-[[(2S,5R)-6-hydroxy-3-methyl-7-oxo-1,6-diazabicyclo[3.2.1]oct-3-en-2-yl]methyl]carbamate (Intermediate 141, 50 mg, 0.18 mmol) and ethyl (2S)-2-bromo-2-fluoro-acetate (Intermediate 174, 0.063 mL, 0.53 mmol) according to the procedure for Intermediate 103 to afford (50 mg, 73.1%) a white solid. The compound is a 1:9 mixture of diastereomers.

MS: 388 ES+(C$_{17}$H$_{26}$FN$_3$O$_6$)

Example 76

(2S)-2-[[(2S,5R)-2-[tert-butoxycarbonylamino)methyl]-3-methyl-7-oxo-1,6-diazabicyclo[3.2.1]oct-3-en-6-yl]oxy]-2-fluoro-acetic acid lithium salt

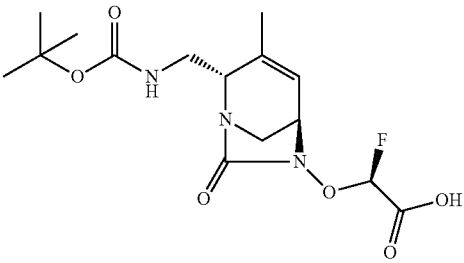 [SMILES: CC1=C[C@@H]2CN(C(=O)N2O[C@@H](F)C(=O)O)[C@@H]1CNC(=O)OC(C)(C)C]

The title compound was prepared from ethyl (2S)-2-(((2S,5R)-2-(((tert-butoxycarbonyl)-amino)methyl)-3-methyl-7-oxo-1,6-diazabicyclo[3.2.1]oct-3-en-6-yl)oxy)-2-fluoroacetate (Intermediate 142, 50 mg, 0.13 mmol) according to the procedure for Example 66 to afford (35 mg, 67.9%) as a white solid after lyophilization.

MS: 360 ES+(C$_{15}$H$_{22}$FN$_3$O$_6$)

$^1$H NMR (300 MHz, D$_2$O) δ: 1.43 (s, 9H); 1.65 (s, 3H); 3.17-3.36 (m, 3H); 3.49 (m, 1H); 3.74 (m, 1H); 4.05 (m, 1H); 5.62-5.81 (d, 1H); 6.08 (m, 1H).

Example 77

(2S)-2-[[(2S,5R)-2-(aminomethyl)-3-methyl-7-oxo-1,6-diazabicyclo[3.2.1]oct-3-en-6-yl]oxy]-2-fluoro-acetic acid

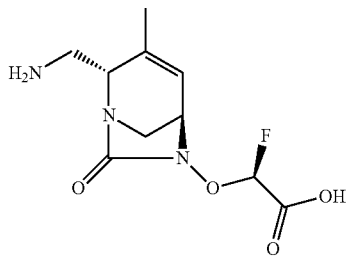

To a solution of (2S)-2-[[(2S,5R)-2-[(tert-butoxycarbonylamino)methyl]-3-methyl-7-oxo-1,6-diazabicyclo[3.2.1]oct-3-en-6-yl]oxy]-2-fluoro-acetic acid (Example 76, 25 mg, 0.07 mmol) in DCM (1 mL) at 0° C. was added trifluoroacetic acid (0.79 g, 6.96 mmol). The reaction mixture was stirred for 2 hours, then concentrated. The residue was dissolved in pH 7 buffer, then loaded on a sepabead column (saturated with water first, then ACN, then washed with water) eluting with (0%-2.5% CAN/water) to afford the title compound (8 mg, 37.7%) as a white solid after lyophilization.

MS: 260 ES+($C_{10}H_{14}FN_3O_4$)

$^1$H NMR (300 MHz, $D_2O$) δ: 1.64 (s, 3H); 3.19-3.30 (m, 3H); 3.44 (m, 1H); 3.96 (m, 1H); 4.09 (m, 1H); 5.64-5.84 (d, 1H); 6.16 (m, 1H).

Intermediate 143: (2S,5R)-2-(aminomethyl)-6-[tert-butyl(dimethyl)silyl]oxy-3-methyl-1,6-diazabicyclo[3.2.1]oct-3-en-7-one

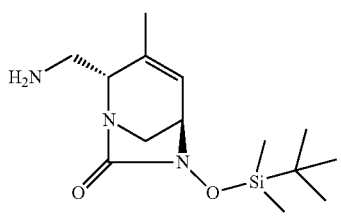 [SMILES: CC1=C[C@@H]2CN(C(=O)N2O[Si](C)(C)C(C)(C)C)[C@@H]1CN]

To a solution of tert-butyl N-[[(2S,5R)-6-[tert-butyl(dimethyl)silyl]oxy-3-methyl-7-oxo-1,6-diazabicyclo[3.2.1]oct-3-en-2-yl]methyl]carbamate (Intermediate 140, 100 mg, 0.25 mmol) in DCM (5 mL) at 0° C. was added $ZnBr_2$ (170 mg, 0.75 mmol). The reaction mixture was stirred at RT for 16 hours, then concentrated and used in the next step without purification.

MS: 298 ES+($C_{14}H_{27}N_3O_2Si$)

Intermediate 144: N-[[(2S,5R)-6-[tert-butyl(dimethyl)silyl]oxy-3-methyl-7-oxo-1,6-diazabicyclo[3.2.1]oct-3-en-2-yl]methyl]acetamide

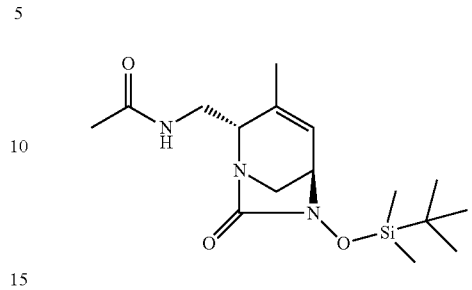

To a solution of (2S,5R)-2-(aminomethyl)-6-[tert-butyl(dimethyl)silyl]oxy-3-methyl-1,6-diazabicyclo[3.2.1]oct-3-en-7-one (Intermediate 143, 74 mg, 0.25 mmol) in pyridine (1 mL) at 0° C. was added $Ac_2O$ (168 mg, 0.75 mmol). The reaction mixture was stirred at RT for 30 minutes, then washed with water, sat. $NaHCO_3$, brine, dried over $MgSO_4$, filtered and concentrated. The residue was purified by silica gel chromatography (0%-100% EtOAc/Hexane) to afford the title compound (70 mg, 78.7%) as a white solid.

MS: 340 ES+($C_{16}H_{29}N_3O_3Si$).

Intermediate 145: N-[[(2S,5R)-6-hydroxy-3-methyl-7-oxo-1,6-diazabicyclo[3.2.1]oct-3-en-2-yl]methyl]acetamide

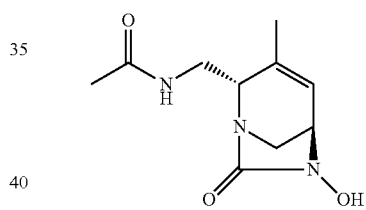

The title compound was prepared from of N-[[(2S,5R)-6-[tert-butyl(dimethyl)silyl]oxy-3-methyl-7-oxo-1,6-diazabicyclo[3.2.1]oct-3-en-2-yl]methyl]acetamide (Intermediate 144, 70 mg, 0.21 mmol) according to the procedure for Intermediate 102 to afford a white gum.

MS: 226 ES+($C_{10}H_{15}N_3O_3$)

Intermediate 146: ethyl (2S)-2-[[(2S,5R)-2-(acetamidomethyl)-3-methyl-7-oxo-1,6-diazabicyclo[3.2.1]oct-3-en-6-yl]oxy]-2-fluoro-acetate

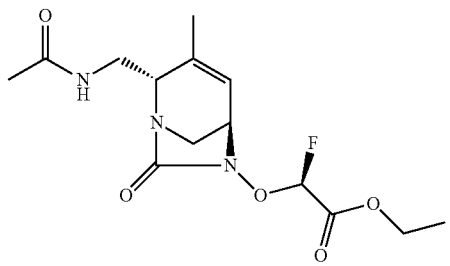 [SMILES: CCOC(=O)[C@H](F)ON1C(=O)N2C[C@H]1C=C(C)[C@H]2CNC(C)=O]

The title compound was prepared from of N-[[(2S,5R)-6-hydroxy-3-methyl-7-oxo-1,6-diazabicyclo[3.2.1] oct-3-en-2-yl]methyl]acetamide (Intermediate 145, 40 mg, 0.18 mmol) and ethyl (2S)-2-bromo-2-fluoro-acetate (Intermediate 174, 0.063 mL, 0.53 mmol) according to the procedure for Intermediate 103 to afford (15 mg, 25.6%) as a white solid after lyophilization. The compound is a 15:85 mixture of diastereomers.

MS: 330 ES+($C_{14}H_{20}FN_3O_5$)

Example 78: (2S)-2-[[(2S,5R)-2-(acetamidomethyl)-3-methyl-7-oxo-1,6-diazabicyclo[3.2.1]oct-3-en-6-yl]oxy]-2-fluoro-acetic acid lithium salt

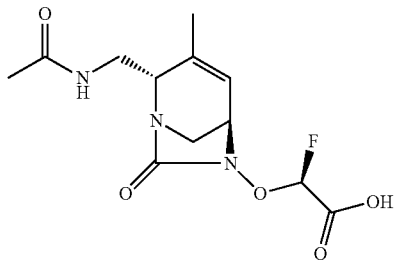 [SMILES: CC(=O)NC[C@@H]1C(C)=C[C@@H]2CN1C(=O)N2O[C@@H](F)C(=O)O]

The title compound was prepared from ethyl (2S)-2-[[(2S,5R)-2-(acetamidomethyl)-3-methyl-7-oxo-1,6-diazabicyclo[3.2.1]oct-3-en-6-yl]oxy]-2-fluoro-acetate (Intermediate 146, 15 mg, 0.05 mmol) according to the procedure for Example 66 to afford (10 mg, 65.6%) a white solid after lyophilization.

MS: 302 ES+($C_{12}H_{16}FN_3O_5$)

$^1$H NMR (300 MHz, D$_2$O) δ: 1.64 (s, 3H); 1.99 (s, 3H); 3.19 (m, 1H); 3.34 (m, 2H); 3.64 (m, 1H); 3.79 (m, 1H); 4.05 (m, 1H); 5.63-5.81 (d, 1H); 6.09 (m, 1H).

Intermediate 147: ethyl (2S)-2-[[(2S,5R)-2-(aminomethyl)-3-methyl-7-oxo-1,6-diazabicyclo[3.2.1]oct-3-en-6-yl]oxy]-2-fluoro-acetate TFA salt

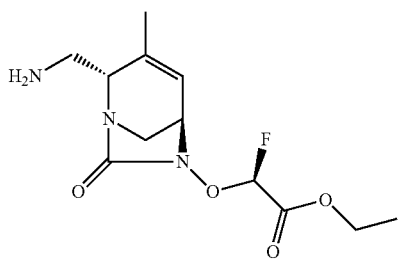 [SMILES: CCOC(=O)[C@H](F)ON1C(=O)N2C[C@H]1C=C(C)[C@H]2CN]

To a solution of ethyl (2S)-2-[[(2S,5R)-2-[(tert-butoxycarbonylamino)methyl]-3-methyl-7-oxo-1,6-diazabicyclo[3.2.1]oct-3-en-6-yl]oxy]-2-fluoro-acetate (Intermediate 142, 97.4 mg, 0.25 mmol) in DCM (2 mL) at 0° C. was added trifluoroacetic acid (2.87 g, 25.2 mmol). The reaction mixture was stirred at 0° C. for 2 hours, then concentrated to afford the title compound as TFA salt.

MS: 288 ES+($C_{12}H_{18}FN_3O_4$)

Intermediate 148: tert-butyl N-chlorosulfonylcarbamate

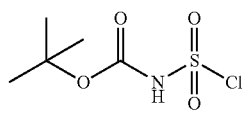

To a stirred solution of tert-butanol (1.9 mL, 20 mmol) in CH$_2$Cl$_2$ (12 mL) at 0° C. was added chlorosulfonyl isocyanate (1.4 mL, 15 mmol) dropwise over the course of 10 minutes. After stirring at 0° C. for 5 minutes, the reaction mixture was warmed to RT and stirred for 20 minutes. The reaction mixture was concentrated in vacuo to one-third volume. The flask was placed back into the 0° C. bath, and the product crystallized out of solution. After 50 minutes, the product was collected by filtration and washed with hexanes to afford the title compound (2.8 g, 80.7%) as a white solid.

Intermediate 149: ethyl (2S)-2-fluoro-2-[[(2S,5R)-3-methyl-7-oxo-2-[[(2,2,2-trifluoroacetyl)amino]methyl]-1,6-diazabicyclo[3.2.1]oct-3-en-6-yl]oxy]acetate

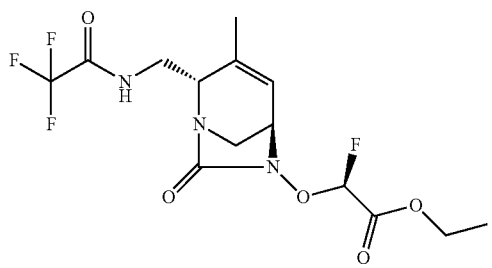 [SMILES: CCOC(=O)[C@H](F)ON1C(=O)N2C[C@H]1C=C(C)[C@H]2CNC(=O)C(F)(F)F]

To a solution of ethyl (2S)-2-[[(2S,5R)-2-(aminomethyl)-3-methyl-7-oxo-1,6-diazabicyclo-[3.2.1]oct-3-en-6-yl]oxy]-2-fluoro-acetate TFA salt (Intermediate 147, 72 mg, 0.25 mmol) in DCM (2 mL) at 0° C. was added tert-butyl N-chlorosulfonylcarbamate (Intermediate 148, 54.0 mg, 0.25 mmol) and triethylamine (63.4 mg, 0.63 mmol). The reaction mixture was stirred at RT for 30 minutes, then diluted with DCM, washed with water, brine, dried over MgSO$_4$, filtered and concentrated. The residue was purified by flash chromatography (0%-100% EtOAc/Hexane) to afford the title compound (38 mg, 39.6%) as a white solid.

MS: 384 ES+($C_{14}H_{17}F_4N_3O_5$)

Example 79

(2S)-2-fluoro-2-[[(2S,5R)-3-methyl-7-oxo-2-[[(2,2,2-trifluoroacetyl)-amino]methyl]-1,6-diazabicyclo[3.2.1]oct-3-en-6-yl]oxy]acetic acid lithium salt

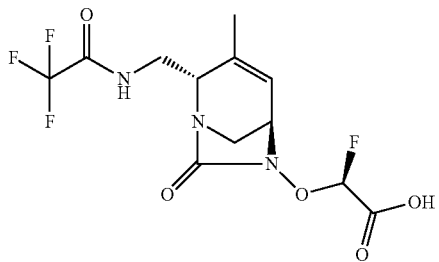 [SMILES: CC1=C[C@@H]2CN(C(=O)N2O[C@@H](F)C(=O)O)[C@@H]1CNC(=O)C(F)(F)F]

The title compound was prepared from ethyl (2S)-2-fluoro-2-[[(2S,5R)-3-methyl-7-oxo-2-[[(2,2,2-trifluoroacetyl)amino]methyl]-1,6-diazabicyclo[3.2.1]oct-3-en-6-yl]oxy]acetate (Intermediate 149, 38 mg, 0.10 mmol) according to the procedure for Example 66 to afford (25 mg, 60.3%) a white solid after lyophilization.

MS: 356 ES+($C_{12}H_{13}FN_3O_5$)
$^1$H NMR (300 MHz, $D_2O$) δ: 1.66 (s, 3H); 3.22 (m, 1H); 3.36 (m, 1H); 3.59 (m, 1H); 3.73 (m, 1H); 3.86 (m, 1H); 4.08 (m, 1H); 5.62-5.83 (d, 1H); 6.11 (m, 1H).

Intermediate 150: (2S,5R)-6-[tert-butyl(dimethyl)silyl]oxy-N-(cyanomethyl)-3-methyl-7-oxo-1,6-diazabicyclo[3.2.1]oct-3-ene-2-carboxamide

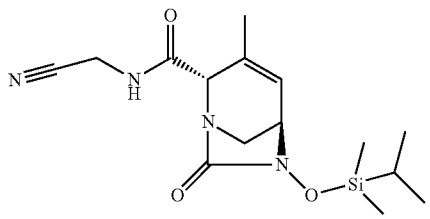 [SMILES: CC1=C[C@@H]2CN(C(=O)N2O[Si](C)(C)C(C)C)[C@@H]1C(=O)NCC#N]

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 700 mg, 2.24 mmol) and aminoacetonitrile hydrochloride (207 mg, 2.24 mmol) according to the procedure for Intermediate 101 to afford (302 mg, 38.4%) a white solid.

MS: 351 ES+($C_{16}H_{26}N_4O_3Si$)

Intermediate 151: (2S,5R)—N-(cyanomethyl)-6-hydroxy-3-methyl-7-oxo-1,6-diazabicyclo[3.2.1]oct-3-ene-2-carboxamide

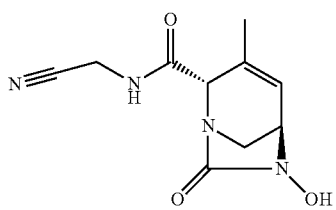 [SMILES: CC1=C[C@@H]2CN(C(=O)N2O)[C@@H]1C(=O)NCC#N]

The title compound was prepared from (2S,5R)-6-[tert-butyl(dimethyl)silyl]oxy-N-(cyanomethyl)-3-methyl-7-oxo-1,6-diazabicyclo[3.2.1]oct-3-ene-2-carboxamide (Intermediate 150, 300 mg, 0.86 mmol) according to the procedure for Intermediate 102 to afford a residue.
MS: 237 ES+($C_{10}H_{12}N_4O_3$)

Example 80 ethyl (2S)-2-fluoro-2-[[(2S,5R)-2-(cyanomethylcarbamoyl)-3-methyl-7-oxo-1,6-diazabicyclo[3.2.1]oct-3-en-6-yl]oxy]acetate

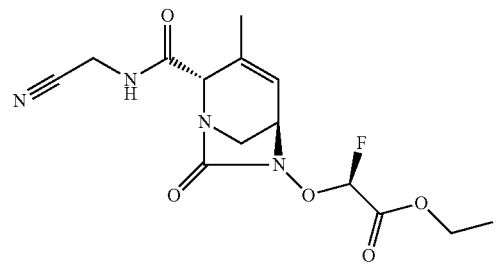 [SMILES: CCOC(=O)[C@H](F)ON1C(=O)N2C[C@H]1C=C(C)[C@H]2C(=O)NCC#N]

To a solution of (2S,5R)—N-(cyanomethyl)-6-hydroxy-3-methyl-7-oxo-1,6-diazabicyclo[3.2.1]oct-3-ene-2-carboxamide (Intermediate 151, 239 mg, 1.01 mmol) in THF (3 mL) and DMF (0.3 mL) at −40° C. was added DBU (0.18 mL, 1.22 mmol) and ethyl (2S)-2-bromo-2-fluoro-acetate (Intermediate 174, 0.18 mL, 1.52 mmol). The reaction mixture was stirred at −40° C. for 30 minutes, then diluted with ethyl acetate and washed three times with 1:1 brine:water. The organics were dried over magnesium sulfate, filtered and concentrated. The residue was purified by flash chromatography (0%-100% EtOAc/Hexane) to give a 1:4 mixture of diastereomers. The diastereomers were separated by reverse phase HPLC (T3 column, 20%-50% ACN/water, 10 minutes) to afford Example 80 (64 mg, 18.2%) and Example 81 (8 mg, 2.3%) as white solids.
MS: 341 ES+($C_{14}H_{17}FN_4O_5$)
$^1$H NMR (300 MHz, DMSO-$d_6$) δ: 1.27 (m, 3H); 1.64 (s, 3H); 3.13 (m, 1H); 3.61 (m, 1H); 3.98 (m, 1H); 4.21 (m, 5H); 6.06-6.26 (m, 1H); 6.10 (m, 1H); 9.18 (m, 1H).

Example 81 ethyl (2R)-2-fluoro-2-[[(2S,5R)-2-(cyanomethylcarbamoyl)-3-methyl-7-oxo-1,6-diazabicyclo[3.2.1]oct-3-en-6-yl]oxy]acetate

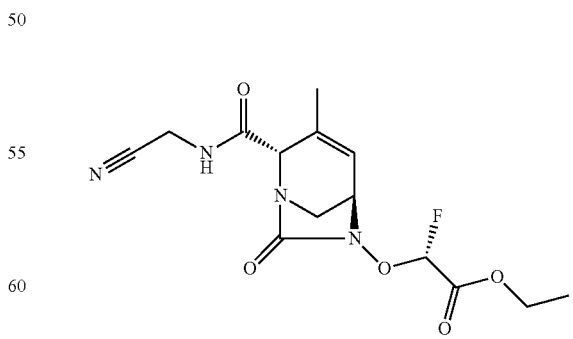

MS: 341 ES+($C_{14}H_{17}FN_4O_5$)
$^1$H NMR (300 MHz, DMSO-$d_6$) δ: 1.21 (m, 3H); 1.65 (s, 3H); 3.12 (m, 1H); 3.60 (m, 1H); 4.07 (m, 1H); 4.22 (m, 5H); 6.08 (m, 1H); 6.15-6.33 (m, 1H); 9.16 (m, 1H).

Example 82

(2S)-2-fluoro-2-[[(2S,5R)-2-(cyanomethylcarbamoyl)-3-methyl-7-oxo-1,6-diazabicyclo[3.2.1]oct-3-en-6-yl]oxy]acetic acid lithium salt

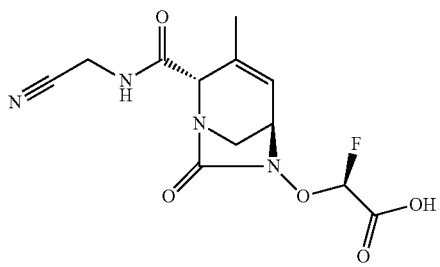 [SMILES: CC1=C[C@@H]2CN(C(=O)N2O[C@@H](F)C(=O)O)[C@@H]1C(=O)NCC#N]

The title compound was prepared from ethyl (2S)-2-fluoro-2-[[(2S,5R)-2-(cyanomethyl-carbamoyl)-3-methyl-7-oxo-1,6-diazabicyclo[3.2.1]oct-3-en-6-yl]oxy]acetate (Example 80, 50 mg, 0.15 mmol) according to the procedure for Example 66 to afford (32 mg, 66.3%) as a white solid after lyophilization.

MS: 313 ES+($C_{12}H_{13}FN_4O_5$)

$^1$H NMR (300 MHz, $D_2O$) δ: 1.74 (s, 3H); 3.35 (m, 2H); 4.12 (m, 1H); 4.25 (m, 2H); 4.42 (m, 1H); 5.63-5.83 (d, 1H); 6.23 (m, 1H).

Example 83 ethyl (2S)-2-fluoro-2-[[(2S,5R)-2-(cyanomethylcarbamoyl)-3-methyl-7-oxo-1,6-diazabicyclo[3.2.1]oct-3-en-6-yl]oxy]acetate

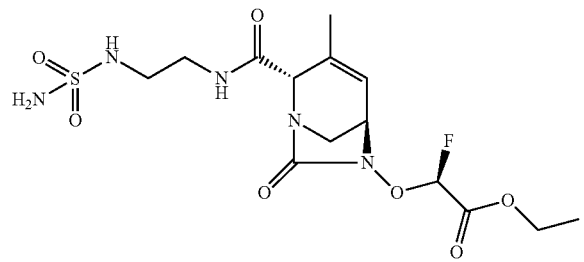 [SMILES: CCOC(=O)[C@H](F)ON1C(=O)N2C[C@H]1C=C(C)[C@H]2C(=O)NCCNS(N)(=O)=O]

Intermediate 138 (230 mg) was separated by reverse phase preparative HPLC (T3 column, ACN/water 20-50% for 10 mins) to afford Example 83 (104 mg) and Example 84 (7 mg) as white solids

MS: 424 ES+($C_{14}H_{22}FN_5O_7S$)

$^1$H NMR (300 MHz, DMSO-$d_6$) δ: 1.27 (m, 3H); 1.63 (s, 3H); 2.97 (m, 2H); 3.10 (m, 1H); 3.26 (m, 2H); 3.73 (m, 1H); 3.96 (m, 1H); 4.21 (m, 3H); 6.06-6.26 (m, 2H); 6.56 (m, 3H); 8.45 (m, 1H).

Example 84 ethyl (2R)-2-fluoro-2-[[(2S,5R)-2-(cyanomethylcarbamoyl)-3-methyl-7-oxo-1,6-diazabicyclo[3.2.1]oct-3-en-6-yl]oxy]acetate

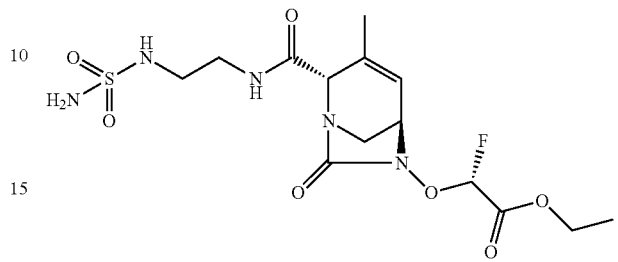

MS: 424 ES+($C_{14}H_{22}FN_5O_7S$)

$^1$H NMR (300 MHz, DMSO-$d_6$) δ: 1.21 (m, 3H); 1.62 (s, 3H); 2.95 (m, 2H); 3.07 (m, 1H); 3.24 (m, 2H); 3.71 (m, 1H); 4.06 (m, 1H); 4.21 (m, 3H); 6.03 (m, 1H); 6.14-6.31 (m, 1H); 6.55 (m, 3H); 8.42 (m, 1H).

Intermediate 152: (2S,5R)-6-[tert-butyl(dimethyl)silyl]oxy-N-(hydroxymethyl)-3-methyl-7-oxo-1,6-diazabicyclo[3.2.1]oct-3-ene-2-carboxamide

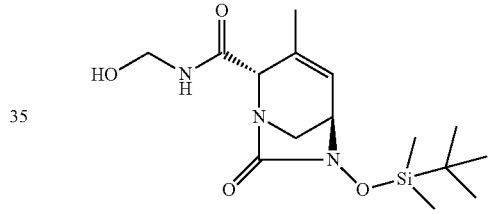

To a solution of (2S,5R)-6-[tert-butyl(dimethyl)silyl]oxy-3-methyl-7-oxo-1,6-diazabicyclo[3.2.1]oct-3-ene-2-carboxamide (Intermediate 192, 1.0 g, 3.21 mmol) was added paraformaldehyde (1.45 g, 16.1 mmol) in 1,4-dioxane (10 mL). The reaction mixture was heated to 90° C. for 16 hours under microwave. The solvent was removed. Silica gel chromatography (0%-80% EtOAc/Hexane) afforded the title compound (0.62 g, 56.5%) as a white solid.

MS: 342 ES+($C_{15}H_{27}N_3O_4Si$)

Intermediate 153: ethyl (2S)-2-fluoro-2-[[(2S,5R)-2-(hydroxymethylcarbamoyl)-3-methyl-7-oxo-1,6-diazabicyclo[3.2.1]oct-3-en-6-yl]oxy]acetate

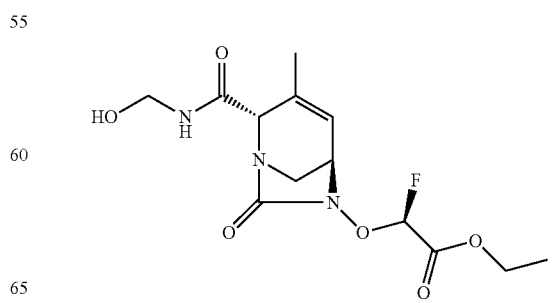

To a solution of (2S,5R)-6-[tert-butyl(dimethyl)silyl]oxy-N-(hydroxymethyl)-3-methyl-7-oxo-1,6-diazabicyclo[3.2.1]oct-3-ene-2-carboxamide (Intermediate 152, 230 mg, 0.67 mmol) and cerium(III) chloride (166 mg, 0.67 mmol) in THF (3 mL) at −78° C. was added TBAF (0.67 mL, 0.67 mmol) (1M in THF). The mixture was stirred for about 10 minutes. To the reaction mixture was added ethyl (2S)-2-bromo-2-fluoro-acetate (Intermediate 174, 24.4 mg, 0.67 mmol). After 5 minutes, the reaction mixture was partitioned between water and EtOAc. The organic layer was collected, washed with water, brine, dried over MgSO$_4$, filtered and concentrated. Silica gel chromatography (0%-80% EtOAc/Hexane) afforded a mixture of two diastereomers in a ratio of 1:3, 180 mg.

Example 85 ethyl (2S)-2-fluoro-2-[[(2S,5R)-2-(hydroxymethyl-carbamoyl)-3-methyl-7-oxo-1,6-diazabicyclo[3.2.1]oct-3-en-6-yl]oxy]acetate

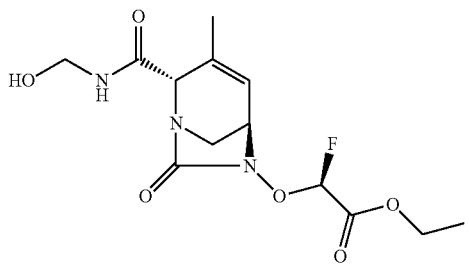 [SMILES: CCOC(=O)[C@H](F)ON1C(=O)N2C[C@H]1C=C(C)[C@H]2C(=O)NCO]

Intermediate 153 (180 mg) was separated by reverse phase preparative HPLC (T3 column, ACN/water 20-50% for 10 mins) to afford Example 85 (43 mg) and Example 86 (2.6 mg) as white solids.

MS: 332 ES+(C$_{13}$H$_{18}$FN$_3$O$_6$)

$^1$H NMR (300 MHz, DMSO-d$_6$) δ: 1.28 (m, 3H); 1.61 (s, 3H); 3.09 (m, 1H); 3.79 (m, 1H); 3.96 (m, 1H); 4.25 (m, 3H); 4.54 (m, 2H); 5.68 (m, 1H); 6.06-6.24 (m, 2H); 8.99 (m, 1H).

Example 86 ethyl (2R)-2-fluoro-2-[[(2S,5R)-2-(hydroxymethyl-carbamoyl)-3-methyl-7-oxo-1,6-diazabicyclo[3.2.1]oct-3-en-6-yl]oxy]acetate

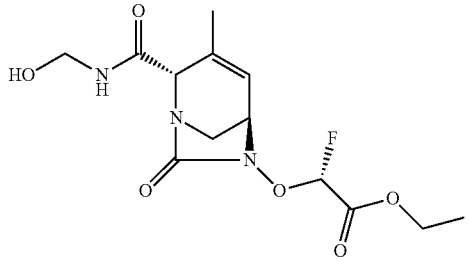 [SMILES: CCOC(=O)[C@@H](F)ON1C(=O)N2C[C@H]1C=C(C)[C@H]2C(=O)NCO]

MS: 332 ES+(C$_{13}$H$_{18}$FN$_3$O$_6$)

$^1$H NMR (300 MHz, DMSO-d$_6$) δ: 1.24 (m, 3H); 1.61 (s, 3H); 2.97 (m, 1H); 3.35 (m, 1H); 4.06 (m, 1H); 4.26 (m, 3H); 4.59 (m, 2H); 5.52 (m, 1H); 6.03 (m, 1H); 6.06-6.24 (m, 1H); 8.99 (m, 1H).

Example 87

(2S)-2-fluoro-2-[[(2S,5R)-2-(hydroxymethylcarbamoyl)-3-methyl-7-oxo-1,6-diazabicyclo[3.2.1]oct-3-en-6-yl]oxy]acetic acid lithium salt

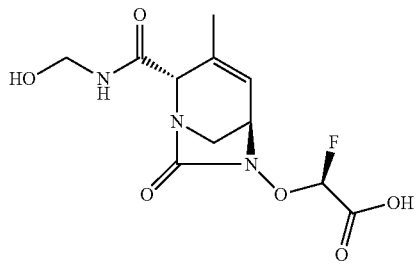 [SMILES: CC1=C[C@@H]2CN(C(=O)N2O[C@@H](F)C(=O)O)[C@@H]1C(=O)NCO]

The title compound was prepared from ethyl (2S)-2-fluoro-2-[[(2S,5R)-2-(hydroxymethylcarbamoyl)-3-methyl-7-oxo-1,6-diazabicyclo[3.2.1]oct-3-en-6-yl]oxy]acetate (Example 85, 15 mg, 0.05 mmol) according to the procedure for Example 66 to afford (8 mg, 55.3%) a white solid after lyophilization.

MS: 304 ES+(C$_{11}$H$_{14}$FN$_3$O$_6$)

$^1$H NMR (300 MHz, D$_2$O) δ: 1.77 (s, 3H); 3.42 (m, 2H); 4.17 (m, 1H); 4.41 (m, 1H); 4.79 (m, 2H); 5.70-5.89 (d, 1H); 6.28 (m, 1H).

Intermediate 154: tert-butyl N-(isocyanatomethyl)carbamate

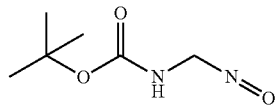

To a stirred solution of BOC-GLY-OH (10 g, 57.08 mmol) in THF (200 mL) at 0° C. was added methyl chloroformate (5.29 mL, 68.5 mmol) dropwise, followed by triethylamine (9.55 mL, 68.5 mmol) dropwise. A white precipitate formed immediately. The mixture was stirred for 45 minutes before the addition of NaN$_3$ (5.58 g, 85.6 mmol) in water (10 mL) at 0° C. The resulting mixture was stirred at 0° C. for 1 hour, then diluted with water. The acyl azide was extracted four times with toluene (4×25 mL) and the combined organic extracts were successively washed with saturated sodium bicarbonate (2×30 mL) and water (50 mL). The organics were dried over MgSO$_4$ at 0° C., filtered and then heated slowly with stirring until nitrogen gas evolution was observed, which occurred at 59° C. for 20 minutes. The temperature was increased and maintained at 64° C. for 1.5 hours, then increased slowly to 70° C. for 20 minutes. The solution was concentrated under reduced pressure to afford the title compound (8.6 g, 87.5%) as a colorless oil.

Intermediate 155: tert-butyl N-(benzyloxycarbonylaminomethyl)carbamate

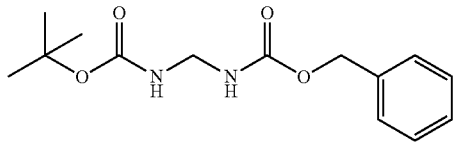 [SMILES: CC(C)(C)OC(=O)NCNC(=O)OCc1ccccc1]

To a solution of tert-butyl N-(isocyanatomethyl)carbamate (Intermediate 154, 8.3 g, 48.2 mmol) in DCE (5 mL) at 0° C. was added benzyl alcohol (7.48 mL, 72.3 mmol) and triethylamine (0.67 mL, 4.82 mmol), dropwise. The reaction mixture was warmed to RT and stirred for 30 minutes. The white solid formed was collected by filtration and washed with hexane to afford the title compound (5.2 g, 38.5%) as a white solid.

MS: 303 ES+Na ($C_{14}H_{20}N_2O_4$).

Intermediate 156: tert-butyl N-(aminomethyl)carbamate

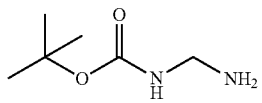

A solution of tert-butyl N-(benzyloxycarbonylaminomethyl)carbamate (Intermediate 155, 1.5 g, 5.35 mmol) in methanol (20 mL) was bubbled with nitrogen gas. Pd/C (10%) (150 mg) was added. The reaction mixture was degassed and then put under hydrogen balloon for 30 minutes. The reaction mixture was filtered through celite. The filtrate was concentrated to afford the title compound as colorless oil.

MS: 147 ES+($C_6H_{14}N_2O_2$)

Intermediate 157: tert-butyl N-[[[(2S,5R)-6-[tert-butyl(dimethyl)silyl]oxy-3-methyl-7-oxo-1,6-diazabicyclo[3.2.1]oct-3-ene-2-carbonyl]amino]methyl]carbamate

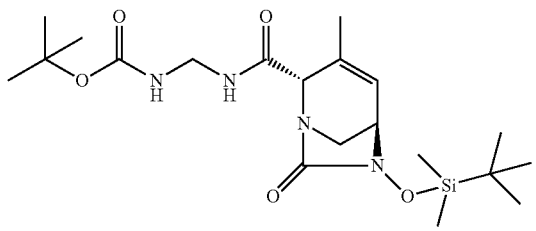 [SMILES: CC1=C[C@@H]2CN(C(=O)N2O[Si](C)(C)C(C)(C)C)[C@@H]1C(=O)NCNC(=O)OC(C)(C)C]

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 350 mg, 1.12 mmol) and tert-butyl N-(aminomethyl)carbamate (Intermediate 156, 246 mg, 1.68 mmol) according to the procedure for Intermediate 101 to afford (170 mg, 34.4%) a white solid.

MS: 441 ES+($C_{20}H_{36}N_4O_5Si$)

Intermediate 158: (2S,5R)—N-(aminomethyl)-6-[tert-butyl(dimethyl)silyl]oxy-3-methyl-7-oxo-1,6-diazabicyclo[3.2.1]oct-3-ene-2-carboxamide

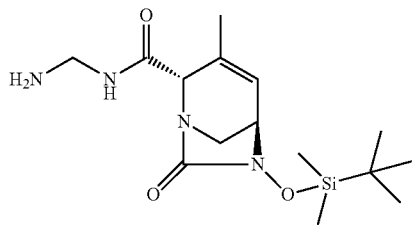 [SMILES: CC1=C[C@@H]2CN(C(=O)N2O[Si](C)(C)C(C)(C)C)[C@@H]1C(=O)NCN]

To a solution of tert-butyl N-[[[(2S,5R)-6-[tert-butyl(dimethyl)silyl]oxy-3-methyl-7-oxo-1,6-diazabicyclo[3.2.1]oct-3-ene-2-carbonyl]amino]methyl]carbamate (Intermediate 157, 170 mg, 0.39 mmol) in DCM (3 mL) at 0° C. was added ZnBr$_2$ (261 mg, 1.16 mmol). The reaction mixture was stirred at RT for 16 hours, then concentrated to afford the title compound.

MS: 341 ES+($C_{15}H_{28}N_4O_3Si$)

Intermediate 159: (2S,5R)—N-(acetamidomethyl)-6-[tert-butyl(dimethyl)silyl]oxy-3-methyl-7-oxo-1,6-diazabicyclo[3.2.1]oct-3-ene-2-carboxamide

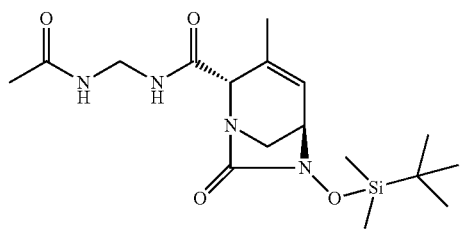 [SMILES: CC(=O)NCNC(=O)[C@@H]1C(C)=C[C@@H]2CN1C(=O)N2O[Si](C)(C)C(C)(C)C]

To a solution of (2S,5R)—N-(aminomethyl)-6-[tert-butyl(dimethyl)silyl]oxy-3-methyl-7-oxo-1,6-diazabicyclo[3.2.1]oct-3-ene-2-carboxamide (Intermediate 158, 131 mg, 0.39 mmol) in pyridine (3 mL) at 0° C. was added acetic anhydride (394 mg, 3.86 mmol). The reaction mixture was stirred at RT for 30 minutes, then partitioned between EtOAc and water. The organic layer washed with water, sat. NaHCO$_3$, brine, dried over MgSO$_4$, filtered and concentrated. Silica gel chromatography (0%-80% EtOAc/Hexane) afforded the title compound (75 mg, 50.8%) as a white solid.

MS: 383 ES+($C_{17}H_{30}N_4O_4Si$)

Intermediate 160: (2S,5R)—N-(acetamidomethyl)-6-hydroxy-3-methyl-7-oxo-1,6-diazabicyclo[3.2.1]oct-3-ene-2-carboxamide

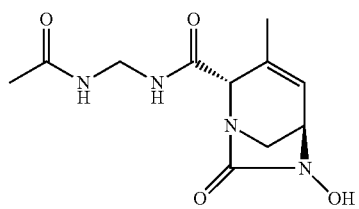 [SMILES: CC(=O)NCNC(=O)[C@@H]1C(C)=C[C@@H]2CN1C(=O)N2O]

The title compound was prepared from (2S,5R)—N-(acetamidomethyl)-6-[tert-butyl(dimethyl)silyl]oxy-3-methyl-7-oxo-1,6-diazabicyclo[3.2.1]oct-3-ene-2-carboxamide (Intermediate 159, 75 mg, 0.20 mmol) according to the procedure for Intermediate 102 to afford a white gum.

MS: 269 ES+($C_{11}H_{16}N_4O_4$)

Intermediate 161: ethyl (2S)-2-fluoro-2-11(2S,5R)-2-(acetamidomethylcarbamoyl)-3-methyl-7-oxo-1,6-diazabicyclo[3.2.1]oct-3-en-6-yl]oxy]acetate

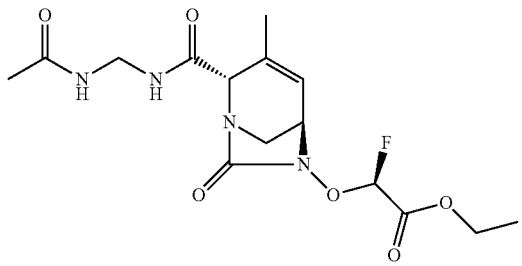 [SMILES: CCOC(=O)[C@H](F)ON1C(=O)N2C[C@H]1C=C(C)[C@H]2C(=O)NCNC(C)=O]

The title compound was prepared from (2S,5R)—N-(acetamidomethyl)-6-hydroxy-3-methyl-7-oxo-1,6-diazabicyclo[3.2.1]oct-3-ene-2-carboxamide (Intermediate 160, 50 mg, 0.19 mmol) and ethyl (2S)-2-bromo-2-fluoro-acetate (Intermediate 174, 0.067 mL, 0.56 mmol) according to the procedure for Intermediate 103 to afford a white solid after sepabead column (saturated with water first, then ACN, then eluting with water) eluting with (0%-15% ACN/water) and lyophilization, 21 mg, 27%. The compound is a 1:4 mixture of diastereomers.

MS: 373 ES+($C_{15}H_{21}FN_4O_6$)

Example 88

(2S)-2-fluoro-2-[[(2S,5R)-2-(acetamidomethylcarbamoyl)-3-methyl-7-oxo-1,6-diazabicyclo[3.2.1]oct-3-en-6-yl]oxy]acetic acid lithium salt

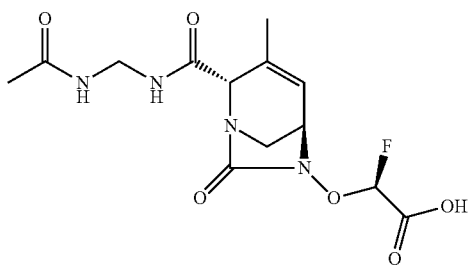 [SMILES: CC(=O)NCNC(=O)[C@@H]1C(C)=C[C@@H]2CN1C(=O)N2O[C@@H](F)C(=O)O]

The title compound was prepared from ethyl (2S)-2-fluoro-2-[[(2S,5R)-2-(acetamido-methylcarbamoyl)-3-methyl-7-oxo-1,6-diazabicyclo[3.2.1]oct-3-en-6-yl]oxy]acetate (Intermediate 161, 21 mg, 0.056 mmol) in water (1 mL) according to the procedure for Example 66 to afford (6.0 mg, 29.3%) a white solid after lyophilization.

MS: 345 ES+($C_{13}H_{17}FN_4O_6$)

$^1$H NMR (300 MHz, $D_2O$) δ: 1.75 (s, 3H); 2.02 (s, 3H); 3.42 (m, 2H); 4.15 (m, 1H); 4.37 (m, 1H); 4.64 (m, 2H); 5.70-5.89 (d, 1H); 6.27 (m, 1H).

Intermediate 162: tert-butyl N-[tert-butoxycarbonylamino)methylsulfamoyl]-carbamate

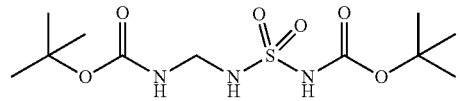 [SMILES: CC(C)(C)OC(=O)NCNS(=O)(=O)NC(=O)OC(C)(C)C]

To a solution of tert-butyl N-(aminomethyl)carbamate (Intermediate 156, 700 mg, 4.79 mmol) in DCM (20 mL) at 0° C. was added triethylamine (0.67 mL, 4.79 mmol). Then tert-butyl N-chlorosulfonylcarbamate (Intermediate 148, 1.03 g, 4.79 mmol) in DCM (5 mL) was added dropwise. The reaction mixture was stirred at 0° C. for 30 minutes, then diluted with DCM, washed with water, brine, dried over $MgSO_4$, filtered and concentrated. The residue was triturated with DCM/Hexane to afford the title compound (650 mg, 41.7%) as a white solid.

MS: 324 ES−($C_{11}H_{23}N_3O_6S$)

Intermediate 163: amino-(sulfamoylamino)methane TFA salt

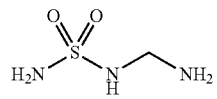

To a solution of tert-butyl N-[(tert-butoxycarbonylamino)methylsulfamoyl]carbamate (Intermediate 162, 650 mg, 2 mmol) in DCM (5 mL) at 0° C. was added trifluoroacetic acid (2.28 g, 19.9 mmol). The reaction mixture was stirred at RT for 30 minutes, then concentrated to afford the title compound as light yellow gum.

Intermediate 164: (2S,5R)-6-[tert-butyl(dimethyl)silyl]oxy-3-methyl-7-oxo-N-[(sulfamoylamino)methyl-1,6-diazabicyclo[3.2.1]oct-3-ene-2-carboxamide

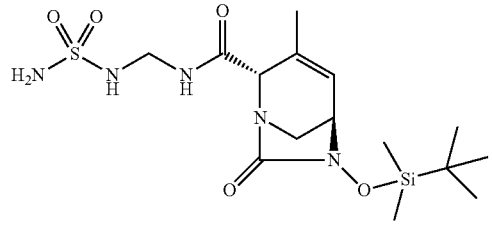 [SMILES: CC1=C[C@@H]2CN(C(=O)N2O[Si](C)(C)C(C)(C)C)[C@@H]1C(=O)NCNS(N)(=O)=O]

The title compound was prepared from (2S,5R)-6-[tert-butyl(dimethyl)silyl]oxy-3-methyl-7-oxo-1,6-diazabicyclo[3.2.1]oct-3-ene-2-carboxylic acid (Intermediate 77, 350 mg, 1.12 mmol) according to the procedure for Intermediate 101 to afford (125 mg, 26.6%) a white solid.

MS: 420 ES+($C_{15}H_{29}N_5O_5SiS$)

Intermediate 165: (2S,5R)-6-hydroxy-3-methyl-7-oxo-N-Rsulfamoylamino)methyl]-1,6-diazabicyclo[3.2.1]oct-3-ene-2-carboxamide

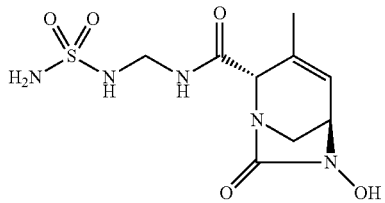

The title compound was prepared from (2S,5R)-6-[tert-butyl(dimethyl)silyl]oxy-3-methyl-7-oxo-N-[(sulfamoylamino)methyl]-1,6-diazabicyclo[3.2.1]oct-3-ene-2-carboxamide (Intermediate 164, 125 mg, 0.30 mmol) according to the procedure for Intermediate 102 to afford a light yellow gum.
MS: 306 ES+($C_9H_{15}N_5O_5S$)

Intermediate 166: ethyl (2S)-2-fluoro-2-[[(2S,5R)-3-methyl-7-oxo-2-[(sulfamoylamino)methylcarbamoyl]-1,6-diazabicyclo[3.2.1]oct-3-en-6-yl]oxy]acetate

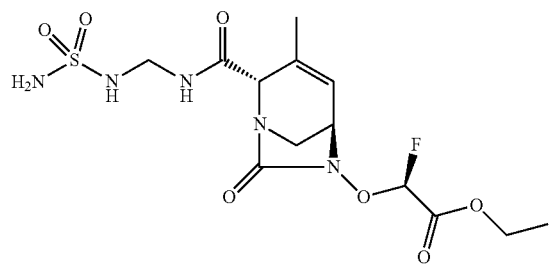 [SMILES: CCOC(=O)[C@H](F)ON1C(=O)N2C[C@H]1C=C(C)[C@H]2C(=O)NCNS(N)(=O)=O]

The title compound was prepared from (2S,5R)-6-hydroxy-3-methyl-7-oxo-N-[(sulfamoylamino)methyl]-1,6-diazabicyclo[3.2.1]oct-3-ene-2-carboxamide (Intermediate 165, 88 mg, 0.29 mmol) and ethyl (2S)-2-bromo-2-fluoroacetate (Intermediate 174, 0.10 mL, 0.86 mmol) according to the procedure for Intermediate 103 to afford (18 mg, 12.2%) a white solid. The compound is a 17:83 mixture of diastereomers.
MS: 410 ES+($C_{13}H_{20}FN_5O_7S$)

Example 89

(2S)-2-fluoro-2-[[(2S,5R)-3-methyl-7-oxo-2-[(sulfamoylamino)-methylcarbamoyl]-1,6-diazabicyclo[3.2.1]oct-3-en-6-yl]oxy]acetic acid lithium salt

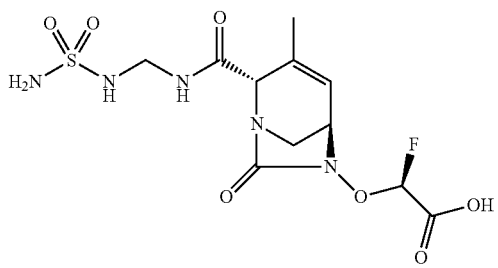 [SMILES: CC1=C[C@@H]2CN(C(=O)N2O[C@@H](F)C(=O)O)[C@@H]1C(=O)NCNS(N)(=O)=O]

The title compound was prepared from ethyl (2S)-2-fluoro-2-[[(2S,5R)-3-methyl-7-oxo-2-[(sulfamoylamino)methylcarbamoyl]-1,6-diazabicyclo[3.2.1]oct-3-en-6-yl]oxy]acetate (Intermediate 166, 18 mg, 0.040 mmol) according to the procedure for Example 66 to afford (5.0 mg, 25.3%) a white solid after lyophilization.
MS: 382 ES+($C_{11}H_{16}F_5O_7S$)
$^1$H NMR (300 MHz, $D_2O$) δ: 1.76 (s, 3H); 3.40 (m, 2H); 4.16 (m, 1H); 4.41 (m, 1H); 4.63 (m, 2H); 5.70-5.89 (d, 1H); 6.28 (m, 1H).

Intermediate 167: racemic 2-bromo-2-fluoroacetic acid

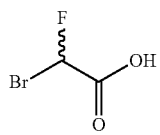

To a 50 L reactor at 0-5° C. was charged a solution of ethyl 2-bromo-2-fluoroacetate (3.5 kg) in tetrahydrofuran (7L, 2V) and a solution of sodium hydroxide (830 g) in water (7L, 2V) dropwise over 1 hour. The resulting solution was stirred at 0-5° C. for 1 hour. HCl (160 mL) was added dropwise at 0-5° C. Water and tetrahydrofuran were removed by concentration under vacuum. The residue was suspended in tetrahydrofuran (35 L, 10V) and conc. HCl (1.57 L, 1.0 eq.) was added dropwise. Anhydrous sodium sulfate was added and the resulting mixture was stirred for 2 hours. The solid was filtered off, and washed with THF (1L×2). The filtrate was concentrated under vacuum to give 2-bromo-2-fluoroacetic acid (2.2 kg) as a yellow oil, which was combined with a previous batch made by the same method (940 g, Purity: 72%) and distilled in vacuum (65-70° C. 100 Pa) to give 2-bromo-2-fluoroacetic acid (2.55 kg, total yield 67%) as a colorless oil.
$^1$H NMR (400 MHz, $CDCl_3$) δ 11.15 (s, 1H), 6.66 (d, 1H, J=68 Hz).

Intermediate 168: (S)-1-phenylethan-1-amine (R)-2-bromo-2-fluoroacetate

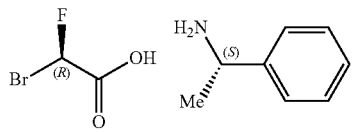

To a 10 L reactor at 0-5° C. was charged a solution of 2-bromo-2-fluoroacetic acid (Intermediate 167, 2.0 kg) in 1 L of chloroform (1V), to which, a solution of (S)-1-phenylethanamine (1.39 kg) in 1 L of chloroform (1V) was added dropwise. The mixture was stirred at room temperature overnight and the resulting white solid was collected by filtration to give a salt of (S)-1-phenylethanamine 2-bromo-2-fluoroacetate (2.5 kg; ee: 6%), which was charged into a 10 L reactor, followed by addition of chloroform (5L, 2V). The resulting mixture was stirred for 2 hours at 50° C. (solid was partially dissolved in chloroform), cooled to 0° C., and was allowed to stand for 2 hours. Solid was collected by filtration, and washed with cooled chloroform (500 mL, 0.2V). The recrystallization procedure was repeated 4 times to afford 1.09 kg (97% ee) of the title compound as a white solid with an overall yield of 31% (2 steps).

Intermediate 169: pentan-3-yl (R)-2-bromo-2-fluoroacetate

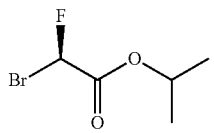

To a 2 L reactor at room temperature was charged (S)-1-phenylethanamine (R)-2-bromo-2-fluoroacetate (Intermediate 168, 450 g), dichloromethane (900 mL, 2V) and iPrOH (2.0 eq.). Chlorotrimethylsilane (1.12 L) was added slowly, and a white precipitate was formed. The resulting mixture was stirred at room temperature overnight. White precipitate was filtered off, and the filter cake was washed with hexane (450 mL, 1V). The combined filtrate was washed with water (3×100 mL). Organic solution was dried with anhydrous sodium sulfate, filtered, concentrated under vacuum. Residue was distilled (54-60° C., 100 Pa) to give the title compound as a colorless oil (290 g, 79% yield, 95% purity).

$^1$H NMR (CDCl$_3$, 400 MHz): δ 6.53 (d, J=51.2 Hz, 1H), 5.17 (m, 1H), 1.32 (m, 6H).

Intermediate 170: ethyl (R)-2-bromo-2-fluoroacetate

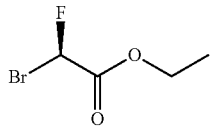

Into a 50 mL 3-necked round-bottom flask, purged and maintained with an inert atmosphere of nitrogen, was placed (1R)-1-phenylethan-1-amine; (2S)-2-bromo-2-fluoroacetic acid (Intermediate 168, 30 g, 107.9 mmol) and ethanol (34.7 g, 755.3 mmol). This was followed by the addition of chlorotrimethylsilane (82 g, 755.3 mmol) dropwise with stirring at room temperature. The resulting solution was stirred for 4 h at room temperature, then quenched by the addition of 10 mL of water/ice. The resulting solution was extracted with 3×20 mL of petroleum ether (30-60 degree) and the organic layers combined. The resulting mixture was washed with 2×20 mL of brine. The mixture was dried over anhydrous sodium sulfate, filtered and concentrated. The residue was applied onto a silica gel column with petroleum ether (30-60 degree). This resulted in 10 g (50%) of the title compound as a colorless oil.

1H NMR (300 MHz, CDCl$_3$): δ 6.58 (d, 1H, J=51 Hz), 4.38 (q, 2H, J=6 Hz), 1.38 (t, 3H, J=6 Hz).

Intermediate 171: (R)-benzyl 2-bromo-2-fluoroacetate

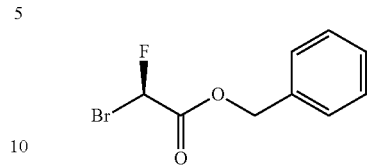

Chlorotrimethylsilane (60 mL, 719.12 mmol) was added portionwise to (S)-1-phenylethanamine (R)-2-bromo-2-fluoroacetate (Intermediate 168, 20 g, 71.91 mmol) and phenylmethanol (60 mL, 71.91 mmol) at 25° C. over a period of 3 minutes under nitrogen. The resulting solution was stirred at 25° C. for 4 hours. The reaction mixture was diluted with heptane (500 mL), then washed with water and brine. The organics were dried over sodium sulfate, filtered and concentrated. Silica gel chromatography (0% to 10% ethyl acetate/petroleum ether) afforded the title compound as a yellow oil, 17.5 g, 98%.

$^1$H NMR (300 MHz, CDCl$_3$-d, 30° C.) δ: 5.30 (s, 2H); 6.60 (d, 1H); 7.40 (m, 5H).

Intermediate 172: (1R)-1-phenylethan-1-amine; (2S)-2-bromo-2-fluoroacetic acid

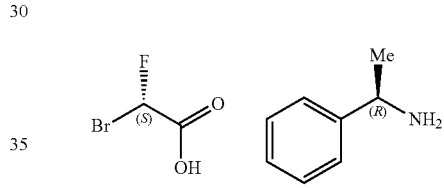

Into a 100-mL round-bottom flask was placed a solution of (1R)-1-phenylethan-1-amine (107.7 g, 0.89 mol) in methanol (325 mL). This was followed by the addition of a solution of 2-bromo-2-fluoroacetic acid (Intermediate 167, 140 g, 0.89 mol) in methanol (420 mL) dropwise with stirring at 0° C. over 30 min. The resulting solution was stirred overnight at room temperature, then concentrated under vacuum. The residue was diluted with CHCl$_3$ (3V). The solids were collected by filtration. The solid was dried under vacuum, then suspended in CHCl$_3$ and heated to 60° C. for 2 hours. The mixture was then was cooled to 0° C. and the solid was filtered. The process was repeated 6 times. This resulted in 80 g (32%) of title compound as a white solid.

$^1$H NMR (300 MHz, d6-DMSO): δ 8.56 (brs, 3H), 7.49-7.46 (m, 2H), 7.42-7.38 (m, 2H), 7.36-7.34 (m, 1H), 6.48 (d, 1H, J=56 Hz), 4.39-4.34 (m, 1H), 1.48 (d, 3H, J=6.8 Hz).

Intermediate 173: (S)-isopropyl 2-bromo-2-fluoroacetate

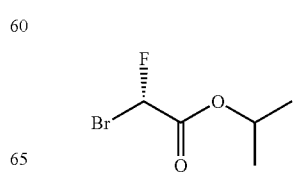

Into a 250-mL 3-necked round-bottom flask, purged and maintained with an inert atmosphere of nitrogen, was placed (R)-1-phenylethanamine (S)-2-bromo-2-fluoroacetate (Intermediate 172, 32.0 g, 116 mmol), and isopropanol (13.9 g, 232 mmol) in DCM (64 mL). This was followed by the dropwise addition of chlorotrimethylsilane (56.4 g, 519 mmol) with stirring at room temperature. The resulting solution was stirred overnight at room temperature, then quenched by the addition of 100 mL of water/ice. The resulting solution was extracted with 3×100 mL of petroleum ether (30-60 degree), and the organic layers combined. The resulting mixture was washed with 3×70 mL of brine. The mixture was dried over anhydrous sodium sulfate and concentrated. The residue was applied onto a silica gel column with petroleum ether (30-60 degree). This resulted in 19 g (83%) of title compound as colorless oil.

$^1$H NMR (CDCl$_3$, 400 MHz): δ 6.53 (d, J=50.8 Hz, 1H), 5.17 (m, 1H), 1.32 (m, 6H).

Intermediate 174: ethyl (2S)-2-bromo-2-fluoroacetate

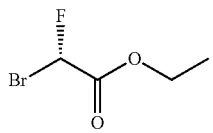

Into a 50 mL 3-necked round-bottom flask, purged and maintained with an inert atmosphere of nitrogen, was placed (1R)-1-phenylethan-1-amine (2S)-2-bromo-2-fluoroacetic acid (Intermediate 172, 20 g, 72 mmol) and ethanol (23.2 g, 504 mmol). This was followed by the dropwise addition of chlorotrimethylsilane (54.8 g, 504 mmol) with stirring at room temperature. The resulting solution was stirred for 4 h at room temperature, then quenched by the addition of 10 mL of water/ice. The resulting solution was extracted with 3×20 mL of petroleum ether (30-60 degree) and the organic layers combined. The resulting mixture was washed with 2×20 mL of brine. The mixture was dried over anhydrous sodium sulfate, filtered and concentrated. The residue was applied onto a silica gel column with petroleum ether (30-60 degree). This resulted in 6 g (45%) of title compound as colorless oil.

$^1$H NMR (300 MHz, d6-DMSO): δ 6.57 (d, 1H, J=56 Hz), 4.37 (q, J=7.2 Hz, 2H), 1.33 (t, 3H, J=7.2 Hz).

Intermediate 175: (E)-but-2-enylboronic acid

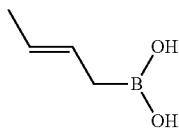

To a solution of (E)-but-2-en-1-ol (59.5 g, 826 mmol) in MeOH (360 mL) at room temperature was added H$_2$PdCl$_4$ (2.06 g, 8.34 mmol), then to the mixture was added B$_2$(OH)$_4$ (81.8 g, 919 mmol) by portion at 30-40° C. The resulting solution was stirred at 30-40° C. for 20 minutes, then filtered through celite.

$^1$H-NMR (DMSO-d$_6$, 400 MHz): δ 5.39-5.49 (m, 1H), 5.16-5.26 (m, 1H), 3.38 (s, 2H), 1.38-1.58 (m, 5H)

Intermediate 176: (S,E)-2-(tert-butylsulfinylimino)acetic acid

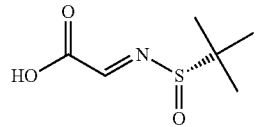

To molecular sieves type 4 Å (500 g) in DCM (600 mL) at room temperature was added (S)-2-methylpropane-2-sulfinamide (100 g, 819 mmol) and 2-oxoacetic acid hydrate (91.2 g, 991 mmol). The resulting solution was stirred at room temperature for overnight, then filtered through celite.

$^1$H-NMR (DMSO-d$_6$, 400 MHz): δ 7.77 (s, 1H), 5.74 (s, 1H), 1.13 (s, 9H)

Intermediate 177: (2S,3R)-2-((S)-1,1-dimethylethylsulfinamido)-3-methylpent-4-enoic acid

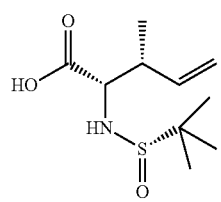

To a solution of the crude product (S,E)-2-(tert-butylsulfinylimino)acetic acid (Intermediate 176) in DCM (600 mL) at 0-15° C. was added dropwise a solution of the (E)-but-2-enylboronic acid (Intermediate 175) in MeOH (360 mL). The resulting solution was stirred at 0-15° C. for 1 hour. The molecular sieves were removed through filtration, and washed with DCM. The filtrate was removed by distillation under vacuum to get crude product. To the crude product was added H$_2$O (600 mL), petroleum ether (240 mL) and methyl tert-butyl ether (120 mL), stirred at room temperature for 1 hour, then filtered and collected the solid and dried under vacuum at 25° C. to afford the product (110 g, 58%) as a white solid. $^1$H-NMR (DMSO-d$_6$, 400 MHz): δ 5.71-5.80 (m, 1H), 5.01-5.07 (m, 2H), 4.94 (d, J=8 Hz, 1H), 3.58-3.62 (m, 1H), 2.56-2.61 (m, 1H), 1.15 (s, 9H), 0.975 (d, J=4 Hz, 3H)

Intermediate 178: (2S,3R)-methyl 2-amino-3-methylpent-4-enoate

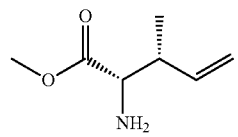

To a solution of (2S,3R)-2-((S)-1,1-dimethylethylsulfinamido)-3-methylpent-4-enoic acid (Intermediate 177, 44 g, 189 mmol) in MeOH (200 mL) was added dropwised SOCl$_2$ (68.6 mL, 944 mmol) at 0° C. The reaction mixture was stirred at 0° C. for 1 hour, then warmed up to 70° C. and stirred overnight. The solvent was removed and the residue diluted with water. To the water phase was added NaHCO$_3$ to neutralize pH to ~8, and extracted with DCM, dried over Na$_2$SO$_4$, filtered and concentrated to give 23 g crude product as a yellow liquid.

$^1$H-NMR (DMSO-d$_6$, 400 MHz): δ 5.71-5.82 (m, 1H), 4.97-5.05 (m, 2H), 3.61 (s, 3H), 3.27 (d, J=8 Hz, 1H), 2.33-2.45 (m, 1H), 1.79 (s, 2H), 0.96 (d, J=8 Hz, 3H)

LCMS: tR=0.682, [M+H]$^+$144.2

Intermediate 179: (2S,3R)-methyl 2-(allylamino)-3-methylpent-4-enoate

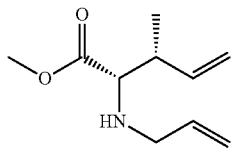

To a solution of (2S,3R)-methyl 2-amino-3-methylpent-4-enoate (Intermediate 178, 23 g, 161 mmol) in DMF (90 mL) at 0° C. was added LiOH (4.248 g, 177 mmol). The mixture was stirred at 0° C. for 30 minutes. Then a solution of 4-bromobut-1-ene (17.5 g, 145 mmol) in DMF (15 mL) was added dropwised. The reaction was stirred at −7° C. for 20 mins, then warmed to room temperature slowly, and stirred overnight. The reaction was quenched with water, extracted with EtOAc. The organic layer was washed with water, brine, dried over Na$_2$SO$_4$, filtered and concentrated to give 28 g crude product as yellow liquid.

$^1$H-NMR (DMSO-d$_6$, 400 MHz): δ 5.65-5.83 (m, 2H), 4.93-5.16 (m, 4H), 3.60 (s, 3H), 3.14-3.22 (m, 1H), 3.06 (d, J=8 Hz, 1H), 2.93-3.01 (m, 1H), 2.34-2.41 (m, 1H), 0.99 (d, J=8 Hz, 3H)

LCMS: tR=0.461, m/z: 184[M+H]

Intermediate 180: (2S,3R)-methyl 2-(allyl(tert-butoxycarbonyl)amino)-3-methylpent-4-enoate

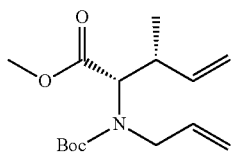 [SMILES: C=CCN(C(=O)OC(C)(C)C)[C@H](C(=O)OC)[C@H](C)C=C]

To a solution of (2S,3R)-methyl 2-(allylamino)-3-methylpent-4-enoate (Intermediate 179, 28 g, 153 mmol) in t-BuOH (150 mL) was added (Boc)$_2$O (33.4 g, 153 mmol). The reaction was stirred at room temperature for 10 minutes, then warmed up to 90° C. and stirred overnight. The reaction mixture was concentrated. The crude product was purified by flash silica chromatography, elution gradient 0 to 6% EtOAc in petroleum ether. Pure fractions were evaporated to afford the product (24 g, 56%) as a light yellow liquid.

$^1$H-NMR (DMSO-d$_6$, 400 MHz): δ 5.71-5.84 (m, 2H), 5.00-5.11 (m, 4H), 3.66-4.43 (m, 3H), 3.58 (s, 3H), 2.81 (s, 1H), 1.39 (s, 9H), 0.93 (d, J=8 Hz, 3H)

LCMS: tR=1.096, 184[M-Boc+H]

Intermediate 181: (2S,3R)-1-tert-butyl 2-methyl 3-methyl-2,3-dihydropyridine-1,2(6H)-dicarboxylate

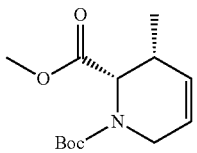 [SMILES: COC(=O)[C@@H]1[C@H](C)C=CCN1C(=O)OC(C)(C)C]

To a solution of (2S,3R)-methyl 2-(allyl(tert-butoxycarbonyl)amino)-3-methylpent-4-enoate (Intermediate 180, 24 g, 84.8 mmol) in DCM (250 mL) was added Grubbs catalyst, 1$^{st}$ generation (886 mg 1.06 mmol) at 0° C. in three batches and stirred for 4 hours. More Grubbs catalyst, 1$^{st}$ generation was added (886 mg 1.06 mmol) at 0° C. in three batches, then warmed up to 25° C. The resulting solution was stirred at room temperature overnight.

LCMS: tR=0.987, 156.2 [M-Boc+H], 295[M+K]

Intermediate 182: (2S,5R)-1-tert-butyl 2-methyl 5-(tert-butoxycarbonyl(hydroxy)amino)-3-methyl-5,6-dihydropyridine-1,2(2H)-dicarboxylate

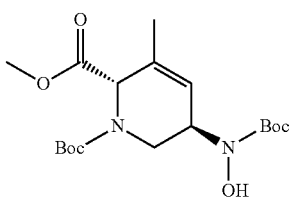 [SMILES: COC(=O)[C@@H]1C(C)=C[C@@H](N(O)C(=O)OC(C)(C)C)CN1C(=O)OC(C)(C)C]

To a solution of (2S,3R)-1-tert-butyl 2-methyl 3-methyl-2,3-dihydropyridine-1,2(6H)-dicarboxylate (Intermediate 181, 21.6 g, 84.8 mmol) in DCM (250 mL) was added BocNHOH (16.9 g, 127 mmol), CuCl (0.419 g, 4.24 mmol) and pyridine (87 mg, 1.1 mmol) and degassed with oxygen. The resulting solution was stirred at room temperature for 44 hours under oxygen. The solid was removed by filtration. The filtrate was washed with water (3×200 mL) and brine, dried over Na$_2$SO$_4$, filtered and concentrated. The crude product was purified by flash silica chromatography, eluting with 0 to 50% DCM in petroleum ether to give the product (29 g, 88%) as brown oil.

$^1$H-NMR (CDCl$_3$, 400 MHz): δ 5.66 (d, J=16 Hz, 1H), 5.31 (s, 1H), 4.90 (d, 1H), 4.51 (d, 1H), 4.11 (t, J=20 Hz, 1H), 3.75 (s, 3H), 3.50-3.61 (m, 1H), 1.90 (d, J=8 Hz, 3H), 1.43-1.51 (m, 18H)

LCMS: tR=0.713, 279 [M-Boc+Na]

Intermediate 183: (2S,5R)-1-tert-butyl 2-methyl 5-(tert-butoxycarbonyl(tert-butyldimethylsilyloxy) amino)-3-methyl-5,6-dihydropyridine-1,2(2H)-dicarboxylate

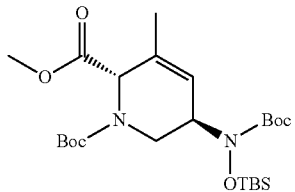 [SMILES: COC(=O)[C@@H]1C(C)=C[C@@H](N(O[Si](C)(C)C(C)(C)C)C(=O)OC(C)(C)C)CN1C(=O)OC(C)(C)C]

To a solution of (2S,5R)-1-tert-butyl 2-methyl 5-(tert-butoxycarbonyl(hydroxy)amino)-3-methyl-5,6-dihydropyridine-1,2(2H)-dicarboxylate (Intermediate 182, 23 g 59.5 mmol) in DCM (180 mL) was added imidazole (8.09 g, 119 mmol). The resulting solution was stirred at room temperature for 10 minutes, then a solution of TBS-Cl (11.6 g, 77.4 mmol) in DCM (20 mL) was added dropwise at 0-5° C. The reaction was stirred at 0° C. for additional 18 hours. The organic phase was washed with water and brine, dried over Na$_2$SO$_4$, filtered and concentrated. The crude product was purified by flash silica chromatography, eluting with petroleum ether and DCM to give product (20 g, 67%) as a brown oil.

$^1$H-NMR(CDCl$_3$, 400 MHz): δ 5.7 (s, 1H), 4.45-4.85 (m, 2H), 4.09 (d, J=20 Hz, 1H), 3.76 (s, 3H), 3.53-3.58 (m, 1H), 1.9 (s, 3H), 1.45-1.54 (m, 18H), 0.92 (d, J=16 Hz, 9H), 0.10 (d, J=20 Hz, 6H).

LCMS: tR=1.467, 523.55[M+Na]

Intermediate 184: (2S,5R)-methyl 5-(tert-butyldimethylsilyloxyamino)-3-methyl-1,2,5,6-tetrahydropyridine-2-carboxylate

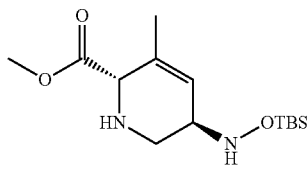 [SMILES: COC(=O)[C@H]1NC[C@H](NO[Si](C)(C)C(C)(C)C)C=C1C]

To a solution of (2S,5R)-1-tert-butyl 2-methyl 5-(tert-butoxycarbonyl(tert-butyldimethylsilyloxy)amino)-3-methyl-5,6-dihydropyridine-1,2(2H)-dicarboxylate (Intermediate 183, 20 g, 40 mmol) in DCM (200 mL) was added ZnBr$_2$ (35.5 g 160 mmol) at 0° C. The resulting solution was stirred at room temperature overnight. The solid was removed through filtration. The filtrate was washed with saturated NaHCO$_3$ to neutralize pH to ~8, extracted with DCM, dried over Na$_2$SO$_4$, filtered and concentrated. The crude product was purified by flash silica chromatography, eluting with 0 to 1% MeOH in DCM to give product (8.4 g, 70%) as a brown oil.

$^1$H-NMR (CDCl$_3$, 400 MHz): δ 5.59-5.62 (m, 1H), 3.82 (s, 1H), 3.75 (s, 3H), 3.14-3.23 (m, 2H), 2.92-2.97 (m, 1H), 1.79 (s, 3H), 0.90 (s, 9H), 0.10 (s, 6H).

LCMS: tR=1.073, 301.2[M+H]

Intermediate 185: methyl (2S,5R)-6-[tert-butyl(dimethyl)silyl]oxy-3-methyl-7-oxo-1,6-diazabicyclo[3.2.1]oct-3-ene-2-carboxylate

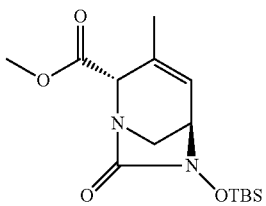 [SMILES: COC(=O)[C@@H]1C(C)=C[C@@H]2CN1C(=O)N2O[Si](C)(C)C(C)(C)C]

To a solution of (2S,5R)-methyl 5-(tert-butyldimethylsilyloxyamino)-3-methyl-1,2,5,6-tetrahydropyridine-2-carboxylate (Intermediate 184, 42 g, 140 mmol) in MeCN (840 mL) was added DIEA (72.2 g 560 mmol) and degassed with nitrogen, then a solution of triphosgene (16.408 g, 56 mmol) in MeCN (120 mL) was added dropwised at 0±5° C. under nitrogen. The resulting solution was stirred at room temperature under nitrogen overnight. The reaction mixture was concentrated, then added EtOAc and washed with 1N citric acid, saturated NaHCO$_3$ and brine, dried over Na$_2$SO$_4$, filtered and concentrated. The crude product was purified by flash C-18 chromatography, eluting with 0 to 38% MeCN in H$_2$O to give product (22 g, 49%) as an orange solid.

$^1$H-NMR (CDCl$_3$, 400 MHz): δ 6.15 (t, J=1.6 Hz, 1H), 4.412 (s, 1H), 3.807 (s, 3H), 3.610-3.629 (m, 1H), 3.506 (d, J=11 Hz, 1H), 3.290-3.322 (m, 1H), 1.722 (s, 3H), 0.962 (s, 9H), 0.195 (s, 3H), 0.172 (s, 3H)

LCMS: tR=1.585, 327.35[M+H]

Intermediate 186: (2S,3R)-2-amino-3-methylpent-4-enamide hydrochloride

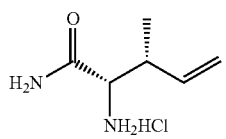

To a solution of (Intermediate 177, 75.2 kg, 322.8 mol, 1.0 eq.) in THF (600 L) was added CDI (61.9 kg, 382.1 mol, 1.2 eq.) in batches at 20±10° C. The mixture was stirred for 2 h at 20±10° C. The mixture was cooled to −40±5° C. NH$_3$ H$_2$O (43.55 kg, 640.4 mol, 2.0 eq., 25 wt. %) was added dropwise at −40±5° C. The mixture was stirred for 10 min at −40±5° C. After completion of the reaction, it was warmed to −10~0° C., then concentrated under vacuum to ~3.0 vol. THF (2.0 vol) was added and concentrated under vacuum to ~3.0 vol. THF was swapped with EtOAc (2.0 vol) two times. EtOAc (6.0 vol) was added to the solution, and cooled to 5±5° C. MeSO$_3$H (148.3 kg, 1543.0 mol, 2.4 eq.) was added dropwise at <10° C., and stirred for 1 h at 5±5° C. The mixture was centrifuged, and the resultant solid cake was washed with EtOAc (1.0 vol) two times. The mother liquor was collected to afford the compound in EtOAc solution, which was used directly in the next step. HCl (gas) was bubbled into the solution at 0±5° C. for 17 h (~4 kg/h). After completion of the reaction, the mixture was centrifuged and the resultant solid cake was washed with EtOAc (1.0 vol) two times. The cake was dried over under vacuum at 25±5° C. for at least 12 h to afford the title compound as a light yellow solid (98 kg, 90% overall yield from 2 steps).

¹H NMR (400 MHz, DMSO): δ 8.24 (s, 2H), 8.00 (s, 1H), 7.56 (s, 1H), 5.84-5.76 (m, 1H), 5.17-5.09 (m, 2H), 3.70-3.68 (m, 1H), 2.77-2.72 (m, 1H), 1.04 (d, J=6.8 Hz, 3H).

Intermediates 187 and 188: allyl((2S,3R)-1-amino-3-methyl-1-oxopent-4-en-2-yl) and tert-butyl allyl ((2S,3R)-1-amino-3-methyl-1-oxopent-4-en-2-yl) carbamate

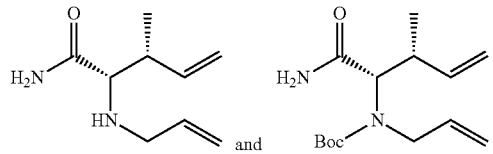 [SMILES: C=CCN[C@H](C(N)=O)[C@H](C)C=C ; C=CCN(C(=O)OC(C)(C)C)[C@H](C(N)=O)[C@H](C)C=C]

To a solution of LiOH (27.55 kg, 1147.9 mol, 2.0 eq.) in DMF (285 L) was added Intermediate 186 (95 kg, 564.67 mol, 1.0 eq.) in batches at 0±5° C. The mixture was stirred for 0.5 h. Allyl bromide (76.76 kg, 634.5 mol, 1.1 eq.) was added dropwise for 9 h at 0±5° C.

The reaction mixture was warmed to 20±5° C. and stirred for at least 8 h. The reaction mixture was cooled to 10±5° C. and soft water was added (3.0 vol). The mixture was extracted with DCM (3.0 vol) three times. The combined organics were washed with brine (2.0 vol). The brine layer was extracted with DCM (3.0 vol). The combined organic layers were concentrated under atmospheric pressure at <60° C. to ~5.0 vol. t-Butyl alcohol (2.0 vol) was added to the solution and concentrated under vacuum at <60° C. to ~5.0 vol. The concentration with t-butyl alcohol (2.0 vol) was repeated once more until the water content ≤0.2% to afford Intermediate 187. t-Butyl alcohol (8.0 vol) was added to the concentrated solution. Boc₂O (138.07 kg, 633.3 mol, 1.1 eq.) was added at 20±5° C. The mixture was warmed to 70±5° C. and stirred for at least 15 h. After completion of the reaction, the mixture was cooled to 40±5° C., then concentrated under vacuum at <60° C. to ~5 vol. The concentrated mixture was cooled to 25±5° C., and soft water (5.0 vol) was added. The mixture was extracted with methyl t-butyl ether (4.0 vol) two times. The combined organics were washed with 0.5 M HCl solution (2.0 vol) once, brine (1.0 vol) three times and concentrated under vacuum at <50° C. to ~2.0 vol. n-Heptane (1.0 vol) was added to the reactor and concentrate under vacuum at <50° C. to ~2.0 vol. This was repeated once more. n-Heptane (1.0 vol) was added to the concentrated solution, cooled to −10±5° C. and stirred for at least 2 h. The mixture was centrifuged and the resultant solid cake washed with cooled n-heptane (0.5 vol). The cake was dried at 25±5° C. under vacuum for at least 12 h to afford Intermediate 188 as a white solid (84.2 kg, 100% purity, 54.4% overall yield from 2 steps).

¹H NMR (400 MHz, DMSO): δ 7.42 (s, 1H), 6.95 (s, 1H), 5.78-5.70 (m, 2H), 5.11-4.98 (m, 4H), 4.33 (d, J=10.8 Hz, 1H), 3.92-3.78 (m, 2H), 2.70 (br, 1H), 1.41 (s, 9H), 0.88 (d, J=6.4 Hz, 3H). LC/MS (ES⁺) m/z 169.2 (M+H)

Intermediates 189: (2S,5R)-tert-butyl 5-(tert-butoxycarbonyl(hydroxy)amino)-2-carbamoyl-3-methyl-5,6-dihydropyridine-1(2H)-carboxylate

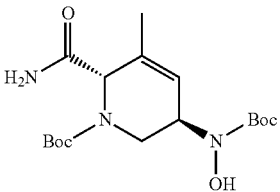 [SMILES: CC1=C[C@@H](N(O)C(=O)OC(C)(C)C)CN(C(=O)OC(C)(C)C)[C@@H]1C(N)=O]

To a solution of Intermediate 188 (81.0 kg, 301.8 mol, 1.0 eq.) in DCM (810 L) was added Grubb's catalyst, 1ˢᵗ generation (1.215 kg, 1.5 mol, 0.005 eq.) in 3 batches at 0±5° C. The reaction mixture was stirred for 1 h at 0±5° C., then warmed to 25±5° C. and stirred for 1 h. The mixture was cooled to 0±5° C. and more catalyst (1.215 kg, 1.5 mol, 0.005 eq.) was added in 3 batches at 0±5° C. The mixture was warmed to 25±5° C. and stirred for at least 8 h.

After completion of the reaction, CuCl (1.46 kg, 14.8 mol, 0.05 eq.), BocNHOH (59.94 kg, 450.7 mol, 1.5 eq.) and pyridine (0.31 kg, 3.9 mol, 0.013 eq.) were added to the solution at 25±5° C. The mixture was stirred for at least 43 h at 25±5° C. under oxygen atmosphere. Once the reaction was complete, EDTA₂Na solution (5.0 vol) was added to the reactor and stirred for at least 4 h at 25±5° C. The layers were separated and the aqueous extracted with DCM (3.0 vol) two times. The organics were combined and concentrate under vacuum at <40° C. to ~3.0 vol. Methyl t-butyl ether (MTBE) (2.0 vol) was added to the reactor and concentrated under vacuum at <40° C. to ~3.0 vol. This was repeated once more. MTBE (2.5 vol), n-heptane (2.5 vol) and soft water (5.0 vol) were added to the concentrated solution and the mixture was slurried at 20±5° C. for at least 2 h. The mixture was centrifuged and the cake was washed with MTBE/n-heptane (0.5 vol, 1:1). The cake was dried under vacuum at 35±5° C. for at least 12 h until the water content ≤1% to afford the title compound as a light-brown solid (70.3 kg, 98% purity, 61.3% overall yield from 2 steps).

¹H NMR (400 MHz, DMSO): δ 8.93-8.78 (m, 1H), 7.49 (s, 1H), 7.07 (s, 1H), 5.57 (s, 1H), 4.62-4.41 (m, 2H), 3.76-3.50 (m, 2H), 1.79 (s, 3H), 1.43 (s, 1H), 1.40 (s, 9H). LC/MS (ES⁺) m/z 272.2 (M+H)

Intermediates 190 and 191: tert-butyl (3R,6S)-3-((tert-butoxycarbonyl)((tert-butyldimethylsilyl)oxy)amino)-6-carbamoyl-5-methyl-3,6-dihydropyridine-1(2H)-carboxylate and (2S,5R)-5-(tert-butyldimethylsilyloxyamino)-3-methyl-1,2,5,6-tetrahydropyridine-2-carboxamide

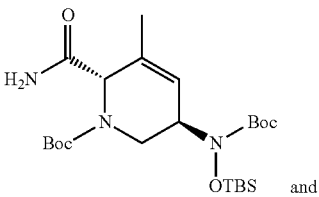

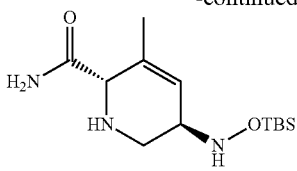

To a solution of Intermediate 189 (50 kg, 134.6 mol, 1.0 eq.) and imidazole (18.5 kg, 268.1 mol, 2.0 eq.) in DCM (500 L) was added TBS-Cl (30.5 kg, 202.0 mol, 1.5 eq.) in DCM solution (1.5 vol) dropwise at 0±5° C. over 4.5 h. The mixture was warmed to 20±5° C. and stirred for at least 5 h. After completion of the reaction, soft water (250 L, 5.0 vol) was added. The layers were separated and the aqueous extracted with DCM (3.0 vol). The combined organic layers were washed with soft water (3.0 vol) two times, then concentrated under atmospheric distillation at <50° C. to ~2.0 vol. DCM (200 L, 4.0 vol) was added to the solution and concentrated under atmospheric distillation at <50° C. to ~2.0 vol, until the water content was ≤1%, affording Intermediate 190. DCM (750 L, 15.0 vol) was added to the solution with stirring at 20±5° C. under nitrogen atmosphere. ZnBr₂ (60.5 kg, 268.9 mol, 2.0 eq.) was added to the solution and stirred for 6 h at 20±5° C. More ZnBr₂ (30.5 kg, 135.6 mol, 1.0 eq.) was added to the reaction mixture ever 6-8 hours until the reaction was complete (~5 eq total of ZnBr₂). The reaction was quenched with NaHCO₃ (113.0 kg, 1345.2 mol, 10.0 eq.) solution (18.0 vol) by addition below 20° C. The mixture was stirred for at least 1 hour at 20±5° C., then centrifuged, and the liquor collected. The resultant solid cake was slurried with dichloromethane (5.0 vol) at 20±5° C. for 1 h, then centrifuged. The liquor was combined with the previous liquor and the layers separated. The aqueous was extracted with DCM (3.0 vol) two times. The combined organics were washed with soft water (4.0 vol) four times, then concentrated the under normal pressure at <50° C. to ~2.0 vol. CH₃CN (2.0 vol) was added to the solution and concentrate under vacuum at <50° C. to ~4.0 vol to afford Intermediate 191 in solution.

LC/MS: (ES⁺) m/z 282.2 (M+H)

Intermediate 192: (2S,5R)-6-(tert-butyldimethylsilyloxy)-3-methyl-7-oxo-1,6-diazabicyclo[3.2.1]oct-3-ene-2-carboxamide

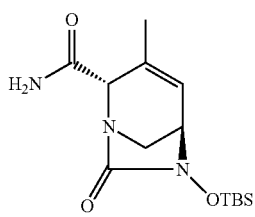 [SMILES: CC1=C[C@@H]2CN(C(=O)N2O[Si](C)(C)C(C)(C)C)[C@@H]1C(N)=O]

To a solution of Intermediate 191 (38.43 kg in theory, 134.6 mol, 1.0 eq.) in CH₃CN (1036 L, 27 vol) was added DIEA (69.56 kg, 539.2 mol, 4.0 eq.) at 20±5° C. The mixture was cooled to 0±5° C., and triphosgene (13.07 kg, 44.0 mol, 0.33 eq.) in CH₃CN (115.2 L, 3.0 vol) was added dropwise. The mixture was warmed to 25±5° C. and stirred for at least 8 h, then cooled to 10±5° C., and quenched with soft water (24.19 kg, 1343.9 mol, 10.0 eq.). The mixture was stirred for at least 1 h, then concentrated under vacuum at <40° C. to ~5.0 vol. The solution was cooled to 10±5° C. and MTBE (384 L, 10 vol) and brine (4.0 vol) were added. The layers were separated, and the organics washed with brine (4.0 vol), and concentrated under vacuum at <40° C. to ~2.0 vol. The MTBE was swapped with n-heptane (1.0 vol) and the solid slurried for 1 h at 20±5° C. The mixture was centrifuged and the cake washed with n-heptane (0.5 vol) two times. The cake was slurried in MTBE (67.5 L) for at least 3 h at 20±5° C., then n-heptane (336 L) was added with stirring for at least 1 h. The mixture was centrifuged and the resultant solid cake washed with n-heptane (1.0 vol). The cake was dried under vacuum at 30±5° C. for 12 h to afford the title compound as a light-brown solid (21.1 kg, 99.6% purity, 49.6% overall yield from 3 steps).

¹H NMR (400 MHz, DMSO): δ 7.80 (s, 1H), 7.33 (s, 1H), 6.06 (t, J=2 Hz, 1H), 4.10 (s, 1H), 3.71-3.69 (m, 1H), 3.65 (d, J=10.8 Hz, 1H), 3.10 (dd, J=10.8 Hz, 2.0 Hz, 1H),1.63 (s, 3H), 0.92 (s, 9H), 0.14 (d, J=0.8 Hz, 1H). LC/MS (ES⁺) m/z 312.2 (M+H)

Intermediate 193: (2S,5R)-tert-butyl 5-(tert-butoxycarbonyl(hydroxy)amino)-2-carbamoyl-3-methyl-5,6-dihydropyridine-1(2H)-carboxylate

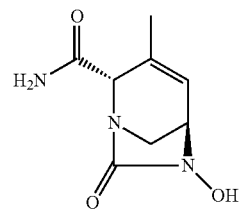

To a solution of Intermediate 192 (18.5 kg, 59.4 mol, 1.0 eq.) in EtOAc (92.5 L, 5 vol) was added HF Py (2.04 kg, 71.4 mol, 1.2 eq., 70 wt. %) at 0±5° C. The mixture was stirred for at least 10 h at 20±5° C., then cooled to 0±5° C. and additional HF Py (0.33 kg, 11.6 mol, 0.2 eq., 70 wt. %) was added. The mixture was stirred for at least 3 h at 20±5° C., then MTBE (27.8 L, 1.5 vol) was added and stirred for 3 h at 10±5° C. The mixture was centrifuged and the cake washed with EtOAc (0.5 vol). The cake was slurried with EtOAc (2.0 V) for at least 1 h at 20±5° C., then centrifuged. The cake was slurried with EtOAc (0.5 vol), then dried under vacuum at 25±5° C. for 12 h to afford the title compound as a yellow solid (11.0 kg, 99.5% purity, 91% yield).

¹H NMR (400 MHz, DMSO): δ 9.56 (s, 1H), 7.79 (s, 1H), 7.32 (s, 1H), 6.10 (d, J=3.2 Hz, 1H), 4.06 (s, 1H), 3.68-3.62 (m, 2H), 3.07 (d, J=8.4 Hz, 1H), 1.61 (s, 3H). LC/MS (ES⁺) m/z 198.1 (M+H)

Intermediate 194: ethyl (S,E)-2-((tert-butylsulfinyl)imino)acetate

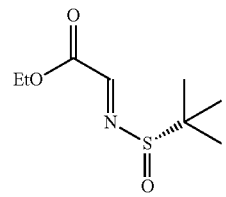

To a solution of ethyl 2-oxoacetate (66 mL, 321 mmol, 50% in toluene) in DCM (1 L) at 0° C. was added (S)-2-methylpropane-2-sulfinamide (30 g, 248 mmol) and molecular sieves (4 Å, 500 g). The resulting solution was stirred at room temperature for 18 hours. Molecular sieves were removed by filtration; filtrate was concentrated by distillation under vacuum to give a crude product, which was purified by flash silica chromatography (0% to 5% EtOAc in petroleum ether) to give a colorless oil, 45 g, 88%.

$^1$HNMR (400 MHz, CDCl3): δ1.28 (s, 9H), 1.39 (t, J=12 Hz, 3H), 4.38 (q, J=12 Hz, 2H), 8.01 (s, 1H).

Intermediate 195: ethyl (S)-1-((S)-tert-butylsulfinyl)-4-methyl-1,2,3,6-tetrahydropyridine-2-carboxylate

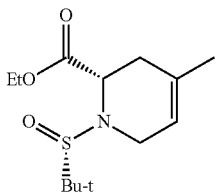

To a solution of (S,E)-ethyl 2-(tert-butylsulfinylimino)acetate (Intermediate 194, 50 g, 244 mmol) in DCM (600 mL), at −78° C. was added isoprene (97.21 mL, 971.91 mmol), followed by addition of TMSOTf (97.42 mL, 416.54 mmol). The resulting solution was stirred at −78° C. for 3 hours and quenched slowly at −78° C. with phosphate buffer solution (pH=7.4, 1 L). After warming to room temperature, the mixture was extracted with DCM (3×500 mL). The combined organic extracts were washed with water (2×500 mL) and brine. The organic layer was dried over Na$_2$SO$_4$, filtered and evaporated to afford 60 g of crude product as a brown oil. The product was used in the next step without further purification.

$^1$HNMR (400 MHz, d6-DMSO): δ1.08 (s, 9H), 1.18 (t, J=12 Hz, 3H), 1.64 (q, J=4 Hz, 3H), 3.59 (m, 2H), 4.11 (dq, J=12, 4 Hz, 2H), 4.30 (dd, J=8, 4 Hz, 1H), 5.39 (ddd, J=4, 8 4 Hz, 1H);

LCMS: (ES$^+$) [M+H]$^+$=274; HPLC tR=1.78 min.

Intermediate 196: 1-(tert-butyl) 2-ethyl (S)-4-methyl-3,6-dihydropyridine-1,2(2H)-dicarboxylate

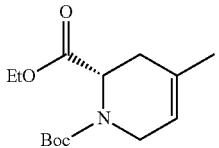

To a solution of the crude (S)-ethyl 1-((S)-tert-butylsulfinyl)-4-methyl-1,2,3,6-tetrahydropyridine-2-carboxylate (Intermediate 195, 100 g) in MeOH (1 L) at 0° C. was added hydrogen chloride (100 mL, 4M in dioxane). The resulting solution was stirred at room temperature for 18 hours. MeOH and HCl/dioxane were removed by distillation under vacuum to give a crude product, which was dissolved in water (1 L) and extracted with EtOAc (3×500 mL). The pH of the aqueous solution was adjusted to 7 with solid NaHCO$_3$.

The aqueous was extracted with EtOAc until LCMS showed no product detected. The organic phases were combined and dried over Na$_2$SO$_4$, filtered and concentrated to afford crude product (30 g, 177 mmol) as a light yellow oil. The oil was dissolved in THF (500 mL) and cooled by ice-water bath. To the cooled solution was added a solution of sodium bicarbonate (22.3 g, 265.5 mmol) in water (500 mL), followed by di-tert-butyl dicarbonate (57.8 g, 265.5 mmol). The resulting solution was stirred at room temperature for 18 hours. The two layers were separated. The aqueous layer was extracted with ethyl acetate. The combined organic layers were dried over Na$_2$SO$_4$, filtered and evaporated. Crude product was purified by flash silica chromatography (0%-30% EtOAc in PE) to afford the title compound 47.5 g, 43% yield from Intermediate 194.

$^1$HNMR (400 MHz, CDCl3): δ 1.24 (t, 3H), 1.50 (m, 9H), 1.71 (s, 3H), 2.46 (m, 2H), 3.73 (m, 1H), 4.10 (m, 3H), 4.95 (m, 1H);

LC-MS: (ES$^+$) [M+Na]$^+$=292; HPLC tR=1.71 min.

Intermediate 197: tert-butyl (S)-2-carbamoyl-4-methyl-3,6-dihydropyridine-1(2H)-carboxylate

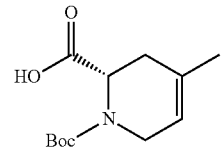

To a solution of 1-(tert-butyl) 2-ethyl (S)-4-methyl-3,6-dihydropyridine-1,2(2H)-dicarboxylate (Intermediate 196, 47.5 g, 176 mmol) in THF (1000 mL) and water (500 mL) at 0° C. was added dropwise lithium hydroxide (1 M, 440 mL, 440 mmol). The reaction mixture was warmed to room temperature and stirred for 16 hours. Solvent was removed; residue was diluted with water. The pH of the solution was adjusted to ~3 with HCl (1N) solution. The mixture was extracted with EtOAc (3×300 mL). Organic layers were combined, washed with water and brine, dried over MgSO$_4$, filtered and concentrated to give a colorless oil, 40.3 g.

$^1$HNMR (300 MHz, d6-DMSO): δ 1.38 (m, 9H), 1.64 (s, 3H), 2.53 (m, 2H), 3.68 (m, 3H), 4.73 (m, 1H), 5.35 (dd, J=3, 15 Hz, 1H), 12.45 (s, 1H);

LCMS: (ES$^+$) [M+Na]$^+$=264; HPLC tR=1.01 min.

Intermediate 198: tert-butyl (S)-2-carbamoyl-4-methyl-3,6-dihydropyridine-1(2H)-carboxylate

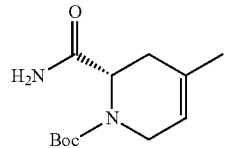

To a solution of (S)-1-(tert-butoxycarbonyl)-4-methyl-1,2,3,6-tetrahydropyridine-2-carboxylic acid (Intermediate 197, 40.3 g, 167.2 mmol) in THF (500 mL) at 0° C. was added N,N'-carbonyldiimidazole (32.5 g, 200.6 mmol) in portions. The crude was stirred at 0° C. for 5 hours. Then ammonium acetate (38.2 g, 502.9 mmol) was added. The reaction was stirred at room temperature for an additional 18 hours, quenched with water and extracted with EtOAc. The combined organic layers were washed with water and brine, dried over Na$_2$SO$_4$, filtered and concentrated. Crude product was purified by flash silica chromatography (0%-30% EtOAc in PE) to give a white solid, 25 g, 62%.

$^1$HNMR (400 MHz, d6-DMSO): δ 1.41 (s, 9H), 1.66 (s, 3H), 2.35 (s, 2H), 3.84 (m, 2H), 4.66 (m, 1H), 5.35 (m, 1H), 6.96 (s, 1H), 7.19 (s, 1H);

LCMS: (ES$^+$) [M+Na]$^+$=263; HPLC tR=0.86 min.

Intermediate 199: tert-butyl (3R,6S)-3-((tert-butoxycarbonyl)(hydroxy)amino)-6-carbamoyl-4-methyl-3,6-dihydropyridine-1(2H)-carboxylate

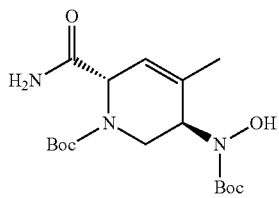 [SMILES: CC1=C[C@@H](C(N)=O)N(C(=O)OC(C)(C)C)C[C@@H]1N(O)C(=O)OC(C)(C)C]

To a solution of tert-butyl (S)-2-carbamoyl-4-methyl-3,6-dihydropyridine-1(2H)-carboxylate (Intermediate 198, 25 g, 104.1 mmol) in DCM (250 mL) was added BocNHOH (70.6 g, 530.9 mmol), CuCl (6.1 g, 62.5 mmol) and pyridine (106.9 mg, 1.3 mmol). The resulting solution was stirred at room temperature for 44 hours under oxygen. The solids were removed by filtration. The filtrate was washed with water (6×500 mL) and brine, dried over Na$_2$SO$_4$, filtered and concentrated. The crude product was purified by flash silica chromatography (0%-50% EtOAc in PE) to give the title compound as a white solid, 40% yield. Starting material was recovered (10 g). The same procedure was repeated three times to afford 15 g of product in total.

LCMS: (ES$^+$) [M+Na]$^+$=394 (C$_{17}$H$_{29}$N$_3$O$_6$)

Intermediate 200: tert-butyl (3R,6S)-3-((tert-butoxycarbonyl)((tert-butyldimethylsilyl)oxy)amino)-6-carbamoyl-4-methyl-3,6-dihydropyridine-1(2H)-carboxylate

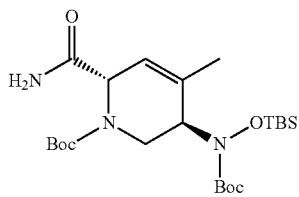 [SMILES: CC1=C[C@@H](C(N)=O)N(C(=O)OC(C)(C)C)C[C@@H]1N(O[Si](C)(C)C(C)(C)C)C(=O)OC(C)(C)C]

To a solution of tert-butyl (3R,6S)-3-((tert-butoxycarbonyl)(hydroxy)amino)-6-carbamoyl-4-methyl-3,6-dihydropyridine-1(2H)-carboxylate (Intermediate 199, 12 g, 32.3 mmol) in DCM (96 mL) at 0±5° C. was added imidazole (4.4 g, 64.6 mmol). The resulting solution was stirred at room temperature for 10 mins, then TBS-Cl (4.8 g, 32.3 mmol) in DCM (10 mL) was added dropwise. The reaction mixture was stirred at 0° C. for an additional 18 hours, washed with water and brine, dried over Na$_2$SO$_4$, filtered and concentrated. The crude product was purified by flash silica chromatography (0%-20% EtOAc in PE) to afford the title compound as a white solid, 10 g, 63%.

LCMS: (ES$^+$) 486 (C$_{23}$H$_{43}$N$_3$O$_6$Si)

Intermediate 201: (2S,5R)-5-(((tert-butyldimethylsilyl)oxy)amino)-4-methyl-1,2,5,6-tetrahydropyridine-2-carboxamide

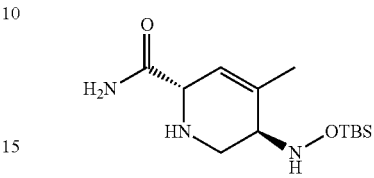

To a solution of tert-butyl (3R,6S)-3-[tert-butoxycarbonyl-tert-butyl(dimethyl)silyl]oxy-amino]-6-carbamoyl-4-methyl-3,6-dihydro-2H-pyridine-1-carboxylate (Intermediate 200, 21.7 g, 44.68 mmol) in DCM (250 mL) at 0° C. was added zinc bromide (40.24 g, 178.71 mmol). The resulting suspension was allowed to warm to room temperature and stir ~66 hours. The reaction mixture was cooled by ice-water bath, to which a slurry of NaHCO$_3$ (38.23 g, 10 equivalent) in water (300 mL) was added. The resulting mixture was stirred for 1 hr. Solid was removed by filtration and washed 3-4 times with DCM until no product was detected from the rinsing solution. The two layers from the filtrate were separated. The aqueous layer was extracted with DCM three times (until no product was detected from aqueous layer). The combined DCM solution was concentrated to remove most of the solvent. The residue was partially dissolved in 10% MeOH in DCM and was loaded onto a short silica gel pad and eluted with 10% MeOH in DCM. The filtrate was evaporated and dried under vacuum to give a yellow foam solid (crude 9.9 g, 77%).

MS: 286 ES+(C$_{13}$H$_{27}$N$_3$O$_2$Si)

Intermediate 202: (2S,5R)-6-((tert-butyldimethylsilyl)oxy)-4-methyl-7-oxo-1,6-diazabicyclo[3.2.1]oct-3-ene-2-carboxamide

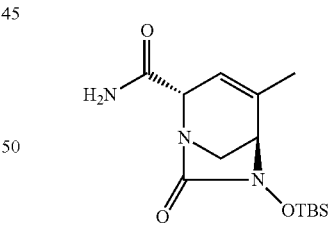

To a clear solution of (3R,6S)-3-[[tert-butyl(dimethyl)silyl]oxyamino]-4-methyl-1,2,3,6-tetrahydropyridine-6-carboxamide (Intermediate 201, 7.66 g, 26.83 mmol) in MeCN (150 mL) and DCM (200 mL) at 0° C. was added N,N'-diisopropylethylamine (19.11 mL, 107.34 mmol) followed by a solution of triphosgene (2.71 g, 9.12 mmol) in MeCN (50 mL) dropwise (2 mL/hour by a syringe pump). After addition, the solution was allowed to warm to room temperature and stirred overnight. The reaction mixture was concentrated to dryness. The resulting residue was diluted with EtOAc and washed with brine. The aqueous layer was extracted with EtOAc. The combined organic extracts were dried over MgSO$_4$, filtered and concentrated. Crude product was purified by silica gel chromatography (0%-100% EtOAc/hexane) to give the title compound as a white solid 4.36 g, 52%.

MS: 312 ES+($C_{14}H_{25}N_3O_3Si$)

Intermediate 203: (2S,5R)-6-hydroxy-4-methyl-7-oxo-1,6-diazabicyclo[3.2.1]oct-3-ene-2-carboxamide

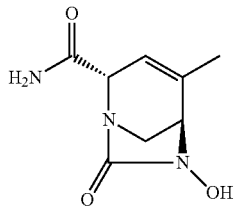

To a solution of (2S,5R)-5-(((tert-butyldimethylsilyl)oxy) amino)-4-methyl-1,2,5,6-tetrahydropyridine-2-carboxamide (Intermediate 202, 165.mg, 0.53 mmol) in ethyl acetate (4 mL) at 0° C. was added HF-pyridine (0.02 mL, 0.64 mmol). The reaction mixture was warmed to room temperature and stirred for 1 hr. Only a small amount of product was observed. Another equivalent of HF-pyridine was added and the reaction mixture was stirred for 3 hrs. The reaction mixture was concentrated to afford an orange solid.

MS: 198 ES+($C_8H_{11}N_3O_3$)

Example 35

(2R)-isopropyl 2-(((2S,5R)-2-carbamoyl-4-methyl-7-oxo-1,6-diazabicyclo[3.2.1]oct-3-en-6-yl)oxy)-2-fluoroacetate

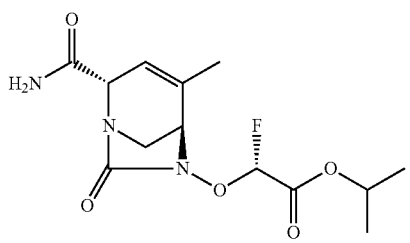 [SMILES: CC1=C[C@@H](C(N)=O)N2C[C@@H]1N(O[C@H](F)C(=O)OC(C)C)C2=O]

To a solution of (2S,5R)-6-hydroxy-4-methyl-7-oxo-1,6-diazabicyclo[3.2.1]oct-3-ene-2-carboxamide (Intermediate 203, 582 mg, 2.95 mmol) in 1,4-dioxane (16 mL) and DMF (2 mL) was added isopropyl (2R)-2-bromo-2-fluoro-acetate (Intermediate 169, 881.1 mg, 4.43 mmol). The reaction mixture was cooled to 0° C. and DBU (0.44 mL, 2.95 mmol) was added dropwise. The reaction mixture was stirred for 10 minutes, then diluted with ethyl acetate and washed with 1:1 brine water twice. The organics were dried over magnesium sulfate, filtered and concentrated. Silica gel chromatography (0%-90% ethyl acetate/hexanes) afforded a white foam. The foam was dissolved in 1:1 acetonitrile:water, frozen and lyophilized to afford a white solid, 614 mg, 66%. There is 6% of the S-diastereomer present.

MS: 316 ES+($C_{13}H_{18}FN_3O_5$)

$^1$H NMR (300 MHz, DMSO-$d_6$) δ: 1.22 (m, 6H); 1.81 (m, 3H); 3.17 (m, 1H); 3.34 (m, 1H); 3.93 (m, 1H); 4.22 (m, 1H); 5.01 (m, 2H); 5.51 (m, 1H); 6.23 (m, 1H); 7.31 (s, 1H); 7.55 (s, 1H).

Example 90 ethyl 2-(((2S,5R)-2-carbamoyl-4-methyl-7-oxo-1,6-diazabicyclo[3.2.1]oct-3-en-6-yl)oxy)-2,2-difluoro-acetate

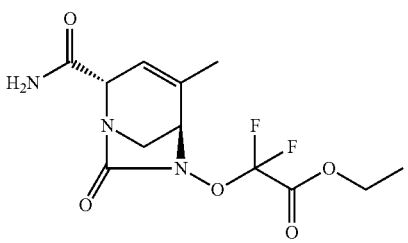 [SMILES: CCOC(=O)C(F)(F)ON1C(=O)N2C[C@H]1C(C)=C[C@H]2C(N)=O]

To a solution of (2S,5R)-6-hydroxy-4-methyl-7-oxo-1,6-diazabicyclo[3.2.1]oct-3-ene-2-carboxamide (Intermediate 203, 64.5 mg, 0.33 mmol) and ethyl bromodifluoroacetate (0.13 mL, 0.98 mmol) in DMF (3 mL) at room temperature was added potassium carbonate (135.62 mg, 0.98 mmol). The mixture was stirred for ~3 hours, then diluted with ethyl acetate and filtered. The filtrate was combined with a previous small batch, washed twice with 1:1 brine:water, dried over magnesium sulfate, filtered and concentrated. Silica gel chromatography (0%-80% ethyl acetate/hexanes) afforded the title compound (52.1 mg, 34%) as an orange solid after lyophilization.

MS: 320 ES+($C_{12}H_{15}F_2N_3O_5$)

$^1$H NMR (300 MHz, DMSO-$d_6$) δ: 1.29 (t, 3H); 1.82 (m, 3H); 3.36 (m, 2H); 3.94 (m, 1H); 4.31 (m, 1H); 4.39 (m, 2H); 5.57 (m, 1H); 7.36 (s, 1H); 7.59 (s, 1H).

Example 91

2-(((2S,5R)-2-carbamoyl-4-methyl-7-oxo-1,6-diazabicyclo[3.2.1]oct-3-en-6-yl)oxy)-2,2-difluoroacetic acid lithium salt

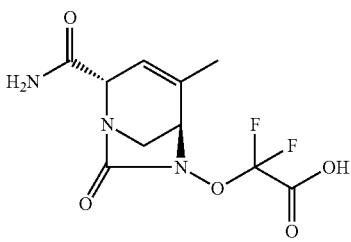 [SMILES: CC1=C[C@@H](C(N)=O)N2C[C@@H]1N(OC(F)(F)C(=O)O)C2=O]

To a solution of ethyl 2-(((2S,5R)-2-carbamoyl-4-methyl-7-oxo-1,6-diazabicyclo[3.2.1]oct-3-en-6-yl)oxy)-2,2-difluoroacetate (Example 90, 46 mg, 0.14 mmol) in THF (2 mL) and water (0.50 mL) at 0° C. was added 1M lithium hydroxide (0.14 mL, 0.14 mmol). The reaction mixture was stirred at 0° C. for 10 minutes. Another 0.2 eq. of lithium hydroxide was added, and after 5 minutes the reaction mixture was neutralized with 0.5N hydrochloric acid, and the THF evaporated. The resulting solution was frozen and lyophilized. Gilson purification (Synergi Polar RP 21.2 mm×100 mm, 4 μm coupled with YMC C30 20 mm×150 mm, 5 μm, 0%-16% acetonitrile/water, 6 min) afforded the title compound (27.2 mg, 64.8%) as an off-white solid.

MS: 292 ES+($C_{10}H_{11}F_2N_3O_5$)

$^1$H NMR (300 MHz, DMSO-$d_6$) δ: 1.81 (m, 3H); 3.30 (m, 2H); 3.84 (m, 1H); 4.20 (m, 1H); 5.48 (m, 1H); 7.29 (s, 1H); 7.55 (s, 1H).

Example 92 ethyl 2-(((2S,5R)-2-carbamoyl-4-methyl-7-oxo-1,6-diazabicyclo[3.2.1]oct-3-en-6-yl)oxy)acetate

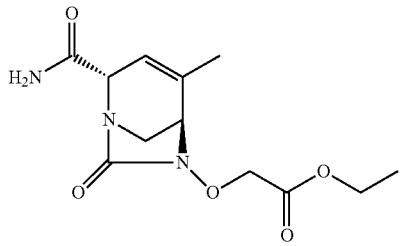

To a solution of (2S,5R)-6-((tert-butyldimethylsilyl)oxy)-4-methyl-7-oxo-1,6-diazabicyclo-[3.2.1]oct-3-ene-2-carboxamide (Intermediate 202, 152 mg, 0.49 mmol) in THF (4 mL) at 0° C. was added TBAF (0.49 mL, 0.49 mmol). The mixture was stirred for ~10 minutes. To the reaction mixture was added ethyl bromoacetate (0.05 mL, 0.49 mmol) and stirred for 10 minutes. More ethyl bromoacetate (0.05 mL, 0.49 mmol) was added and stirred 30 minutes. Additional ethyl bromoacetate (0.05 mL, 0.49 mmol) was added, and the reaction mixture was warmed to room temperature and stirred for 1 hour. The reaction mixture was concentrated onto silica gel and purified (0%-90% ethyl acetate/hexanes) to afford a colorless oil. The oil was dissolved in 1:1 acetonitrile:water, frozen and lyophilized to afford the title compound as a white solid, 78.5 mg, 56%.

MS: 284 ES+($C_{12}H_{17}N_3O_5$)

$^1$H NMR (300 MHz, DMSO-$d_6$) δ: 1.23 (t, 3H); 1.84 (m, 3H); 3.19 (m, 2H); 3.97 (m, 1H); 4.17 (m, 3H); 4.53 (m, 2H); 5.46 (m, 1H); 7.29 (s, 1H); 7.50 (s, 1H).

Example 93

2-(((2S,5R)-2-carbamoyl-4-methyl-7-oxo-1,6-diazabicyclo[3.2.1]oct-3-en-6-yl)oxy)acetic acid lithium salt

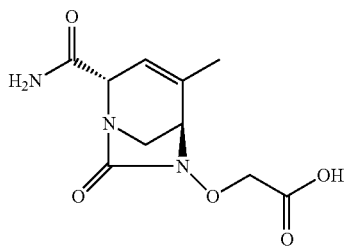

To a solution of ethyl 2-(((2S,5R)-2-carbamoyl-4-methyl-7-oxo-1,6-diazabicyclo[3.2.1]oct-3-en-6-yl)oxy)acetate (Example 92, 57.4 mg, 0.2 mmol) in THF (2 mL) and water (1 mL) at 0° C. was added 1M lithium hydroxide (0.66 mL, 0.66 mmol). The reaction mixture was stirred at 0° C. for 10 minutes. Another 0.2 equivalents of lithium hydroxide was added and after 10 minutes the reaction is complete. The reaction mixture was neutralized with 0.5N hydrochloric acid and 1 eq of sodium bicarbonate in water was added at 0° C. The resulting solution was frozen and lyophilized. Gilson purification (0%-16%, 6 min) afforded the title compound as a white solid, 18.3 mg, 35%.

MS: 256 ES+($C_{10}H_{13}N_3O_5$)

$^1$H NMR (300 MHz, DMSO-$d_6$) δ: 1.85 (m, 3H); 3.11 (m, 2H); 3.88 (m, 2H); 4.07 (m, 1H); 4.24 (m, 1H); 5.39 (m, 1H); 7.24 (s, 1H); 7.48 (s, 1H).

Intermediate 204: (2S,5R)-6-((tert-butyldimethylsilyl)oxy)-4-methyl-7-oxo-1,6-diazabicyclo[3.2.1]oct-3-ene-2-carbonitrile

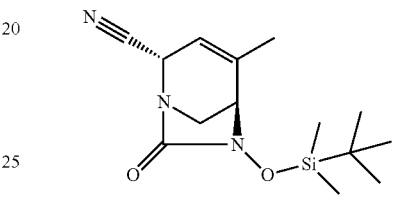

The title compound was prepared from (2S,5R)-6-((tert-butyldimethylsilyl)oxy)-4-methyl-7-oxo-1,6-diazabicyclo[3.2.1]oct-3-ene-2-carboxamide (Intermediate 202, 0.205 g, 0.66 mmol) according to the procedure for Intermediate 139 to afford the title compound (159 mg, 82%) as a white solid.

MS: 294 ES+($C_{14}H_{23}N_3O_2Si$)

Example 94 ethyl (2R)-2-(((2S,5R)-2-cyano-4-methyl-7-oxo-1,6-diazabicyclo[3.2.1]oct-3-en-6-yl)oxy)-2-fluoroacetate

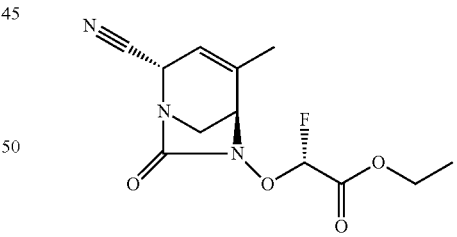

The title compound was prepared from (2S,5R)-6-((tert-butyldimethylsilyl)oxy)-4-methyl-7-oxo-1,6-diazabicyclo[3.2.1]oct-3-ene-2-carbonitrile (Intermediate 204, 152 mg, 0.49 mmol) according to the alternate procedure for Example 35 to afford (26.9 mg, 19%) a colorless oil. There was approximately 9% S-diastereomer present.

MS: 284 ES+($C_{12}H_{14}FN_3O_4$)

$^1$H NMR (300 MHz, DMSO-$d_6$) δ: 1.09 (t, 3H); 1.72 (m, 3H); 3.26 (m, 2H); 3.97 (m, 1H); 4.11 (m, 2H); 4.94 (m, 1H); 5.30 (m, 1H); 6.16 (m, 1H).

Example 95

(2R)-2-(((2S,5R)-2-cyano-4-methyl-7-oxo-1,6-diaz-abicyclo[3.2.1]oct-3-en-6-yl)oxy)-2-fluoroacetic acid lithium salt

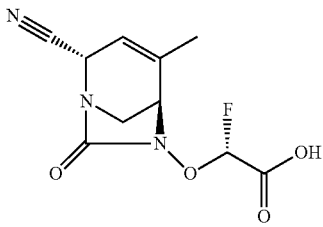

The title compound was prepared from ethyl (2R)-2-(((2S,5R)-2-cyano-4-methyl-7-oxo-1,6-diazabicyclo[3.2.1]oct-3-en-6-yl)oxy)-2-fluoroacetate (Example 94, 22 mg, 0.08 mmol) according to the procedure for Example 91 to afford (3.8 mg, 15%) a light yellow solid.
MS: 256 ES+($C_{10}H_{10}FN_3O_4$)
$^1$H NMR (300 MHz, DMSO-$d_6$) δ: 1.81 (m, 3H); 3.30 (m, 2H); 4.00 (m, 1H); 4.92 (m, 1H); 5.27 (m, 1H); 5.28 (m, 1H).

Example 96 isopropyl 2-(((2S,5R)-2-carbamoyl-4-methyl-7-oxo-1,6-diazabicyclo[3.2.1]oct-3-en-6-yl)oxy)acetate

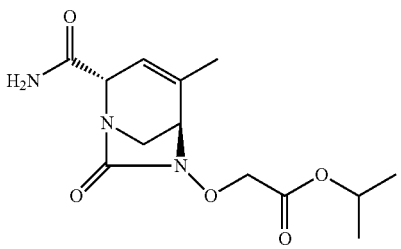 [SMILES: CC1=C[C@@H](C(N)=O)N2C[C@@H]1N(OCC(=O)OC(C)C)C2=O]

To a solution of (2S,5R)-6-hydroxy-4-methyl-7-oxo-1,6-diazabicyclo[3.2.1]oct-3-ene-2-carboxamide (Intermediate 203, 93.38 mg, 0.47 mmol) and isopropyl bromoacetate (0.18 mL, 1.42 mmol) in DMF (4 mL) at room temperature was added potassium carbonate (196.35 mg, 1.42 mmol). The reaction mixture was stirred for ~3 hours, then diluted with ethyl acetate and filtered. The filtrate was washed twice with 1:1 brine:water, dried over magnesium sulfate, filtered and concentrated. Silica gel chromatography (0%-80% ethyl acetate/hexanes) afforded the title compound as an off-white solid after lyophilization in acetonitrile, 106.6 mg, 72%.
MS: 298 ES+($C_{13}H_{19}N_3O_5$)
$^1$H NMR (300 MHz, DMSO-$d_6$) δ: 1.23 (m, 6H); 1.84 (m, 3H); 3.19 (m, 2H); 3.97 (m, 1H); 4.16 (m, 1H); 4.35 (m, 1H); 4.62 (m, 1H); 5.00 (m, 1H); 5.46 (m, 1H); 7.29 (s, 1H); 7.50 (s, 1H).

Biological Examples

Example 102

Inhibition of Beta-Lactamase Enzymes

A buffer consisting of 0.1 M sodium phosphate (pH 7.0), 10 mM NaHCO$_3$, and 0.005% Triton X-100 was used for all enzymes. The chromogenic substrate nitrocefin (SynGene, Bangalore, India) was used at 100 μM. Enzyme activity was monitored by the 490 nm absorbance increase upon nitrocefin hydrolysis. Assays were performed in clear polystyrene 384-well plates (Greiner Bio-One, Monroe, N.C.). Absorbance was measured for 1 hour at 30-s intervals using a Spectramax absorbance plate reader (Molecular Devices, Sunnyvale, Calif.). Measurement of beta-lactamase inhibition by INHIBITOR employed serial 3-fold dilutions of the inhibitor in assay buffer, ranging from 100 μM to 62.7 pM. A background absorbance progress curve for a control lacking enzyme and inhibitor was subtracted from each progress curve.

The complete set of progress curves for one enzyme with all inhibitor concentrations was subjected to numerical integration with the program Kintek Global Kinetic Explorer (Kintek Corp, Snowshoe Pa.) to obtain a best-fit to the mechanism shown in Scheme 10.

Scheme 10

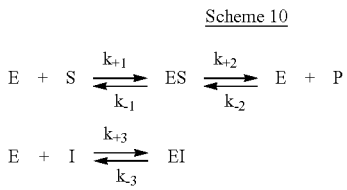

where E, S, ES, P, I, and EI are the concentrations of the enzyme, nitrocefin, the enzyme-nitrocefin complex, the nitrocefin hydrolysis product, INHIBITOR, and the enzyme-INHIBITOR complex respectively. The measured value of $K_m$(nitrocefin) was used to define the fixed values of $k_{+1}$, $k_{-1}$, and $k_{+2}$, where $k_{+1}=k_{-1}=1$ and $k_{+2}=K_m-1$. The values of $k_{+2}$, $k_{+3}$, and $k_{-3}$ were fit. Concentration series offsets of the absorbance measurements were used to correct for slight absorbance baseline differences between wells. The parameter $k_{+3}$ is equivalent to the second order rate constant $k_{inact}/K_i$. In some cases, the inhibition was in rapid equilibrium on the experimental time scale, so that only the ratio $k_{-3}/k_{+3}=K_i$ could be determined. Although $k_{-3}$ represents reversal of inhibitor binding in Scheme 10, hydrolysis of the enzyme-inhibitor complex could not be excluded based on kinetic measurements.

Best-fit absorbance values from the above procedure at each time point for each compound concentration were exported to Excel. To calculate the 60-min IC$_{50}$, the % inhibition at each inhibitor concentration at 60 min was calculated based on the best-fit absorbance values at that time, using the equation $$\% \text{ inhibition} = 100 \times (1 - A_{inhib}/A_{max})$$

where A is the best-fit absorbance without inhibitor and $A_{inhib}$ is the best-fit absorbance in the presence of the inhibitor. IC$_{50}$ was calculated from the set of % inhibition values by nonlinear least-squares regression using the equation $$\% \text{ inhibition} = 100[I]^n/(IC_{50}^n + [I]^n)$$

where [I] is the inhibitor concentration and n is the Hill coefficient. The Excel add-in XLfit (ID Business Solutions) was used for nonlinear regression.

Table 1 lists IC$_{50}$s of exemplar compounds (μM)

TABLE 1
| Example | Class A TEM-1 60 min IC$_{50}$ (μM) | Class C AmpC 60 min IC$_{50}$ (μM) | Class D OXA-48 60 min IC$_{50}$ (μM) |
| --- | --- | --- | --- |
| 3 | 0.019 | 0.071 | 0.015 |
| 4 | 0.00135 | 0.011 | 0.015 |
| 5 | 0.0044 | 0.02 | 0.017 |
| 8 | 0.0015 | 0.012 | 0.014 |
| 10 | 0.43 | 1.2 | 0.051 |
| 11 | 0.23 | 0.4 | 22 |
| 27 | 0.047 | 0.0083 | 0.018 |
| 30 | 0.081 | 0.0018 | 0.14 |
| 33 | 0.0032 | 0.16 | 0.077 |
| 34 | 0.026 | 0.3 | 0.019 |
| 41 | 0.0035 | 0.022 | 0.0064 |
| 42 | 0.024 | 0.095 | 0.0052 |
| 55 | 0.024 | 0.18 | 0.0073 |
| 56 | 0.093 | 0.14 | 0.22 |
| 57 | 0.057 | 0.0041 | 0.41 |
| 62 | 0.21 | 0.41 | 0.87 |
| 63 | 0.11 | 0.04 | 0.23 |
| 66 | 0.66 | 0.054 | 0.012 |
| 67 | 0.064 | 0.0073 | 0.34 |
| 68 | 0.31 | 0.0093 | 0.078 |
| 69 | 0.18 | 0.002 | 0.11 |
| 70 | 0.026 | 0.13 | 0.087 |
| 71 | 0.11 | 0.0044 | 0.075 |
| 72 | 0.077 | 0.053 | 0.11 |
| 73 | 0.73 | 0.01 | 0.53 |
| 74 | 0.28 | 0.022 | 0.59 |
| 75 | 0.083 | 0.014 | 0.42 |
| 76 | 0.94 | 44 | 0.22 |
| 77 | >100 | >100 | >100 |
| 78 | 3.6 | >100 | 0.69 |
| 79 | 4.2 | >100 | 5.7 |
| 82 | 0.085 | 0.014 | 0.028 |
| 87 | 0.15 | 0.017 | 0.011 |
| 88 | 0.054 | 0.0031 | 0.045 |
| 89 | 0.033 | 0.0021 | 0.15 |
| 91 | 0.00047 | 0.036 | 0.018 |
| 93 | 0.15 | 4.6 | 0.053 |
| 95 | 0.035 | 0.59 | 0.0013 |
| Comparator 98 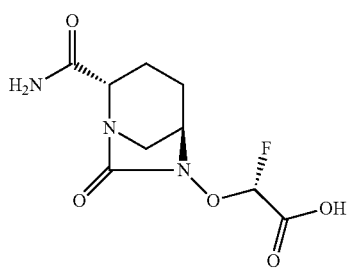 [SMILES: NC(=O)[C@@H]1CC[C@@H]2CN1C(=O)N2O[C@H](F)C(=O)O] | 0.0013 | 2 | 2.6 |
| Comparator 99 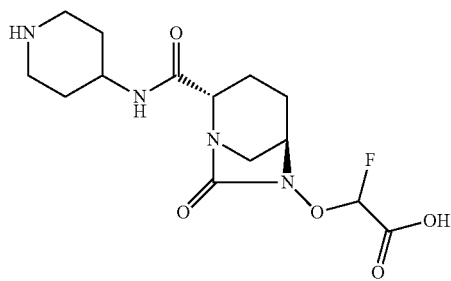 [SMILES: O=C(O)C(F)ON1C(=O)N2C[C@H]1CC[C@H]2C(=O)NC1CCNCC1] | 0.03 | 1.6 | 82 |

Example 103

Restoration of Activity of Cefpodoxime in Presence of Fixed Concentration of 4 ug/mL of BLI The minimal inhibitory concentration (MIC) values against each organism and drug combination were determined using the Clinical and Laboratory Standards Institute guidelines (CLSI) broth microdilution methodology (CLSI M07-A10). The recommended quality control (QC) bacterial strains *E. coli* ATCC 25922, *E. coli* ATCC 35218 and *Klebsiella pneumoniae* ATCC 700603 were incorporated into each test according to the CLSI guidelines to assure that there was no variation between test dates (CLSI M100-S25). The MICs of these QC strains were within QC range on all test occasions. Drug containing plates were made using the master plate method. A cefpodoxime solution was prepared to 20× concentration and 2-fold serial dilutions were made in cation adjusted Mueller-Hinton Broth. Equal volumes of 20× examplar compounds at a fixed concentration were added to the master plate. 10 uL was stamped into daughter plates using a Tecan EVO robot. Organism suspensions were adjusted to a 0.5 McFarland standard and further diluted to yield a final inoculum between $3\times10^5$ and $7\times10^5$ colony-forming units (CFU)/mL. Bacterial inocula were made in sterile, cation adjusted Mueller-Hinton Broth (Beckton Dickinson). An inoculum volume of 1.1× concentration of 90 uL was added to wells (using a Tecan EVO robot). All inoculated microdilution plates were incubated in ambient air at 35° C. for 18-24 hours. Following incubation, the lowest concentration of the drug that prevented visible growth as read at OD600 nm was recorded as the MIC (Table 2, all MICs are in μg/mL and all beta-lactamase inhibitors were tested at a fixed concentration of 4 μg/ml).

TABLE 2

| | Compound | | | |
|---|---|---|---|---|
| | | | | *Klebsiella pneumoniae* |
| | *C.* | *E. coli* | | SHV-18, |
| | *freundii* | | AmpC, | OXA-2, | KPC-2, |
| | AmpC, | WT | OXA-1, | OKP-6 | SHV-11, |
| | TEM-1, | (ATCC | CTX-M- | (ATCC | TEM-1 |
| Beta-lactamase content: | CMY65 | 25922) | 15, TEM-1 | 700603) | OXA-9 |
| Cefpodoxime alone | <64 | 1 | <64 | 16 | <64 |
| +3 | ≤1 | ≤0.5 | 1 | 2 | 0.5 |
| +4 | ≤0.125 | ≤0.06 | 0.06 | 0.25 | 0.06 |
| +5 | <0.03125 | <0.03125 | <0.03125 | 0.0625 | <0.03125 |
| +10 | 2 | 0.5 | 4 | 2 | 1 |
| +11 | 16 | 0.5 | 2 | 2 | 4 |
| +27 | <0.03125 | <0.03125 | <0.03125 | 0.25 | <0.03125 |
| +28 | 32 | 1 | 4 | 1 | 2 |
| +30 | 0.5 | 0.03125 | 0.5 | 2 | 1 |
| +33 | <0.03125 | ≤0.03125 | <0.03125 | ≤0.0625 | <0.03125 |
| +34 | <0.03125 | ≤0.03125 | <0.03125 | ≤0.125 | ≤0.0625 |
| +41 | <0.00012 | <0.00012 | 0.00024 | 0.25 | 0.01117 |
| +42 | 4 | 0.5 | 2 | 2 | 1 |
| +43 | 0.13 | 0.016 | 0.0039 | 1 | 0.063 |
| +55 | >32 | 0.0625 | 2 | 2 | 32 |
| +56 | 8 | <0.03125 | <0.03125 | 0.125 | 0.0625 |
| +57 | <0.0625 | <0.0625 | <0.0625 | 1 | 0.0625 |
| +62 | <0.03125 | <0.03125 | <0.03125 | ≤0.0625 | <0.03125 |
| +63 | >32 | 0.25 | 32 | 8 | >32 |
| +66 | 16 | 0.5 | >32 | 4 | 8 |
| +67 | 0.5 | <0.03125 | <0.03125 | 4 | 1 |
| +68 | >32 | 0.5 | >32 | 4 | 8 |
| +69 | >32 | 0.25 | 16 | 4 | 8 |
| +70 | >32 | 0.5 | 16 | 4 | >32 |
| +71 | 0.25 | 0.5 | 2 | 2 | 1 |
| +72 | >32 | <0.03125 | 4 | 4 | 8 |
| +73 | >32 | 0.25 | 32 | ND | 16 |
| +74 | 0.5 | <0.03125 | <0.03125 | 2 | 0.03125 |
| +75 | <0.03125 | <0.03125 | <0.03125 | 0.125 | <0.03125 |
| +76 | >32 | 1 | >32 | 16 | >32 |
| +77 | <0.03125 | <0.03125 | <0.03125 | <0.03125 | <0.03125 |
| +78 | >32 | 1 | >32 | 8 | >32 |
| +79 | >32 | 1 | >32 | 16 | >32 |
| +82 | <0.03125 | <0.03125 | <0.03125 | 0.0625 | <0.03125 |
| +87 | <0.03125 | <0.03125 | <0.03125 | 0.125 | <0.03125 |
| +88 | <0.03125 | <0.03125 | <0.03125 | 2 | <0.03125 |
| +89 | <0.03125 | <0.03125 | <0.03125 | 0.0625 | <0.03125 |
| +91 | ≤0.03 | ≤0.03 | ≤0.03 | ≤0.03 | ≤0.03 |
| +93 | ≤0.03 | ≤0.03 | ≤0.03 | 0.125 | ≤0.03 |
| +95 | 32 | 0.25 | 1 | 2 | 2 |

TABLE 2-continued

| Beta-lactamase content: | C. freundii AmpC, TEM-1, CMY65 | E. coli WT (ATCC 25922) | E. coli AmpC, OXA-1, CTX-M-15, TEM-1 | Klebsiella pneumoniae SHV-18, OXA-2, OKP-6 (ATCC 700603) | KPC-2, SHV-11, TEM-1 OXA-9 |
|---|---|---|---|---|---|
| 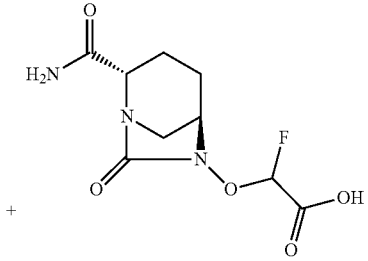 [SMILES: NC(=O)[C@@H]1CC[C@@H]2CN1C(=O)N2OC(F)C(=O)O] Comparator 97 | >32 | 1 | 2 | 2 | 2 |
| 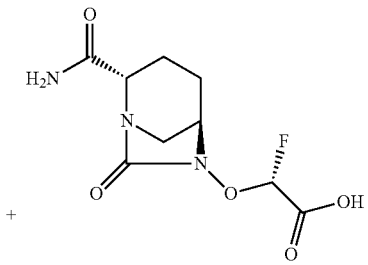 Comparator 98 | 16 | 0.5 | 2 | 2 | 0.5 |
| 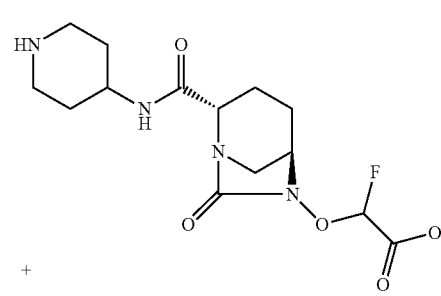 Comparator 99 | >32 | 0.5 | 8 | 2 | 4 |

Example 104

Restoration of Activity of Various Oral Beta-Lactams in Presence of Fixed Concentration of 4 ug/mL of BLI Following the procedure from Example 103, MICs were determined for several beta-lactams in presence of a fixed concentration (4 μg/mL) of exemplar compounds (Table 3) against 3 Enterobacteriaceae strains.

TABLE 3

| Compound | C. freundii AmpC, TEM-1, CMY65 | E. coli WT (ATCC 25922) | Klebsiella pneumoniae SHV-18, OXA-2, OKP-6 (ATCC 700603) |
|---|---|---|---|
| Cefpodoxime | >64 | 1 | 16 |
| Cefpodoxime + Ex. 3 (4 μg/ml) | 0.5 | 0.125 | 2 |
| Cefpodoxime + Ex. 4 (4 μg/ml) | ≤0.125 | ≤0.06 | 0.25 |

TABLE 3-continued

| Compound | C. freundii AmpC, TEM-1, CMY65 | E. coli WT (ATCC 25922) | Klebsiella pneumoniae SHV-18, OXA-2, OKP-6 (ATCC 700603) |
|---|---|---|---|
| Cefpodoxime + Ex. 33 (4 µg/ml) | <0.03125 | ≤0.03125 | 0.25 |
| Cefpodoxime + Ex. 34 (4 µg/ml) | <0.03125 | ≤0.03125 | 0.25 |
| Cefpodoxime + Ex. 93 (4 µg/ml) | ≤0.06 | ≤0.06 | 0.25 |
| Cefuroxime | >64 | 4 | 32 |
| Cefuroxime + Ex. 3 (4 µg/ml) | 1 | 0.02 | ND |
| Cefuroxime + Ex. 4 (4 µg/ml) | 0.02 | 0.02 | ND |
| Cefuroxime + Ex. 33 (4 µg/ml) | <0.03125 | <0.03125 | 4 |
| Cefuroxime + Ex. 34 (4 µg/ml) | <0.03125 | <0.03125 | 1 |
| Tigemonam | 4 | 1 | 32 |
| Tigemonam + Ex. 3 (4 µg/ml) | 0.125 | 1 | 2 |
| Tigemonam + Ex. 4 (4 µg/ml) | ≤0.06 | ≤0.06 | 0.5 |
| Tigemonam + Ex. 33 (4 µg/ml) | ≤0.06 | ≤0.06 | 0.5 |
| Tigemonam + Ex. 34 (4 µg/ml) | ≤0.06 | ≤0.06 | 0.5 |
| Tigemonam + Ex. 93 (4 µg/ml) | 0.125 | 0.125 | 1 |
| Tebipenem | 0.125 | ≤0.06 | 0.125 |
| Tebipenem + Ex. 3 (4 µg/ml) | ≤0.06 | ≤0.06 | 0.125 |
| Tebipenem + Ex. 4 (4 µg/ml) | ≤0.06 | ≤0.06 | ≤0.06 |
| Tebipenem + Ex. 33 (4 µg/ml) | ≤0.06 | ≤0.06 | 0.125 |
| Tebipenem + Ex. 34 (4 µg/ml) | ≤0.06 | ≤0.06 | ≤0.06 |
| Tebipenem + Ex. 93 (4 µg/ml) | ≤0.06 | ≤0.06 | ≤0.06 |
| Faropenem | 8 | 0.5 | 8 |
| Faropenem + Ex. 3 (4 µg/ml) | 0.25 | 0.25 | 2 |
| Faropenem + Ex. 4 (4 µg/ml) | ≤0.06 | ≤0.06 | 1 |
| Faropenem + Ex. 33 (4 µg/ml) | ≤0.06 | ≤0.06 | 0.5 |
| Faropenem + Ex. 34 (4 µg/ml) | ≤0.06 | ≤0.06 | 0.5 |
| Faropenem + Ex. 93 (4 µg/ml) | ≤0.06 | ≤0.06 | 1 |
| Cefixime | >64 | 0.5 | 8 |
| Cefixime + Ex. 3 (4 µg/ml) | 1 | 0.125 | 0.5 |
| Cefixime + Ex. 4 (4 µg/ml) | ≤0.06 | ≤0.06 | ≤0.06 |
| Cefixime + Ex. 33 (4 µg/ml) | ≤0.06 | ≤0.06 | ≤0.06 |
| Cefixime + Ex. 34 (4 µg/ml) | ≤0.06 | ≤0.06 | ≤0.06 |
| Cefixime + Ex. 93 (4 µg/ml) | ≤0.06 | ≤0.06 | 0.125 |
| Loracarbef | >64 | 2 | 32 |
| Loracarbef + Ex. 3 (4 µg/ml) | 1 | 0.5 | 0.5 |
| Loracarbef + Ex. 4 (4 µg/ml) | ≤0.06 | ≤0.06 | 0.125 |
| Loracarbef + Ex. 33 (4 µg/ml) | ≤0.06 | ≤0.06 | 0.125 |
| Loracarbef + Ex. 34 (4 µg/ml) | ≤0.06 | ≤0.06 | 0.125 |
| Loracarbef + Ex. 93 (4 µg/ml) | ≤0.06 | ≤0.06 | 0.25 |

Example 105

Stability/Conversion in the Absence or Presence of Metabolizing Enzymes

The human intestinal S9 with the absence of PMSF, human liver S9, rat intestinal S9, and rat liver S9 preparations were obtained from Xenotech (Lenexa, Kans.). The 500-µL incubation solution contained 0.8 mg/mL of enzyme (or no enzyme for buffer stability), 10 µM of test compounds in 100 mM of HEPES buffer, pH 7.4. The hydrolysis reactions were conducted in a 1-mL glass insert (Analytical Sales, Pompton Plains, N.J.) in a shake water bath at 37° C. At 0, 2, 5, 10, 15, 30 and 60 min, the reaction was terminated by pipetting 50 µL incubate to a 96 DeepWell plate (Thermo Fisher Scientific, Rochester, N.Y.) containing 100 µL of acetonitrile with 250 ng/mL of Carbutamide (Sigma-Aldrich, St. Louis, Miss.) as the internal standard. The crashed solutions were then vortexed well followed by centrifuge at 4000 rpm for 15 min at 4° C. The extract was transferred to a new 96 DeepWell plate for LC-MS/MS analysis.

LC-MS/MS analysis was done using an AB Sciex QTrap 6500 mass spectrometer under positive ionization mode, coupled to a Schimadzu Nexera LC system.

A Waters Atlantis T3 (3 µm, 3.0×50 mm) column was used for separation. The mobile phase consisted 0.1% formic acid in water (A) and 0.1% formic acid in acetonitrile (B) with a flow rate set at 1.2 mL/min. For the prodrug analysis, the Multiple Reaction Monitoring (MRM) specific for each compound was set up so that both prodrug and its hydrolyzed active can be monitored simultaneously.

Table 4 lists the first-order half-lives of the exemplar compounds ($T_{1/2}$ in minutes). Half-lives listed are based on disappearance of starting ester. As can be seen from Table 4, there is a good correlation between the rat and human enzymes. The data in Table 4 indicates that there is generally more rapid conversion of ester into the active compound by rat and human liver S9 enzymes, while the esters are predominantly stable in the presence of buffer and intestinal S9.

TABLE 4

| Example | pH 7.4 Buffer | Rat Intestinal S9 | Rat Liver S9 | Human Intestinal S9 | Human Liver S9 |
|---|---|---|---|---|---|
| 1 | 41 | 39 | 4.4 | 38 | 6.5 |
| 2 | 29 | 24 | 1.4 | 21 | 1.9 |
| 7 | 3.9 | 3.9 | 0.5 | 2.4 | 0.8 |
| 9 | 18.3 | 27.3 | 1.4 | 17.8 | 2.9 |
| 12 | 236 | 233 | 14 | 132 | 16 |
| 13 | 55 | ND | ND | 44 | 1 |
| 15 | 98 | >100 | 1.5 | >100 | 12.4 |
| 18 | 18 | 16 | 7 | 15 | 9.2 |
| 20 | 39 | 54 | 6.1 | 40 | 5.1 |
| 22 | 38 | 56 | 9.2 | 43 | 4.6 |
| 24 | >100 | ND | ND | 34 | 9 |
| 31 | 44 | 42 | 20 | 35 | 27 |
| 32 | 22 | 18 | 2.4 | 6.9 | 2.4 |
| 35 | 186 | 240 | 32 | 163 | 39 |
| 36 | 91 | 68 | 3 | 36 | 8.5 |
| 45 | 33 | 17 | 0.22 | 2 | 0.39 |
| 47 | 12 | 11 | 1.8 | 8.2 | 2.3 |
| 48 | 62 | 50 | 3 | 42 | 6.1 |
| 49 | 68 | 26 | 1.8 | 32 | 6.9 |
| 50 | 120 | 30 | 2.8 | 73 | 3.5 |
| 51 | 75 | 4.1 | 1.7 | 1.5 | 6.4 |
| 52 | 76 | 39 | 0.45 | 5.7 | 0.84 |
| 53 | 4.8 | 4.2 | 2 | <1.0 | 1.7 |
| 54 | 22 | 19 | 0.9 | 5 | 1.9 |
| 60 | 29 | 21 | 10 | 22 | 9.9 |
| 64 | 1.2 | 1.1 | <1.0 | <1.0 | <1.0 |

TABLE 4-continued

| Example | pH 7.4 Buffer | Rat Intestinal S9 | Rat Liver S9 | Human Intestinal S9 | Human Liver S9 |
|---|---|---|---|---|---|
| 65 | 1.7 | 1.3 | <1.0 | <1.0 | <1.0 |
| 85 | 26 | 21 | 3.8 | 20 | 3.5 |
| 86 | 39 | 43 | 23 | 36 | 24 |
| 90 | 2.9 | 3.3 | 0.7 | 1 | 0.7 |
| 92 | 160.9 | 397 | 11 | 193.1 | 24.8 |
| 94 | 46.9 | 25.9 | 1.3 | 10.6 | 0 |
| 96 | >100 | 210.7 | 10.3 | 1475.6 | 57 |

ND = not determined

Example 106

Rat PK

Intravenous rat pharmacokinetics of exemplar compounds were determined in jugular vein cannulated Sprague-Dawley rats (n=3) (Harlan Laboratories, Indianapolis, Ind.) at a dose of 10 mg/kg. Compounds were dissolved and administered intravenously in 0.9% saline, pH 6.5 at a dose volume of 2 mL/kg. Blood samples (~100 µL) were obtained via the jugular vein catheter prior to dosing and at 0.08, 0.17, 0.25, 0.5, 1, 2, 4, and 8 hpd and prepared for plasma in K$_2$EDTA microtainers. Oral pharmacokinetic studies were conducted with exemplar compounds at 10 mg/kg equivalents of carboxylic acids. Doses were dissolved and administered orally in 25:75 PEG400: water for injection, pH 4.5 at a dose volume of 10 mL/kg. Blood samples were obtained via the jugular vein catheter prior to dosing and at 0.25, 0.5, 1, 2, 4, 8, and 24 hpd and prepared for plasma in K$_2$EDTA microtainers. Plasma samples were stored at −80° C. prior to bioanalysis.

Sample Preparation for LC/MS/MS Analysis

Plasma samples were thawed on ice prior to processing. Samples (30 µL) were diluted and proteins precipitated with 180 µL of acetonitrile containing 0.1% formic acid and 250 ng/mL of carbutamide (N1-(butylcarbanoyl)-sulfanilamide, Sigma-Aldrich Catalog # S385433) as an internal standard. Samples were vortexed for 30 seconds, centrifuged at 3400 g for 10 minutes and the supernatant transferred to injection vials.

LC/MS/MS Conditions

Rapid hydrolysis precluded satisfactory analysis of circulating concentrations of Examples 12 and 35. LC/MS/MS analysis was completed on an AB Sciex QTrap 6500 mass spectrometer in positive ionization mode, coupled to a Schimadzu Nexera LC system. A Waters Atlantis T3 (3 µm, 3.0×50 mm) column was used for chromatographic separation. Injection volume was 1 The mobile phase consisted 0.1% formic acid in water (A) and 0.1% formic acid in acetonitrile (B), with a gradient of 2-98% B:A over two minutes.

Pharmacokinetic Analysis

Plasma concentration vs. time profiles following intravenous (IV) administration and oral (PO) administration of exemplar compounds were analyzed by non-compartment analysis using WinNonLin 6.4. Mean AUC and F % are summarized in Table 5. Absolute oral bioavailability (F %) of analytes following administration of their respective esters was determined as:

$$F\% = 100 * (\mathrm{AUC}_{po} * \mathrm{Dose}_{iv}) / (\mathrm{AUC}_{iv} * \mathrm{Dose}_{po}).$$

In general, the exemplar compounds exhibit increased AUC upon oral dosing as compared with sulfate-derived beta-lactamase inhibitors, resulting in favorable F %.

TABLE 5

| Example administered | Route | Analyte | AUC, µM*h | F % |
|---|---|---|---|---|
| 4 | IV | 4 | 19.1 | |
| 3 | IV | 3 | 34.9 | |
| 13 | PO | 3 | 18.3 | 53 |
| 12 | PO | 4 | 8.2 | 38 |
| 2 | PO | 3 | 18.5 | 58 |
| 1 | PO | 4 | 8.4 | 45 |
| 60 | PO | 62 | 2.2 | 6.3 |
| 33 | IV | 33 | 26.3 | |
| 34 | IV | 34 | 16.1 | |
| 36 | PO | 34 | 13.5 | 84 |
| 35 | PO | 33 | 25.8 | 98 |
| 32 | PO | 34 | 11.5 | 71 |
| 31 | PO | 33 | 19.8 | 75 |
| 53 | PO | 4 | 2.2 | 11 |
| 65 | PO | 4 | 2.8 | 15 |
| | PO | ETX2514 | 0.44 | |

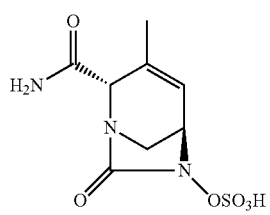

ETX2514

TABLE 5-continued

| Example administered | Route | Analyte | AUC, μM*h | F % |
|---|---|---|---|---|
| Relebactam (structure) | PO | Relebactam | 0.29 | |
| WCK 4234 (structure) | PO | WCK 4234 | 0.45 | |

Example 106

**In Vivo Oral Efficacy of Cefpodoxime Proxetil in Combination with Example 35 vs. *E. coli* (Beta-Lactamase Content: AmpC, CTX-M-14)**

The oral in vivo efficacy of Example 35 was evaluated in combination with cefpodoxime proxetil in a mouse neutropenic thigh infection model versus a relevant clinical isolate. The isolate, *E. coli* ARC2687, expresses the beta-lactamases AmpC and CTX-M-14, both of which can readily hydrolyze cefpodoxime resulting in non-susceptible MICs in excess of 512 μg/mL. In combination with Example 33 (4 μg/mL), the cefpodoxime MIC is reduced to <0.03 μg/mL. Dose setting for the study was based upon targeting cefpodoxime exposure above an MIC of 0.03 μg/mL for at least 50% of the dosing interval for all treatment arms while titrating increasing doses of the compound from Example 35. CD-1 mice (Charles River, Wilmington US) were housed in shoebox type cages with contact bedding and acclimated to the facility for a minimum of 2 days prior to use. The animal room was maintained at 70° F., with 50+/−10% relative humidity and a 12-hour light/dark cycle. The study was conducted using an IACUC-approved protocol in accordance with Title 9 of the Code of Federal Regulations. Animals were rendered neutropenic with two intraperitoneal doses of cyclophosphamide (150 mg/kg—4 days and 100 mg/kg—1 day prior to infection (Gerber et al. (1983) *J Infect Dis* 147(5); 910-917)). Animals were infected via an intramuscular challenge of ~1×10$^6$ CFU administered within 100 μL of 0.9% saline. The inoculum was prepared from a 25 mL overnight culture of *E. coli* ARC 2687 in tryptic soy broth media. Following an OD$_{600}$ determination, the inoculum was diluted in 0.9% saline to a concentration of ~1.0×10$^6$ CFU/mL prior to inoculation into the left and right thigh. Oral therapy with cefpodoxime proxetil alone and in combination with Example 35 was initiated 2 hours post bacterial challenge. Doses were suspended in 0.5% HPMC/0.1% Tween 80 and administered by oral gavage at a dose volume of 10 mL/kg. A terminal endpoint was obtained at 24 hr to determine bacterial counts in thigh tissue (CFU/gm). Animals were ethically euthanized, thighs were aseptically removed, weighed and homogenized in 1 mL of saline. Bacterial burden enumeration of tissue homogenate was performed by serial dilution on tryptic soy agar plates which were incubated overnight at 37° C. prior to colony (CFU) counting. The lower limit of detection was ~2.6 log$_{10}$ CFU/gm of tissue.

As summarized in Table 6, bacterial burden in the thighs of mice receiving cefpodoxime proxetil alone at 50 mg/kg q6h or Example 35 at 10 mg/kg q6h demonstrated greater than 3 log$_{10}$ CFU/gm of growth after 24 hours of therapy. In combination with cefpodoxime proxetil, increasing dose of the compound from Example 35 resulted in dose dependent reduction of bacterial burden with maximal kill of −0.75 log$_{10}$ CFU/gm (relative to initiation of therapy) achieved at 50 mg/kg cefpodoxime proxetil+100 mg/kg Example 35 q6h. Meropenem used as a positive control achieved just over 1-log$_{10}$ reduction in CFU relative to initiation of therapy at 600 mg/kg q6h administered subcutaneously.

TABLE 6

| Group | Dose (mg/kg) | Route/Regimen | log$_{10}$CFU/gm thigh | Std. Dev | CFU Change from 2 hr | CFU Change from 26 hr |
|---|---|---|---|---|---|---|
| Initiation of Rx | n/a | n/a | 6.27 | 0.35 | — | −4.59 |
| 26 hr Growth Control | vehicle | PO/q6h | 10.86 | 0.19 | +4.59 | — |
| Cefpodoxime proxetil alone | 50 | PO/q6h | 10.24 | 0.15 | +3.97 | −0.62 |
| Example 35 alone | 10 | PO/q6h | 9.56 | 0.29 | +3.29 | −1.30 |
| Example 35 + cefpodoxime proxetil | 10 + 50 | PO/q6h | 5.77 | 0.14 | −0.50 | −5.09 |
| Example 35 + cefpodoxime proxetil | 25 + 50 | PO/q6h | 5.59 | 0.17 | −0.68 | −5.27 |
| Example 35 + cefpodoxime proxetil | 100 + 50 | PO/q6h | 5.52 | 0.20 | −0.75 | −5.34 |
| Meropenem | 600 | SC/q6h | 5.17 | 0.27 | −1.10 | −5.69 |

We claim:

1. A compound according to Formula (I):

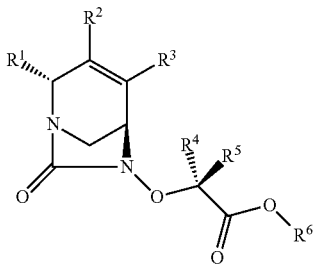

or a pharmaceutically acceptable salt thereof; wherein:
$R^1$ is —C(O)NR$^7$R$^8$, —CN, phenyl, a 5-6 membered heteroaryl (containing at least one heteroatom selected from nitrogen, sulfur, and oxygen), —C(O)NR'NR'C(O)R$^9$, —C(O)NR'OR$^{10}$, or a $C_1$-$C_6$ alkyl group, wherein the alkyl group is substituted with one to three groups selected from halo, $C_1$-$C_3$ alkoxy, —OH, —CN, —NR$^7$R$^8$, —NR$^7$COR$^9$, a 5-6 membered heteroaryl (containing at least one heteroatom selected from nitrogen, sulfur, and oxygen), and a 5-7 membered monocyclic saturated or partially saturated non-aromatic heterocyclyl (containing at least one heteroatom selected from nitrogen, sulfur, and oxygen), and wherein the phenyl and heteroaryl represented by $R^1$ are optionally and independently substituted with 1-3 groups selected from halo, —OH, $C_1$-$C_3$ alkoxy, —CN, —NR$^7$R$^8$, and —CONR$^7$R$^8$;
$R^2$ and $R^3$ are independently selected from hydrogen, halo, $C_1$-$C_3$ alkyl, and $C_3$-$C_6$ cycloalkyl;
$R^4$ and $R^5$ are independently selected from hydrogen, halo, —CN, —CO$_2$R$^9$, $C_1$-$C_3$ alkyl, and $C_1$-$C_3$ haloalkyl;
$R^6$ is hydrogen, $C_1$-$C_{12}$ alkyl, $C_1$-$C_4$ alkyl-$C_1$-$C_3$ alkoxy-(NR'C$_1$-$C_6$ alkyl)-$C_1$-$C_3$ alkoxy, $C_1$-$C_4$ alkyl-$C_1$-$C_3$ alkoxy-$C_1$-$C_3$ alkoxy, $C_2$-$C_{12}$ alkenyl, $C_3$-$C_{10}$cycloalkyl, a 5-6 membered heteroaryl (containing at least one heteroatom selected from nitrogen, sulfur, and oxygen), and a 5-7 membered monocyclic saturated or partially saturated non-aromatic heterocyclyl (containing at least one heteroatom selected from nitrogen, sulfur, and oxygen), wherein the alkyl, alkenyl, cycloalkyl, heteroaryl and heterocyclyl are optionally and independently substituted with 1-6 groups selected from a carboxyl, halo, $C_1$-$C_6$ alkoxy, $C_1$-$C_6$ alkyl and phenyl;
each $R^7$ and $R^8$ are independently hydrogen, $C_1$-$C_3$ alkyl, $C_1$-$C_3$ alkoxy, phenyl, $C_3$-$C_6$ cycloalkyl, 4-7 membered monocyclic saturated or partially saturated non-aromatic heterocyclyl (containing at least one heteroatom selected from nitrogen, sulfur, and oxygen), or 5-6 membered heteroaryl (containing at least one heteroatom selected from nitrogen, sulfur, and oxygen), wherein the alkyl, alkoxy, phenyl, cycloalkyl, heterocyclyl or heteroaryl represented by $R^7$ or $R^8$ is optionally and independently substituted with 1-6 groups selected from a 5-6 membered monocyclic saturated or partially saturated non-aromatic heterocyclyl (containing at least one heteroatom selected from nitrogen, sulfur, and oxygen) optionally substituted with one or two —F atoms, carboxyl or —CO(OC$_{1-6}$ alkyl), 5-6 membered heteroaryl (containing at least one heteroatom selected from nitrogen, sulfur, and oxygen), —CN, —OH, $C_1$-$C_3$ alkyl optionally substituted with —NH$_2$ or —OH, $C_1$-$C_3$ haloalkyl, $C_1$-$C_3$ haloalkoxy, $C_1$-$C_3$ alkoxy —NHCO($C_1$-$C_3$alkyl), —NHCO($C_1$-$C_3$alkoxy), —S(O)$_2$NR'R'', —NHS(O)$_2$NR'R'', —NHS(O)$_2$($C_1$-$C_3$alkyl), —NR'R'', and —C(O)NR'R'';
each $R^9$ is $C_1$-$C_6$ alkyl, $C_1$-$C_6$ haloalkyl, $C_1$-$C_6$ haloalkoxy or $C_1$-$C_6$ alkoxy;
each $R^{10}$ is a $C_1$-$C_3$ alkyl optionally substituted with 1-6 groups selected from a 5-6 membered monocyclic saturated or partially saturated non-aromatic heterocyclyl (containing at least one heteroatom selected from nitrogen, sulfur, and oxygen) optionally substituted with one or two —F atoms, carboxyl or —CO(OC$_{1-6}$ alkyl), a $C_3$-$C_6$ cycloalkyl, a 5-6 membered heteroaryl (containing at least one heteroatom selected from nitrogen, sulfur, and oxygen), —CN, —OH, —NHCO($C_1$-$C_3$ alkyl), —NHCO($C_1$-$C_3$ alkoxy), —S(O)$_2$NR'R'', —NHS(O)$_2$NR'R'', —NHS(O)$_2$($C_1$-$C_3$ alkyl), —NR'R'', or —C(O)NR'R''; and
each R' and R'' is independently hydrogen, methyl, ethyl or propyl; or R' and R'' are taken together with the nitrogen to which they are attached to form a 5-6 membered monocyclic saturated or partially saturated non-aromatic heterocyclyl (containing at least one heteroatom selected from nitrogen, sulfur, and oxygen);
provided that at least one of $R^2$ and $R^3$ is other than hydrogen.

2. The compound of claim 1 or a pharmaceutically acceptable salt thereof, wherein $R^6$ is $C_1$-$C_{12}$ alkyl, $C_1$-$C_4$ alkyl-$C_1$-$C_3$ alkoxy-(NR'C$_1$-$C_6$ alkyl)-$C_1$-$C_3$ alkoxy, $C_1$-$C_4$ alkyl-$C_1$-$C_3$ alkoxy-$C_1$-$C_3$ alkoxy, $C_2$-$C_{12}$ alkenyl, $C_3$-$C_{10}$ cycloalkyl, a 5-6 membered heteroaryl (containing at least one heteroatom selected from nitrogen, sulfur, and oxygen), and a 5-7 membered monocyclic saturated or partially saturated non-aromatic heterocyclyl (containing at least one heteroatom selected from nitrogen, sulfur, and oxygen), wherein the alkyl, alkenyl, cycloalkyl, heteroaryl and heterocyclyl are optionally and independently substituted with 1-6 groups selected from a carboxyl, halo, $C_1$-$C_6$ alkoxy, $C_1$-$C_6$ alkyl and phenyl.

3. The compound of claim 2, according to formula (III):

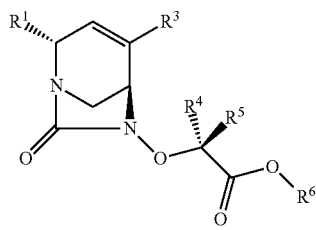

or a pharmaceutically acceptable salt thereof.

4. The compound according to claim 2 or a pharmaceutically acceptable salt thereof, wherein $R^3$ is $C_1$-$C_3$ alkyl.

5. The compound according to claim 4 or a pharmaceutically acceptable salt thereof, wherein $R^3$ is methyl.

6. The compound of claim 1 or a pharmaceutically acceptable salt thereof, wherein $R^1$ is —C(O)NR$^7$R$^8$.

7. The compound of claim 6 or a pharmaceutically acceptable salt thereof, wherein $R^7$ and $R^8$ are both hydrogen.

8. The compound of claim 3, according to formula (V):

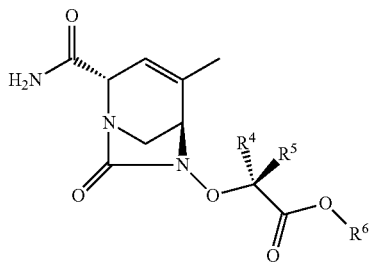

or a pharmaceutically acceptable salt thereof.

9. The compound of claim 8 or a pharmaceutically acceptable salt thereof, wherein $R^6$ is $C_1$-$C_{12}$ alkyl.

10. The compound of claim 9 or a pharmaceutically acceptable salt thereof, wherein $R^6$ is ethyl, isopropyl, 2-butyl or isopentyl.

11. The compound of claim 10 or a pharmaceutically acceptable salt thereof, wherein $R^6$ is isopropyl.

12. The compound according to claim 9 or a pharmaceutically acceptable salt thereof, wherein $R^4$ and $R^5$ are independently H, methyl or fluoro.

13. The compound according to claim 12 or a pharmaceutically acceptable salt thereof, wherein one of $R^4$ and $R^5$ is hydrogen, and the other is fluoro.

14. The compound according to claim 12 or a pharmaceutically acceptable salt thereof, wherein $R^4$ is fluoro and $R^5$ is hydrogen.

15. A pharmaceutical composition comprising a compound or a pharmaceutically acceptable salt thereof, as claimed in claim 1, and at least one pharmaceutically acceptable carrier, diluent or excipient.

16. The pharmaceutical composition according to claim 15, further comprising a beta-lactam antibiotic.

17. The pharmaceutical composition according to claim 16, wherein the beta-lactam antibiotic is cefpodoxime proxetil.

18. A method for treating a bacterial infection in a subject in need thereof, comprising administering to the subject an effective amount of a compound according to claim 1, or a pharmaceutically acceptable salt thereof, and a beta-lactam antibiotic.

19. The method of claim 18, wherein said beta-lactam antibiotic is cefpodoxime proxetil.

20. The method of claim 18, wherein the bacterial infection is selected from the group consisting of complicated urinary tract infection, uncomplicated urinary tract infection, kidney infection, lower respiratory tract infection, hospital-acquired bacterial pneumonia (HAP), pneumonia, acute bacterial prostatitis, acute bacterial skin and soft tissue infection, sepsis, intra-abdominal infection, and diabetic foot infection.

21. A compound of the formula:

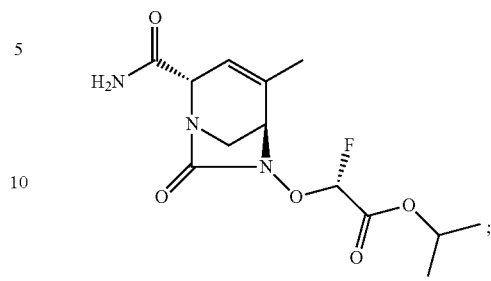

or a pharmaceutically acceptable salt thereof.

22. A method for treating a bacterial infection in a subject in need thereof, comprising administering to the subject an effective amount of a compound of the formula:

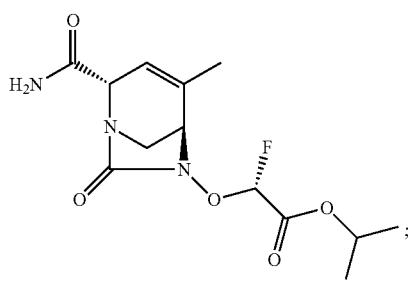 [SMILES: CC1=C[C@@H](C(N)=O)N2C[C@@H]1N(O[C@H](F)C(=O)OC(C)C)C2=O]

or a pharmaceutically acceptable salt thereof, and a beta-lactam antibiotic.

23. The method of claim 22, wherein said beta-lactam antibiotic is cefpodoxime proxetil.

24. The compound of claim 1, wherein the compound is of the formula:

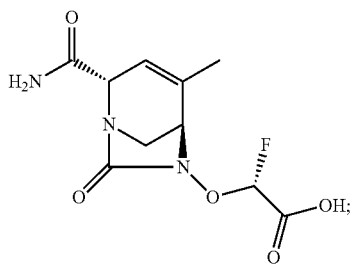 [SMILES: CC1=C[C@@H](C(N)=O)N2C[C@@H]1N(O[C@H](F)C(=O)O)C2=O]

or a pharmaceutically acceptable salt thereof.

25. A pharmaceutical composition comprising the compound of claim 21, or a pharmaceutically acceptable salt thereof, and at least one pharmaceutically acceptable carrier, diluent or excipient.

* * * * *